(12) United States Patent
Snoonian et al.

(10) Patent No.: US 10,577,317 B2
(45) Date of Patent: *Mar. 3, 2020

(54) CRYSTAL FORMS AND PRODUCTION METHODS THEREOF

(71) Applicant: Sunovion Pharmaceuticals Inc., Marlborough, MA (US)

(72) Inventors: John R. Snoonian, Bolton, MA (US); Harold Scott Wilkinson, Westborough, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/449,103

(22) Filed: Jun. 21, 2019

(65) Prior Publication Data

US 2019/0315686 A1 Oct. 17, 2019

Related U.S. Application Data

(63) Continuation of application No. 16/209,263, filed on Dec. 4, 2018, now Pat. No. 10,377,708.

(60) Provisional application No. 62/650,542, filed on Mar. 30, 2018, provisional application No. 62/594,851, filed on Dec. 5, 2017.

(51) Int. Cl.
*C07D 207/09* (2006.01)

(52) U.S. Cl.
CPC ........ *C07D 207/09* (2013.01); *C07B 2200/13* (2013.01)

(58) Field of Classification Search
CPC .................................................. C07D 207/09
See application file for complete search history.

(56) References Cited

U.S. PATENT DOCUMENTS

| | | | |
|---|---|---|---|
| 4,294,828 A | 10/1981 | Thominet et al. | |
| 5,955,500 A | 9/1999 | Logstreth et al. | |
| 6,069,165 A | 5/2000 | Andrieu et al. | |
| 6,169,094 B1 | 1/2001 | Perrault et al. | |
| 6,187,807 B1 | 2/2001 | Perrault et al. | |
| 6,861,072 B1 | 3/2005 | Alaux et al. | |
| 6,897,242 B1 | 5/2005 | Somerville et al. | |
| 7,825,156 B2 | 11/2010 | Azorin | |
| 8,394,790 B2 | 3/2013 | Portnoy et al. | |
| 8,575,172 B2 | 11/2013 | Wilding et al. | |
| 9,173,953 B2 | 11/2015 | Rau et al. | |
| 10,369,134 B2 | 8/2019 | Hopkins et al. | |
| 10,377,708 B2* | 8/2019 | Snoonian ............. | C07D 207/09 |
| 2003/0096264 A1 | 5/2003 | Altar et al. | |
| 2003/0130334 A1 | 7/2003 | Muller | |
| 2005/0085463 A1 | 4/2005 | Weiner et al. | |
| 2005/0171086 A1 | 8/2005 | Brodney et al. | |
| 2005/0250767 A1 | 11/2005 | Weiner et al. | |
| 2005/0281752 A1 | 12/2005 | Dugger, III | |
| 2006/0150989 A1 | 7/2006 | Migaly | |
| 2006/0153925 A1 | 7/2006 | Andre et al. | |
| 2006/0167068 A1 | 7/2006 | Feuerstein et al. | |
| 2006/0167074 A1 | 7/2006 | Muller | |
| 2008/0188464 A1 | 8/2008 | Green et al. | |
| 2008/0188537 A1 | 8/2008 | Azorin | |
| 2008/0280886 A1 | 11/2008 | Grant et al. | |
| 2008/0319041 A1 | 12/2008 | Digenis et al. | |
| 2009/0208979 A1 | 8/2009 | Silver et al. | |
| 2009/0269770 A1 | 10/2009 | Silver et al. | |
| 2010/0069356 A1 | 3/2010 | Gant et al. | |
| 2010/0069399 A1 | 3/2010 | Gant et al. | |
| 2010/0074973 A1 | 3/2010 | Gant et al. | |
| 2010/0119622 A1 | 5/2010 | Gant et al. | |
| 2010/0119624 A1 | 5/2010 | Gant et al. | |
| 2010/0143507 A1 | 6/2010 | Gant et al. | |
| 2010/0159033 A1 | 6/2010 | Gant et al. | |
| 2010/0266711 A1 | 10/2010 | Gant et al. | |
| 2011/0130390 A1 | 6/2011 | Muller | |
| 2011/0136742 A1 | 6/2011 | Mickle et al. | |
| 2013/0096319 A1 | 4/2013 | Paghdar et al. | |
| 2013/0281410 A1 | 10/2013 | Renshaw | |
| 2014/0031372 A1 | 1/2014 | Fong et al. | |
| 2014/0113912 A1 | 4/2014 | Loebel et al. | |
| 2015/0018360 A1 | 1/2015 | Halse et al. | |
| 2015/0099741 A1 | 4/2015 | Li et al. | |
| 2015/0272946 A1 | 10/2015 | Sato et al. | |
| 2016/0032390 A1 | 2/2016 | Hakonarson et al. | |
| 2016/0060702 A1 | 3/2016 | Li et al. | |
| 2016/0081987 A1 | 3/2016 | Lawton et al. | |
| 2016/0348101 A1 | 12/2016 | Chen et al. | |

(Continued)

FOREIGN PATENT DOCUMENTS

| CN | 1018988991 | 12/2010 |
|---|---|---|
| CN | 104725292 | 6/2015 |

(Continued)

OTHER PUBLICATIONS

Abbas et al., "Amisulpride is a potent 5-HT7 antagonist: relevance for antidepressant actions in vivo," Psychopharmacology, Jul. 2009, 205(1)119-128.
Babichev, "Interaction between regions of the hypothalamus regulating hypophyseal gonadotropic function in female rats," Neurosci Behav Physiol., Jul.-Sep. 1972, 5(3):195-199.
Bard et al., "Cloning of a novel human serotonin receptor (5-HT7) positively linked to adenylate cyclase," J Biol Chem, Nov. 5, 1993, 268(31):23422-23426.
BioOrganics, "R-Amisulpride," [retrieved on Mar. 22, 2018], retrieved from: <www.bioorganics.biz/product_details.php?id=BO%ADA67%AD009#1/2>, 2 pages.
No Author, "Dementia and Mental Illness: Findings on Dementia Detailed by Investigators at Department of Medicine (Antipsychotic Drug Use and the Risk of Seizures: Follow-up Study with a nested Case-Control Analysis)," Biotech Week; Atlanta, ProQuest document ID 1715999653, Sep. 30, 2015, 3 pages.
Bonaventure et al., "Translational evaluation of JNJ-18038683, a 5-hydroxytryptamine type 7 receptor antagonist, on rapid eye movement sleep and in major depressive disorder.," Aug. 2012, J Pharmacol Exp Ther., 342(2):429-440.

(Continued)

*Primary Examiner* — Rebecca L Anderson
(74) *Attorney, Agent, or Firm* — Fish & Richardson P.C.

(57) ABSTRACT

The various aspects present inventions provide various crystalline forms of (S)-(−)-amisulpride, (R)-(+)-amisulpride, and solvates thereof and methods of making same. In various aspects, the inventions also provide methods of resolving racemic amisulpride.

42 Claims, 40 Drawing Sheets

(56) References Cited

U.S. PATENT DOCUMENTS

| | | | |
|---|---|---|---|
| 2019/0167635 A1 | 6/2019 | Hopkins et al. | |
| 2019/0169123 A1 | 6/2019 | Hopkins et al. | |
| 2019/0314331 A1 | 10/2019 | Hopkins et al. | |

FOREIGN PATENT DOCUMENTS

| | | |
|---|---|---|
| CN | 106995397 | 8/2017 |
| EP | 1944295 | 7/2008 |
| EP | 1946777 | 7/2008 |
| EP | 2030619 | 3/2009 |
| EP | 2959895 | 3/2009 |
| GB | 2456183 | 7/2009 |
| WO | WO 98/47506 | 10/1998 |
| WO | WO 00/32558 | 6/2000 |
| WO | WO 2002/053140 | 7/2002 |
| WO | WO 2002/102297 | 12/2002 |
| WO | WO 2003/042654 | 5/2003 |
| WO | WO 2005/084654 | 9/2005 |
| WO | WO 2005/092392 | 10/2005 |
| WO | WO 2006/079547 | 8/2006 |
| WO | WO 2006/106425 | 10/2006 |
| WO | WO 2007/137224 | 11/2007 |
| WO | WO 2008/038003 | 4/2008 |
| WO | WO 2008/050341 | 5/2008 |
| WO | WO 2008/065500 | 6/2008 |
| WO | WO 2008/070296 | 6/2008 |
| WO | WO 2008/116024 | 9/2008 |
| WO | WO 2008/155357 | 12/2008 |
| WO | WO 2009/017453 | 2/2009 |
| WO | WO 2009/035473 | 3/2009 |
| WO | WO 2009/036056 | 3/2009 |
| WO | WO 2009/039461 | 3/2009 |
| WO | WO 2009/126931 | 10/2009 |
| WO | WO 2010/020642 | 2/2010 |
| WO | WO 2010/058314 | 5/2010 |
| WO | WO 2010/075275 | 7/2010 |
| WO | WO 2010/085452 | 7/2010 |
| WO | WO 2011/012722 | 2/2011 |
| WO | WO 2011/057199 | 5/2011 |
| WO | WO 2011/060363 | 5/2011 |
| WO | WO 2011/082337 | 5/2011 |
| WO | WO 2011/110854 | 9/2011 |
| WO | WO 2012/002583 | 1/2012 |
| WO | WO 2012/065102 | 5/2012 |
| WO | WO 2012/065110 | 5/2012 |
| WO | WO 2012/088441 | 6/2012 |
| WO | WO 2012/118562 | 9/2012 |
| WO | WO 2012/158492 | 11/2012 |
| WO | WO 2013/003586 | 1/2013 |
| WO | WO 2013/016727 | 1/2013 |
| WO | WO 2013/040164 | 3/2013 |
| WO | WO 2014/065437 | 5/2014 |
| WO | WO 2015/085004 | 6/2015 |
| WO | WO 2015/154025 | 10/2015 |
| WO | WO 2015/154030 | 10/2015 |
| WO | WO 2016/020573 | 2/2016 |
| WO | WO 2016/109359 | 7/2016 |
| WO | WO 2016/162695 | 10/2016 |
| WO | WO 2016/166679 | 10/2016 |
| WO | WO 2016/186968 | 11/2016 |
| WO | WO 2012/037457 | 5/2018 |

OTHER PUBLICATIONS

Bonaventure et al., "Selective blockade of 5-hydroxytryptamine (5-HT)7 receptors enhances 5-HT transmission, antidepressant-like behavior, and rapid eye movement sleep suppression induced by citalopram in rodents.," J Pharmacol Exp Ther., May 2007, 321(2):690-698.

Boulu, "Behavioral and neurochemical methods in research on new psychotropics," Ann Pharm Fr, 1998, 56(2):54-59.

Cassano et al., "Efficacy and safety of amisulpride 50 mg versus paroxetine 20 mg in major depression: a randomized, double-blind, parallel group study," Int Clin Psychopharmacol., Jan. 2002, 17(1):27-32.

Carta et al., "An Open Label Follow-up Study on Amisulpride in the add-on Treatment of Bipolar 1 Patients," Clinical Practive and Epidemiology in Mental Health, Aug. 24, 2006, 2:19.

Castelli et al., "(-)S amisulpride binds with high affinity to cloned dopamine D(3) and D(2) receptors," Euro Journal of Pharma., Nov. 5, 2001, 432:143-147.

Cates et al., "Effects of lurasidone in behavioral models of depression. Role of the 5-HT$_7$ receptor subtype," Neuropharmacology, Jul. 2013, 70:211-217.

Chaggar et al., "Effect of antipsychotic medications on glucose and lipid levels," J Clin Pharmacol, May 2011, 51(5):631-638.

Chen et al., "Second-generation antipsychotics in major depressive disorder: update and clinical perspective," Curr Opin Psychiatry., Jan. 2011, 24(1):10-17

Clinicaltrials.gov, Search Results, Jul. 25, 2018, 25 pages.

Clinicaltrials.gov, "A Four-week Clinical Trial Investigating Efficacy and Safety of Cannabidiol as a Treatment for Acutely Ill Schizophrenic Patients," NCT02088060, Mar. 8, 2018, [retrieved on Dec. 4, 2018] retrieved from URL<https://clinicaltrials.gov/ct2/show/NCT02088060>, 8 pages Clinicaltrials.gov, "A Randomized, Double-blind, Comparison of the Efficacy and Safety of Amisulpride Versus Low-dose Amisulpride Plus Low-dose Sulpiride in the Treatment of Schizophrenia," NCT01615185, Mar. 1, 2016, [retrieved on Dec. 3, 2018] retrieved from URL<https://clinicaltrials.gov/ct2/show/NCT01615185>, 8 pages.

Clinicaltrials.gov, "Amisulpride Augmentation in Clozapine-unresponsive Schizophrenia (AMICUS)," NCT01246232, Apr. 1, 2015, [retrieved on Dec. 3, 2018] retrieved from URL<https://clinicaltrials.gov/ct2/show/NCT01246232>, 8 pages Clinicaltrials.gov, "Amisulpride Augmentation Therapy for Clozapine-resistant Schizophrenic Patients (M1106)," NCT01105481, Apr. 16, 2010, [retrieved on Dec. 3, 2018] retrieved from URL<https://clinicaltrials.gov/ct2/show/NCT01105481>, 7 pages Clinicaltrials.gov, "Amisulpride in Schizophrenic Patients," NCT0033 1981, Apr. 10, 2008, [retrieved on Dec. 3, 2018] retrieved from URL<https://clinicaltrials.gov/ct2/show/NCT00331981>, 5 pages Clinicaltrials.gov, "Amisulpride in Schizophrenic Acute Phase Patients (ASAP)," NCT00436371, Sep. 5, 2008, [retrieved on Dec. 3, 2018] retrieved from URL<https://clinicaltrials.gov/ct2/show/NCT00436371>, 5 pages Clinicaltrials.gov, "An Investigation of Early life Stress and Depression", NCT 017101258, Dec. 28, 2016, [retrieved on Jul. 22, 2017] retrieved from URL<https://clinicaltrials.gov/ct2/show/NCT01701258?term=amisulpride&draw=1>, 6 pages Clinicaltrials.gov, "An Observational Drug Utilization Study of Asenapine in the United Kingdom (P08308)," NCT01498770, Jun. 7, 2017, [retrieved on Jul. 22, 2017] retrieved from URL<https://clinicaltrials.gov/ct2/show/NCT01498770?term=amisulpride&draw=1>, 6 pages Clinicaltrials.gov, "An Observational Study on Atypical Antipsychotics Long-term Treatment Patients With Schizophrenia," NCT02640911, Aug. 1, 2017, [retrieved on Dec. 4, 2018] retrieved from URL<https://clinicaltrials.gov/ct2/show/NCT02640911>, 6 pages Clinicaltrials.gov, "An Observational Study on Metabolic Syndrome Parameters in Schizophrenia Patients Treated With Atypical Antipsychotics (MESSAGE)," NCT00448630, Jul. 7, 2010, [retrieved Dec. 4, 20018] retrieved from URL<https://clinicaltrials.gov/ct2/show/NCT00448630>, 8 pages.

Clinicaltrials.gov, "Antipsychotic Induced Structural and Functional Brain Changes (APIC)," NCT02435095, Dec. 22, 2017, [retrieved on Dec. 4, 2018] retrieved from URL<https://clinicaltrials.gov/ct2/show/NCT02435095>, 10 pages.

Clinicaltrials.gov, "Association of Amisulpride Response in Schizophrenia With Brain Image (ARB)," NCT02095938, Mar. 26, 2014, [retrieved Dec. 3, 2018] retrieved from URL<https://clinicaltrials.gov/ct2/show/NCT02095938>, 9 pages.

Clinicaltrials.gov,"Benzamide Derivates as Treatment of Clozapine-induced Hypersalivation (CIH)," NCT00534573, Jul. 26, 2012, Jul. 26, 2012, [retrieved on Dec. 3, 2018] retrieved from URL<https://clinicaltrials.gov/ct2/show/NCT00534573>, 6 pages.

(56) References Cited

OTHER PUBLICATIONS

Clinicaltrials.gov, "Bergen Psychosis Project 2—The Best Intro Study (BP2)," NCT01446328, Jan. 30, 2018, [retrieved on Dec. 4, 2018] retrieved from URL<https://clinicaltrials.gov/ct2/show/NCT01446328>, 7 pages.

Clinicaltrials.gov, "Cannabidiol as a Different Type of an Antipsychotic: Drug Delivery and Interaction Study (CBD-IS)," NCT02051387, Mar. 8, 2018, [retrieved on Dec. 4, 2018] retrieved from URL<https://clinicaltrials.gov/ct2/show/NCT02051387>, 7 pages.

Clinicaltrials.gov, "Clinical Trial to Evaluate the Efficacy of Treatment vs Discontinuation in a First Episode of Non-affective Psychosis (NONSTOP)," NCT01765829, Dec. 5, 2014, [retrieved on Dec. 4, 2018] retrieved from URL<https://clinicaltrials.gov/ct2/show/NCT01765829>, 10 pages.

Clinicaltrials.gov, "Clozapine Versus Amisulpride in Treatment-resistant Schizophrenia Patients (ClozAmi)," NCT01448499, Dec. 9, 2015, [retrieved on Dec. 3, 2018] retrieved from URL<https://clinicaltrials.gov/ct2/show/NCT01448499>, 7 pages.

Clinicaltrials.gov, "Characterize the Modulatory Effects of Dopamine D2/D3 Receptor Agonist and Antagonist Drugs on Compulsive Behaviors," NCT00471588, Sep. 15, 2014, [retrieved on Dec. 4, 2018] retrieved from URL<https://clinicaltrials.gov/ct2/show/NCT00471588>, 7 pages.

Clinicaltrials.gov, "Comparison of Antipsychotic Combination Treatment of Olanzapine and Amisulpride to Monotherapy," NCT01609153, Jan. 23, 2017, [retrieved on Jul. 22, 2017] retrieved from URL<https://clinicaltrials.gov/ct2/show/NCT01609153?term=amisulpride&draw=1>, 7 pages.

Clinicaltrials.gov, "Comparison of Valproate-Amisulpride and Valproate-Haloperidol in Bipolar I Patients," NCT00126009, Apr. 8, 2008, [retireved on Jul. 22, 2017] retrieved from URL<https://clinicaltrials.gov/ct2/show/NCT00126009?term=amisulpride&draw=1>, 5 pages.

Clinicaltrials.gov, "Dopamine and Opioid Receptor Antagonists Reduce Cue-induced Reward Responding and Reward Impulsivity," NCT02557984, Sep. 23, 2015, [retrieved on Dec. 4, 2018] retrieved from URL<https://clinicaltrials.gov/ct2/show/NCT02557984>, 8 pages.

Clinicaltrials.gov, "Early Pharmacological and Psychological Intervention for Late Prodromal States of Psychosis," NCT00204061, Dec. 24, 2014, [retrieved on Dec. 4, 2018] retrieved from URL<https://clinicaltrials.gov/ct2/show/NCT00204061>, 7 pages.

Clinicaltrials.gov, "Effect of Atypical Antipsychotic Drugs Olanzapine and Amisulpride on Glucose Metabolism," NCT01160991, Aug. 3, 2010, [retrieved on Dec. 3, 2018] retrieved from URL https://clinicaltrials.gov/ct2/show/NCT01160991>, 7 pages.

Clinicaltrials.gov, "Effectiveness and Safety of Amisulpride in Chinese Patients With Schizophrenia (ESCAPE)," NCT01795183, Jan. 22, 2015, [retrieved on Dec. 3, 2018] retrieved from URL<https://clinicaltrials.gov/ct2/show/NCT01795183>, 6 pages.

Clinicaltrials.gov, "Efficacy of an Early Antipsychotic Switch in Case of Poor Initial Response to the Treatment of Schizophrenia," NCT01029769, May 27, 2015, [retrieved on Jul. 22, 2018], retrieved from URL<https://clinicaltrials.gov/ct2/show/NCT01029769?term=amisulpride&draw=1>, 4 pages.

Clinicaltrials.gov, "Efficacy Study on Cognitive Functions in Schizophrenic Patients (AMIMIND)," NCT00761670, Dec. 9, 2010, [retrieved on Dec. 3, 2018] retrieved from URL<https://clinicaltrials.gov/ct2/show/NCT00761670>, 7 pages.

Clinicaltrials.gov, "Enhancing Recovery in Early Schizophrenia," NCT02926859, Mar. 8, 2018, [retrieved on Dec. 4, 2018] retrieved from URL<https://clinicaltrials.gov/ct2/show/NCT02926859>, 9 pages.

Clinicaltrials.gov, "European Phase III Study of APD421 in PONV," NCT01991821, Jan. 12, 2015, [retrieved on Dec. 4, 2018] retrieved from URL<https://clinicaltrials.gov/ct2/show/NCT01991821>, 5 pages.

Clinicaltrials.gov, "Evaluation of the Antipsychotic Efficacy of Cannabidiol in Acute Schizophrenic Psychosis (CBD-CT1)," NCT00628290, Mar. 18, 2008, [retrieved on Dec. 4, 2018] retrieved from URL<https://clinicaltrials.gov/ct2/show/NCT00628290>, 6 pages.

Clinicaltrials.gov, "Evaluation of Negative Symptoms and Cognitive Function After Administration of Antipsychotics in Healthy Volunteer," NCT01185418, Aug. 20, 2010, [retrieved on Dec. 4, 2018] retrieved from URL<https://clinicaltrials.gov/ct2/show/NCT01185418>, 6 pages.

Clinicaltrials.gov, "Evaluation of the Necessity of Long-term Pharmacological Treatment with Antipsychotics in Schizophrenic Patients," NCT02307396, Feb. 29, 2016, [retreived on Jul. 22, 2017] retrieved from URL<https://clinicaltrials.gov/ct2/show/NCT02307396?term=amisulpride&draw=1>, 5 pages.

Clinicaltrials.gov, "Identification and Treatment Response Prediction of Antipsychotic-Related Metabolic Syndrome," NCT00956189, Jan. 3, 2013, [retrieved on Dec. 3, 2018] retrieved from URL<https://clinicaltrials.gov/ct2/show/NCT00956189>, 6 pages.

Clinicaltrials.gov, "Investigation of the Safety, Tolerability and Potential Therapeutic Effects of JNJ-40411813 in Patients With Schizophrenia," NCT01323205, May 30, 2014, [retrieved on Dec. 4, 2018] retrieved from URL<https://clinicaltrials.gov/ct2/show/NCT01323205>, 8 pages.

Clinicaltrials.gov, "Metabolic Side-effects for Second-generation Antipsychotics," NCT01280396, Jan. 28, 2011, [retrieved on Jul. 22, 2017] retrieved from URL<https://clinicaltrials.gov/ct2/show/NCT01280396?term=amisulpride&draw=1>, 4 pages.

Clinicaltrials.gov, "Metoclopramide as Treatment of Clozapine-induced Hypersalivation," NCT02222220, Aug. 21, 2014, [retrieved on Dec. 4, 2018] retrieved from URL<https://clinicaltrials.gov/ct2/show/NCT02222220>, 7 pages.

Clinicaltrials.gov, "Modulation of Regional Brain Activation in Schizophrenic Patients by Pharmacological Therapy," NCT00419653, Sep. 16, 2008, [retrieved on Dec. 4, 2018] retrieved from URL<https://clinicaltrials.gov/ct2/show/NCT00419653>, 6 pages.

Clinicaltrials.gov, "Optimisation of Antipsychotic Drug Use in Older People," NC01454453, Oct. 19, 2011, [retrieved on Dec. 4, 2018] retrieved from URL<https://clinicaltrials.gov/ct2/show/NCT01454453>, 6 pages.

Clinicaltrials.gov, "Optimization of Treatment and Management of Schizophrenia in Europe (OPTIMISE): Substudy Site Copenhagen," NCT0155814, Oct. 25, 2016, [retrieved Jul. 22, 2017] retrieved from URL<https://clinicaltrials.gov/ct2/show/NCT01555814?term=amisulpride&draw=1>, 5 pages.

Clinicaltrials.gov, "Optimization of Treatment and Management of Schizophrenia in Europe (OPTIMISE)," NCT01248195, Nov. 3, 2016, [retrieved Jul. 22, 2017] retrieved from URL<https://clinicaltrials.gov/ct2/show/NCT01248195?term=amisulpride&draw=1>, 6 pages.

Clinicaltrials.gov, "Pan European Collaboration on Antipsychotic Naive Schizophrenia (PECANS) (PECANS)," NCT01154829, May 26, 2016, [retrieved on Dec. 4, 2018] retrieved from URL<https://clinicaltrials.gov/ct2/show/NCT01154829>, 7 pages.

Clinicaltrials.gov, "Pharmacovigilance in Gerontopsychiatric Patients (GAP)," NCT02374567, Feb. 23, 2017, [retrieved on Jul. 22, 2017] retrieved from URL<https://clinicaltrials.gov/ct2/show/NCT02374567?term=amisulpride&draw=1>, 8 pages.

Clinicaltrials.gov, "Phase IIIb Study of APD421 in Combination as PONV Prophylaxis," NCT02337062, Aug. 4, 2017, [retrieved on Dec. 4, 2018] retrieved from URL<https://clinicaltrials.gov/ct2/show/NCT02337062>, 7 pages.

Clinicaltrials.gov. "Safety and Efficacy of Aripiprazole and Ziprasidone Among Schizophrenic Patients With Metabolic Syndrome," NCT01714011, Nov. 27, 2012, [retrieved on Dec. 4, 2018] retrieved from URL<https://clinicaltrials.gov/ct2/show/NCT01714011>, 8 pages.

Clinicaltrials.gov, "SOLIACS: Solian Solution in the Acute Setting," NCT00245674, Apr. 10, 2008, [retrieved on Dec. 3, 2018] retrieved from URL<https://clinicaltrials.gov/ct2/show/NCT00245674>, 5 pages.

Clinicaltrials.gov, "SOLMANIA—Comparison of Valproate-Amisulpride and Valproate-Haloperidol in Bipolar I Patients," NCT00126009, Apr. 10, 2008, [retrieved on Dec. 3, 2018] retrieved from URL<https://clinicaltrials.gov/ct2/show/NCT00126009>, 7 pages.

Clinicaltrials.gov, "Study Assessing SEP-363856 in Male and Female Volunteers With High or Low Schizotype Characteristics," NCT01972711, Feb. 23, 2016, [retrieved Dec. 4, 2018] retrieved from URL<https://clinicaltrials.gov/ct2/show/NCT01972711>, 9 pages.

(56) References Cited

OTHER PUBLICATIONS

Clinicaltrials.gov, "Study of APD421 as PONV Treatment (Prior Prophylaxis)," NCT02646566, Jan. 24, 2017, [retrieved Dec. 4, 2018] retrieved from URL<https://clinicaltrials.gov/ct2/show/NCT02646566>, 7 pages.
Clinicaltrials.gov, "Study of APD421 as PONV Treatment (no Prior Prophylaxis)," NCT024492914, Aug. 5, 2016, [retrieved Dec. 4, 2018] retrieved from URL<https://clinicaltrials.gov/ct2/show/NCT02449291>, 6pages.
Clinicaltrials.gov, "SWitching to Abilify Trial (SWAT)," NCT00304616, Dec. 17, 2009, [retrieved on Dec. 4, 2018] retirieved from URL<https://clinicaltrials.gov/ct2/show/NCT00304616>, 6 pages.
Clinicaltrials.gov, "Tardive Dyskinesia and Cognitive Function (TD)," NCT00926965, Jun. 24, 2009, [retrieved on Dec. 4, 2018] retrieved from URL<https://clinicaltrials.gov/ct2/show/NCT00926965>, 6 pages.
Clinicaltrials.gov, "The Effects of Dopamine on Reward Processing," NCT01253421, Dec. 27, 2016, [retrieved on Jul. 22, 2017] retrieved from URL<https://clinicaltrials.gov/ct2/show/NCT01253421?term=amisulpride&draw=1>, 5 pages.
Clinicaltrials.gov, "Thorough QT Study of Intravenous Amisulpride," NCT02661594, Nov. 29, 2018, [retrieved on Dec. 3, 2018] retrieved from URL<https://clinicaltrials.gov/ct2/show/NCT02661594>, 11 pages.
Clinicaltrials.gov, "US Phase III Study of APD421 in PONV," NCT01991860, Sep. 6, 2018, [retrieved on Dec. 4, 2018] retrieved from URL<https://clinicaltrials.gov/ct2/show/NCT01991860>, 5 pages.
Clinicaltrials.gov, "[18 Fluorine(F)]DOPA Determinants and Predictors of Treatment Response in Psychosis (DPTP)," NCT02880995, Aug. 26, 2016, [retrieved on Dec. 4, 2018] retrieved from URL<https://clinicaltrials.gov/ct2/show/NCT02880995>, 8 pages.
Coukell et al., "A Review of its Pharmacodynamic and Pharmacokinetic Properties and Therapeutic Efficacy in the Management of Schizophrenia," Drug Evaluation, Sep. 1996, 6(3):237-256.
Coulouvrat et al., "Safety of amisulpride (Solian): a review of 11 clinical studies," International Clinical Psychopharmacology, Jul. 1999, 14(4):209-218.
DeVane et al., "Clinical Pharmacokinetics of Quetiapine," Drug Disposition, 2001, 40(7):509-522.
Donahue, "Amisulpride is a potent 5-HT7 antagonist: relevance for antidepressant actions in vivo," Psychopharmacology, Jul. 2009, 205(1):119-128.
Donahue, Characterization of the Decriminative Stimulus Properties of the Atypical Antipsychotic Amisulpride in C57BL/6 Mice:, Thesis or the degree of Doctor of Philosophy, Virginia Commonwealth University, Department of Psychology, Nov. 2014, 141 pages.
Donahue, "Discriminative stimulus properties of he atypical antipsychotic amisulpride: comparison to its isomers and to other benzamide derivatives, antipsychotic, antidepressant, and antianxiety drugs in C57BL/6 mice," Psychopharmacology, Dec. 2017, 234(23-24):3507-3520.
Donahue et al., "(S)-amisulpride as a discriminative stimulus in C57BL/6 mice and its comparison to the stimulus effects of typical and atypical antipsychotics," Eur J Pharmacolo., Jul. 5 2014, 734(1):15-22.
Farde et al., "Positron emission tomographic analysis of central D1 and D2 dopamine receptor occupancy in patients treated with classical neuroleptics and clozapine. Relation to extrapyramidal side effects," Arch Gen Psychiatry., Jul. 1992, 49:538-544.
Gao et al., "Efficacy of typical and atypical antipsychotics for primary and comorbid anxiety symptoms or disorders: a review," J Clin Psychiatry, Sep. 2006, 67(9):13727-1340.
Grunder et al., "The 'atypicality' of antipsychotics: a concept re-examined and re-defined," Nat Rev Drug Discov., Mar. 2009, 8(3):197-202.
Guscott et al., "Genetic knockout and pharmacological blockade studies of the 5-HT7 receptor suggest therapeutic potential in depression," Neuropharmacology, Mar. 2005, 48(4):492-502.

Hardoy et al., "Adjunctive amisulpride to fluvoxamine in major depression: Early ssri onset of action," European psychiatry, 2000, 15:s325.
Harvey et al., "Effect of lurasidone on neurocognitive performance in patients with schizophrenia: a short-term placebo- and active-controlled study followed by a 6-month double-blind extension," Eur Neuropsychopharmocol., Nov. 2013, 23(11):1373-1382.
Harvey et al., "Effect of lurasidone dose on cognition in patients with schizophrenia: post-hoc analysis of a long-term, double-blind continuation study," Schizophr Res., Aug. 2015, 166(1-3):334-338.
Hedlund et al., "The 5-HT7 receptor and disorders of the nervous system: an overview," Psycopharmacology, Oct. 2009, 206(3):345-354.
Hedlund et al., "5-HT7 receptor inhibition and inactivation induce antidepressantlike behavior and sleep pattern," Biol Psychiatry., Nov. 15, 2005, 58(10):831-837.
International Search Report and Written Opinion in International Application No. PCT/US2018/63865, dated Mar. 25, 2019, 13 pages.
International Search Report and Written Opinion in International Application No. PCT/US2018/63859, dated Mar. 26, 2019, 23 pages.
Jakovcevska-Kujundziska et al., "Amisulpride in combination with maprotiline in the treatment of psychotic depression—a clinical experience," European NeuroPsychopharmacology, Oct. 2003, 13:s193.
Kapur et al., "Clinical and Theoretical Implications of 5-HT2 and D2 Receptor Occupancy of Clozapine, Risperidone, and Olanzapine in Schizophrenia," Am J Psychiatry, Feb. 1999, 156:2.
Kapur et al., "A Positron Emission Tomography Study of Quetiapine in Schizophrenia," Arch Gen Psychiatry, Jun. 2000, 57:553-559.
Kaul et al., "Comparative evaluation of amisulpride and escitalopram on Hamilton Depression Rating Scale among depression patients in a tertiary care teaching hospital in Nepal," Int J Med Sci Public Health., 2015, 4(5):642-646.
Keshipeddy et al., "Nonracemic Antifolates Stereoselectively Recruit Alternate Cofactors and Overcome Resistance in *S. aureus*", Journal of the American Chemical Society, Jun. 22, 2015, 137:8983-8990.
Komossa et al., "Second-generation antipsychotics for major depressive disorder and dysthymia," Cochrane Database Syst Rev., Dec. 8, 2010, (12):CD008121.
La Fougere et al., "D2 receptor occupancy during high- and low-dose therapy with the atypical antipsychotic amisulpride: a 123I-iodobenzamide SPECT study.," J Nucl Med., Jun. 2005, 46(6):1028-1033.
Lecrubier et al., "Amisulpride versus imipramine and placebo in dysthymia and major depression. Amisulpride Study Group," J Affect Disord., Apr. 1997, 43(2):95-103.
Leopoldo et al., "Serotonin 5-HT7 receptor agents: Structure-activity relationships and potential therapeutic applications in central nervous system disorders," Pharmacol Ther., Feb. 2011, 129(2):120-148.
Leucht et al., "Comparative efficacy and tolerability of 15 antipsychotic drugs in schizophrenia: a multiple-treatments meta-analysis," Lancet, Sep. 14, 2013, 382(9896):951-962.
Lopez-Monoz et al., "Bipolar disorder as an emerging pathology in the scientific literature: a bibliometric approach," J Affect Disorder, Jun. 2006, 92(2-3):161-170.
Lovenberg et al., "A novel adenylyl cyclase-activating serotonin receptor (5-HT7) implicated in the regulation of mammalian circadian rhythms," Neuron, Sep. 1993, 11(3):449-458.
Mamo et al., "Quetiapine Extended-Release Versus Immediate-Release Formulation: A Positron Emission Tomography Study," J Clin PsyChiatry, Jan. 2008, 69(1):81-86.
Marchese et al., "Effect of the Amisulpride Isomers on Rat Catalepsy," European Journal of Pharmacology, May 24, 2002, 444(1-2):69-74.
Moller et al., "Antipsychotic and antidepressive effects of second generation antipsychotics," Eur Arch Psychiatry Clin Neurosci., Jun. 2005, 255(3):190-201.
Montgomery, "Dopaminergic deficit and the role of amisulpride in the treatment of mood disorders," Int Clin Psychopharmacol., Dec. 2002, 17 Suppl 4:S9-15.

(56) References Cited

OTHER PUBLICATIONS

Morgan et al., "Characterization of the Antiociceptive Effects of the Individual Isomers of Methadone After Acute and Chronic Administrations," Behav Pharmacol., Sep. 2011, 22(5-6):548-557.
Morita et al., "HTR7 Mediates Seratonergic Acute and Chronic Itch," Neuron, Jul. 1, 2015, 87(1):124-138.
Nelson et al., "Atypical antipsychotic augmentation in major depressive disorder: a meta-analysis of placebo-controlled randomized trials," Am J Psychiatry, Sep. 2009, 166(9):980-991.
Nikiforuk, "Targeting the Serotonin 5-HT7 Receptor in the Search for Treatments for CNS Disorders: Rationale and Progress to Date," CNS Drugs, Apr. 2015, 29(4):265-275.
Nikiforuk et al., "Effects of the selective 5-HT7 receptor antagonist SB-269970 and amisulpride on ketamine-induced schizophrenia-like deficits in rats," PLoS One., Jun. 11, 2013, 8(6):e66695.
Nyberg et al., "Suggested Minimal Effective Dose of Risperidone Based on PET-Measured D2 5-HT2A Receptor Occupancy in Schizophrenic Patients," Am J Psychiatry., Jun. 1999, 156:873-875.
Office Action (Final) in U.S. Appl. No. 14/344,665, dated Oct. 28, 2016, 32 pages.
Palovics et al., "Separation of the Mixtures of Chiral Compounds by Crystallization," Advances in Crystallization Processes, Apr. 27, 2012, retrieved from URL <https://www.intechopen.com/books/advances-in-crystallization-processes/separation-of-the-mixtures-of-chiral-compounds-by-crystallization>, pp. 1-38.
Papp and Wieronska, "Antidepressant-like activity of amisulpride in two animal models of depression," Journal of Psychopharmacology, 2000, 14(1):46-52.
Pawar et al., "Evaluation of antidepressant like property of amisulpride per se and its comparison with fluoxetine and olanzapine using forced swimming test in albino mice," Acta Pol Pharma., May-Jun. 2009, 66(3):327-331.
Popovic et al., "Number needed to treat analyses of drugs used for maintenance treatment of bipolar disorder,", Psychopharmacology, Feb. 2011, 213(4):657-667.
Barrett, "Aspects of cognitive function in healthy volunteers administered antipsychotic drugs and in patients with bipolar disorder," Queen's University Belfast (United Kingdom), ProQuest Dissertations Publishing, 2001. U151775. (Abstract only).
Roix et al., "Effect of the antipsychotic agent amisulpride on clucose lowering and insulin secretion," Diabetes, Obesity and Metabolism, Apr. 2012, 14(4):329-334.
Rybakowski et al., "Treatment of depression in first episode of schizophrenia: results from EUFEST," Eur Neuropsychopharmacol., Dec. 2012, 22(12):875-882.
Sarkisyan et al., "The 5-HT(7) receptor as a mediator and modulator of antidepressant-like behavior," Behave Brain Res., May 1, 2010, 209(1):99-108.
Smeraldi, "Amisulpride versus fluoxetine in patients with dysthymia or major depression in partial remission: a double-blind, comparative study," J Affect Disord., Feb. 1998, 48(1):47-56.

Spina et al., "Metabolic drug interactions with newer antipsychotics: a comparative review," Basic Clin Pharmacol Toxicol, Jan. 2007, 100(1):4-22.
Suppes et al., "Lurasidone for the Treatment of Major Depressive Disorder With Mixed Features: A Randomized, Double-Blind, Placebo-Controlled Study," Am J Psychiatry., Apr. 1, 2016, 174(4):400-407.
Taubel et al., "Thorough QT study of the effect of intravenous amisulpride on QTc Interval in Caucasian and Japanese healthy subjects," British Journal of Clinical Pharmacology, Feb. 2017, 83(2):339-348.
Toronto Research Chemicals, "R-Amisulpride," 2017, [retrieved on Mar. 20, 2017], retrieved from: URL<https://www.trc-canada.com/product-detail/?CatNum=A633255&CAS=71675-90-6&Chemical_Name=R-Amisulpride&Mol_Formula=$C_{17}H_{27}N_3O_4S$>, 2 pages.
Thomas et al., "Amisulpride Plus Valproate vs Haloperidol Plus Valproate in the Treatment of Acute Mania of Bipolar I Patients: A Multicenter, Open-label Randomized, Comparative Trial," Original Research, 2008, 4(3):675-686.
Thomas et al., "SB-656104-A, A Novel Selective 5-HT7 Receptor Antagonist, Modulates REM Sleep in Rats," British Journal of Pharmacology, Jun. 2003, 139(4):705-714.
Vanelle et al., "Metabolic control in patients with comorbidschizophrenia and depression treated with amisulpride or olanzapine," European Neuropsychopharmacology, Oct. 2004, 14(3):S284.
Vernaleken et al., "High striatal occupancy of D2-like dopamine receptors by amisulpride in the brain of patients with schizophrenia," Int J Neuropsychopharmacol., Dec. 2004, 7(4):421-430.
Vieta et al. "An open-label study of amisulpride in the treatment of mania," The Journal of Clinical Psychiatry, May 2005, 66(5):575-8.
Wesolowska et al., "Enhancement of the anti-immobility action of antidepressants by a selective 5-HT7 receptor antagonist in the forced swimming test in mice," Eur J Pharmacol., Jan. 19 2007, 555(1):43-47.
Willner et al., "Dopaminergic mechanism of antidepressant action in depressed patients," J Affect Disord., May 2005, 86(1):37-45.
Winter et al., "Structure of the Neuropeptic Drug 4-Amino-N-1-[(1-ethyl-2-pyrrolidinyl)methyl]-5-(ethylsulfonyl)-2-methoxybenzamide (Amisulpride)," Acta Cryst., Feb. 15, 1990, 46(2):313-317.
Yatham et al., "Canadian Network for Mood and Anxiety Treatments (CANMAT) and International Society for Bipolar Disorders (ISBD) collaborative update of CANMAT guidelines for the management of patients with bipolar disorder: update 2009," Bipolar Disord., May 2009, 11(3):225-255.
Zhang et al., "Crystal Structures and physicochemical properties of amisulpride polymorphs," Journal of Pharmacautical and Biomedicinal Analysis, Jun. 5, 2017, 140:252-257.
Zhou et al., "Atypical Antipsychotic Augmentation for Treatment-Resistant Depression: A Systematic Review and Network Meta-Analysis," Int J Neuropsychopharmacol, May 25, 2015, 18(11):pyv060.

* cited by examiner

CRYSTAL FORMS AND PRODUCTION METHODS THEREOF

FIELD OF THE INVENTION

The present inventions relate to crystal forms of enantiomeric amisulpride and to methods of producing the same.

BACKGROUND

Amisulpride is a member of the chemical class benzamide, and has the chemical name 4-amino-N-[(1-ethylpyrrolidin-2-yl)methyl]-5-ethylsulfonyl-2-methoxy-benzamide. The chemical structure of amisulpride is as follows:

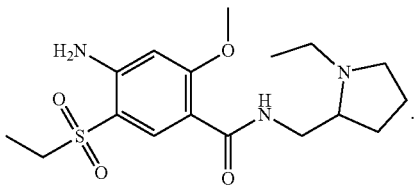 [SMILES: CCN1CCCC1CNC(=O)c1cc(S(=O)(=O)CC)c(N)cc1OC]

Drug substances are most frequently administered orally by means of solid dosage forms such as tablets. Tablets remain popular because of the advantages afforded both to the manufacturer (e.g., simplicity and economy of preparation, stability and convenience in packaging, shipping and dispensing) and to the patient (e.g., accuracy of dosage, compactness, portability, and ease of administration). The preparation of tablets typically requires that the active pharmaceutical ingredient (API) be a solid. In the manufacture of solid APIs, it is necessary to obtain products with reproducible properties, including chemical purity and composition. For crystalline solid enantiomeric APIs, it is important to produce the desired polymorph with high chemical and enantiomeric purity. A reliable, reproducible process for preparing pure crystalline amisulpride enantiomers would be highly desired.

SUMMARY

The present inventions relate to substantially pure crystalline forms of amisulpride enantiomers and methods of producing same. Amisulpride has a single asymmetric center and as a result exists in two enantiomeric forms: R-4-Amino-N-[(1-ethyl-2-pyrrolidinyl)methyl]-5-(ethylsulfonyl)-2-methoxybenzamide (also referred to as: (R)-(+)-4-amino-N-[(1-ethylpyrrolidin-2-yl)methyl]-5-(ethylsulfonyl)-2-methoxybenzamide, and under the IUPAC name as 4-amino-5-(ethanesulfonyl)-N-{[(2R)-1-ethylpyrrolidin-2-yl]methyl}-2-methoxybenzamide), abbreviated herein as (R)-(+)-amisulpride or (R)-amisulpride; and S-4-Amino-N-[(1-ethyl-2-pyrrolidinyl)methyl]-5-(ethylsulfonyl)-2-methoxybenzamide (also referred to as: (S)-(−)-4-amino-N-[(1-ethylpyrrolidin-2-yl)methyl]-5-(ethylsulfonyl)-2-methoxybenzamide, and under the IUPAC name as 4-amino-5-(ethanesulfonyl)-N-{[(2S)-1-ethylpyrrolidin-2-yl]methyl}-2-methoxybenzamide), abbreviated herein as (S)-(−)-amisulpride or (S)-amisulpride. These two enantiomeric forms have the following chemical structures:

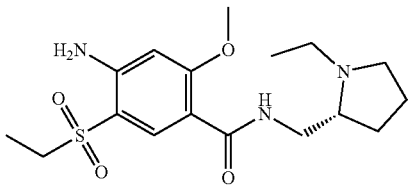 [SMILES: CCN1CCC[C@@H]1CNC(=O)c1cc(S(=O)(=O)CC)c(N)cc1OC]

R-4-Amino-N-[(1-ethyl-2-pyrrolidinyl)methyl]-5-(ethylsulfonyl)-2-methoxybenzamide (R)-amisulpride

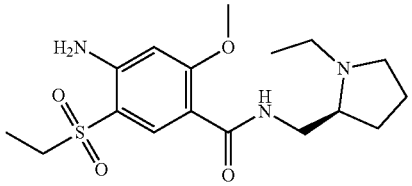 [SMILES: CCN1CCC[C@H]1CNC(=O)c1cc(S(=O)(=O)CC)c(N)cc1OC]

S-4-Amino-N-[(1-ethyl-2-pyrrolidinyl)methyl]-5-(ethylsulfonyl)-2-methoxybenzamide (S)-amisulpride In various aspects, the present inventions relate to crystal forms of amisulpride enantiomers and in various aspects, the present inventions relate to crystal forms of solvates of amisulpride enantiomers. In various aspects, the present inventions provide methods of making crystal forms of amisulpride enantiomers and in various aspects, the present inventions relate to methods of resolving amisulpride enantiomers from a racemic or non-enantiomerically pure amisulpride.

In the course of several experiments, the inventors have unexpectedly discovered that (R)-amisulpride and (S)-amisulpride can independently be prepared as a new and advantageous free base crystalline form, which for the sake of identification herein is referred to as Form A for the free base crystalline form of (R)-amisulpride, and Form A' for the free base crystalline form of (S)-amisulpride. In addition, it has now been unexpectedly discovered that (R)-amisulpride and (S)-amisulpride can independently be prepared as a new and advantageous ethyl acetate solvate crystalline form, which for the sake of identification herein is referred as Form B for the ethyl acetate solvate crystalline form of (R)-amisulpride, and Form B' for the ethyl acetate solvate crystalline form of (S)-amisulpride.

In various embodiments, crystalline forms of the present inventions have several advantageous physical properties. For example, in contrast to the crystalline form (S)-amisulpride D-tartrate, the (R)-amisulpride Form A and (S)-amisulpride Form A' crystalline forms are substantially non-hygroscopic, exhibiting less than a 0.5% maximum mass change in water sorption isotherms, at 25° C. scanned over 0 to 95% relative humidity, as measured by dynamic vapor sorption (DVS), whereas crystalline (S)-amisulpride D-tartrate was found to be highly hygroscopic, exhibiting a 52±9% (n=4, σ=18.25) maximum mass change in water sorption isotherms, at 25° C. scanned over 0 to 95% relative humidity, as measured by DVS. In various embodiments, Form A and Form A' are anhydrous, e.g., substantially free of water and solvents.

In addition, Forms A and A' were found to be thermodynamically stable, not substantially converting to other polymorphs or amorphous form after 4 months at 25° C. and 60% relative humidity (RH). Forms B and B' were found to desolvate upon drying and heating about 30° C. to convert to Form A or Form A' (respectively) and amorphous, indicating that Forms A and A' are thermodynamically favored over Forms B and B' and potentially other polymorphs of (R)-amisulpride free base and (S)-amisulpride free base.

It is to be understood that various embodiments of the present inventions provide crystalline enantiomeric amisulpride of Form A and Form A' and crystalline enantiomeric amisulpride ethyl acetate solvates of Form B and Form B', that have both high chiral purity and high chemical purity.

In various embodiments the present inventions provide substantially enantiomerically pure crystalline forms of (R)-amisulpride of Form A. For example, in various embodiments, the present inventions provide crystalline forms of amisulpride that contain greater than about 90% (R)-amisulpride and less than about 10% of (S)-amisulpride, greater than about 95% (R)-amisulpride and less than about 5% of (S)-amisulpride, greater than about 97% (R)-amisulpride and less than about 3% of (S)-amisulpride, greater than about 99% (R)-amisulpride and less than about 1% of (S)-amisulpride, greater than about 99.5% (R)-amisulpride and less than about 0.5% of (S)-amisulpride, greater than about 99.7% (R)-amisulpride and less than about 0.3% of (S)-amisulpride, or greater than about 99.9% (R)-amisulpride and less than about 0.1% of (S)-amisulpride.

In various embodiments the present inventions provide substantially chemically pure crystalline forms of (R)-amisulpride of Form A. For example, in various embodiments, the present inventions provide crystalline (R)-amisulpride of Form A that has a greater than about 80% chemical purity, greater than about 90% chemical purity, greater than about 95% chemical purity, greater than about 97% chemical purity, greater than about 99% chemical purity, greater than about 99.5% chemical purity, greater than about 99.7% chemical purity, or greater than about 99.9% chemical purity. In various embodiments, provided is crystalline (R)-amisulpride of Form A that has less than about 8000 ppm residual solvents, less than about 6000 ppm residual solvents, less than about 4000 ppm residual solvents, less than about 2000 ppm residual solvents, less than about 1000 ppm residual solvents, less than about 800 ppm residual solvents, or less than about 500 ppm residual solvents.

In various embodiments the present inventions provide substantially enantiomerically pure crystalline forms of (S)-amisulpride of Form A'. For example, in various embodiments, the present inventions provide crystalline forms of amisulpride that contain greater than about 90% (S)-amisulpride and less than about 10% of (R)-amisulpride, greater than about 95% (S)-amisulpride and less than about 5% of (R)-amisulpride, greater than about 97% (S)-amisulpride and less than about 3% of (R)-amisulpride, greater than about 99% (S)-amisulpride and less than about 1% of (R)-amisulpride, greater than about 99.5% (S)-amisulpride and less than about 0.5% of (R)-amisulpride, greater than about 99.7% (S)-amisulpride and less than about 0.3% of (R)-amisulpride, or greater than about 99.9% (S)-amisulpride and less than about 0.1% of (R)-amisulpride.

In various embodiments the present inventions provide substantially chemically pure crystalline forms of (S)-amisulpride of Form A'. For example, in various embodiments, the present inventions provide crystalline (S)-amisulpride of Form A' that has a greater than about 80% chemical purity, greater than about 90% chemical purity, greater than about 95% chemical purity, greater than about 97% chemical purity, greater than about 99% chemical purity, greater than about 99.5% chemical purity, greater than about 99.7% chemical purity, or greater than about 99.9% chemical purity. In various embodiments, provided is crystalline (S)-amisulpride of Form A' that has less than about 8000 ppm residual solvents, less than about 6000 ppm residual solvents, less than about 4000 ppm residual solvents, less than about 2000 ppm residual solvents, less than about 1000 ppm residual solvents, less than about 800 ppm residual solvents, or less than about 500 ppm residual solvents.

In various embodiments the present inventions provide substantially enantiomerically pure crystalline forms of (R)-amisulpride ethyl acetate solvate of Form B. For example, in various embodiments, the present inventions provide crystalline forms of (R)-amisulpride ethyl acetate solvate of Form B having a chiral purity of greater than about 90%, a chiral purity of greater than about 95%, a chiral purity of greater than about 97%, a chiral purity of greater than about 99%, a chiral purity of greater than about 99.5%, a chiral purity of greater than about 99.7%, or a chiral purity of greater than about 99.9%.

In various embodiments the present inventions provide substantially chemically pure crystalline forms of (R)-amisulpride ethyl acetate solvate of Form B. For example, in various embodiments, the present inventions provide crystalline (R)-amisulpride ethyl acetate solvate of Form B that have a greater than about 95% chemical purity, greater than about 97% chemical purity, greater than about 99% chemical purity, greater than about 99.5% chemical purity, greater than about 99.7% chemical purity, or greater than about 99.9% chemical purity.

In various embodiments the present inventions provide substantially enantiomerically pure crystalline forms of (S)-amisulpride ethyl acetate solvate of Form B'. For example, in various embodiments, the present inventions provide crystalline forms of (S)-amisulpride ethyl acetate solvate of Form B' having a chiral purity of greater than about 90%, a chiral purity of greater than about 95%, a chiral purity of greater than about 97%, a chiral purity of greater than about 99%, a chiral purity of greater than about 99.5%, a chiral purity of greater than about 99.7%, or a chiral purity of greater than about 99.9%.

In various embodiments the present inventions provide substantially chemically pure crystalline forms of (S)-amisulpride ethyl acetate solvate of Form B'. For example, in various embodiments, the present inventions provide crystalline (S)-amisulpride ethyl acetate solvate of Form B' that have a greater than about 95% chemical purity, greater than about 97% chemical purity, greater than about 99% chemical purity, greater than about 99.5% chemical purity, greater than about 99.7% chemical purity, or greater than about 99.9% chemical purity.

In various aspects, the present inventions provide methods of making crystal forms of amisulpride enantiomers having a powder x-ray crystal pattern comprising peaks, in terms of 2-theta, at least at 7.0±0.2°, 9.7±0.2°, and 19.4±0.2°, comprising the steps of: (a) providing a starting material comprising either R-4-Amino-N-[(1-ethyl-2-pyrrolidinyl)methyl]-5-(ethylsulfonyl)-2-methoxybenzamide or S-4-Amino-N-[(1-ethyl-2-pyrrolidinyl)methyl]-5-(ethylsulfonyl)-2-methoxybenzamide; (b) solvating the starting material with a first solvent to form a solvate of the starting material and first solvent, wherein the first solvent is a carbonyl containing compound having 5 carbons or less; (c) freeing the solvated starting material from the first solvent by adding a second solvent other than water to form a mixture with a starting material solubility of less than about 20 wt/wt %; and (d) isolating from the mixture comprising the free base of the starting material a crystalline form of the starting material having a powder x-ray crystal pattern comprising peaks, in terms of 2-theta, at least at 7.0±0.2°, 9.7±0.2°, and 19.4±0.2°.

In various aspects, the present inventions provide methods of making crystal forms of amisulpride enantiomers of Form A and Form A' of high crystal form, enantiomeric and chemical purity. In various embodiments these methods provide enantiomerically pure crystalline forms of (R)-amisulpride of Form A having a chiral purity of greater than about 90%, a chiral purity of greater than about 95%, a chiral purity of greater than about 97%, a chiral purity of greater than about 99%, a chiral purity of greater than about 99.5%, a chiral purity of greater than about 99.7%, or a chiral purity of greater than about 99.9%. In various embodiments these methods provide crystalline forms of (R)-amisulpride of Form A that have a greater than about 95% chemical purity, greater than about 97% chemical purity, greater than about 99% chemical purity, greater than about 99.5% chemical purity, greater than about 99.7% chemical purity, or greater than about 99.9% chemical purity. In various embodiments, these methods provide crystalline (R)-amisulpride of Form A that has less than about 8000 ppm residual solvents, less than about 6000 ppm residual solvents, less than about 4000 ppm residual solvents, less than about 2000 ppm residual solvents, less than about 1000 ppm residual solvents, less than about 800 ppm residual solvents, or less than about 500 ppm residual solvents.

In various embodiments, the methods of making crystal forms of amisulpride enantiomers of Form A' provide enantiomerically pure crystalline forms of (S)-amisulpride of Form A' having a chiral purity of greater than about 90%, a chiral purity of greater than about 95%, a chiral purity of greater than about 97%, a chiral purity of greater than about 99%, a chiral purity of greater than about 99.5%, a chiral purity of greater than about 99.7%, or a chiral purity of greater than about 99.9%. In various embodiments these methods provide crystalline (S)-amisulpride of Form A' that have a greater than about 95% chemical purity, greater than about 97% chemical purity, greater than about 99% chemical purity, greater than about 99.5% chemical purity, greater than about 99.7% chemical purity, or greater than about 99.9% chemical purity. In various embodiments, these methods provide crystalline (S)-amisulpride of Form A' that has less than about 8000 ppm residual solvents, less than about 6000 ppm residual solvents, less than about 4000 ppm residual solvents, less than about 2000 ppm residual solvents, less than about 1000 ppm residual solvents, less than about 800 ppm residual solvents, or less than about 500 ppm residual solvents.

In various aspects, the present inventions provide methods of making ethyl acetate solvated crystal forms of amisulpride enantiomers, the solvated crystalline form of amisulpride having a powder x-ray crystal pattern comprising peaks, in terms of 2-theta, at least at 6.4±0.2°, 8.3±0.2°, and 20.8±0.2°, comprising the steps of: (a) providing a starting material comprising either R-4-Amino-N-[(1-ethyl-2-pyrrolidinyl)methyl]-5-(ethylsulfonyl)-2-methoxybenzamide or S-4-Amino-N-[(1-ethyl-2-pyrrolidinyl)methyl]-5-(ethylsulfonyl)-2-methoxybenzamide; (b) solvating the starting material with a ethyl acetate to form an ethyl acetate solvate with the starting material and first solvent; and (c) isolating from the mixture of step (b) an ethyl acetate solvated crystalline form of the starting material having a powder x-ray crystal pattern comprising peaks, in terms of 2-theta, at least at 6.4±0.2°, 8.3±0.2°, and 20.8±0.2°.

In various aspects, the present inventions provide methods of making crystal forms of amisulpride ethyl acetate solvate of Form B and Form B'. In various embodiments these methods provide crystalline (R)-amisulpride ethyl acetate solvate of Form B having a chiral purity of greater than about 90%, a chiral purity of greater than about 95%, a chiral purity of greater than about 97%, a chiral purity of greater than about 99%, a chiral purity of greater than about 99.5%, a chiral purity of greater than about 99.7%, or a chiral purity of greater than about 99.9%. In various embodiments these methods provide crystalline forms of (R)-amisulpride ethyl acetate solvate of Form B that have a greater than about 95% chemical purity, greater than about 97% chemical purity, greater than about 99% chemical purity, greater than about 99.5% chemical purity, greater than about 99.7% chemical purity, or greater than about 99.9% chemical purity.

In various embodiments the methods of making crystal forms of amisulpride ethyl acetate solvate of Form B' provide crystalline (S)-amisulpride ethyl acetate solvate of Form B' having a chiral purity of greater than about 90%, a chiral purity of greater than about 95%, a chiral purity of greater than about 97%, a chiral purity of greater than about 99%, a chiral purity of greater than about 99.5%, a chiral purity of greater than about 99.7%, or a chiral purity of greater than about 99.9%. In various embodiments these methods provide crystalline forms of (S)-amisulpride ethyl acetate solvate of Form B' that have a greater than about 95% chemical purity, greater than about 97% chemical purity, greater than about 99% chemical purity, greater than about 99.5% chemical purity, greater than about 99.7% chemical purity, or greater than about 99.9% chemical purity.

In various aspects, the present inventions provide methods of resolving amisulpride enantiomers from a racemic or non-enantiomerically pure amisulpride. In various embodiments, these methods can resolve the R and S enantiomers to a respective chiral purity of greater than about 90%, a chiral purity of greater than about 95%, a chiral purity of greater than about 97%, a chiral purity of greater than about 99%, a chiral purity of greater than about 99.5%, a chiral purity of greater than about 99.7%, or a chiral purity of greater than about 99.9%.

These and other objects, features, and advantages of the inventions will become apparent from the following detailed description of the various aspects and embodiments of the inventions taken in conjunction with the accompanying tables and drawings.

BRIEF DESCRIPTION OF THE DRAWINGS

In the accompanying drawings like reference numerals indicate like elements and features in the various figures. For clarity, not every element may be labeled in every figure. In addition, the drawings are not necessarily complete when viewed without reference to the text, emphasis instead being placed upon illustrating the principles of the inventions.

The following abbreviations are used herein. The abbreviation "DSC" refers to differential scanning calorimetry; the abbreviation XRPD refers to x-ray powder diffraction, the abbreviation NMR refers to nuclear magnetic resonance, the abbreviation DVS refers to, dynamic vapor sorption, the abbreviation HPLC refers to high performance liquid chromatography, and the abbreviation GC refers to gas chromatography. The abbreviations (R)-(+)-amisulpride and (R)- amisulpride refer to R-4-Amino-N-[(1-ethyl-2-pyrolidinyl) methyl]-5-(ethylsulfonyl)-2-methoxybenzamide. The abbreviations (S)-(−)-amisulpride and (S)-amisulpride refer to S-4-Amino-N-[(1-ethyl-2-pyrrolidinyl)methyl]-5-(ethylsulfonyl)-2-methoxybenzamide. Other abbreviations not explicitly described herein have their normal meanings in the art.

Figure 1A:
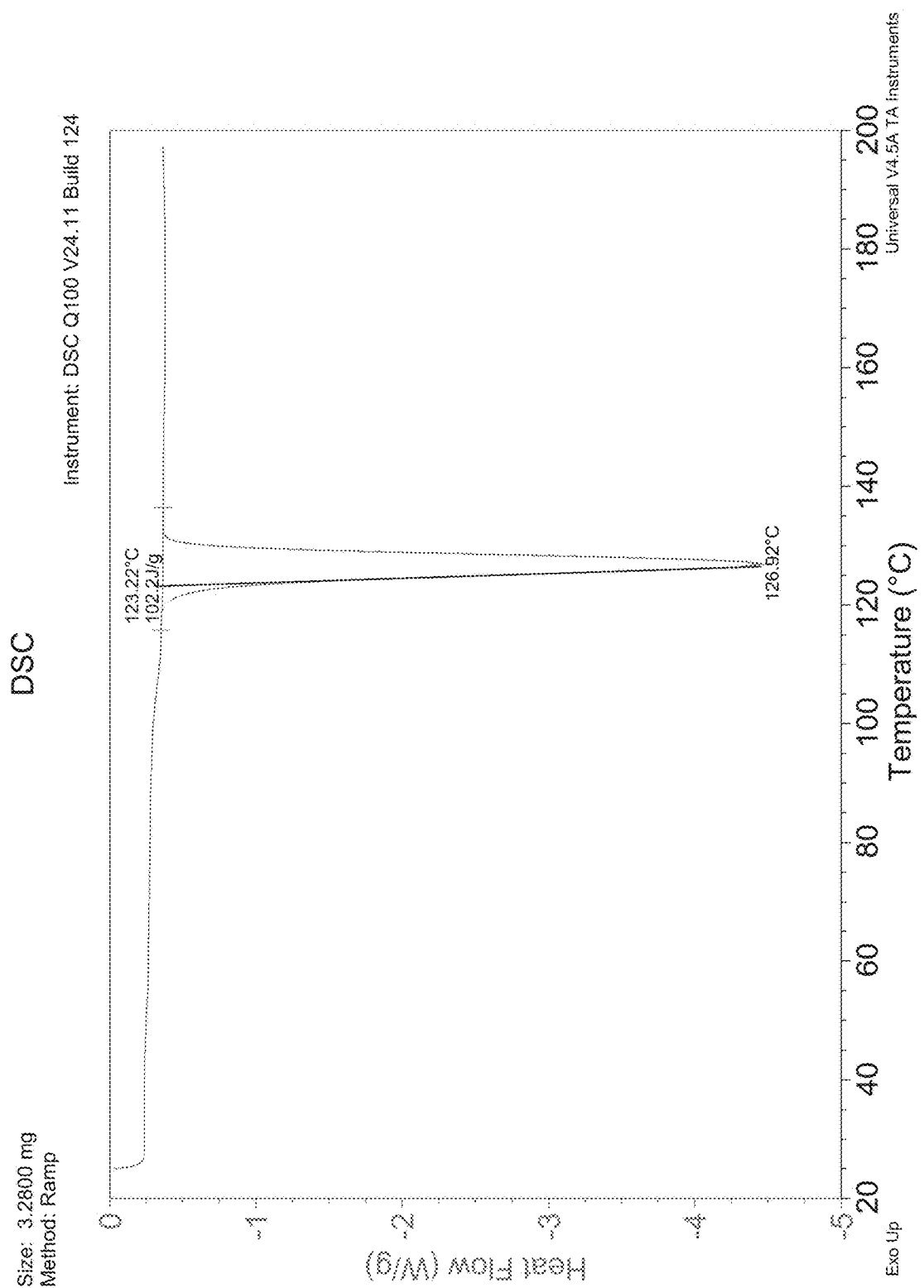
Figure 1B:
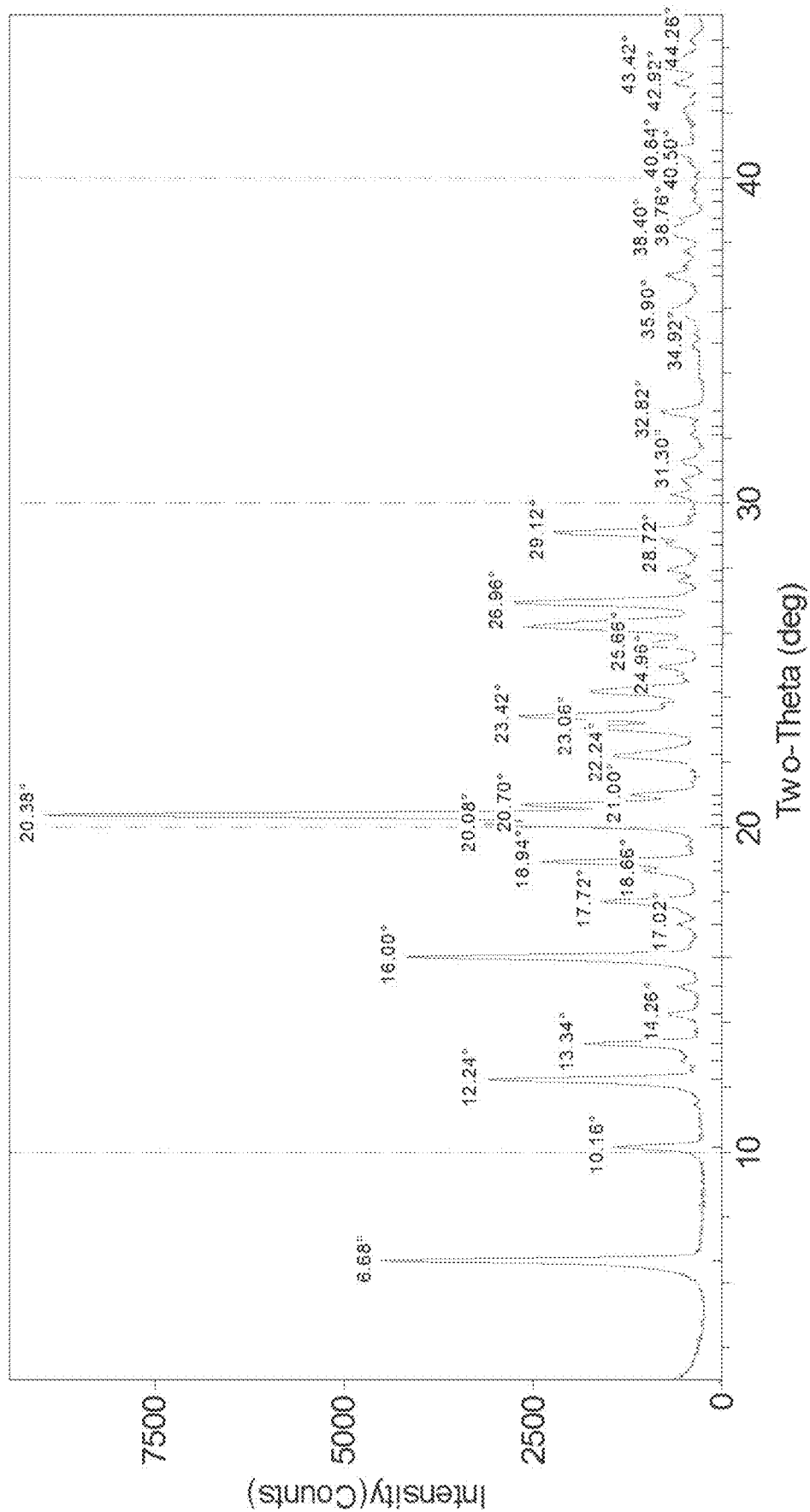
Figure 1C:
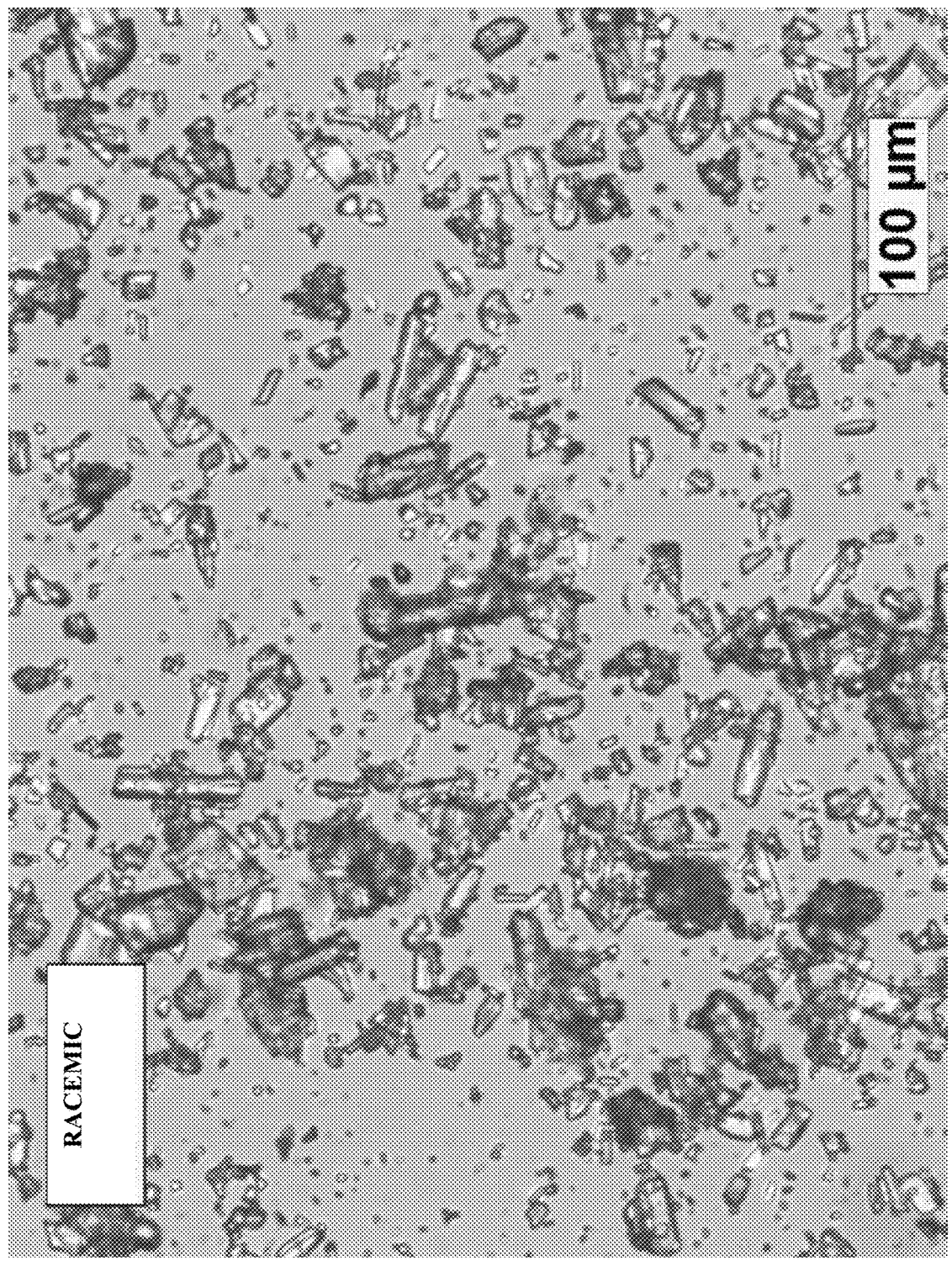

FIGS. 1A, 1B and 1C present various analytical data and images for crystalline racemic amisulpride, where FIG. 1A presents a DSC thermogram; FIG. 1B presents a XRPD pattern; and FIG. 1C presents a micrograph image.

Figure 2A:
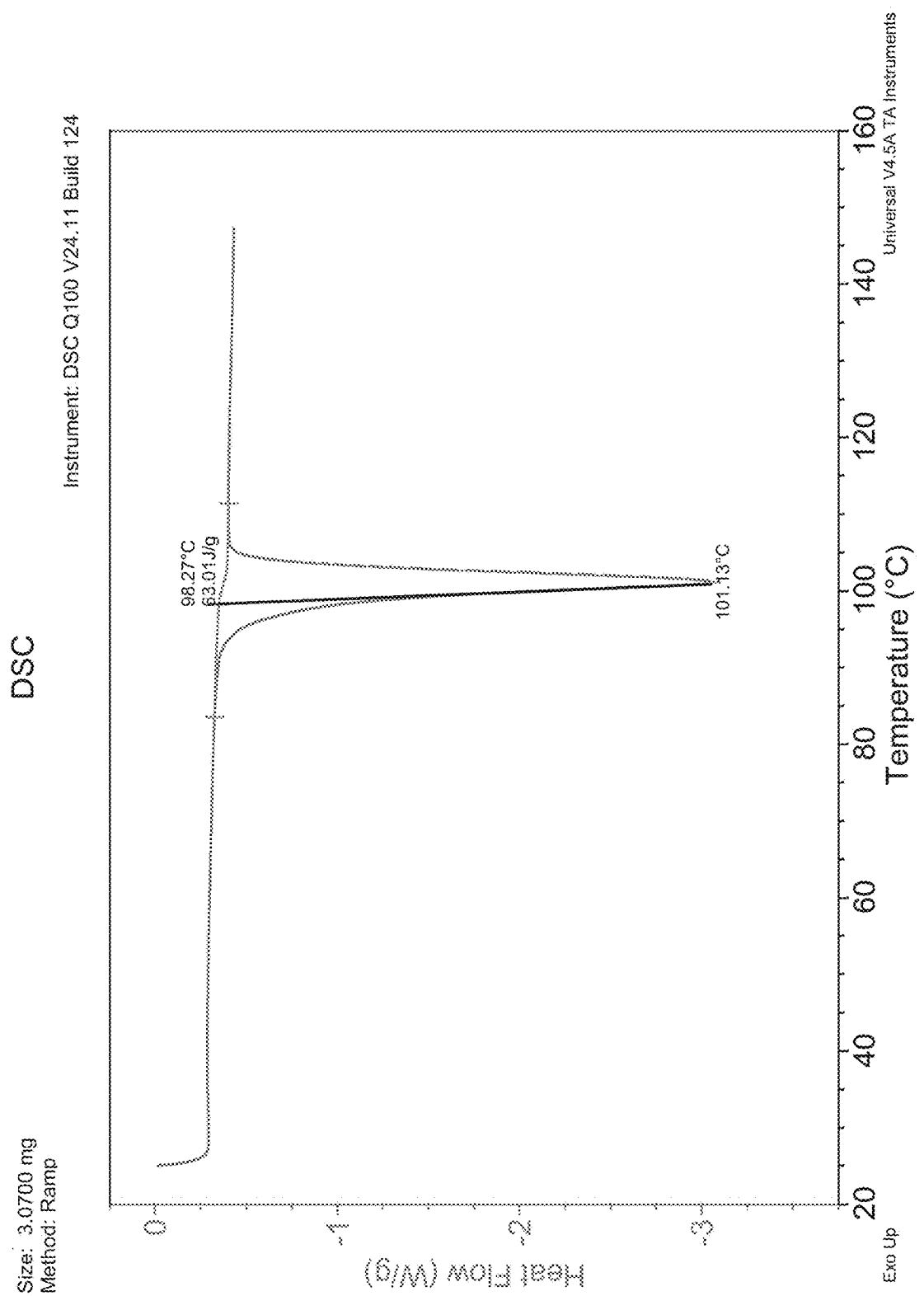
Figure 2B:
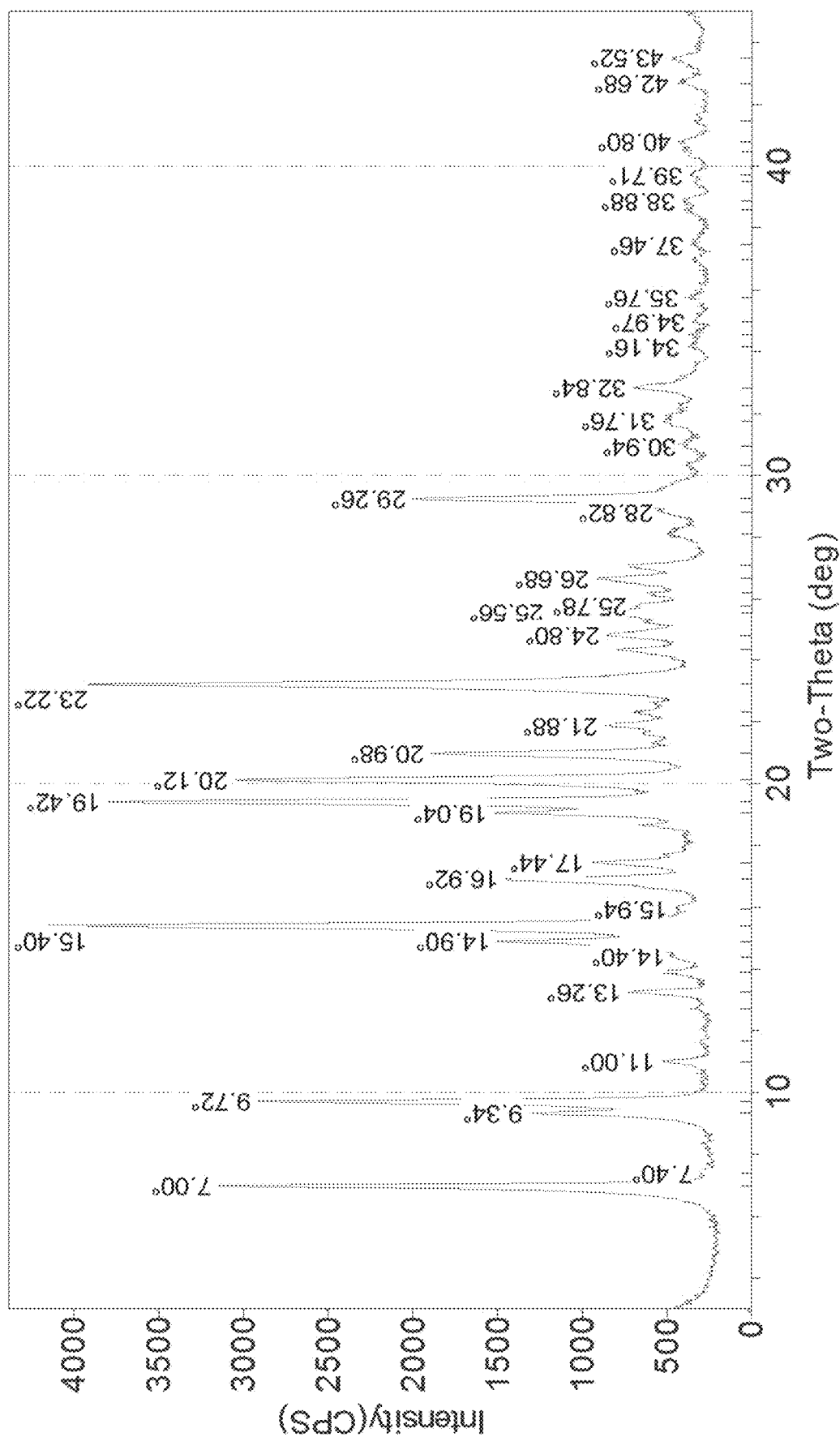
Figure 2C:
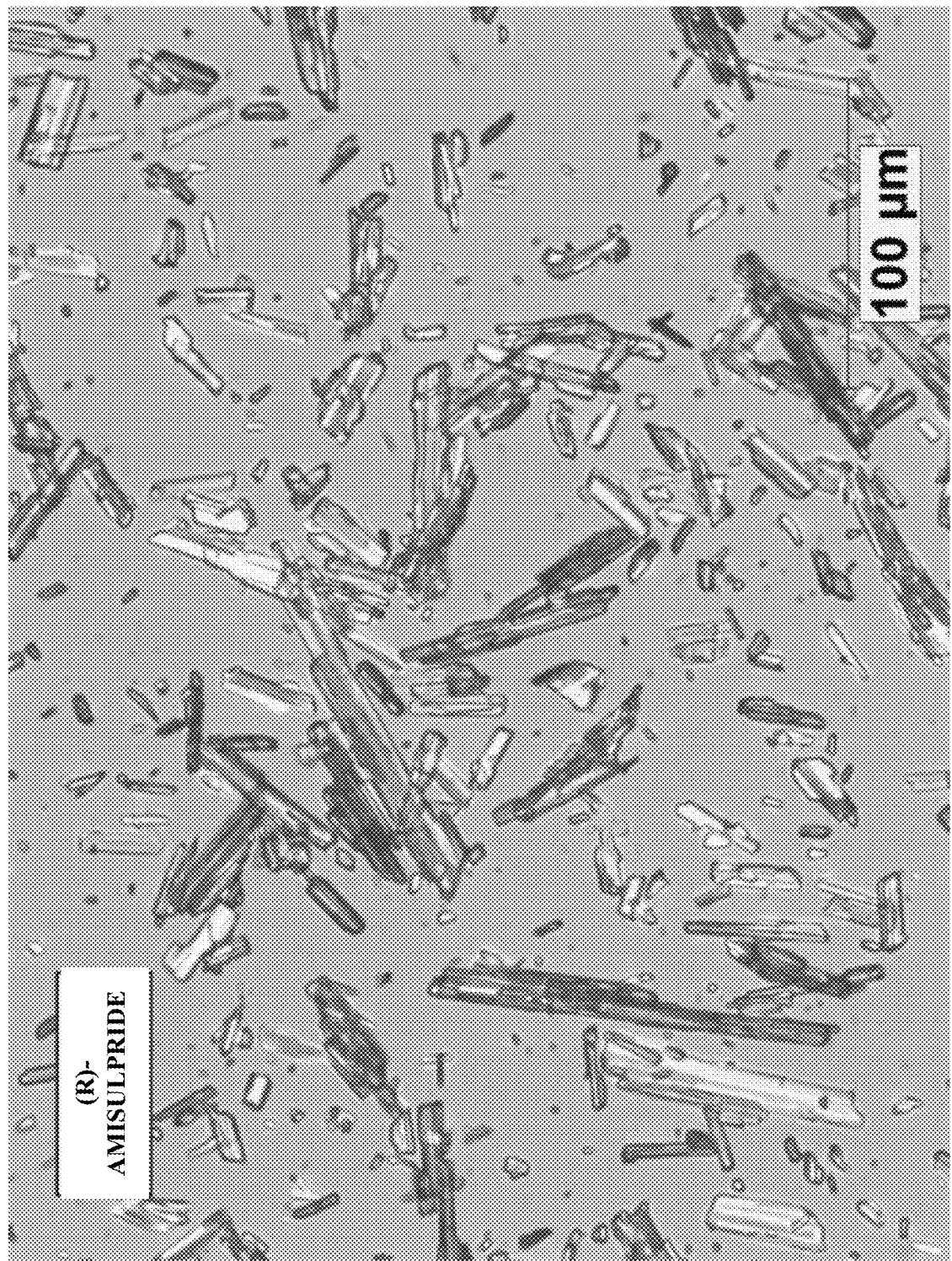
Figure 2D:
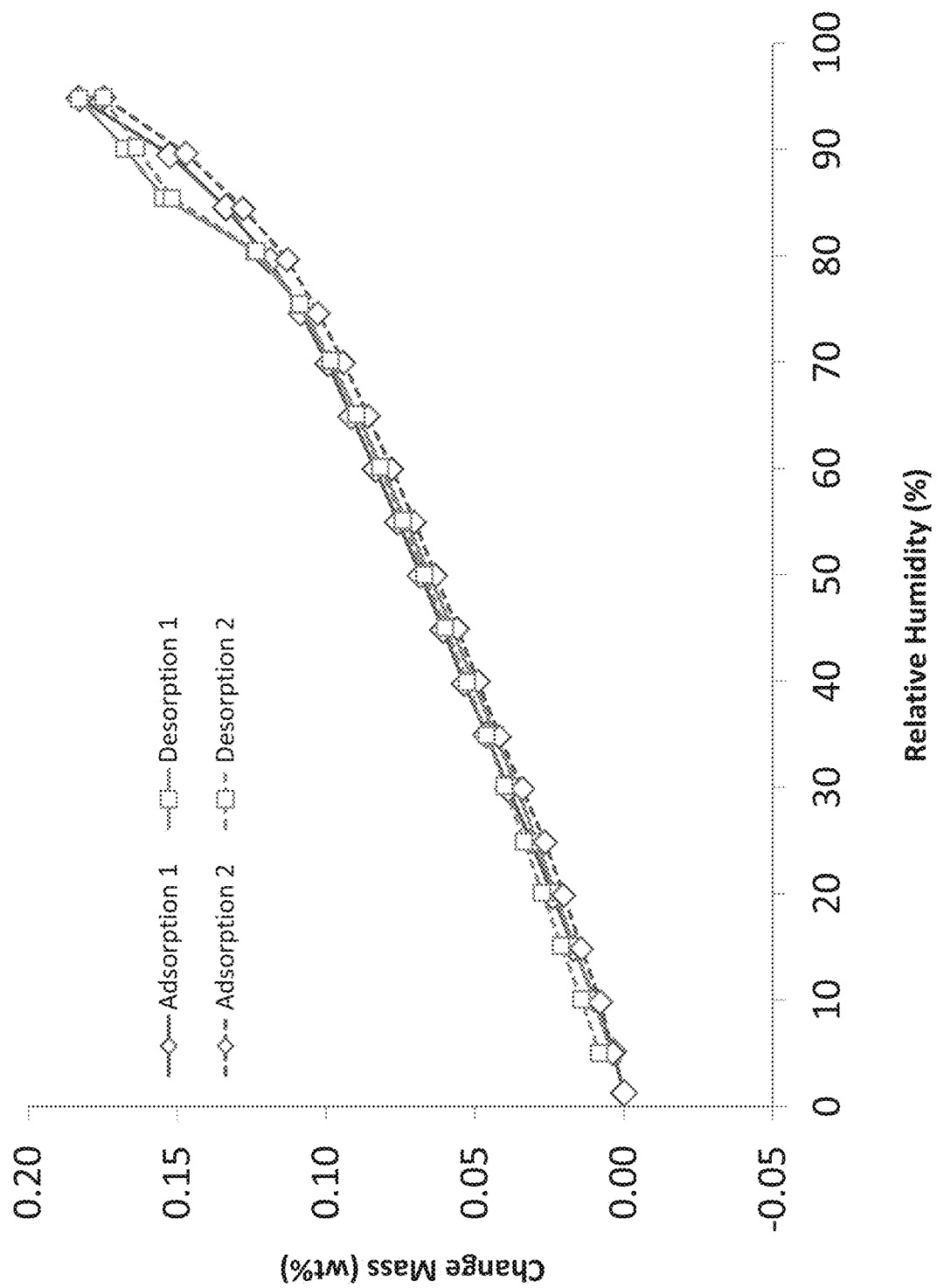
Figure 2E:
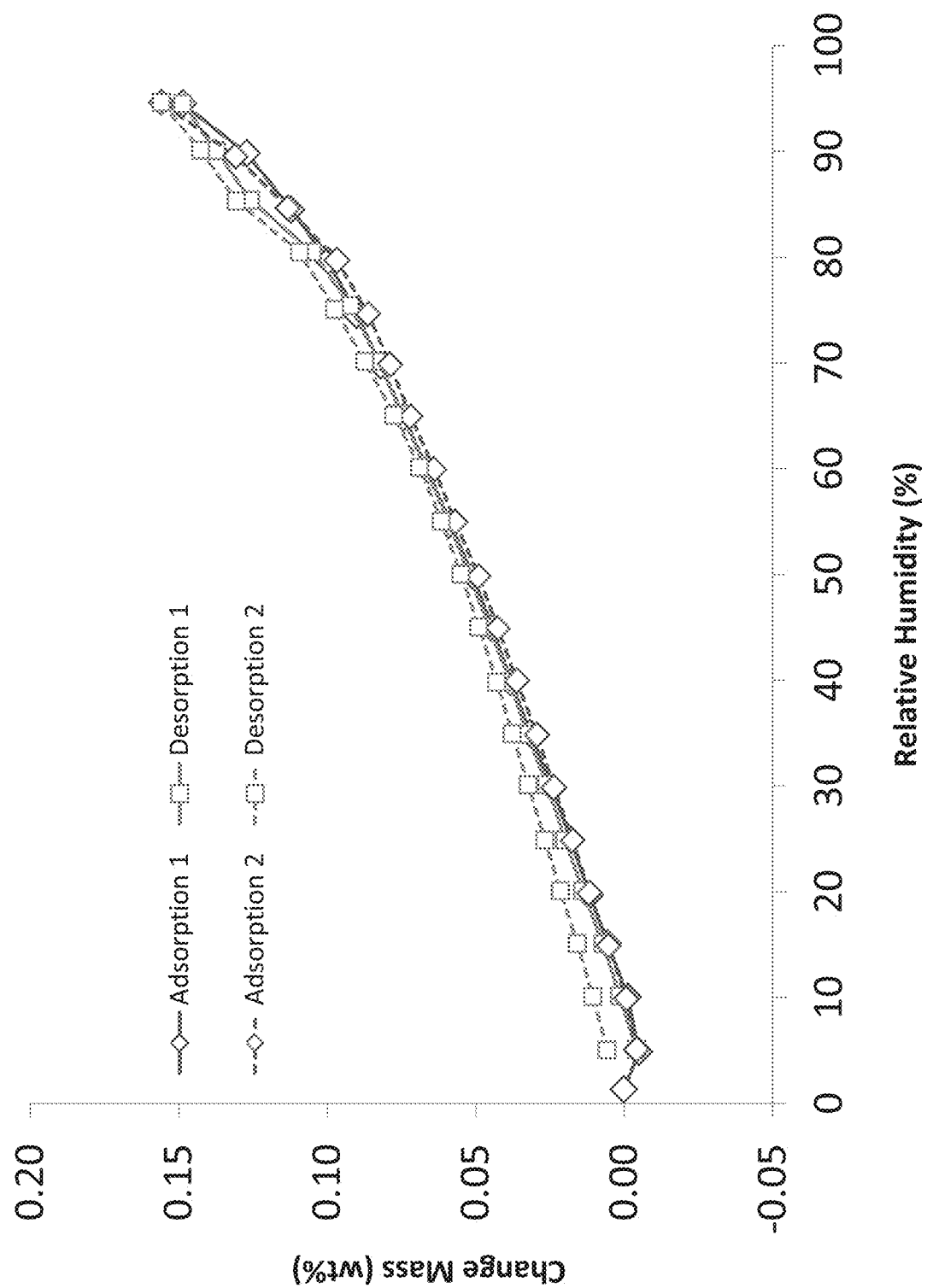

FIGS. 2A, 2B, 2C, 2D and 2E present various analytical data and images for Form A crystals of (R)-amisulpride, where FIG. 2A presents a DSC thermogram; FIG. 2B presents a XRPD pattern; and FIG. 2C presents a micrograph image; and FIGS. 2D and 2E present DVS water sorption isotherms.

Figure 3A:
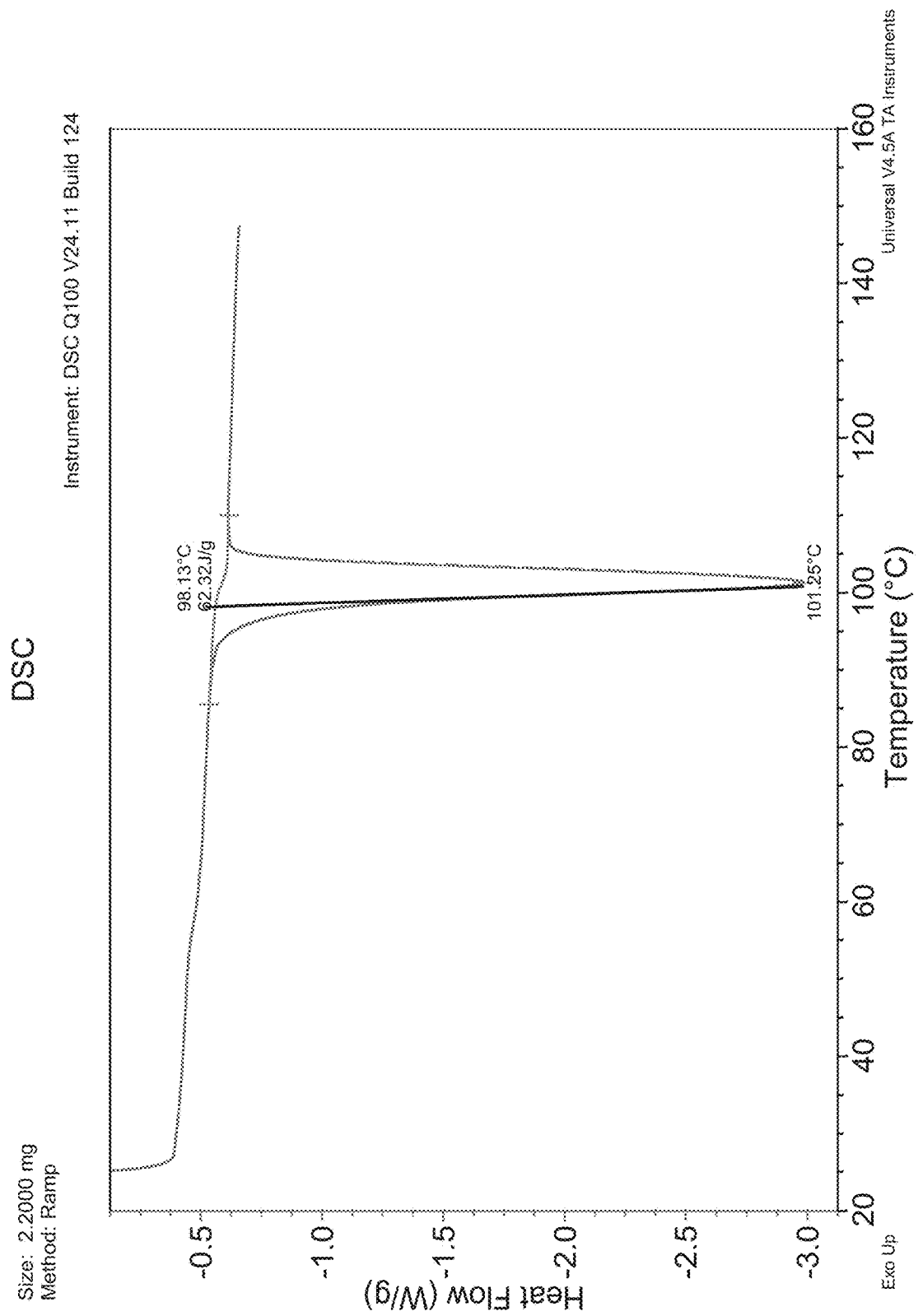
Figure 3B:
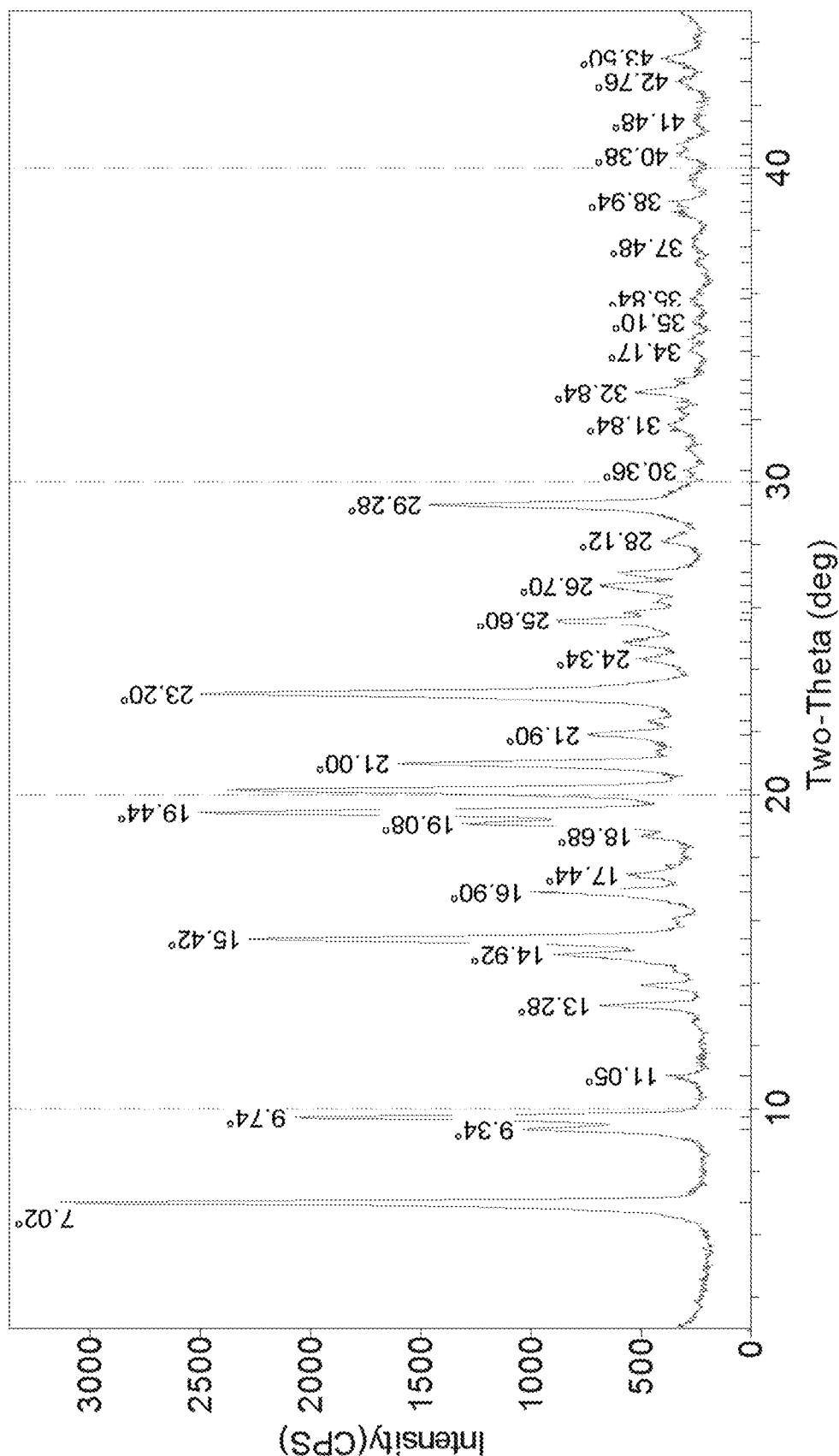
Figure 3C:
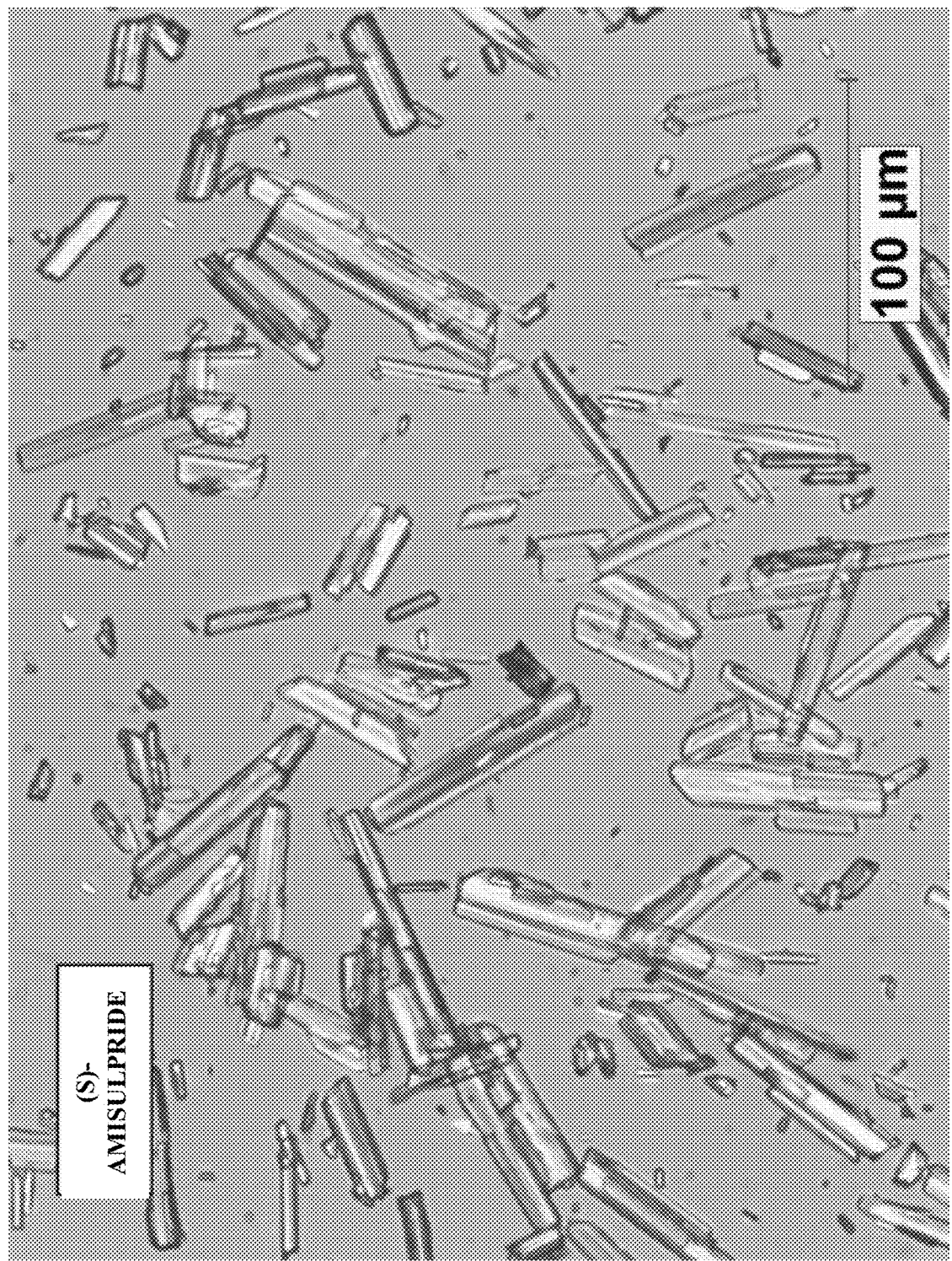
Figure 3D:
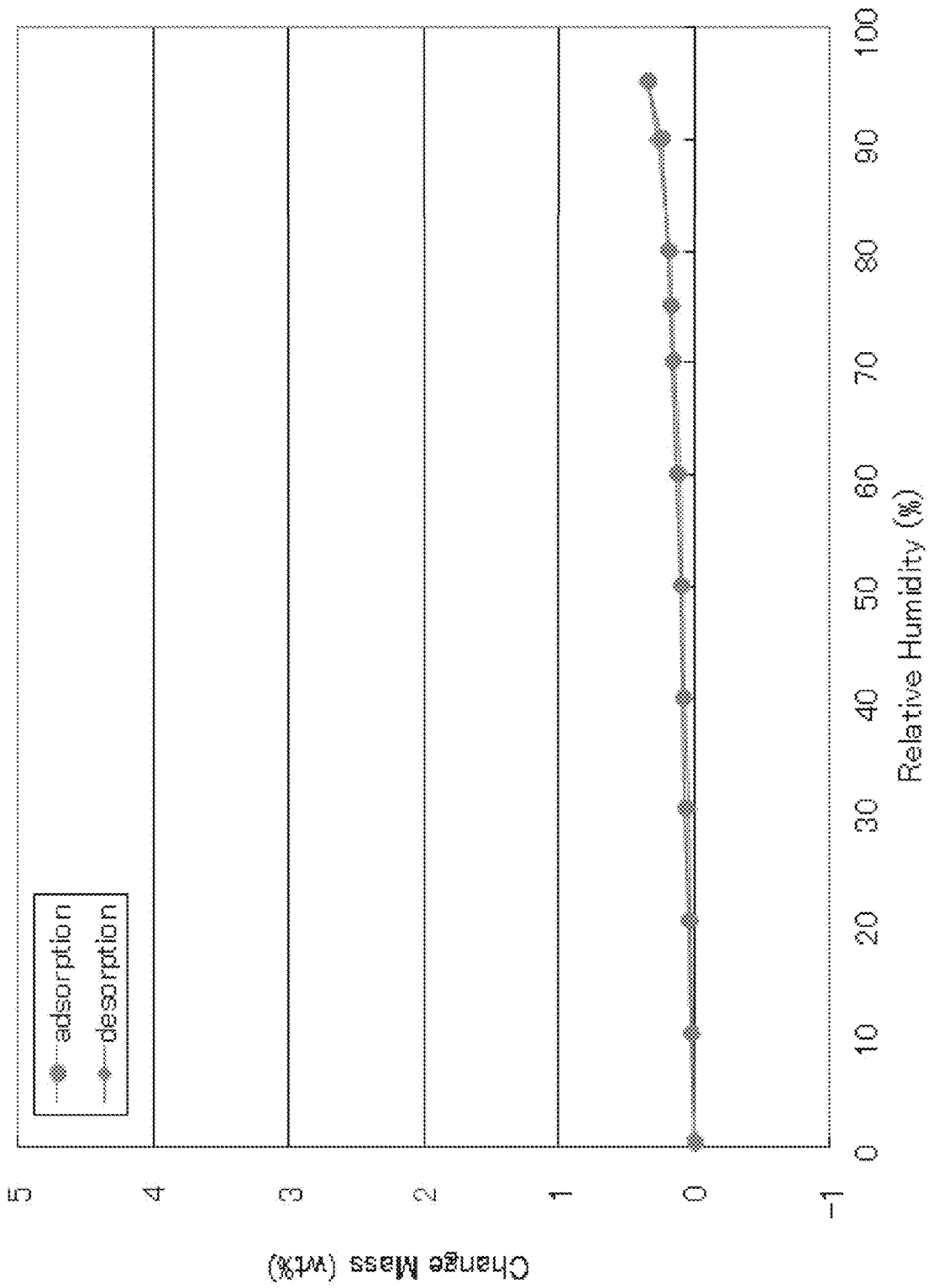
Figure 3E:
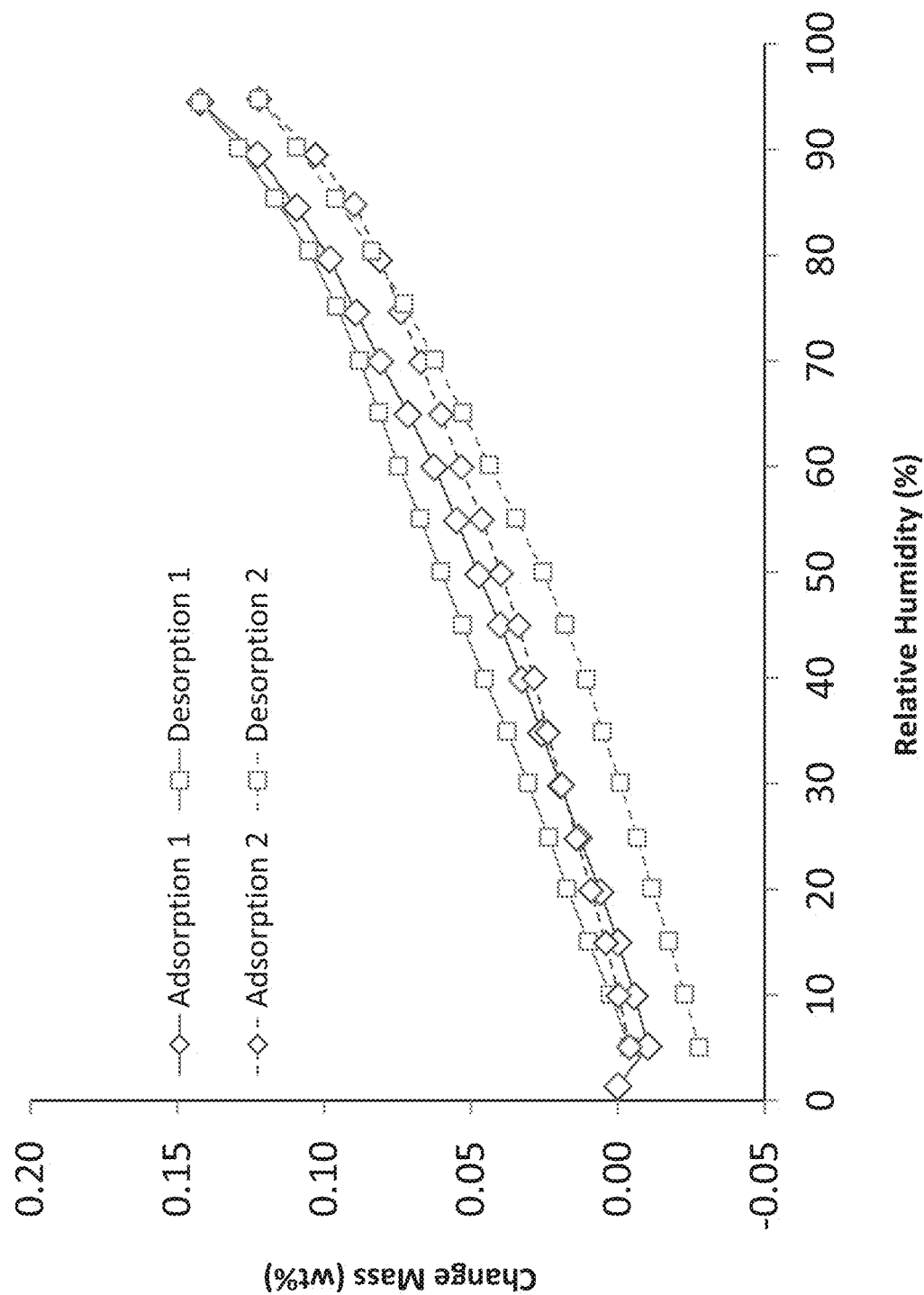
Figure 3F:
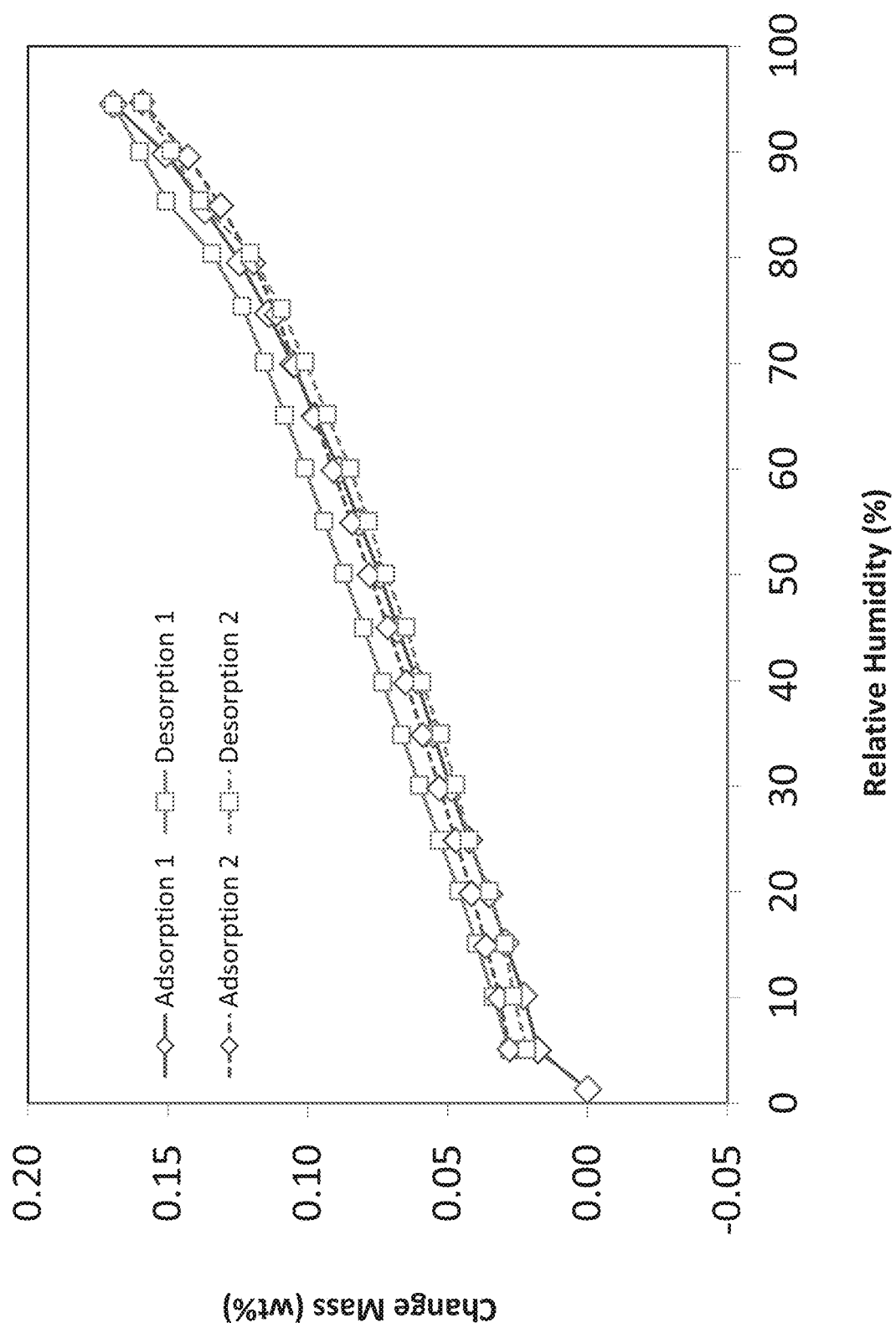

FIGS. 3A, 3B, 3C, 3D, 3E and 3F present various analytical data and images for Form A' crystals of (S)-amisulpride, where FIG. 3A presents a DSC thermogram; FIG. 3B presents a XRPD pattern; FIG. 3C presents a micrograph image; and FIGS. 3D, 3E and 3F present DVS water sorption isotherms.

Figure 4A:
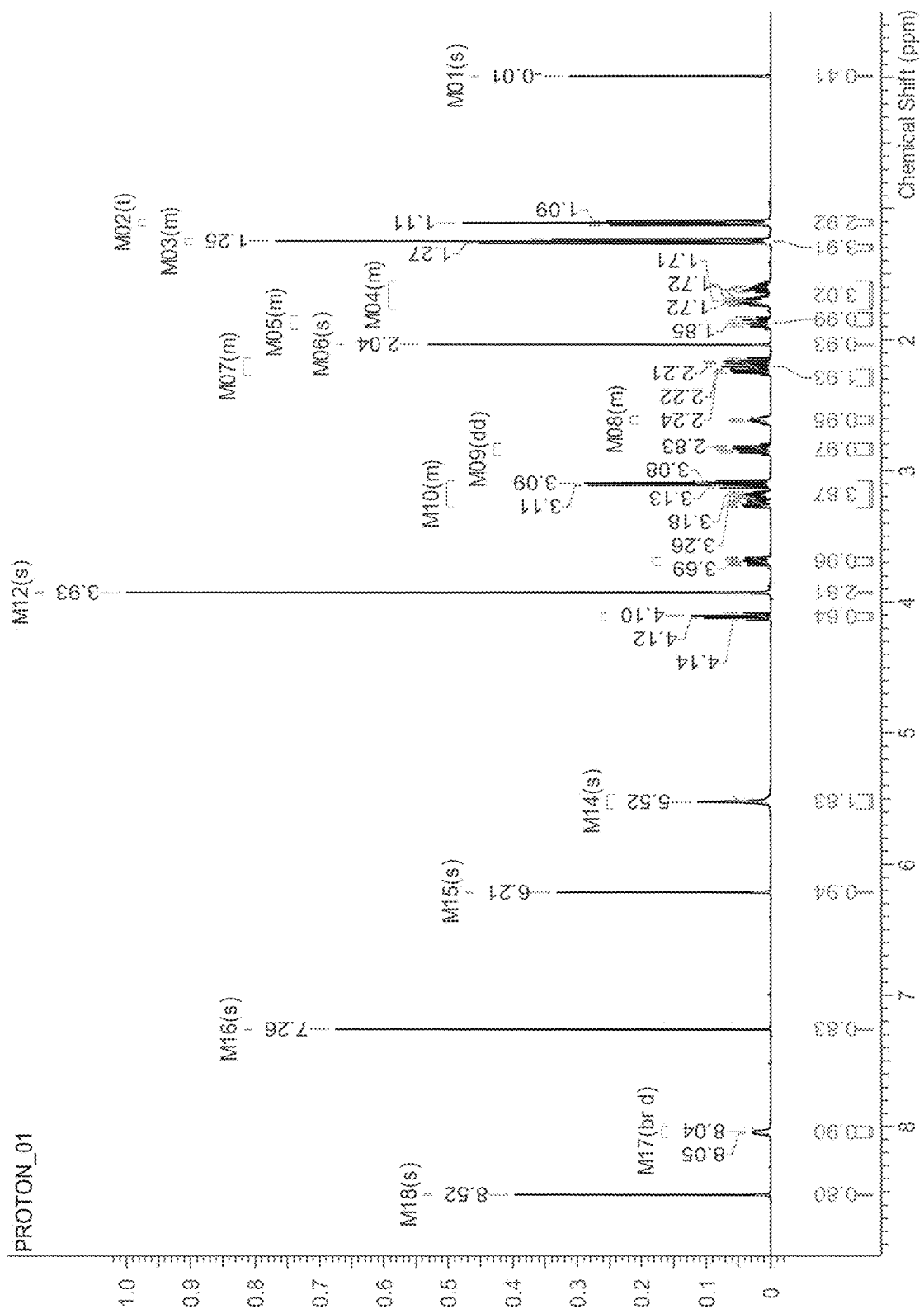
Figure 4B:
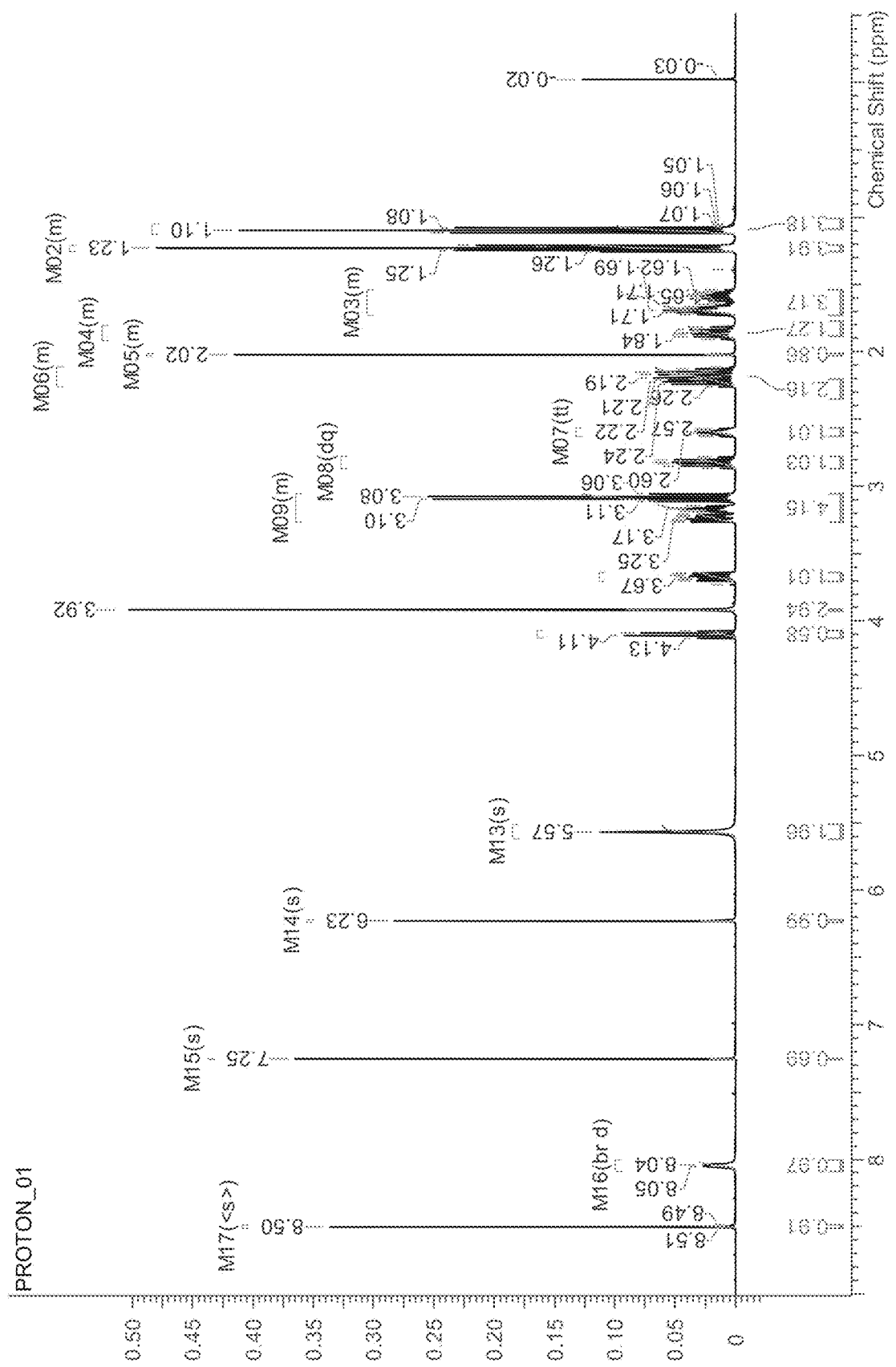

FIGS. 4A and 4B are NMR spectrum of an (R)-4-Amino-N-[(1-ethyl-2-pyrrolidinyl)methyl]-5-(ethylsulfonyl)-2-methoxybenzamide ethyl acetate solvate.

Figure 5:
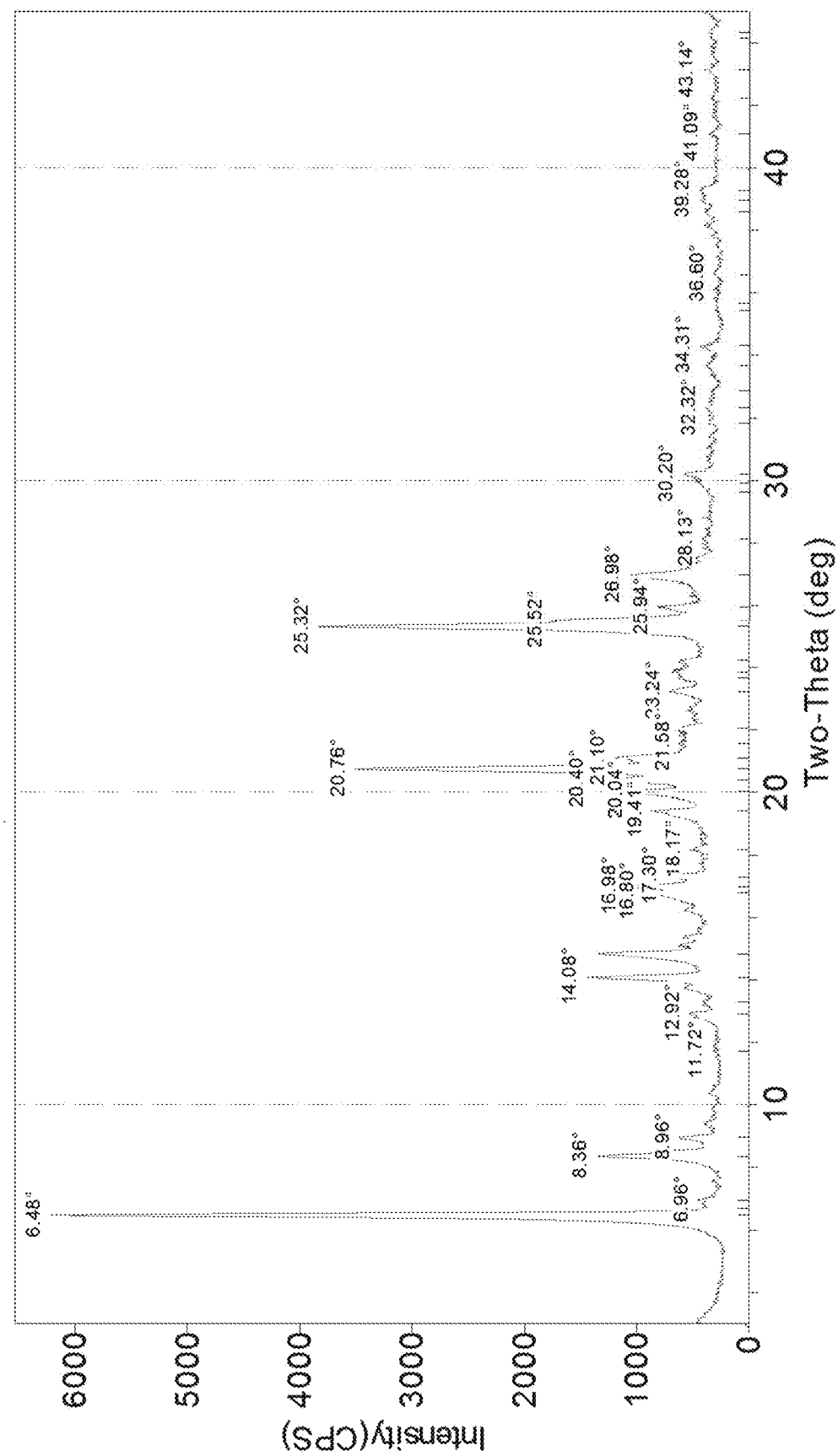

FIG. 5 presents a XRPD for a crystalline (R)-amisulpride ethyl acetate solvate of Form B.

Figure 6:
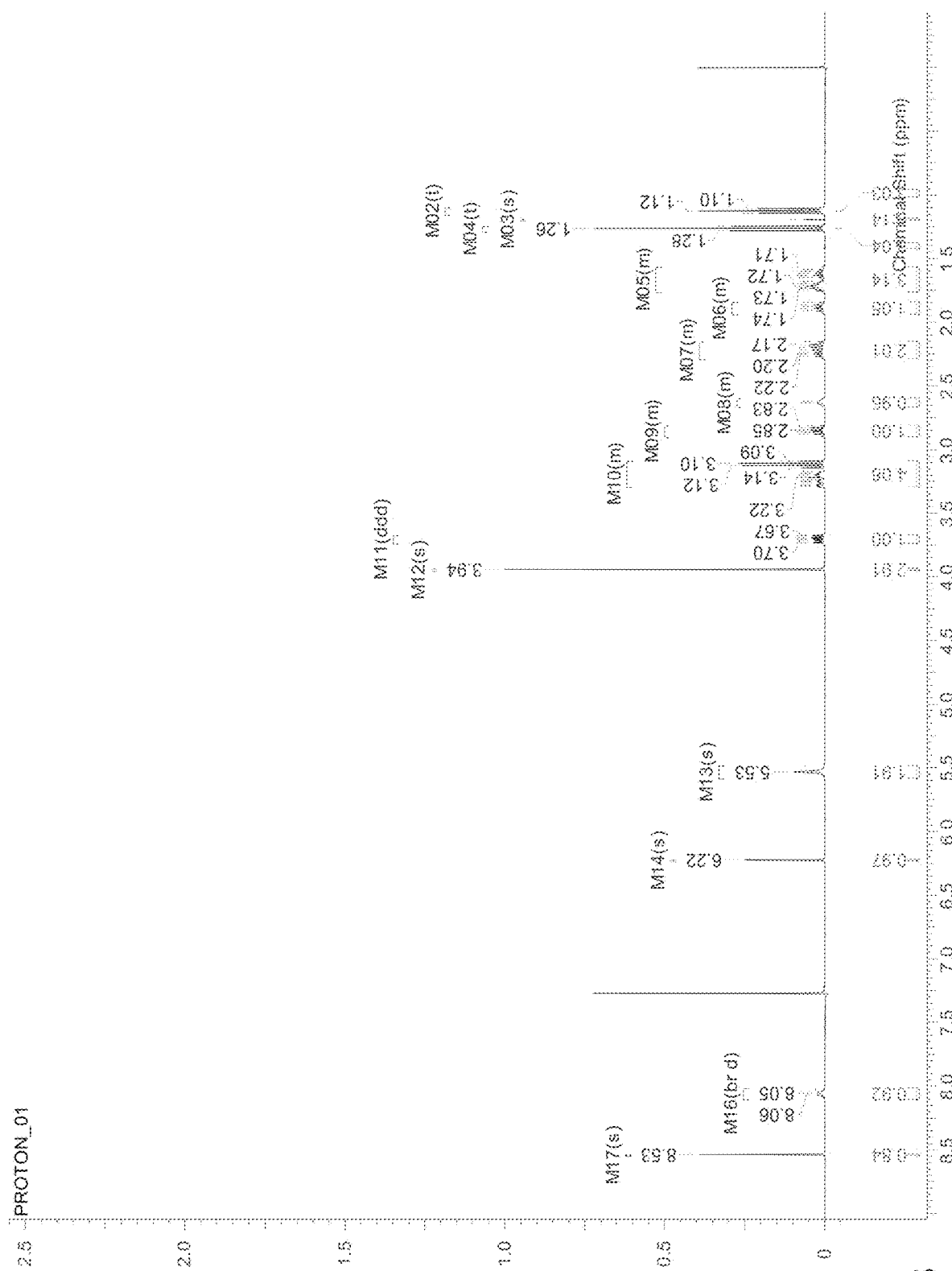

FIG. 6 is an NMR spectrum of an R-4-Amino-N-[(1-ethyl-2-pyrrolidinyl)methyl]-5-(ethylsulfonyl)-2-methoxybenzamide freebase of crystal Form A'.

Figure 7:
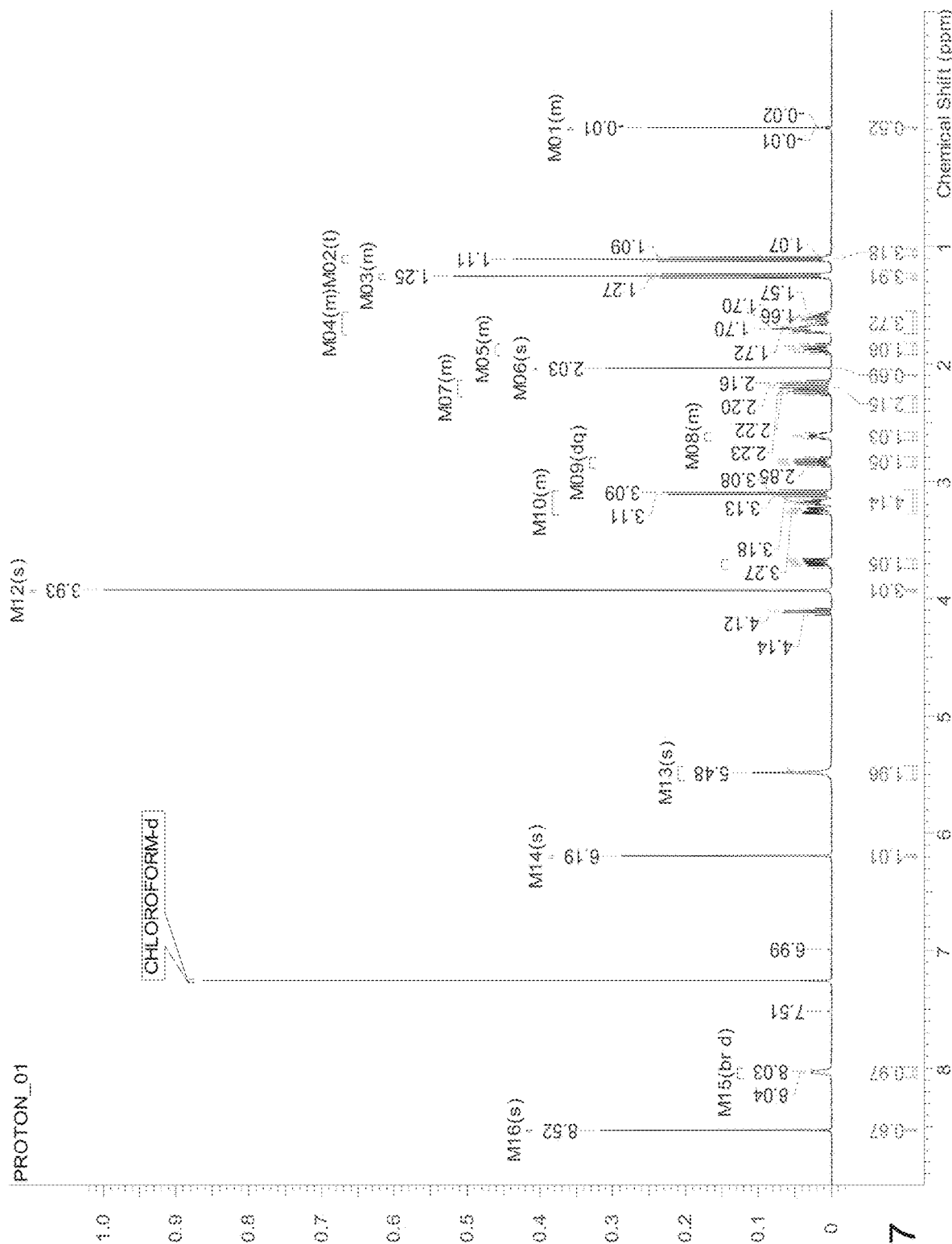

FIG. 7 is an NMR spectrum of an S-4-Amino-N-[(1-ethyl-2-pyrrolidinyl)methyl]-5-(ethylsulfonyl)-2-methoxybenzamide ethyl acetate solvate.

Figure 8:
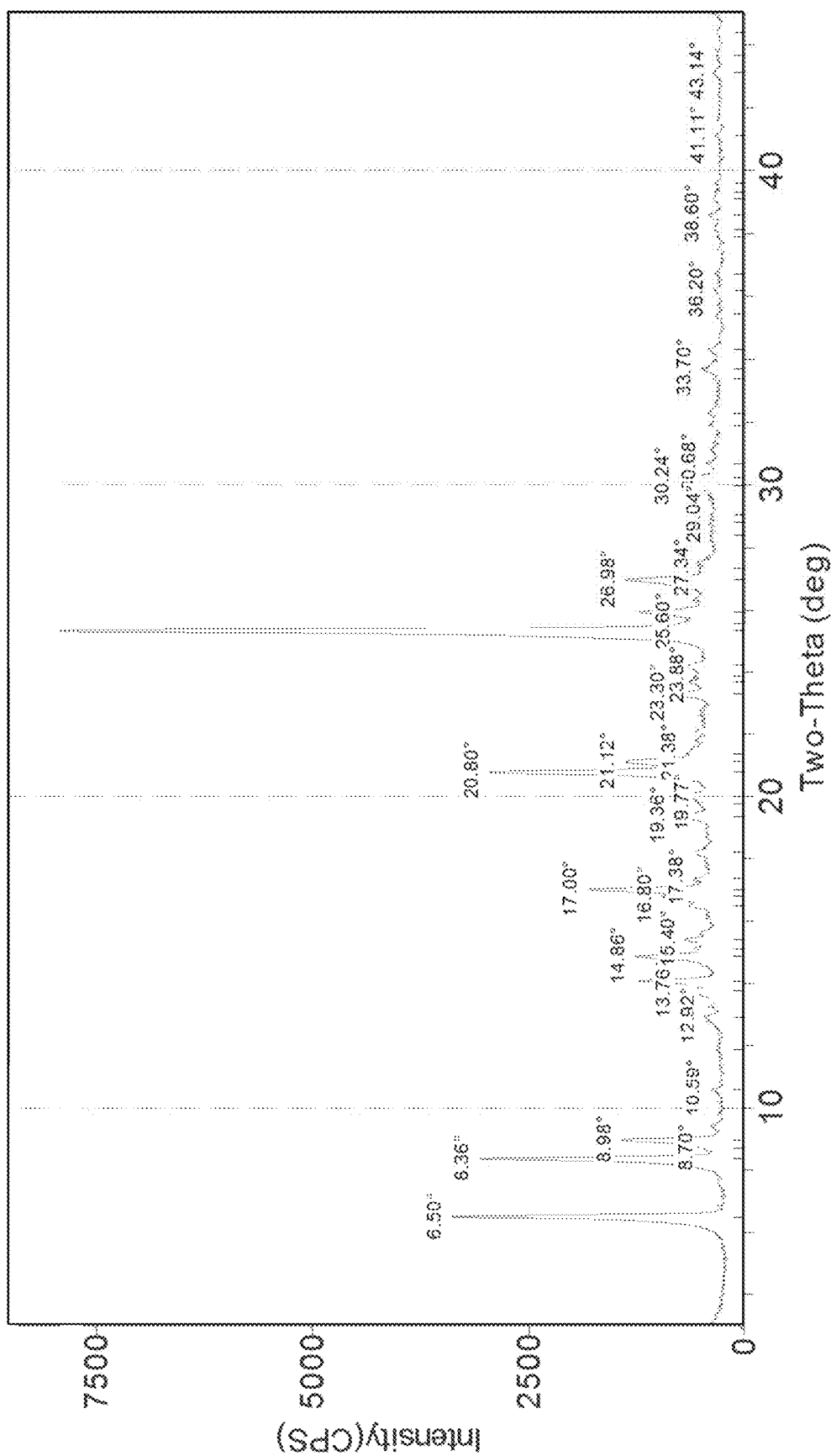

FIG. 8 presents a XRPD for a crystalline (S)-amisulpride ethyl acetate solvate of Form B'.

Figure 9:
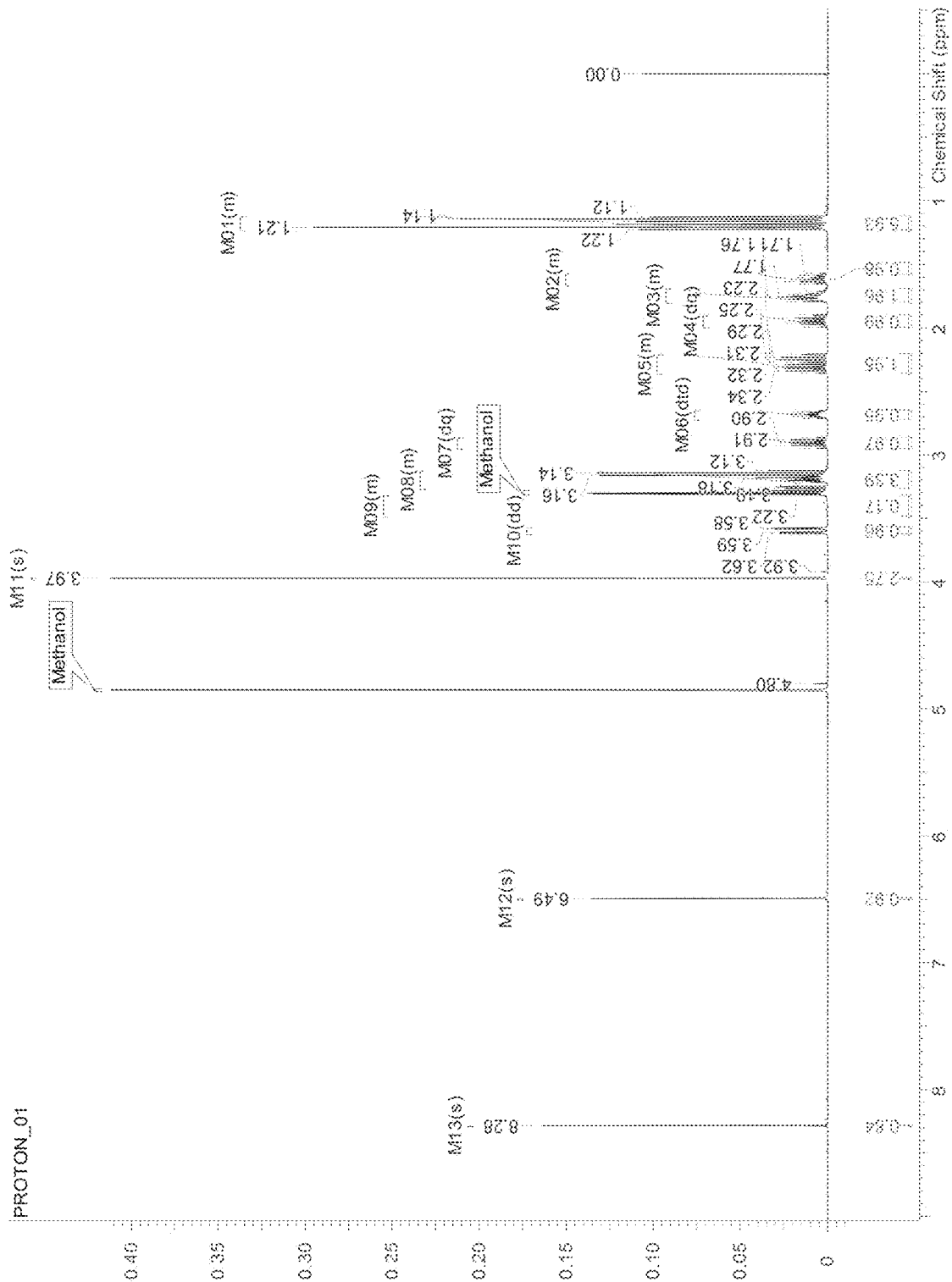

FIG. 9 is an NMR spectrum of an S-4-Amino-N-[(1-ethyl-2-pyrrolidinyl)methyl]-5-(ethylsulfonyl)-2-methoxybenzamide freebase of crystal Form A'.

Figure 10:
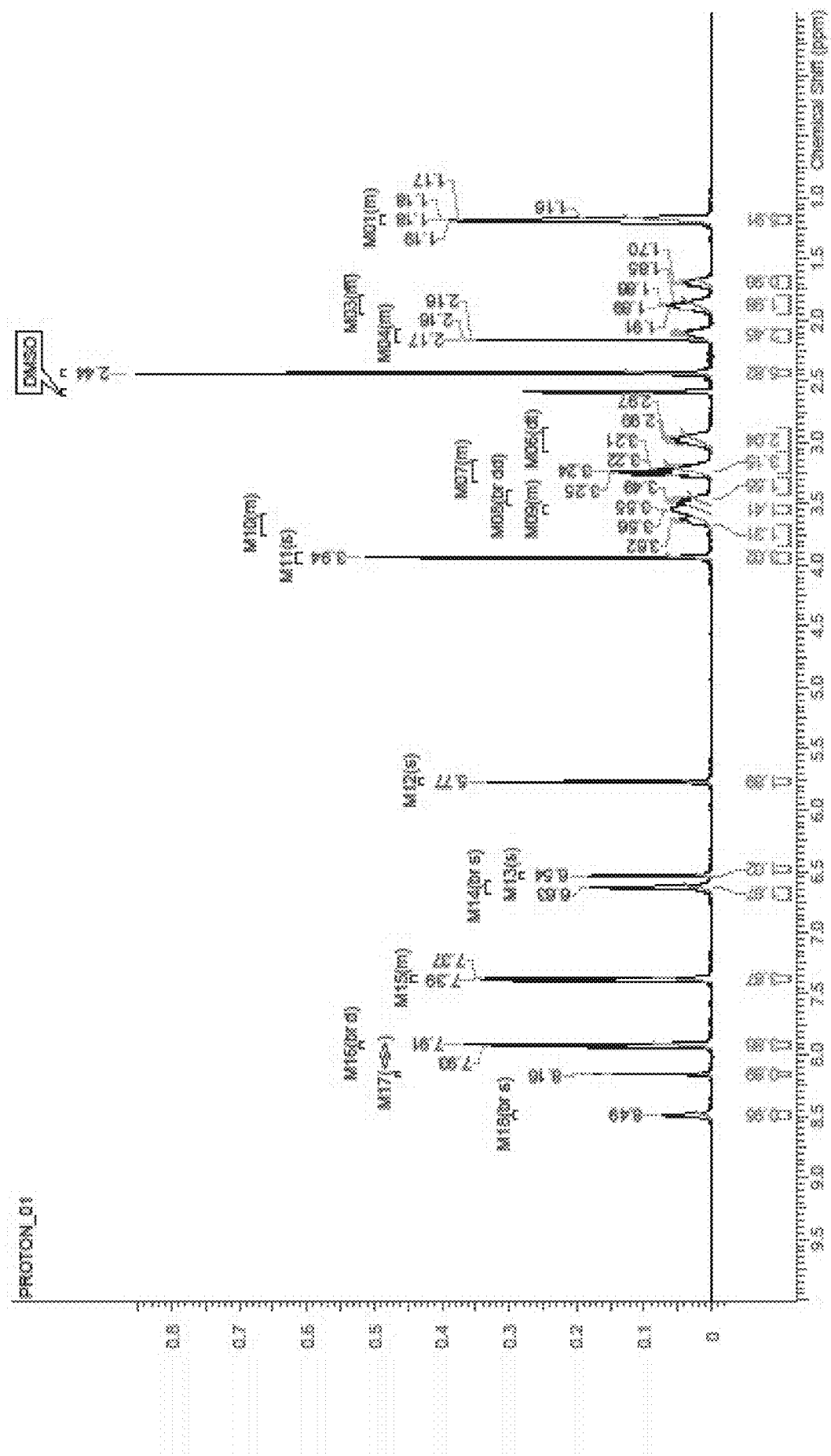

FIG. 10 is an NMR spectrum of an (S)-4-amino-N-((1-ethylpyrrolidin-2-yl)methyl)-5-(ethylsulfonyl)-2-methoxybenzamide (2R,3R)-bis((4-methylbenzoyl)oxy)succinic acid salt.

Figure 11A:
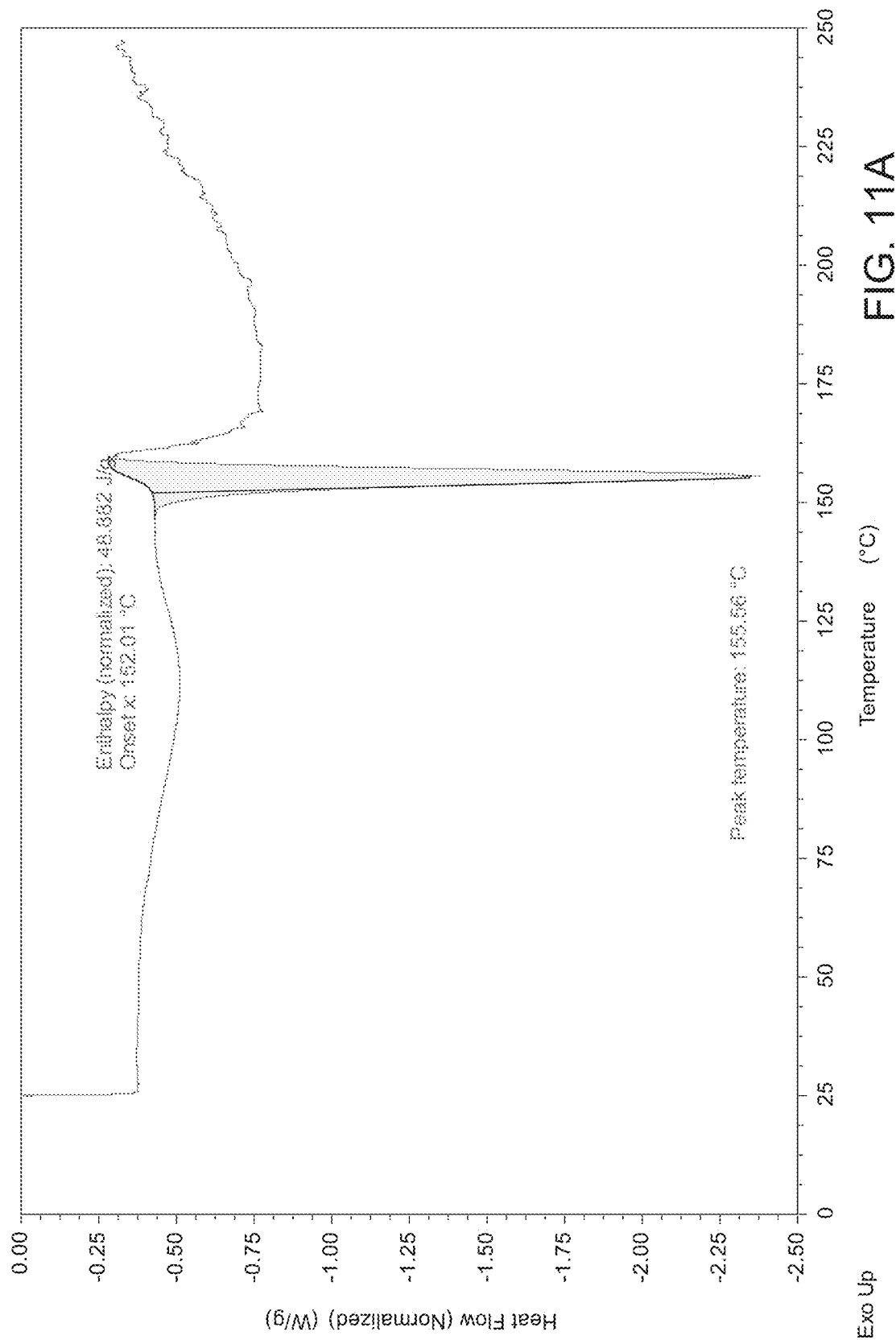
Figure 11B:
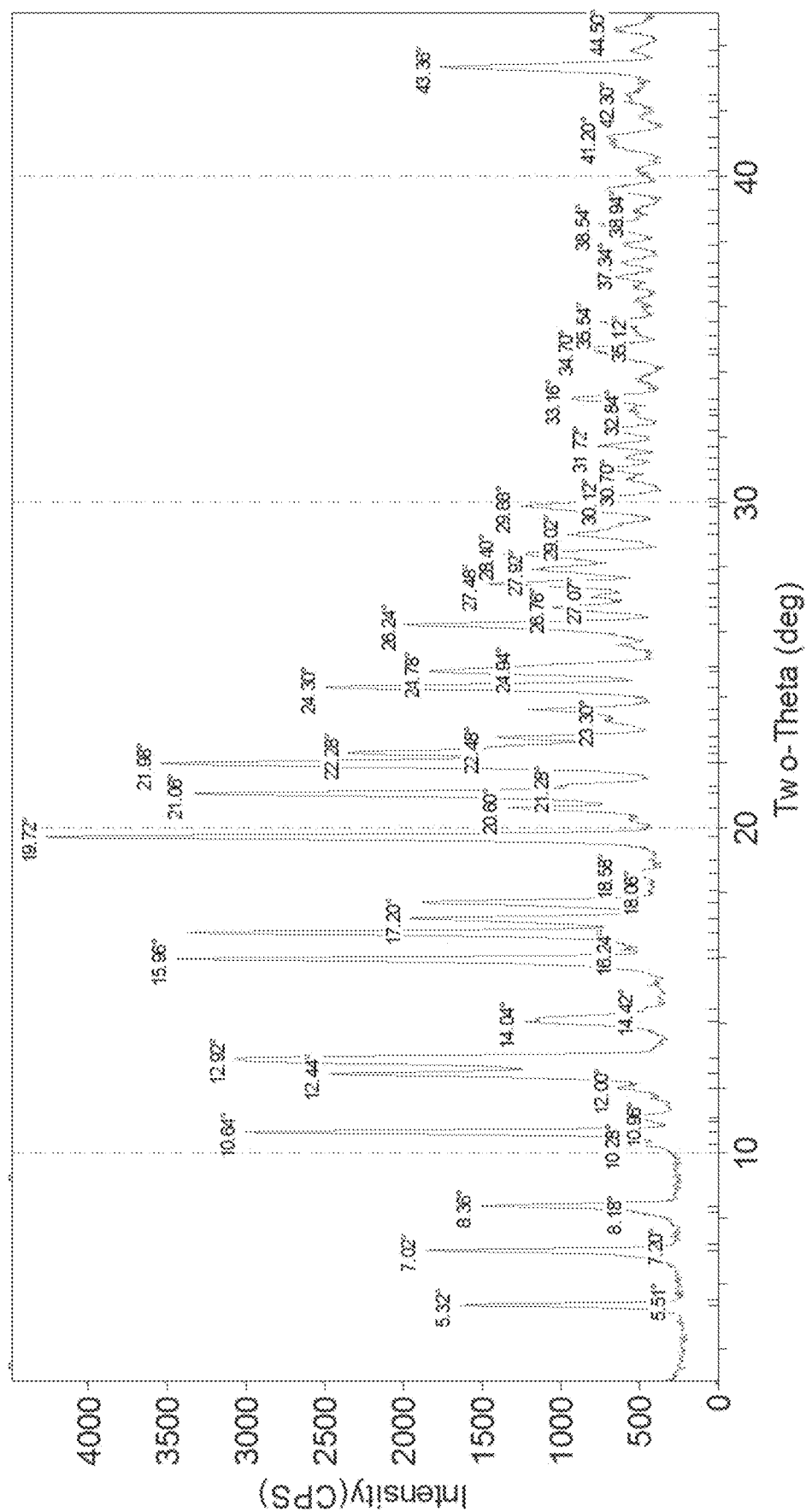

FIGS. 11A and 11B present various analytical data for (S)-4-amino-N-((1-ethylpyrrolidin-2-yl)methyl)-5-(ethylsulfonyl)-2-methoxybenzamide (2R,3R)-bis((4-methylbenzoyl)oxy)succinic acid salt, where FIG. 11A presents a DSC thermogram; and FIG. 11B presents a XRPD pattern.

Figure 12A:
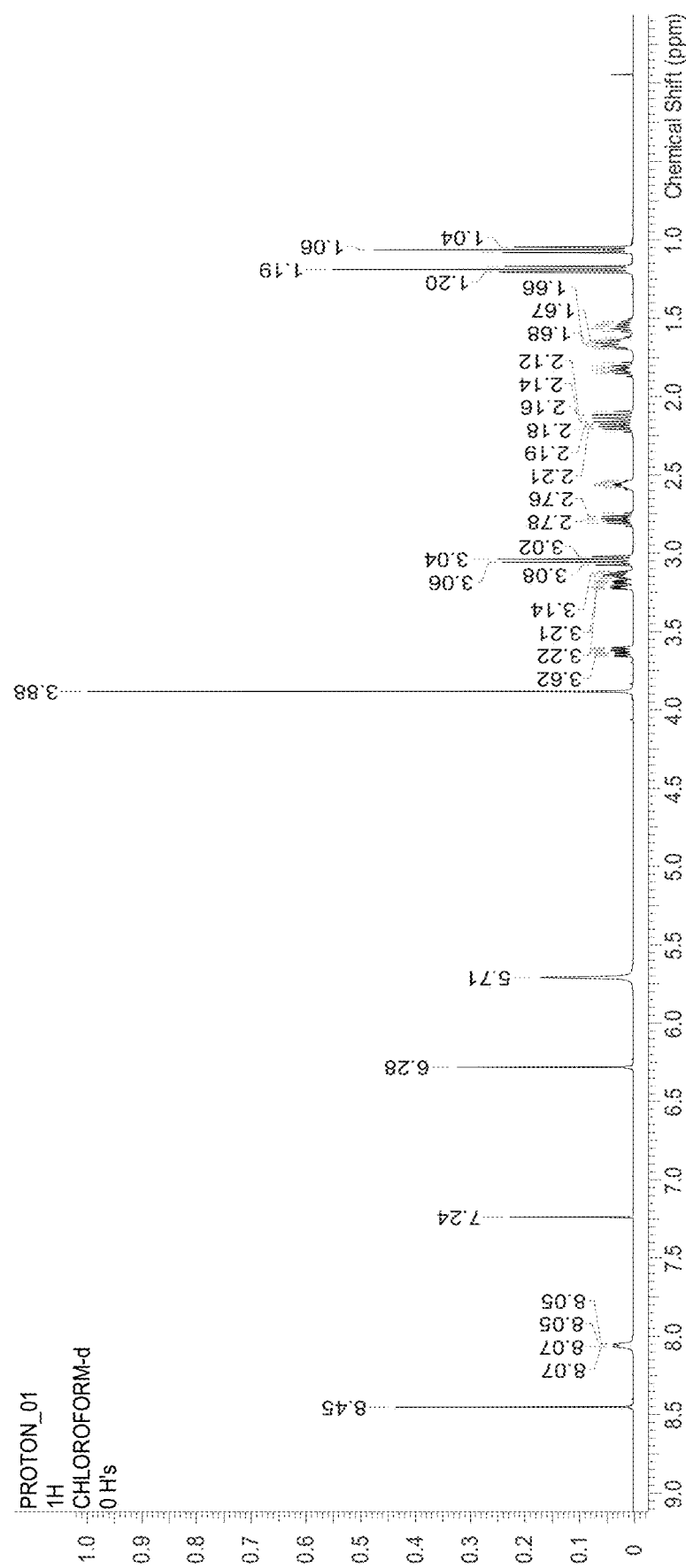
Figure 12B:
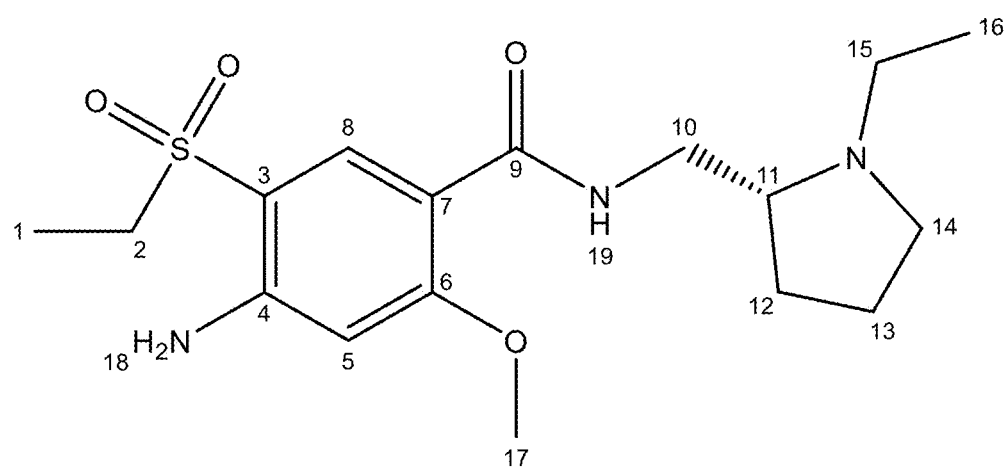

FIG. 12A is an NMR spectrum of an R-4-Amino-N-[(1-ethyl-2-pyrrolidinyl)methyl]-5-(ethylsulfonyl)-2-methoxybenzamide freebase of crystal Form A, and FIG. 12B illustrates the number sequence used for the assignment of peaks in FIG. 12A.

Figure 13A:
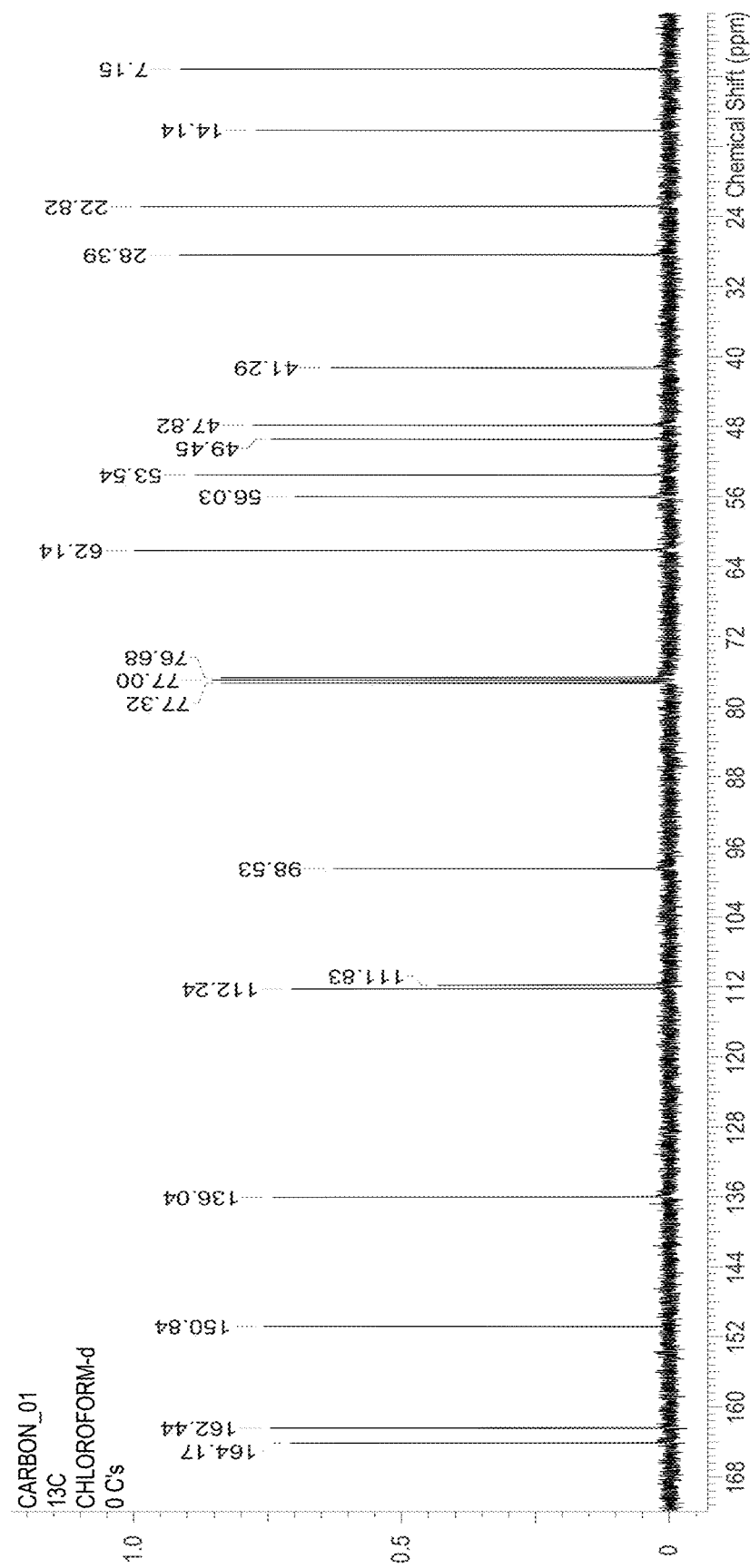
Figure 13B:
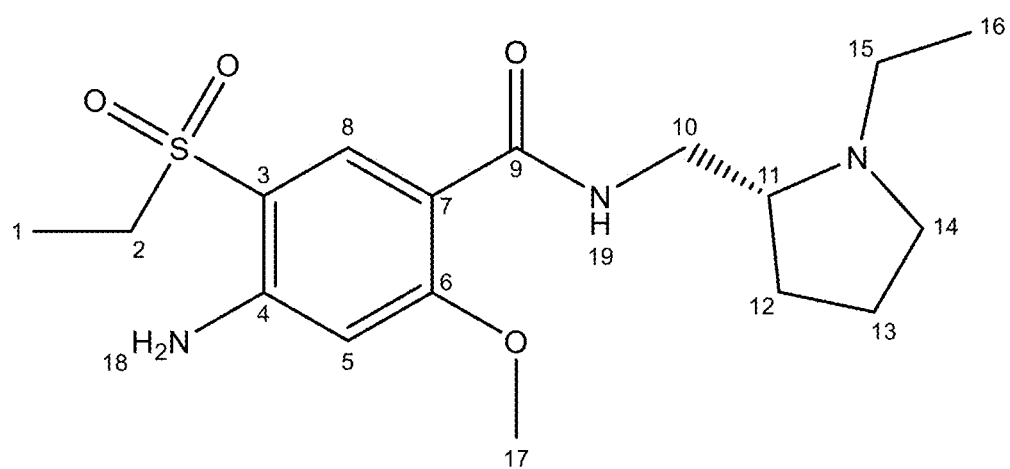

FIG. 13A is an $^{13}$C NMR spectrum of an R-4-Amino-N-[(1-ethyl-2-pyrrolidinyl)methyl]-5-(ethylsulfonyl)-2-methoxybenzamide freebase of crystal Form A, and FIG. 13B illustrates the number scheme used for the assignment of peaks in FIG. 13A.

Figure 14A:
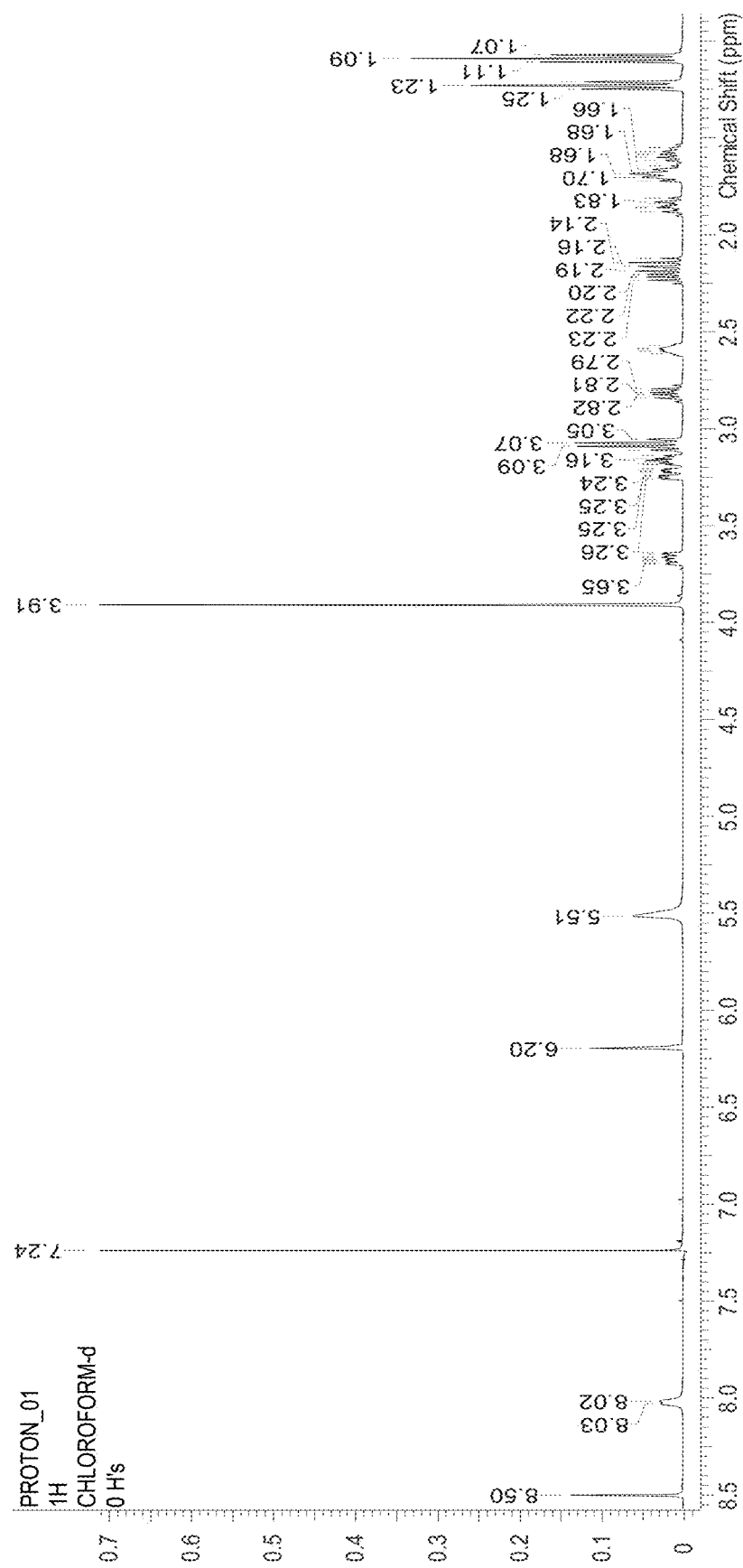
Figure 14B:
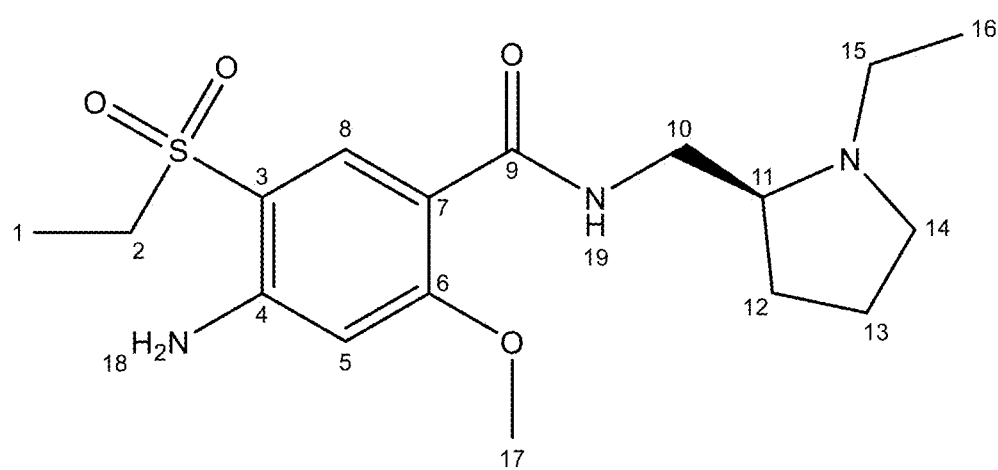

FIG. 14A is an NMR spectrum of an S-4-Amino-N-[(1-ethyl-2-pyrrolidinyl)methyl]-5-(ethylsulfonyl)-2-methoxybenzamide freebase of crystal Form A', and FIG. 14B illustrates the number sequence used for the assignment of peaks in FIG. 14A.

Figure 15A:
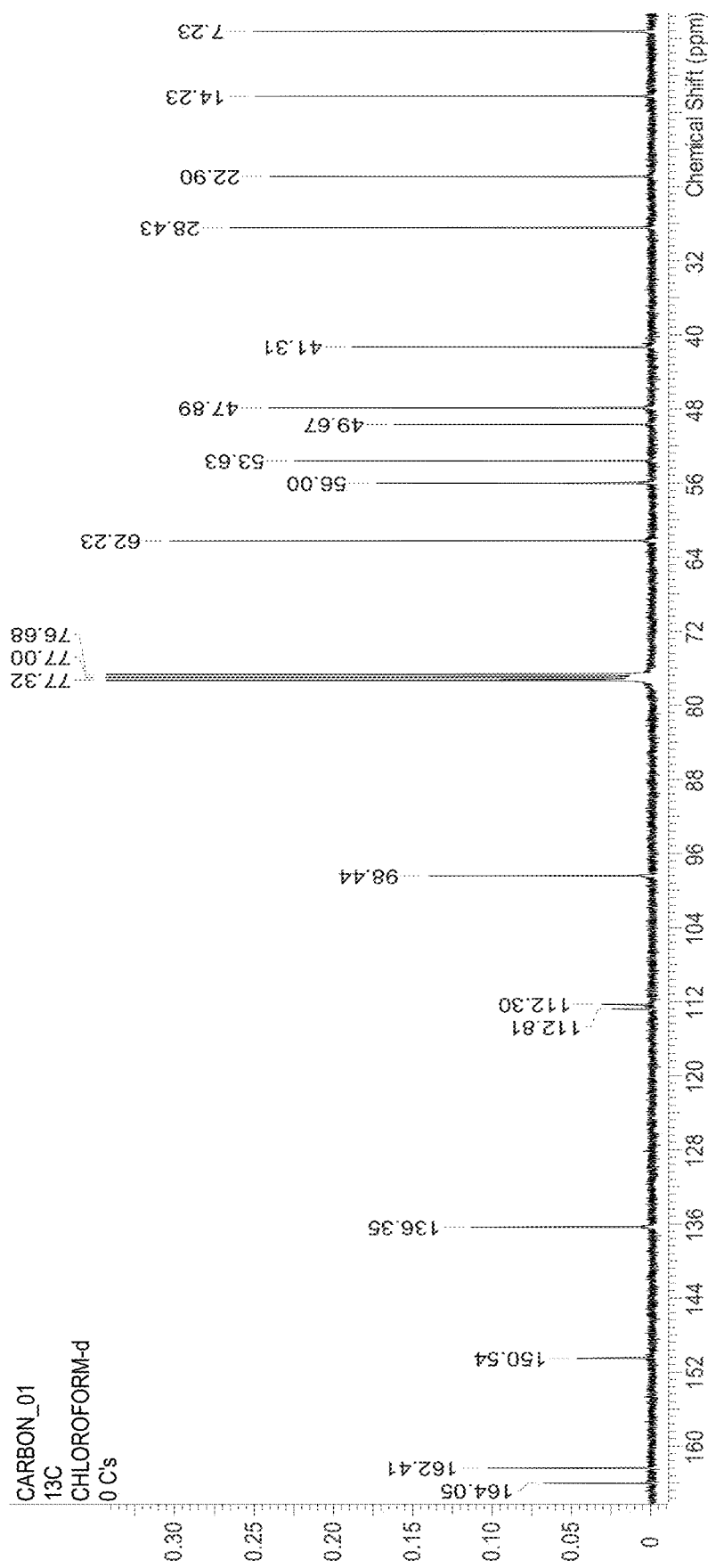
Figure 15B:
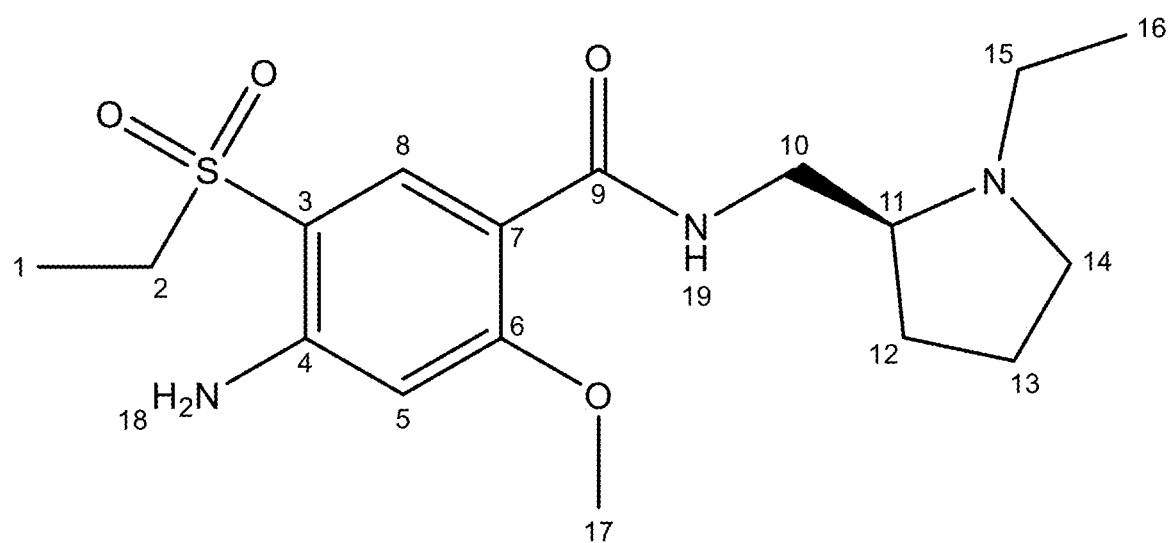

FIG. 15A is an $^{13}$C NMR spectrum of an S-4-Amino-N-[(1-ethyl-2-pyrrolidinyl)methyl]-5-(ethylsulfonyl)-2-methoxybenzamide freebase of crystal Form A', and FIG. 15B illustrates the number scheme used for the assignment of peaks in FIG. 15A.

Figure 16:
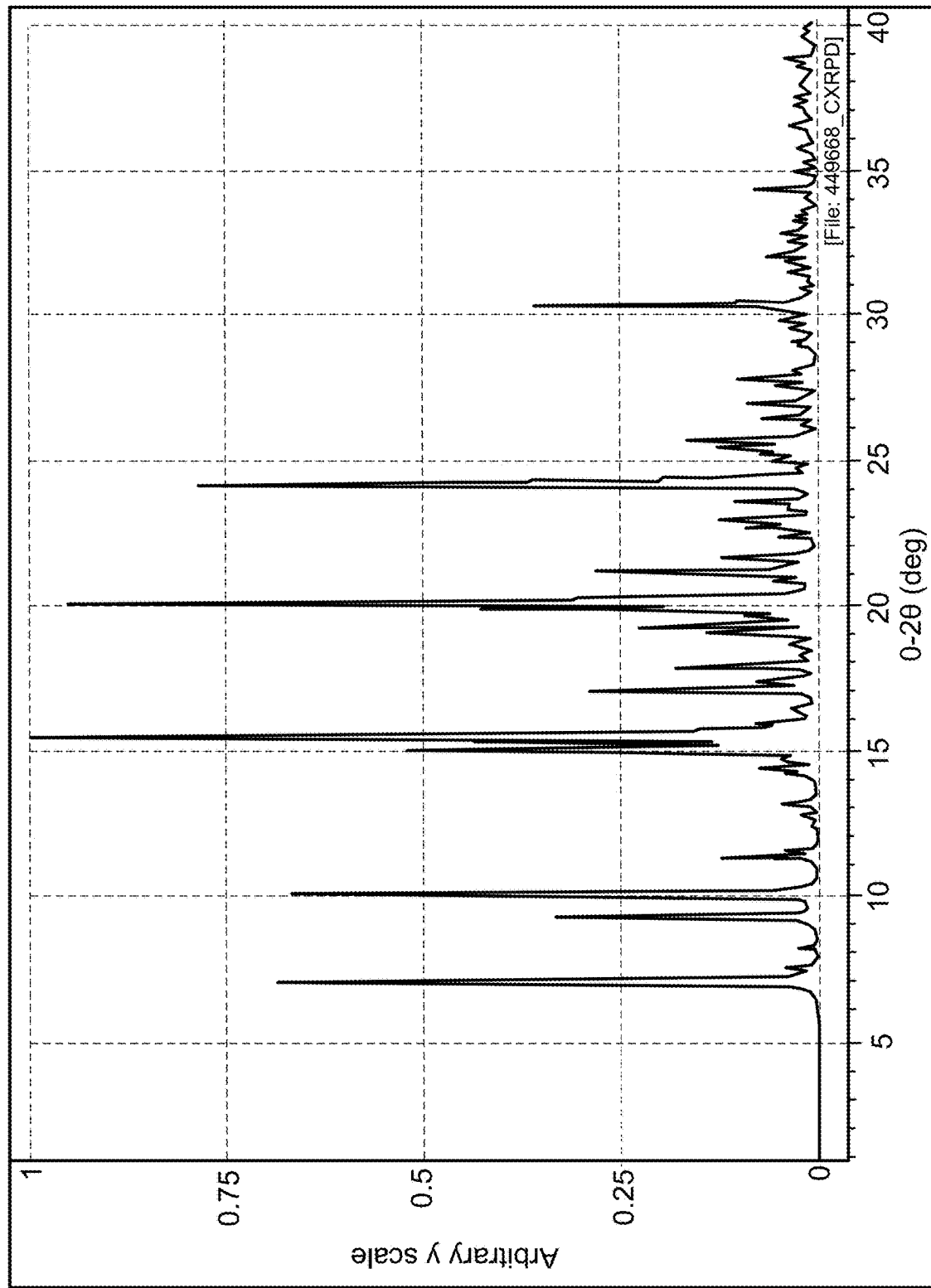

FIG. 16 presents a calculated XRPD pattern based on single crystal structure determination for (R)-amisulpride Form A.

Figure 17:
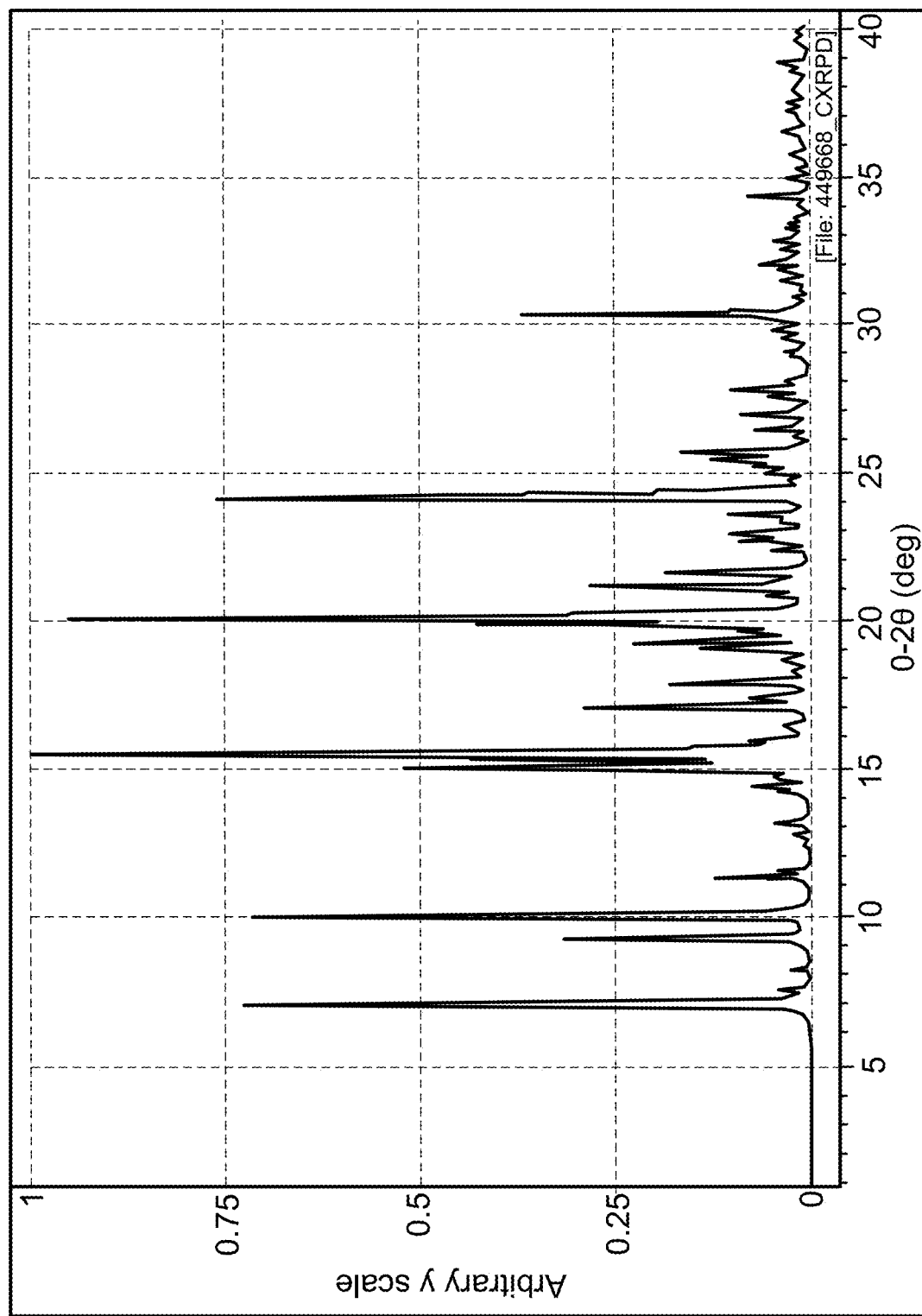

FIG. 17 presents a calculated XRPD pattern based on single crystal structure determination for (S)-amisulpride Form A'.

Figure 18:
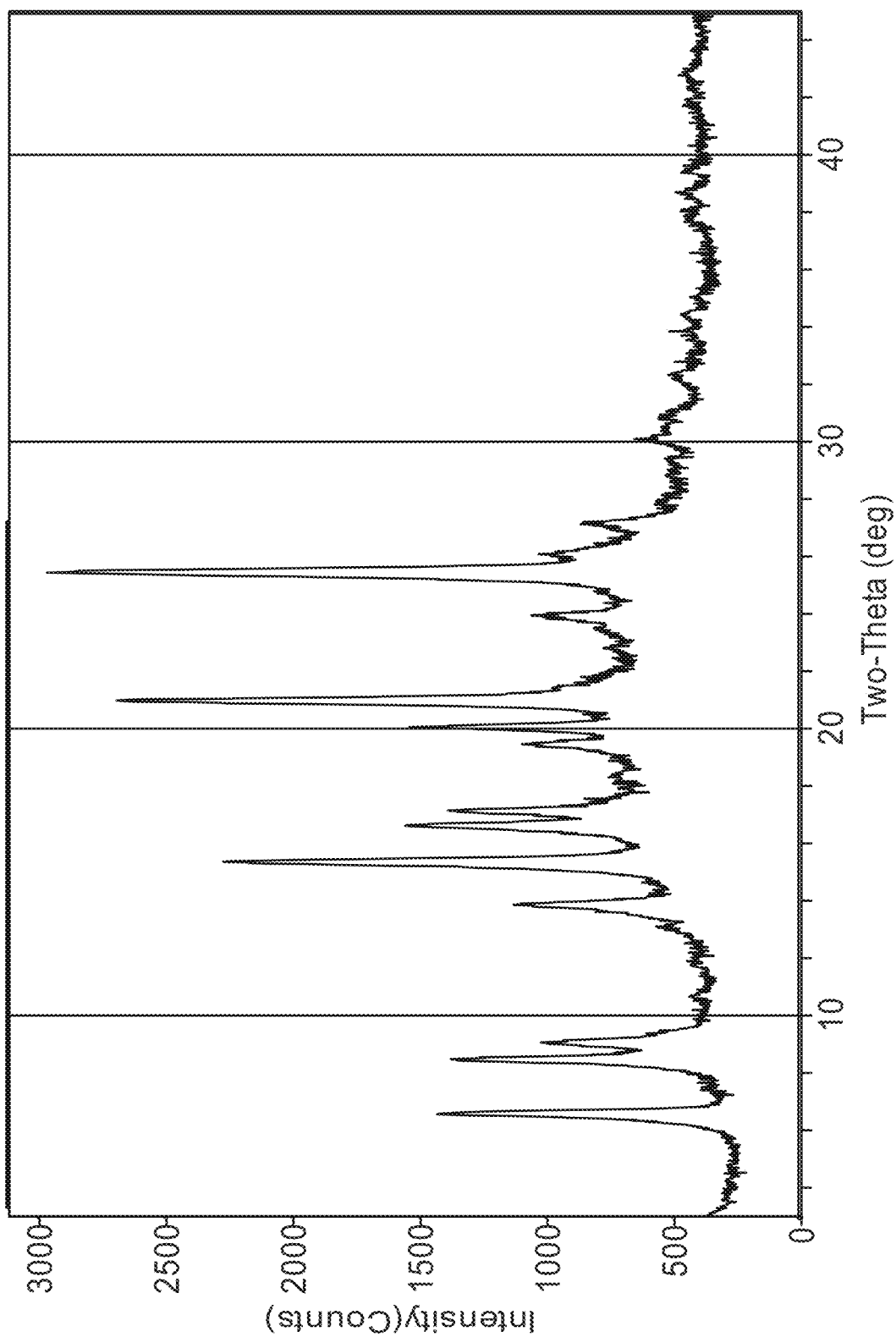

FIG. 18 presents a XRPD pattern of (R)-amisulpride 2-butanone solvate.

Figure 19:
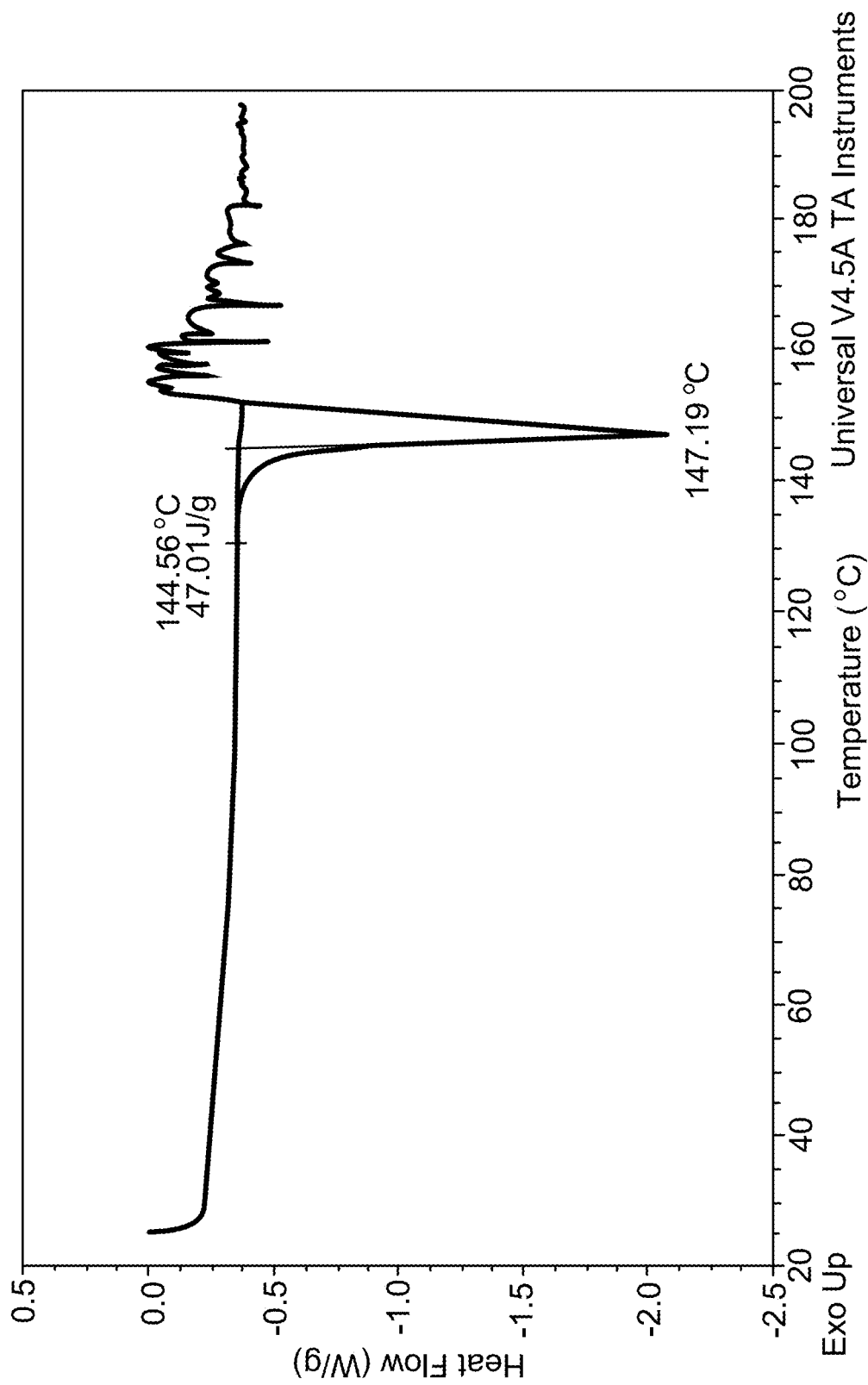

FIG. 19 presents a DSC thermogram of crystalline (R)-amisulpride 2-butanone solvate.

Figure 20:
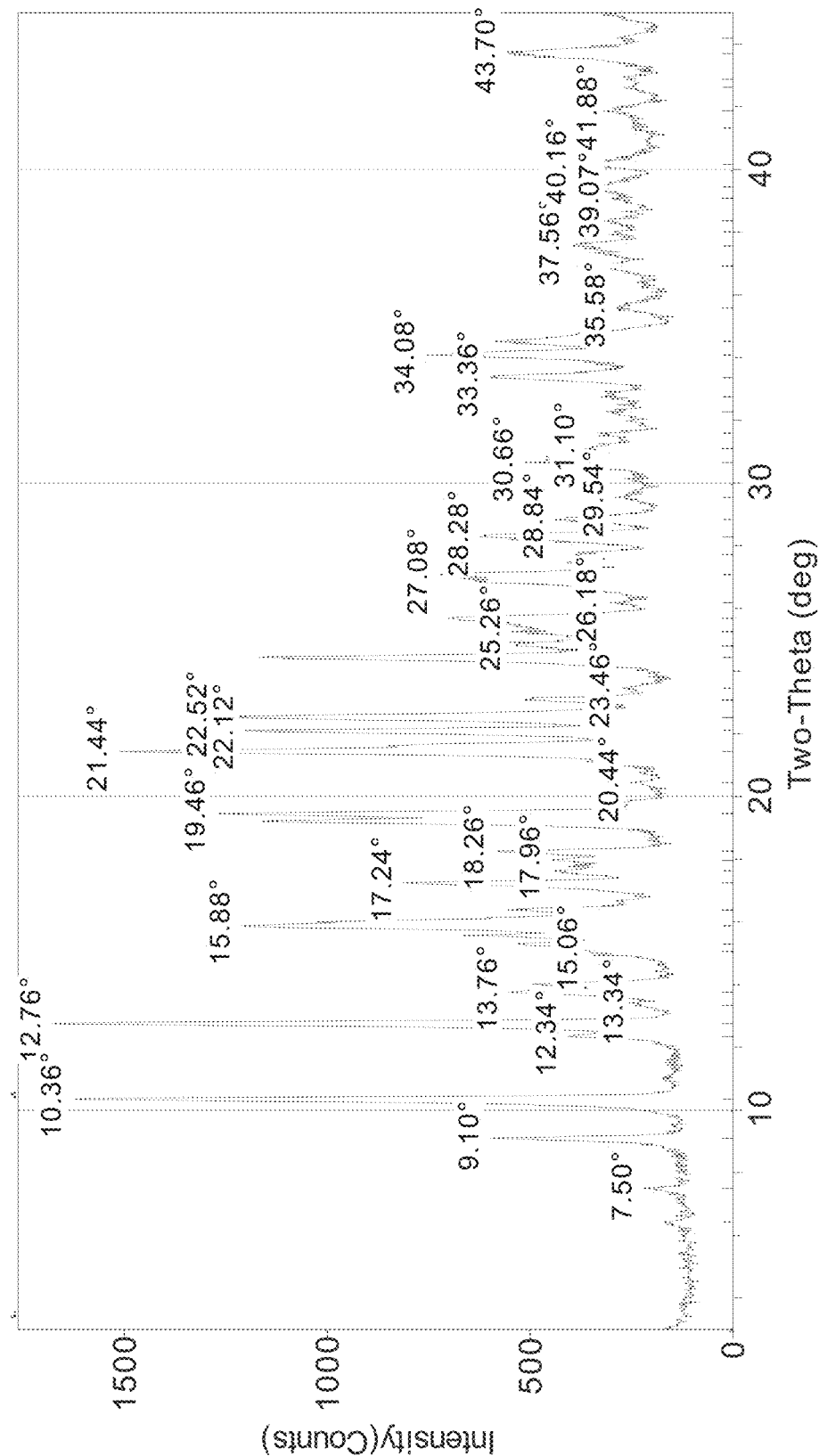

FIG. 20 presents an XRPD pattern of D-tartrate of S-(−)-4-Amino-N-[(1-ethyl-2-pyrrolidinyl)methyl]-5-(ethylsulfonyl)-2-methoxybenzamide.

Figure 21:
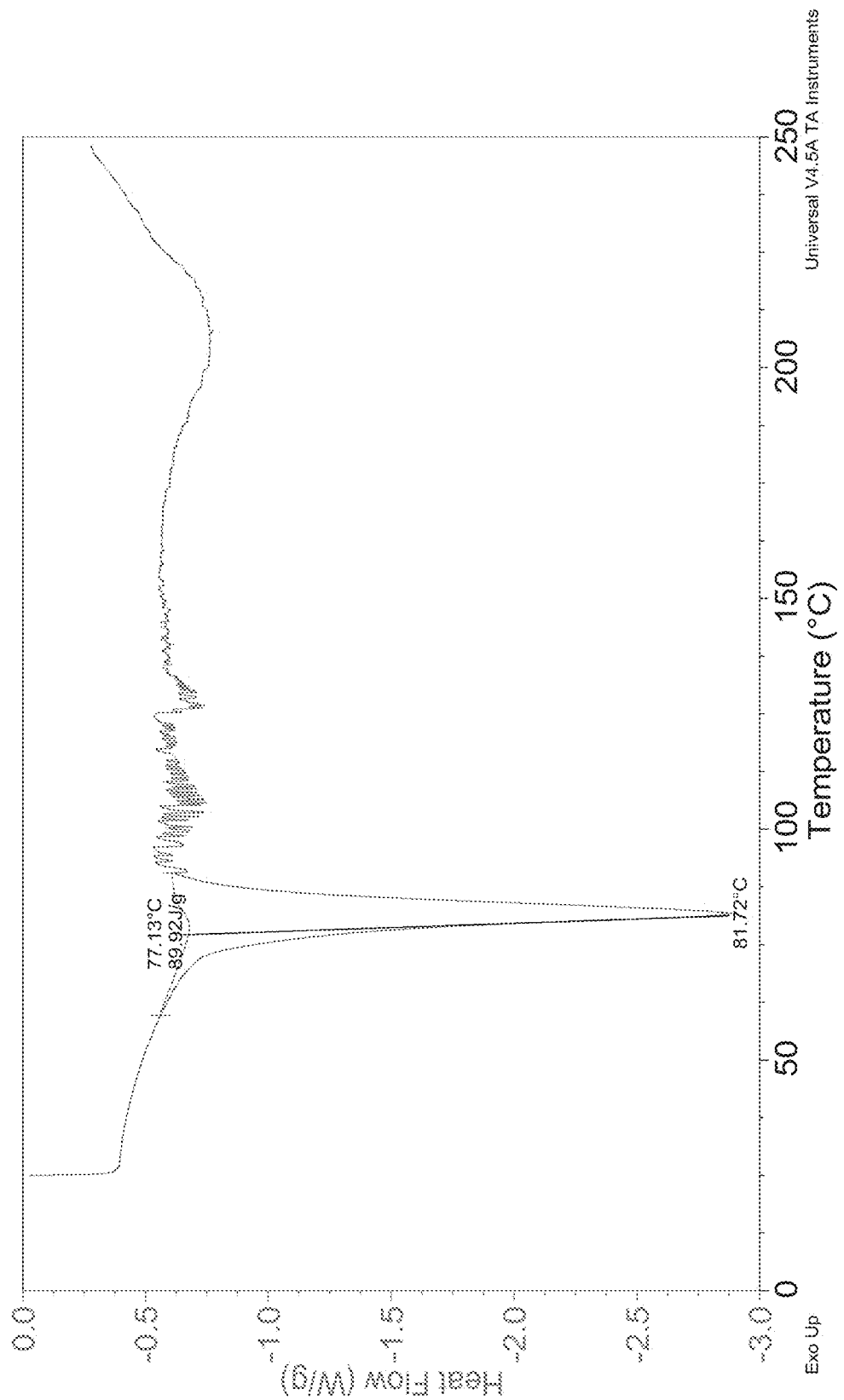

FIG. 21 presents a DSC thermogram of D-tartrate of S-(−)-4-Amino-N-[(1-ethyl-2-pyrrolidinyl)methyl]-5-(ethylsulfonyl)-2-methoxybenzamide.

Figure 22:
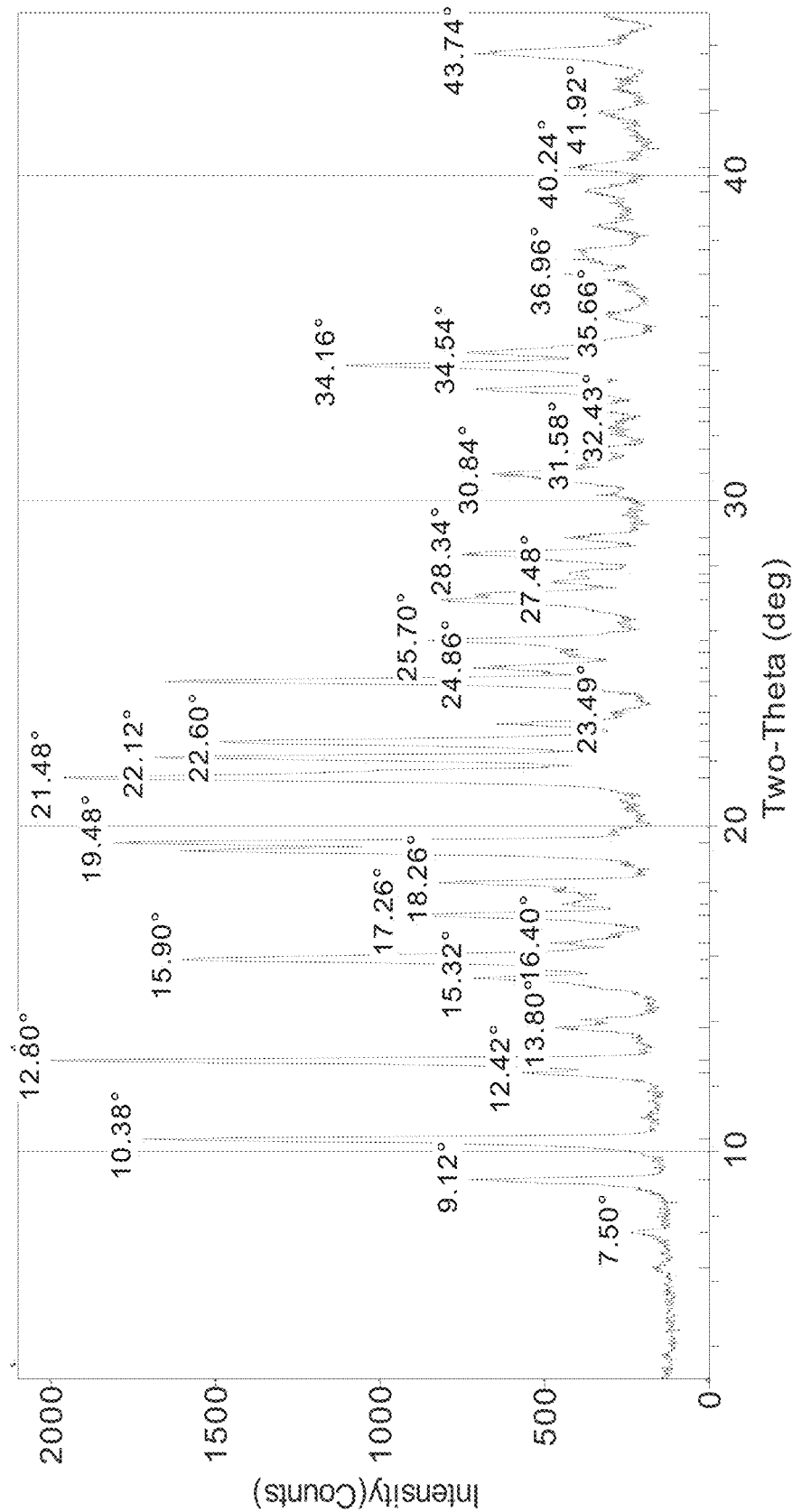

FIG. 22 presents an XRPD pattern of L-tartrate of R-(+)-4-Amino-N-[(1-ethyl-2-pyrrolidinyl)methyl]-5-(ethylsulfonyl)-2-methoxybenzamide.

Figure 23:
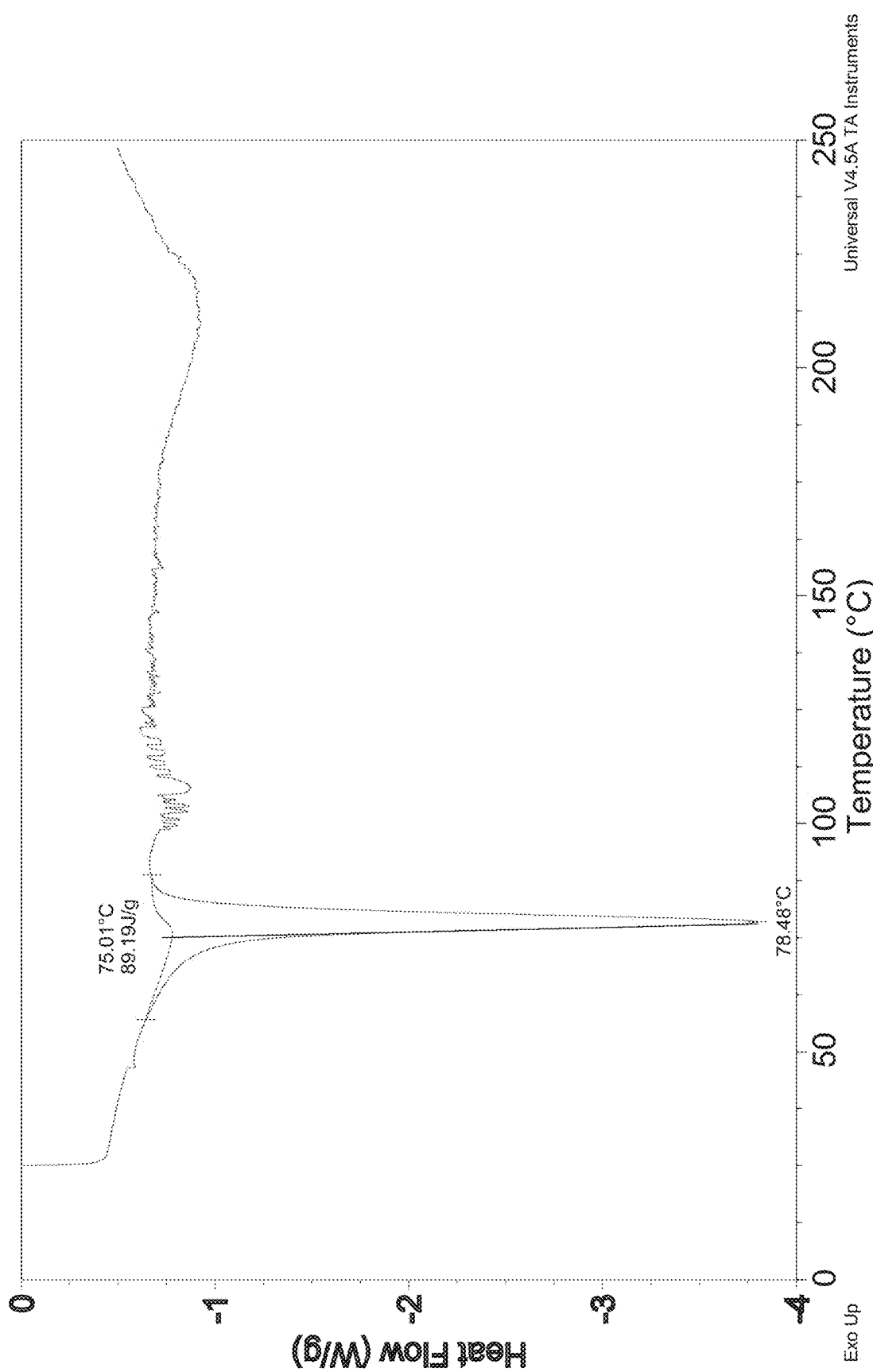

FIG. 23 presents a DSC thermogram of L-tartrate of R-(+)-4-Amino-N-[(1-ethyl-2-pyrrolidinyl)methyl]-5-(ethylsulfonyl)-2-methoxybenzamide.

DETAILED DESCRIPTION

All published documents cited herein are hereby incorporated herein by reference in their entirety.

Reference in the specification to "one embodiment," "an embodiment," "one aspect," or "an aspect" means that a particular, feature, structure or characteristic described in connection with the embodiment or aspect is included in at least one embodiment or aspect of the teachings.

Polymorphism is the ability of an element or compound to crystallize into distinct crystalline phases. Although the term polymorph implies more than one morphology, the term is still used in the art, and herein, to refer to a crystalline structure of a compound as a polymorph even when only one crystalline phase is currently known. Thus, polymorphs are distinct solids sharing the same molecular formula as other polymorphs and the amorphous (non-crystalline) phase, however since the properties of any solid depends on its structure, polymorphs often exhibit physical properties distinct from each other and the amorphous phase, such as different solubility profiles, different melting points, different dissolution profiles, different thermal stability, different photostability, different hygroscopic properties, different shelf life, different suspension properties and different physiological absorption rates. Inclusion of a solvent in the crystalline solid leads to solvates, and in the case of water as a solvent, hydrates, often leads to a distinct crystalline form with one or more physical properties that are distinctly different from the non-solvated and non-hydrated (e.g., free base) crystalline form.

As used herein, the term "polymorph" refers to different crystal structures achieved by a particular chemical entity. As used herein, the term "solvate" refers to a crystal form where a stoichiometric or non-stoichiometric amount of solvent, or mixture of solvents, is incorporated into the crystal structure. Similarly, the term "hydrate" refers to a crystal form where a stoichiometric or non-stoichiometric amount of water is incorporated into the crystal structure.

In various embodiments of the present inventions, (R)-amisulpride and (S)-amisulpride are independently provided in a free base crystal form, and thus without any water or solvent incorporated into the crystal structure. It has been found that (R)-amisulpride and (S)-amisulpride can exist in at least one such free base crystal form, or polymorph, which is referred to herein as Form A for crystalline (R)-amisulpride, and Form A' for crystalline (S)-amisulpride.

In various embodiments of the present inventions, (R)-amisulpride and (S)-amisulpride are independently provided in crystal form incorporating ethyl acetate, and thus as crystalline (R)-amisulpride ethyl acetate solvate and crystalline (S)-amisulpride ethyl acetate solvate forms. It has been found that ethyl acetate solvates can exist in at least one such form, or polymorph, which is referred to herein as Form B for crystalline (R)-amisulpride ethyl acetate solvate, and Form B' for crystalline (S)-amisulpride ethyl acetate solvate.

As used herein the term "polymorph purity" refers to the weight % that is the specified polymorph form. For example, when a crystalline (R)-amisulpride of Form A is characterized as having greater than 95% polymorph purity, that means that greater than 95% by weight of the substance is crystalline (R)-amisulpride of Form A and less than 5% by weight of any other polymorph or amorphous form of (R)-amisulpride.

As used herein the terms "chiral purity" and "enantiomeric purity" are used interchangeably and refers to the weight % that is the specified enantiomer. For example, when a (R)-amisulpride containing substance (such as a compound or crystal) is characterized as having greater than 90% chiral purity, that means that greater than 90% by weight of the amisulpride in the substance is the (R)-amisulpride and less than 10% by weight is in any other enantiomeric form of amisulpride.

As used herein the term "chemical purity" refers to the weight % that is the specified chemical entity, including specified polymorph form. For example, when a crystalline amisulpride Form A' is characterized as having greater than 95% chemical purity, that means that greater than 95% by weight of the substance is crystalline amisulpride Form A' and less than 5% by weight of other compound including other polymorphs.

For example, when a crystalline (R)-amisulpride Form A is characterized as having greater than 99% chemical purity and greater than 97% chiral purity, that means greater than 97% by weight of the substance is of enantiomeric form (R)-amisulpride Form A and less than 3% by weight of any other amisulpride enantiomer, and that greater than 99% by weight of the substance is amisulpride and less than 1% by weight of other compounds. For example, when a crystalline (R)-amisulpride Form A is characterized as having greater than 99% chemical purity, greater than 97% chiral purity and greater than 95% polymorph purity, that means that greater than 95% by weight of the substance is crystalline (R)-amisulpride of Form A and less than 5% by weight of any other polymorph or amorphous form of (R)-amisulpride, greater than 97% by weight of the substance is of enantiomeric form (R)-amisulpride and less than 3% by weight of any other amisulpride enantiomer, and that greater than 99% by weight of the substance is amisulpride and less than 1% by weight of other compounds.

Crystal forms of amisulpride, enantiomeric amisulpride, and crystalline forms of their salts, hydrates and solvates, including those of the present inventions, may be characterized and differentiated using a number of conventional analytical techniques, including but not limited to X-ray powder diffraction (XRPD) patterns, nuclear magnetic resonance (NMR) spectra, Raman spectra, Infrared (IR) absorption spectra, dynamic vapor sorption (DVS), Differential Scanning calorimetry (DSC), and melting point. Chemical purity may be characterized using a number of conventional analytical techniques, including but not limited to high performance liquid chromatography (HPLC) and gas chromatography (GC). For example, one skilled in the art could use a reverse phase gradient HPLC method or a reverse phase isocratic HPLC method to determine organic impurities, a headspace GC method to determine residual solvents, coulometric titration (Karl Fischer) to determine water content, and a reverse phase isocratic HPLC method or a polar organic phase isocratic HPLC method to determine the amount of drug product in a sample. Chiral purity (also known as enantiomeric purity) may be characterized using a number of conventional analytical techniques, including but not limited to chiral high performance liquid chromatography (HPLC). Water content may be characterized using a number of conventional analytical techniques, including but not limited to coulometric titration.

In various embodiments, the crystal forms of racemic amisulpride, enantiomeric amisulpride, and enantiomeric amisulpride solvates are characterized by X-ray powder diffraction (XRPD). XRPD is a technique of characterizing a powdered sample of a material by measuring the diffraction of X-rays by the material. The result of an XRPD experiment is a diffraction pattern. Each crystalline solid produces a distinctive diffraction pattern containing sharp peaks as a function of the scattering angle 2θ (2-theta). Both the positions (corresponding to lattice spacing) and the relative intensity of the peaks in a diffraction pattern are indicative of a particular phase and material. This provides a "fingerprint" for comparison to other materials. In contrast to a crystalline pattern comprising a series of sharp peaks, amorphous materials (liquids, glasses etc.) produce a broad background signal in a diffraction pattern.

It is to be understood that with the apparatus employed, humidity, temperature, orientation of the powder crystals, and other parameters involved in obtaining an XRPD pattern may cause some variability in the appearance, intensities, and positions of the lines in the diffraction pattern. An XRPD pattern that is "substantially in accord with" that of a FIG. provided herein (e.g., FIG. 2B) is an XRPD pattern that would be considered by one skilled in the art to represent a compound possessing the same crystal form as the compound that provided the XRPD pattern of that FIG. That is, the XRPD pattern may be identical to that of the FIG., or more likely it may be somewhat different. Such an XRPD pattern may not necessarily show each of the lines of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns.

For example, one skilled in the art could use a chiral HPLC method (e.g. polar organic mode isocratic HPLC) to determine the enantiomeric identity of an amisulpride sample and if, for example, the sample is identified as (R)-amisulpride, one skilled in the art can overlay an XRPD pattern of the amisulpride sample with FIG. 2B and/or FIG. 3B, and using expertise and knowledge in the art, readily determine whether the XRPD pattern of the sample is substantially in accordance with the XRPD pattern of crystalline (R)-amisulpride of Form A presented in FIG. 2B. If, for example, HPLC identifies the sample as being (R)-amisulpride and the sample XRPD pattern is substantially in accord with FIG. 2B, the sample can be readily and accurately identified as (R)-amisulpride of Form A.

In various embodiments, the crystal forms of racemic amisulpride, enantiomeric amisulpride, and enantiomeric amisulpride solvates are characterized by melting point. Melting points were determined by conventional methods such as capillary tube and may exhibit a range over which complete melting occurs, or in the case of a single number, a melting point of that temperature ±2° C. In some embodiments, the melting point is of that temperature ±3° C.

In various embodiments, the crystal forms of racemic amisulpride, enantiomeric amisulpride, and enantiomeric amisulpride solvates are characterized by differential scanning calorimetry (DSC). DSC is a thermoanalytical technique in which the difference in the amount of heat required to increase the temperature of a sample and a reference is measured as a function of temperature. Both the sample and reference are maintained at substantially the same temperature throughout the experiment. The result of a DSC experiment is a curve of heat flow versus temperature, called a DSC thermogram. The temperature readings (e.g., an endothermic event or an exothermic event) in connection with DSC can vary about ±2° C. depending on the instrument, particular settings, sample preparation, etc. In some embodiments, the temperature reading can vary about ±3° C.

In various embodiments, the hygroscopicity of crystal forms of racemic amisulpride, enantiomeric amisulpride, and enantiomeric amisulpride solvates are characterized by dynamic vapor sorption (DVS). DVS is a gravimetric technique that measures how much of a solvent is absorbed by a sample by varying the vapor concentration surrounding the sample (e.g., relative humidity) and measuring the change in mass. In the present application, DVS is used to generate water sorption isotherms, which represent the equilibrium amount of vapor sorbed as a function of steady state relative vapor pressure at a constant temperature.

As used herein, the term "substantially non-hygroscopic" refers to a compound exhibiting less than a 1% maximum mass change in water sorption isotherms, at 25° C. scanned over 0 to 95% relative humidity, as measured by dynamic vapor sorption (DVS).

The compounds disclosed herein can include isotopes. Isotopes include those atoms having the same atomic number but different mass numbers. For example, isotopes of hydrogen include tritium and deuterium. In some embodiments, one or more atoms of the compounds can be replaced or substituted with isotopes of the atoms in natural or non-natural abundance. In some embodiments, one or more hydrogen atoms in a compound of the present disclosure can be replaced or substituted by deuterium.

As used herein, and unless otherwise specified, the term "about", when used in connection with a numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values. In some embodiments, the numeric value or range of values vary by 5%.

In various embodiments, the present inventions relate to new crystalline forms of enantiomeric amisulpride, Form A and Form A'. Forms A and A' have been found to be a distinct polymorph, different from the crystalline form of a racemic amisulpride, Forms A and A' having distinctly different structure and XRPD pattern, as well as physical properties. In various embodiments, Form A and A' are anhydrous, e.g., substantially free of water and solvent. Table 1 compares various properties and data on crystalline racemic amisulpride, Form A crystals of (R)-amisulpride, and Form A' crystals of (S)-amisulpride where the FIG. references are to figures in the present application. The Specific Rotation data was obtained by polarimetry, the subject compound was dissolved in methanol at nominal concentration of c=1 using the 589 nm (Sodium Line). It is to be understood that upon dissolution of the compound it is no longer of a crystalline form, thus one of ordinary skill in the art will understand that the specific rotation in Table 1 refers to that of the non-crystalline compound.

TABLE 1

| | Compound | | |
| --- | --- | --- | --- |
| Physical Property | crystalline racemic amisulpride | (R)-amisulpride Form A | (S)-amisulpride Form A' |
| # of Solid Phases | 1 | 1 | 1 |
| Melting Point, ° C. | 126 | 102 | 102 |
| DSC Thermograph | FIG. 1A | FIG. 2A | FIG. 3A |
| XRPD Pattern | FIG. 1B | FIG. 2B | FIG. 3B |
| Micrograph Image | FIG. 1C | FIG. 2C | FIG. 3C |
| Specific Rotation | — | $[\alpha]^{20}_D = 5.1 \cdot 10^1$ (MeOH, c = 1) | $[\alpha]^{20}_D = -5.0 \cdot 10^1$ (MeOH, c = 1) |
| Solubility (mg/mL): | | | |
| Water (solution pH) | <1 | 2 (10.2) | 2 (10.3) |
| 0.05M Acetate Buffer (solution pH) | | >100 (4.5) | >100 (4.5) |
| Ethyl Acetate | 0.5 | 3.9 | 3.9 |
| Acetone/MtBE 1:4 | 0.4 | 8 | 8 |
| Acetone/MtBE 1:9 | 0.2 | 2 | 2 |
| Simulated Gastric Fluid (no enzyme) | | >100 (pH adjusted to 1.1) | >100 (pH adjusted to 1.2) |
| Simulated Intestinal Fluid (no enzyme) | | >100 (pH adjusted to 6.7) | >100 (pH adjusted to 6.9) |

The present inventors have discovered that crystalline enantiomeric amisulpride of Forms A and A' cannot be formed from crystalline racemic amisulpride. It is believed, without being held to theory, that the higher melting point of crystalline racemic amisulpride, relative to crystalline enantiomeric amisulpride of Forms A and A', is indicative of the greater thermodynamic stability of crystalline racemic amisulpride. In addition, the present inventors have observed that dissolution of a 95:5 mixture of (R)-amisulpride Form A:(S)-amisulpride Form A' followed by recrystallization, results not in formation of Form A or Form A' from recrystallization but rather a 90:10 mixture of (R)-amisulpride Form A:crystalline racemic amisulpride.

In various embodiments, the present inventions provide a crystalline form of (R)-amisulpride characterized by an XRPD pattern comprising peaks, in terms of 2-theta, at 7.0±0.2°, 9.7±0.2°, and 19.4±0.2°. In various embodiments, the present inventions provide a crystalline form of (R)-amisulpride characterized by three or more peaks in its XRPD pattern selected from those at 7.0±0.2°, 9.7±0.2°, 15.4±0.2°, 19.4±0.2°, 20.1±0.2°, 21.0±0.2°, 23.2±0.2°, and 29.3±0.2°, in terms of 2-theta. In various embodiments, the present inventions provide a crystalline form of (R)-amisulpride characterized by an XRPD pattern substantially in accord with FIG. 2B.

In various embodiments, the present inventions provide a crystalline form of (R)-amisulpride characterized by the following properties, an XRPD pattern comprising peaks, in terms of 2-theta, at 7.0±0.2°, 9.7±0.2°, and 19.4±0.2°, a melting point of 102±3° C., a chiral purity of greater than about 99%, a chemical purity greater than about 99%, a residual solvent content of less than about 1000 ppm, and is substantially non-hygroscopic.

In various embodiments, the present inventions provide a crystalline form of (R)-amisulpride characterized by the following properties, an XRPD pattern comprising peaks, in terms of 2-theta, at 7.0±0.2°, 9.7±0.2°, and 19.4±0.2° and one or more of the following:
(a) the powder x-ray diffraction pattern further comprising peaks, in terms of 2-theta, at 15.4±0.2° and 29.3±0.2°;
(b) the powder x-ray diffraction pattern further comprising peaks, in terms of 2-theta, at 20.1±0.2°, 21.0±0.2°, and 23.2±0.2°;
(c) a melting point of 102±3° C.;
(d) a differential scanning calorimetry thermogram comprising a peak at 101±3° C.;
(e) a differential scanning calorimetry thermogram substantially in accord with FIG. 2A;
(f) a chiral purity of greater than about: (i) 90%, (ii) 95%, (iii) 97%, (iv) 99%, (v) 99.5%, (vi) 99.7%, or (vii) 99.9%;
(g) a chemical purity of greater than about: (i) 80%, (ii) 90%, (iii) 95%, (iv) 97%, (v) 99%, (vi) 99.5%, (vii) 99.7%, or (viii) 99.9%;
(h) residual solvents present in an amount less than about: (i) 8000 ppm, (ii) 6000 ppm, (iii) 4000 ppm, (iv) 2000 ppm, (v) 1000 ppm, (vi) 800 ppm, or 500 ppm; and
(i) as measured by dynamic vapor sorption (DVS), at 25° C. scanned over 0 to 95% relative humidity, a maximum mass change in water sorption isotherms of less than about (i) 2%, (ii) 1%, (iii) 0.5%, or (iv) 0.4%.

In various embodiments, the present inventions provide a crystalline form of (S)-amisulpride characterized by an XRPD pattern comprising peaks, in terms of 2-theta, at 7.0±0.2°, 9.7±0.2°, and 19.4±0.2°. In various embodiments, the present inventions provide a crystalline form of (S)-amisulpride characterized by three or more peaks in its XRPD pattern selected from those at 7.0±0.2°, 9.7±0.2°, 15.4±0.2°, 19.4±0.2°, 20.1±0.2°, 21.0±0.2°, 23.2±0.2°, and 29.3±0.2°, in terms of 2-theta. In various embodiments, the present inventions provide a crystalline form of (S)-amisulpride characterized by an XRPD pattern substantially in accord with FIG. 3B.

In various embodiments, the present inventions provide a crystalline form of (S)-amisulpride characterized by the following properties, an XRPD pattern comprising peaks, in terms of 2-theta, at 7.0±0.2°, 9.7±0.2°, and 19.4±0.2°, a melting point of 102±3° C., a chiral purity of greater than about 99%, a chemical purity greater than about 99%, a residual solvent content of less than about 1000 ppm, and is substantially non-hygroscopic.

In various embodiments, the present inventions provide a crystalline form of (S)-amisulpride characterized by the following properties, an XRPD pattern comprising peaks, in terms of 2-theta, at 7.0±0.2°, 9.7±0.2°, and 19.4±0.2° and two or more of the following:
(a) the powder x-ray diffraction pattern further comprising peaks, in terms of 2-theta, at 15.4±0.2° and 29.3±0.2°;
(b) the powder x-ray diffraction pattern further comprising peaks, in terms of 2-theta, at 20.1±0.2°, 21.0±0.2°, and 23.2±0.2°;
(c) a melting point of 102±3° C.;
(d) a differential scanning calorimetry thermogram comprising a peak at 101±3° C.;
(e) a differential scanning calorimetry thermogram substantially in accord with FIG. 3A;
(f) a chiral purity of greater than about: (i) 90%, (ii) 95%, (iii) 97%, (iv) 99%, (v) 99.5%, (vi) 99.7%, or (vii) 99.9%;
(g) a chemical purity of greater than about: (i) 80%, (ii) 90%, (iii) 95%, (iv) 97%, (v) 99%, (vi) 99.5%, (vii) 99.7%, or (viii) 99.9%;
(h) residual solvents present in an amount less than about: (i) 8000 ppm, (ii) 6000 ppm, (iii) 4000 ppm, (iv) 2000 ppm, (v) 1000 ppm, (vi) 800 ppm, or 500 ppm; and
(i) as measured by dynamic vapor sorption (DVS), at 25° C. scanned over 0 to 95% relative humidity, a maximum mass change in water sorption isotherms of less than about (i) 2%, (ii) 1%, (iii) 0.5%, or (iv) 0.4%.

In various embodiments, provided herein is a crystalline form of (R)-(+)-amisulpride characterized by a powder x-ray diffraction pattern comprising peaks, in terms of 2-theta, at 7.0±0.2°, 9.7±0.2°, and 15.4±0.2°. In some embodiment, the crystalline form of (R)-(+)-amisulpride is further characterized by the powder x-ray diffraction pattern further comprising peaks, in terms of 2-theta, at 9.3±0.2°, and 19.4±0.2°. In some embodiment, the crystalline form of (R)-(+)-amisulpride is further characterized by the powder x-ray diffraction pattern further comprising peaks, in terms of 2-theta, at 14.9±0.2°, 16.9±0.2°, and 20.1±0.2°. In some embodiment, the crystalline form of (R)-(+)-amisulpride is further characterized by the powder x-ray diffraction pattern further comprising peaks, in terms of 2-theta, at 19.0±0.2°, 21.0±0.2°, and 23.2±0.2°.

In various embodiments, provided herein is a crystalline form of (S)-(−)-amisulpride characterized by a powder x-ray diffraction pattern comprising peaks, in terms of 2-theta, at 7.0±0.2°, 9.7±0.2°, and 15.4±0.2°. In some embodiments, the crystalline form of (S)-(−)-amisulpride is further characterized by the powder x-ray diffraction pattern further comprising peaks, in terms of 2-theta, at 9.3±0.2°, and 19.4±0.2°. In some embodiments, the crystalline form of (S)-(−)-amisulpride is further characterized by the powder x-ray diffraction pattern further comprising peaks, in terms of 2-theta, at 14.9±0.2°, 16.9±0.2°, and 20.2±0.2°. In some embodiments, the crystalline form of (S)-(−)-amisulpride is further characterized by the powder x-ray diffraction pattern further comprising peaks, in terms of 2-theta, at 19.1±0.2°, 21.0±0.2°, and 23.2±0.2°.

The DSC thermograms of FIGS. 1A, 2A, 3A, and 11A were obtained using TA Instruments Q100 differential scanning calorimeter. Each sample was heated in a sealed pan under a 50 mL/min nitrogen purge at a heating rate of 10°

C./min, from a starting temperature of 25° C. up to a final temperature of 150° C. or 200° C.

The micrograph images of FIGS. 1C, 2C, and 3C were obtained using the Nikon Microphot polarizing light microscope. Samples were prepared in Isopar G/3% Lecithin, and imaged using cross-polarized light with a quarter wave plate.

Racemic amisulpride has been found to have a distinctly different structure from crystal Form A and Form A' of the single enantiomers. For example, the XRPD pattern of the crystalline racemic amisulpride of FIG. 1B, comprises a prominent peak, in terms of 2-theta, at about 6.7° that is notably absent in the XRPD patterns for either Form A of the (R)-amisulpride enantiomer (FIG. 2B) or Form A' of the (S)-amisulpride enantiomer (FIG. 3B), that is to the extent a signal is discernable at 6.7° it has a peak height that is less than 5%, and even less than 1%, of the highest peak in FIG. 2B or 3B.

Accordingly, in various embodiments, provided are crystalline enantiomeric amisulpride characterized at least in part by having an XRPD pattern comprising peaks, in terms of 2-theta, at 7.0±0.2°, 9.7±0.2°, and 19.4±0.2° and not having a peak, in terms of 2-theta, at 6.6±0.3° that has a height greater than about 5% of the highest of the peaks at 7.0±0.2°, 9.7±0.2°, and 19.4±0.2°.

In various embodiments, XRPD information and patterns are used to characterize Form A and Form A'. FIGS. 2B and 3B XRPD patterns for, respectively, (R)-amisulpride Form A and (S)-amisulpride Form A'. Tables 2-5 present further information and details on XRPD patterns obtained for Form A and Form A'.

The XRPD patterns of both (R)-amisulpride Form A (FIG. 2B) and (S)-amisulpride Form A' (FIG. 3B) show prominent peaks, in terms of 2-theta, at 7.0±0.2°, 9.7±0.2°, 15.4±0.2°, 19.4±0.2°, 20.1±0.2°, 21.0±0.2°, 23.2±0.2°, and 29.3±0.2°.

The XRPD patterns of FIGS. 1B, 2B, 3B, 5, 8, and 11B were performed using a Rigaku MiniFlex II Desktop X-Ray diffractometer using Cu radiation. The tube voltage and amperage were set to 30 kV and 15 mA, respectively. The scattering slit was fixed at 1.25° and the receiving slit was fixed at 0.3 mm. Diffracted radiation was detected by a NaI scintillation detector. A θ-2θ continuous scan at 1.0°/min with a step size of 0.02-0.05° from 3 to 45° 2θ was used. Data were collected and analyzed using Jade 8.5.4. Each sample was prepared for analysis by placing it in a low background, round, 0.1 mm indent sample holder. In FIGS. 1B, 2B, 3B, 5, 8, and 11B 2-Theta angles in degrees (x-axis) are plotted against peak intensity in terms of the count rate per second (y-axis).

Crystals of (R)-amisulpride Form A

For single crystal structure determination, a colorless needle having approximate dimensions of 0.25×0.04×0.02 mm³, was mounted on a polymer loop in random orientation. Preliminary examination and data collection were performed on a Rigaku SuperNova diffractometer, equipped with a copper anode microfocus sealed X-ray tube (Cu Kα λ=1.54184 Å) and a Dectris Pilatus3 R 200K hybrid pixel array detector. Cell constants and an orientation matrix for data collection were obtained from least-squares refinement using the setting angles of 16528 reflections in the range 3.5080°<θ<77.2950°. The data was collected to a maximum diffraction angle (2θ) of 155.296°, at a temperature of 100 K. A total of 35826 reflections were collected, of which 12849 were unique. Lorentz and polarization corrections were applied to the data. The linear absorption coefficient is 1.728 mm⁻¹ for Cu Kα radiation. An empirical absorption correction using CRYSALISPRO was applied (CrysAlisPro 1.171.38.41r (Rigaku Oxford Diffraction, 2015). Transmission coefficients ranged from 0.659 to 1.000. Intensities of equivalent reflections were averaged. The agreement factor for the averaging was 5.72% based on intensity.

A calculated XRPD pattern was generated for Cu radiation using MERCURY and the atomic coordinates, space group, and unit cell parameters from the single crystal structure (Macrae, C. F. et a., J. J. Appl. Cryst., 2006, 39, 453-457). It is to be understood that because the single crystal data are collected at low temperatures (100 K), peak shifts may be evident between the pattern calculated from low temperature data and room temperature experimental powder diffraction patterns, particularly at high diffraction angles. FIG. 16 shows the calculated XRPD pattern of Form A, which is consistent with the experimental XRPD pattern of Form A in FIG. 2B.

In various embodiments, the crystal system of (R)-amisulpride Form A crystals is triclinic and the space group is P1. Referring to FIG. 2C, by microscopy the solids consisted of birefringent spherulites of long needles. Further details of the crystal data and crystallographic data collection parameters are summarized in Table 2 and a listing of the peaks of the experimental XRPD of FIG. 2B are listed in Table 3. The calculated XRPD pattern of Form A is shown in FIG. 16.

In some embodiment, the crystalline form of (R)-(+)-amisulpride is characterized by single crystal x-ray diffraction having a P1 space group and cell formula units (Z) of 4. In some embodiments, crystalline form of (R)-(+)-amisulpride has unit cell parameters: a is about 12.3 Å, b is about 12.8 Å, c is about 14.1 Å, α is about 64.0°, β is about 73.4°, and γ is about 75.9°.

TABLE 2

(R)-amisulpride Form A Single Crystal Data and Data Collection Parameters

| | |
|---|---|
| Empirical formula | $C_{17}H_{27}N_3O_4S$ |
| Molecular weight (g mol⁻¹) | 369.47 |
| Temperature (K) | 100 |
| Wavelength (Å) | 1.54184 |
| Crystal system | triclinic |
| Space group | P1 |
| Unit cell parameters | |
| a = 12.3348(4) Å | α = 64.033(4)° |
| b = 12.8343(6) Å | β = 73.431(3)° |
| c = 14.1403(6) Å | γ = 75.881(3)° |
| Unit cell volume (Å³) | 1910.47(15) |
| Cell formula units, Z | 4 |
| Calculated density (g cm⁻³) | 1.285 |
| Absorption coefficient (mm⁻¹) | 1.728 |
| F(000) | 792 |
| Crystal size (mm³) | 0.25 × 0.04 × 0.02 |
| Reflections used for cell measurement | 16528 |
| θ range for cell measurement | 3.5080°-77.2950° |
| Total reflections collected | 35826 |
| Index ranges | −15 ≤ h ≤ 15; −16 ≤ k ≤ 16; −17 ≤ l ≤ 17 |
| θ range for data collection | $θ_{min}$ = 3.552°, $θ_{max}$ = 77.648° |
| Completeness to $θ_{max}$ | 97.6% |
| Completeness to $θ_{full}$ = 67.684° | 99.8% |
| Absorption correction | multi-scan |
| Transmission coefficient range | 0.659-1.000 |
| Refinement method | full matrix least-squares on $F^2$ |
| Independent reflections | 12849 [$R_{int}$ = 0.0572, $R_σ$ = 0.0533] |
| Reflections [I > 2σ(I)] | 11460 |
| Reflections/restraints/parameters | 12849/3/954 |
| Goodness-of-fit on $F^2$ | S = 1.02 |
| Final residuals [I > 2σ(I)] | R = 0.0607, $R_w$ = 0.1675 |
| Final residuals [all reflections] | R = 0.0658, $R_w$ = 0.1739 |
| Largest diff. peak and hole (e Å⁻³) | 0.640, −0.670 |
| Max/mean shift/standard uncertainty | 0.000/0.000 |

TABLE 2-continued (R)-amisulpride Form A Single Crystal Data and Data Collection Parameters

| Absolute structure determination | Flack parameter: 0.009(18) |
| --- | --- |
| | Hooft parameter: 0.007(12) |
| | Friedel coverage: 60.2% |

TABLE 3

(R)-amisulpride Form A XRPD (FIG. 2B) Peak List

| 2-Theta | Relative Height |
| --- | --- |
| 7.00 | 75 |
| 7.42 | 1.6 |
| 9.34 | 26.9 |
| 9.72 | 68.3 |
| 9.95 | 1.5 |
| 11.00 | 6.7 |
| 11.66 | 1.2 |
| 12.72 | 2.3 |
| 13.26 | 11.3 |
| 13.90 | 5.2 |
| 14.41 | 4.8 |
| 14.72 | 13.5 |
| 14.90 | 31 |
| 15.40 | 100 |
| 15.94 | 4 |
| 16.64 | 7.9 |
| 16.92 | 28 |
| 17.44 | 14.8 |
| 17.70 | 4 |
| 18.66 | 7.5 |
| 19.04 | 29.3 |
| 19.42 | 87 |
| 20.12 | 63.7 |
| 20.98 | 34.8 |
| 21.62 | 3.5 |
| 21.88 | 7.8 |
| 22.32 | 3.8 |
| 22.61 | 2.5 |
| 23.22 | 89.3 |
| 24.34 | 8.1 |
| 24.80 | 8.7 |
| 25.26 | 3 |
| 25.56 | 17 |
| 25.78 | 4.3 |
| 26.20 | 3.2 |
| 26.68 | 15.8 |
| 27.10 | 11.3 |
| 28.12 | 3.5 |
| 28.28 | 2.6 |
| 28.82 | 5.2 |
| 29.26 | 42.2 |
| 29.56 | 5.9 |
| 29.76 | 3.7 |
| 30.32 | 1.9 |
| 30.92 | 1.7 |
| 31.02 | 2.6 |
| 31.70 | 4.3 |
| 31.94 | 3.8 |
| 32.26 | 2.2 |
| 32.84 | 8.9 |
| 33.22 | 2.7 |
| 34.16 | 2.7 |
| 34.55 | 2.2 |
| 34.97 | 1.7 |
| 35.24 | 1.1 |
| 35.48 | 0.9 |
| 35.76 | 2.9 |
| 37.00 | 1.9 |
| 37.44 | 1.3 |
| 38.58 | 3.2 |
| 38.88 | 3.4 |
| 39.50 | 1.6 |
| 39.76 | 2.1 |
| 40.38 | 2.5 |
| 40.80 | 3.7 |
| 41.39 | 1.4 |
| 41.68 | 1.5 |
| 42.68 | 3.7 |
| 43.28 | 2.8 |
| 43.52 | 4.7 |

Crystals of (S)-amisulpride Form A'

For single crystal structure determination, a colorless needle having approximate dimensions of 0.20×0.04×0.02 mm$^3$, was mounted on a polymer loop in random orientation. Preliminary examination and data collection were performed on a Rigaku SuperNova diffractometer, equipped with a copper anode microfocus sealed X-ray tube (Cu Kα λ=1.54184 Å) and a Dectris Pilatus3 R 200K hybrid pixel array detector. Cell constants and an orientation matrix for data collection were obtained from least-squares refinement using the setting angles of 14943 reflections in the range 3.5170°<θ<77.9740°. The data was collected to a maximum diffraction angle (2θ) of 156.71°, at a temperature of 100 K. A total of 36278 reflections were collected, of which 12840 were unique. Lorentz and polarization corrections were applied to the data. The linear absorption coefficient is 1.728 mm$^{-1}$ for Cu Kα radiation. An empirical absorption correction using CRYSALISPRO was applied (CrysAlisPro 1.171.38.41r (Rigaku Oxford Diffraction, 2015). Transmission coefficients ranged from 0.791 to 1.000. Intensities of equivalent reflections were averaged. The agreement factor for the averaging was 5.83% based on intensity.

A calculated XRPD pattern was generated for Cu radiation using MERCURY and the atomic coordinates, space group, and unit cell parameters from the single crystal structure (Macrae, C. F. et al., J. J. Appl. Cryst., 2006, 39, 453-457). It is to be understood that because the single crystal data are collected at low temperatures (100 K), peak shifts may be evident between the pattern calculated from low temperature data and room temperature experimental powder diffraction patterns, particularly at high diffraction angles. FIG. 17 shows the calculated XRPD pattern of Form A', which is consistent with the experimental XRPD pattern of Form A' in FIG. 3B.

1e;.5qIn various embodiments, the crystal system of (S)-amisulpride Form A' crystals is triclinic and the space group is P1. Referring to FIG. 3C, by microscopy the solids consisted of birefringent spherulites of long needles. Further details of the crystal data and crystallographic data collection parameters are summarized in Table 4 and a listing of the peaks of the experimental XRPD of FIG. 3B are listed in Table 5. The calculated XRPD pattern of Form A' is shown in FIG. 17.

In some embodiments, the crystalline form of (S)-(−)-amisulpride is characterized by single crystal x-ray diffraction having a P1 space group and cell formula units (Z) of 4. In some embodiments, the crystalline form of (S)-(−)-amisulpride has unit cell parameters: a is about 12.4 Å, b is about 12.8 Å, c is about 14.1 Å, α is about 64.2°, β is about 73.6°, and γ is about 75.8°.

TABLE 4

(S)-amisulpride Form A' Single Crystal Data and Data Collection Parameters

| Empirical formula | $C_{17}H_{27}N_3O_4S$ |
| --- | --- |
| Formula weight (g mol$^{-1}$) | 369.47 |

TABLE 4-continued (S)-amisulpride Form A' Single Crystal Data and Data Collection Parameters

| | |
|---|---|
| Temperature (K) | 100 |
| Wavelength (Å) | 1.54184 |
| Crystal system | triclinic |
| Space group | P1 |
| Unit cell parameters | |
| a = 12.3795(4) Å | α = 64.246(3)° |
| b = 12.7526(4) Å | ß = 73.598(3)° |
| c = 14.1438(4) Å | γ = 75.797(3)° |
| Unit cell volume (Å$^3$) | 1909.71(11) |
| Cell formula units, Z | 4 |
| Calculated density (g cm$^{-3}$) | 1.285 |
| Absorption coefficient (mm$^{-1}$) | 1.728 |
| F(000) | 792 |
| Crystal size (mm$^3$) | 0.2 × 0.04 × 0.02 |
| Reflections used for cell measurement | 14943 |
| ϑ range for cell measurement | 3.5170°-77.9740° |
| Total reflections collected | 36278 |
| Index ranges | −15 ≤ h ≤ 14; −16 ≤ k ≤ 16; −17 ≤ l ≤ 17; |
| ϑ range for data collection | ϑ$_{min}$ = 3.542°, ϑ$_{max}$ = 78.355° |
| Completeness to θ$_{max}$ | 97.6% |
| Completeness to θ$_{full}$ = 67.684° | 99.9% |
| Absorption correction | multi-scan |
| Transmission coefficient range | 0.791-1.000 |
| Refinement method | full matrix least-squares on F$^2$ |
| Independent reflections | 12840 [R$_{int}$ = 0.0583, R$_\sigma$ = 0.0539] |
| Reflections [I > 2σ(I)] | 11066 |
| Reflections/restraints/parameters | 12840/3/956 |
| Goodness-of-fit on F$^2$ | S = 1.08 |
| Final residuals [I > 2σ(I)] | R = 0.0613, R$_w$ = 0.1732 |
| Final residuals [all reflections] | R = 0.0694, R$_w$ = 0.1817 |
| Largest diff. peak and hole (e Å$^{-3}$) | 0.470, −0.468 |
| Max/mean shift/standard uncertainty | 0.000/0.000 |
| Absolute structure determination | Flack parameter: 0.008(18) Hooft parameter: 0.019(12) Friedel coverage: 58.8% |

TABLE 5

(S)-amisulpride Form A' XRPD (FIG. 3B) Peak List

| 2-Theta | Relative Height |
|---|---|
| 7.02 | 100 |
| 9.34 | 28 |
| 9.74 | 62 |
| 11.05 | 5.6 |
| 13.28 | 15.2 |
| 13.94 | 7.8 |
| 14.92 | 20 |
| 15.42 | 66.2 |
| 16.90 | 23.9 |
| 17.44 | 8.9 |
| 18.68 | 7.4 |
| 19.08 | 34.2 |
| 19.44 | 74.4 |
| 20.16 | 70 |
| 21.00 | 41.2 |
| 21.90 | 12 |
| 22.36 | 3.1 |
| 23.20 | 72.1 |
| 24.34 | 5.7 |
| 24.87 | 7 |
| 25.60 | 16.9 |
| 25.84 | 6.2 |
| 26.17 | 2.3 |
| 26.70 | 14.8 |
| 27.12 | 12.1 |
| 28.12 | 5.2 |
| 29.28 | 40.4 |
| 30.36 | 2.2 |
| 31.84 | 3.8 |
| 32.30 | 2.4 |
| 32.84 | 9 |
| 33.26 | 3.7 |
| 34.17 | 2.5 |
| 34.64 | 2 |
| 35.10 | 1.8 |
| 35.84 | 2.8 |
| 36.14 | 1.6 |
| 37.00 | 1.6 |
| 37.48 | 2.1 |
| 38.60 | 4.8 |
| 38.94 | 5.2 |
| 39.52 | 1.6 |
| 39.75 | 2.1 |
| 40.38 | 4.1 |
| 40.76 | 4.2 |
| 41.48 | 1.8 |
| 42.76 | 3.6 |
| 43.50 | 5.7 |
| 44.12 | 1.1 |

In various embodiments, the present inventions provide a crystalline form of (R)-amisulpride characterized by an XRPD pattern comprising peaks, in terms of 2-theta, at two or more of 7.0±0.2°, 9.7±0.2°, and 19.4±0.2°, and a DSC thermogram having a peak at 101±3° C. In various preferred embodiments, the DSC thermogram has a single peak at 101±3° C.

In various embodiments, the present inventions provide a crystalline form of (R)-amisulpride characterized by an XRPD pattern comprising peaks, in terms of 2-theta, at two or more of 7.0±0.2°, 9.7±0.2°, and 19.4±0.2°, and a differential scanning calorimetry thermogram substantially in accord with FIG. 2A.

In various embodiments, the present inventions provide a crystalline form of (S)-amisulpride characterized by an XRPD pattern comprising peaks, in terms of 2-theta, at two or more of 7.0±0.2°, 9.7±0.2°, and 19.4±0.2°, and a DSC thermogram having a peak at 101±3° C. In various preferred embodiments, the DSC thermogram has a single peak at 101±3° C.

In various embodiments, the present inventions provide a crystalline form of (S)-amisulpride characterized by an XRPD pattern comprising peaks, in terms of 2-theta, at two or more of 7.0±0.2°, 9.7±0.2°, and 19.4±0.2°, and a differential scanning calorimetry thermogram substantially in accord with FIG. 3A.

In various embodiments, the present inventions provide a crystalline form of enantiomeric amisulpride that is the substantially non-hygroscopic. In various embodiments, the present inventions provide a crystalline (R)-amisulpride of Form A that has a maximum mass change of less than about 2%, less than about 1%, or less than about 0.5%, in water sorption isotherms as measured by dynamic vapor sorption (DVS), at 25° C. scanned over 0 to 95% relative humidity. In various embodiments, the present inventions provide a crystalline (S)-amisulpride of Form A' that has a maximum mass change of less than about 2%, less than about 1%, or less than about 0.5%, in water sorption isotherms as measured by dynamic vapor sorption (DVS), at 25° C. scanned over 0 to 95% relative humidity.

Tables 6A-6E present DVS water sorption for crystalline enantiomeric amisulpride of Form A and Form A'. Tables 6A-6C providing data on crystalline (S)-amisulpride of Form A' and Tables 6D and 6E providing data on crystalline (R)-amisulpride of Form A FIG. 3D shows a DVS water sorption isotherm for 19.077 mg of (S)-amisulpride crystal Form A' and Table 6A lists the data plotted in FIG. 3D; FIG. 3E shows a DVS water sorption isotherm for 24.2193 mg of (S)-amisulpride crystal Form A' and Table 6B lists the data plotted in FIG. 3E; and FIG. 3F shows a DVS water sorption isotherm for 27.6204 mg of (S)-amisulpride crystal Form A' and Table 6C lists the data plotted in FIG. 3F. As can be seen, crystalline (S)-amisulpride Form A' is substantially non-hygroscopic, exhibiting a maximum mass change of only 0.35%, and an average maximum mass change of only about 0.22%, and an average of about 0.16% based on the data of Tables 6B and 6C.

TABLE 6A (S)-amisulpride Form A' DVS Water Sorption Isotherm of FIG. 3D

| Relative Humidity % | Change Mass (wt %) | Elapse time (min) |
|---|---|---|
| 0 | 0.00 | 60.72 |
| 10 | 0.03 | 33.25 |
| 20 | 0.05 | 31.89 |
| 30 | 0.07 | 32.20 |
| 40 | 0.09 | 31.53 |
| 50 | 0.11 | 31.95 |
| 60 | 0.13 | 31.87 |
| 70 | 0.16 | 31.10 |
| 75 | 0.18 | 31.28 |
| 80 | 0.19 | 31.43 |
| 90 | 0.25 | 31.97 |
| 95 | 0.34 | 32.77 |
| 95 | 0.35 | 36.47 |
| 90 | 0.28 | 31.35 |
| 80 | 0.17 | 32.11 |
| 75 | 0.16 | 31.01 |
| 70 | 0.14 | 31.50 |
| 60 | 0.11 | 32.10 |
| 50 | 0.08 | 32.12 |
| 40 | 0.07 | 31.41 |
| 30 | 0.05 | 62.67 |
| 20 | 0.03 | 32.05 |
| 10 | 0.01 | 31.00 |
| 1 | −0.01 | 32.02 |

TABLE 6B (S)-amisulpride Form A' DVS Water Sorption Isotherm of FIG. 3E

| Relative Humidity % | Change Mass (wt %) | Elapse Time (min) |
|---|---|---|
| 1.33 | 0.000 | 60.4 |
| 5.15 | −0.010 | 243.7 |
| 9.91 | −0.006 | 260.3 |
| 14.99 | 0.000 | 270.3 |
| 19.74 | 0.006 | 278.3 |
| 24.92 | 0.013 | 287.8 |
| 29.82 | 0.019 | 296.8 |
| 34.80 | 0.026 | 305.8 |
| 39.84 | 0.033 | 314.8 |
| 45.02 | 0.040 | 325.8 |
| 49.78 | 0.047 | 334.8 |
| 54.90 | 0.055 | 345.8 |
| 59.94 | 0.062 | 356.8 |
| 65.00 | 0.071 | 365.8 |
| 69.95 | 0.081 | 376.8 |
| 74.60 | 0.089 | 385.8 |
| 79.61 | 0.098 | 394.8 |
| 84.52 | 0.109 | 403.8 |
| 89.49 | 0.123 | 412.8 |
| 94.51 | 0.142 | 421.8 |
| 90.18 | 0.129 | 430.8 |
| 85.43 | 0.117 | 439.8 |
| 80.44 | 0.105 | 448.8 |

TABLE 6B-continued (S)-amisulpride Form A' DVS Water Sorption Isotherm of FIG. 3E

| Relative Humidity % | Change Mass (wt %) | Elapse Time (min) |
|---|---|---|
| 75.19 | 0.096 | 457.9 |
| 70.05 | 0.088 | 468.9 |
| 65.14 | 0.081 | 479.9 |
| 60.08 | 0.075 | 490.9 |
| 55.12 | 0.067 | 501.9 |
| 50.10 | 0.060 | 512.9 |
| 45.04 | 0.053 | 523.9 |
| 39.92 | 0.045 | 533.9 |
| 34.95 | 0.038 | 543.9 |
| 30.09 | 0.031 | 551.4 |
| 24.95 | 0.024 | 558.9 |
| 20.10 | 0.017 | 566.9 |
| 15.08 | 0.010 | 574.9 |
| 10.06 | 0.003 | 582.9 |
| 5.09 | −0.004 | 590.9 |
| 9.94 | 0.000 | 598.9 |
| 14.90 | 0.004 | 606.9 |
| 19.88 | 0.009 | 614.9 |
| 24.83 | 0.014 | 623.9 |
| 29.84 | 0.019 | 632.9 |
| 34.87 | 0.024 | 641.9 |
| 39.94 | 0.028 | 650.9 |
| 44.92 | 0.034 | 659.9 |
| 49.88 | 0.040 | 668.9 |
| 54.96 | 0.046 | 679.9 |
| 59.95 | 0.053 | 688.9 |
| 64.92 | 0.060 | 699.9 |
| 69.90 | 0.067 | 710.9 |
| 74.67 | 0.074 | 719.9 |
| 79.52 | 0.081 | 728.9 |
| 84.80 | 0.090 | 737.9 |
| 89.52 | 0.103 | 746.9 |
| 94.81 | 0.122 | 756.0 |
| 90.24 | 0.109 | 765.0 |
| 85.39 | 0.096 | 774.0 |
| 80.43 | 0.084 | 783.0 |
| 75.43 | 0.073 | 792.0 |
| 70.16 | 0.062 | 803.0 |
| 65.13 | 0.053 | 814.0 |
| 60.19 | 0.044 | 823.0 |
| 55.14 | 0.035 | 834.0 |
| 50.07 | 0.026 | 845.0 |
| 45.07 | 0.018 | 856.1 |
| 39.90 | 0.011 | 865.6 |
| 34.94 | 0.005 | 875.6 |
| 30.10 | −0.001 | 884.1 |
| 24.90 | −0.007 | 891.6 |
| 20.12 | −0.012 | 899.6 |
| 15.12 | −0.017 | 907.6 |
| 10.08 | −0.023 | 915.6 |
| 5.06 | −0.028 | 923.6 |

TABLE 6C (S)-amisulpride Form A' DVS Water Sorption Isotherm of FIG. 3F

| Relative Humidity % | Change Mass (wt %) | Elapse Time (min) |
|---|---|---|
| 1.31 | 0.000 | 104.3 |
| 5.02 | 0.018 | 292.6 |
| 10.14 | 0.023 | 301.1 |
| 15.17 | 0.029 | 309.1 |
| 19.77 | 0.035 | 317.2 |
| 24.90 | 0.042 | 326.2 |
| 29.81 | 0.049 | 335.2 |
| 34.95 | 0.055 | 344.2 |
| 40.00 | 0.061 | 353.2 |
| 44.81 | 0.068 | 362.2 |
| 49.95 | 0.074 | 373.2 |
| 54.94 | 0.081 | 382.2 |
| 59.92 | 0.089 | 393.2 |

TABLE 6C-continued (S)-amisulpride Form A' DVS Water Sorption Isotherm of FIG. 3F

| Relative Humidity % | Change Mass (wt %) | Elapse Time (min) |
|---|---|---|
| 64.98 | 0.097 | 404.2 |
| 69.97 | 0.105 | 413.2 |
| 74.69 | 0.114 | 422.2 |
| 79.58 | 0.124 | 431.2 |
| 84.53 | 0.137 | 440.2 |
| 89.83 | 0.151 | 449.2 |
| 94.52 | 0.170 | 458.3 |
| 90.05 | 0.160 | 467.3 |
| 85.35 | 0.151 | 476.3 |
| 80.40 | 0.134 | 485.3 |
| 75.42 | 0.123 | 494.3 |
| 70.13 | 0.115 | 505.3 |
| 65.10 | 0.108 | 516.3 |
| 60.09 | 0.101 | 527.3 |
| 55.07 | 0.094 | 538.3 |
| 50.14 | 0.087 | 547.3 |
| 45.01 | 0.080 | 558.3 |
| 39.84 | 0.073 | 567.8 |
| 34.89 | 0.066 | 577.8 |
| 30.11 | 0.060 | 586.3 |
| 24.90 | 0.053 | 593.8 |
| 20.12 | 0.046 | 601.8 |
| 15.12 | 0.040 | 609.8 |
| 10.09 | 0.034 | 617.8 |
| 5.07 | 0.028 | 625.8 |
| 9.91 | 0.031 | 633.8 |
| 14.86 | 0.036 | 641.9 |
| 19.87 | 0.041 | 649.9 |
| 24.86 | 0.047 | 658.9 |
| 29.83 | 0.053 | 667.9 |
| 34.85 | 0.059 | 676.9 |
| 39.80 | 0.065 | 685.9 |
| 45.01 | 0.071 | 696.9 |
| 49.96 | 0.078 | 707.9 |
| 54.92 | 0.084 | 718.9 |
| 59.85 | 0.091 | 729.9 |
| 64.90 | 0.098 | 740.9 |
| 69.85 | 0.105 | 751.9 |
| 74.64 | 0.111 | 760.9 |
| 79.56 | 0.119 | 769.9 |
| 84.91 | 0.131 | 778.9 |
| 89.53 | 0.143 | 787.9 |
| 94.71 | 0.159 | 797.0 |
| 90.15 | 0.149 | 806.0 |
| 85.40 | 0.139 | 815.0 |
| 80.44 | 0.121 | 824.0 |
| 75.16 | 0.109 | 833.0 |
| 70.15 | 0.101 | 844.0 |
| 65.18 | 0.093 | 855.0 |
| 60.09 | 0.085 | 866.0 |
| 55.07 | 0.078 | 877.0 |
| 50.08 | 0.072 | 888.0 |
| 45.07 | 0.065 | 899.0 |
| 39.84 | 0.059 | 908.5 |
| 34.97 | 0.052 | 918.5 |
| 30.15 | 0.047 | 927.0 |
| 24.92 | 0.042 | 934.5 |
| 20.09 | 0.035 | 942.5 |
| 15.11 | 0.029 | 950.5 |
| 10.15 | 0.026 | 958.5 |
| 5.10 | 0.022 | 966.5 |

FIG. 2D shows a DVS water sorption isotherm for 30.1733 mg of (R)-amisulpride crystal Form A and Table 6D lists the data plotted in FIG. 2D; and FIG. 2E shows a DVS water sorption isotherm for 26.5614 mg of (R)-amisulpride crystal Form A and Table 6E lists the data plotted in FIG. 2E. As can be seen, crystalline (R)-amisulpride Form A is substantially non-hygroscopic, exhibiting a maximum mass change of only 0.183%, and an average maximum mass change of only about 0.17%.

TABLE 6D (R)-amisulpride Form A DVS Water Sorption Isotherm of FIG. 2D

| Relative Humidity % | Change Mass (wt %) | Elapse Time (min) |
|---|---|---|
| 1.28 | 0.000 | 173.0 |
| 5.19 | 0.004 | 181.6 |
| 10.07 | 0.010 | 189.1 |
| 14.91 | 0.017 | 196.6 |
| 19.83 | 0.024 | 204.6 |
| 24.98 | 0.031 | 213.7 |
| 29.88 | 0.039 | 222.7 |
| 34.97 | 0.046 | 231.7 |
| 39.80 | 0.054 | 240.7 |
| 44.82 | 0.061 | 249.7 |
| 49.98 | 0.068 | 258.7 |
| 55.01 | 0.076 | 269.7 |
| 59.95 | 0.084 | 278.7 |
| 64.92 | 0.091 | 289.7 |
| 69.88 | 0.099 | 300.7 |
| 74.64 | 0.108 | 309.7 |
| 79.56 | 0.119 | 318.7 |
| 84.52 | 0.134 | 327.8 |
| 89.51 | 0.152 | 336.8 |
| 94.80 | 0.183 | 347.8 |
| 90.09 | 0.168 | 356.8 |
| 85.47 | 0.155 | 365.8 |
| 80.45 | 0.124 | 374.8 |
| 75.39 | 0.109 | 383.8 |
| 70.09 | 0.099 | 394.8 |
| 65.16 | 0.090 | 405.8 |
| 60.08 | 0.081 | 416.8 |
| 55.07 | 0.073 | 427.8 |
| 50.07 | 0.065 | 438.8 |
| 45.17 | 0.058 | 447.9 |
| 39.88 | 0.050 | 457.4 |
| 34.93 | 0.043 | 467.4 |
| 30.13 | 0.036 | 475.9 |
| 24.89 | 0.029 | 483.4 |
| 20.10 | 0.023 | 491.4 |
| 15.10 | 0.017 | 499.4 |
| 10.08 | 0.010 | 507.4 |
| 5.03 | 0.004 | 515.4 |
| 9.87 | 0.008 | 523.4 |
| 14.89 | 0.014 | 531.4 |
| 19.90 | 0.020 | 539.4 |
| 24.87 | 0.027 | 548.4 |
| 29.89 | 0.034 | 557.4 |
| 34.83 | 0.042 | 566.4 |
| 39.99 | 0.049 | 577.4 |
| 44.93 | 0.056 | 586.4 |
| 49.96 | 0.063 | 597.5 |
| 54.98 | 0.070 | 606.5 |
| 59.95 | 0.078 | 617.5 |
| 64.91 | 0.086 | 628.5 |
| 69.98 | 0.094 | 639.5 |
| 74.63 | 0.103 | 648.5 |
| 79.66 | 0.113 | 657.5 |
| 84.45 | 0.128 | 666.5 |
| 89.63 | 0.147 | 675.5 |
| 94.89 | 0.175 | 684.5 |
| 90.20 | 0.164 | 693.5 |
| 85.43 | 0.152 | 702.5 |
| 80.45 | 0.123 | 711.5 |
| 75.48 | 0.109 | 720.5 |
| 70.18 | 0.098 | 731.5 |
| 65.11 | 0.090 | 742.5 |
| 60.16 | 0.082 | 753.5 |
| 55.14 | 0.074 | 764.5 |
| 50.04 | 0.067 | 775.5 |
| 45.05 | 0.060 | 786.5 |
| 39.95 | 0.053 | 796.5 |
| 34.94 | 0.046 | 806.5 |
| 30.15 | 0.040 | 815.0 |
| 24.93 | 0.033 | 822.5 |
| 20.13 | 0.028 | 830.5 |
| 15.15 | 0.021 | 838.6 |
| 10.10 | 0.014 | 846.6 |
| 5.05 | 0.008 | 854.6 |

TABLE 6E (R)-amisulpride Form A DVS Water Sorption Isotherm of FIG. 2E

| Relative Humidity % | Change Mass (wt %) | Elapse Time (min) |
|---|---|---|
| 1.32 | 0.000 | 170.4 |
| 4.91 | −0.005 | 352.8 |
| 10.10 | −0.001 | 363.3 |
| 15.14 | 0.006 | 375.8 |
| 19.69 | 0.012 | 383.8 |
| 24.95 | 0.018 | 392.9 |
| 29.81 | 0.024 | 401.9 |
| 34.97 | 0.032 | 412.9 |
| 39.81 | 0.038 | 421.9 |
| 44.97 | 0.044 | 432.9 |
| 49.81 | 0.051 | 441.9 |
| 54.81 | 0.059 | 450.9 |
| 59.91 | 0.066 | 461.9 |
| 64.88 | 0.074 | 472.9 |
| 69.81 | 0.082 | 483.9 |
| 74.59 | 0.090 | 492.9 |
| 79.63 | 0.100 | 501.9 |
| 84.55 | 0.112 | 510.9 |
| 89.85 | 0.127 | 519.9 |
| 94.52 | 0.149 | 528.9 |
| 90.10 | 0.137 | 537.9 |
| 85.39 | 0.126 | 546.9 |
| 80.52 | 0.105 | 555.9 |
| 75.44 | 0.092 | 564.9 |
| 70.16 | 0.083 | 575.9 |
| 65.19 | 0.075 | 586.9 |
| 60.10 | 0.067 | 598.0 |
| 55.04 | 0.059 | 609.0 |
| 50.10 | 0.052 | 618.0 |
| 45.03 | 0.046 | 627.0 |
| 39.88 | 0.038 | 636.5 |
| 34.91 | 0.033 | 646.5 |
| 30.14 | 0.026 | 655.0 |
| 24.91 | 0.020 | 662.6 |
| 20.10 | 0.014 | 670.6 |
| 15.11 | 0.007 | 678.6 |
| 10.17 | 0.002 | 686.6 |
| 5.10 | −0.004 | 694.6 |
| 9.91 | −0.001 | 702.6 |
| 14.90 | 0.005 | 710.6 |
| 19.91 | 0.012 | 718.6 |
| 24.87 | 0.017 | 727.6 |
| 29.85 | 0.024 | 736.6 |
| 34.86 | 0.029 | 745.6 |
| 39.96 | 0.036 | 756.6 |
| 44.93 | 0.043 | 767.6 |
| 49.83 | 0.049 | 776.6 |
| 54.99 | 0.057 | 787.6 |
| 59.98 | 0.064 | 798.7 |
| 64.95 | 0.072 | 807.7 |
| 69.88 | 0.079 | 818.7 |
| 74.62 | 0.086 | 827.7 |
| 79.72 | 0.097 | 836.7 |
| 84.65 | 0.113 | 845.7 |
| 89.55 | 0.131 | 854.7 |
| 94.65 | 0.156 | 865.7 |
| 90.11 | 0.143 | 874.7 |
| 85.33 | 0.131 | 883.7 |
| 80.48 | 0.109 | 892.7 |
| 75.08 | 0.098 | 901.7 |
| 70.14 | 0.087 | 912.7 |
| 65.08 | 0.078 | 923.7 |
| 60.15 | 0.069 | 934.7 |
| 55.04 | 0.062 | 945.7 |
| 50.05 | 0.055 | 954.7 |
| 45.04 | 0.049 | 965.8 |
| 39.84 | 0.043 | 975.3 |
| 34.96 | 0.038 | 985.3 |
| 30.14 | 0.032 | 993.8 |
| 24.91 | 0.027 | 1001.3 |
| 20.09 | 0.021 | 1009.3 |
| 15.12 | 0.016 | 1017.3 |
| 10.10 | 0.011 | 1025.3 |
| 5.05 | 0.006 | 1033.3 |

In various embodiments, the present inventions provide a crystalline form of (R)-amisulpride ethyl acetate solvate characterized by an XRPD pattern comprising peaks, in terms of 2-theta, at 6.4±0.2°, 8.3±0.2°, and 20.8±0.2°. In various embodiments, the present inventions provide a crystalline form of (R)-amisulpride ethyl acetate solvate characterized by three or more peaks in its XRPD pattern selected from those at 6.4±0.2°, 8.3±0.2°, 14.1±0.2°, 20.8±0.2°, and 25.3±0.2°. In various embodiments, the present inventions provide a crystalline form of (R)-amisulpride ethyl acetate solvate characterized by an XRPD pattern substantially in accord with FIG. 5.

In various embodiments, the present inventions provide a crystalline form of (R)-amisulpride ethyl acetate solvate characterized by the following properties, an XRPD pattern comprising peaks, in terms of 2-theta, at 6.4±0.2°, 8.3±0.2°, and 20.8±0.2°, a chiral purity of greater than about 99%, and a chemical purity greater than about 99%.

In various embodiments, the present inventions provide a crystalline form of (R)-amisulpride ethyl acetate solvate characterized by the following properties, an XRPD pattern comprising peaks, in terms of 2-theta, at 6.4±0.2°, 8.3±0.2°, and 20.8±0.2° and one or more of the following:
(a) the powder x-ray diffraction pattern further comprising a peak, in terms of 2-theta, at 14.1±0.2°;
(b) the powder x-ray diffraction pattern further comprising peaks, in terms of 2-theta, at 25.3±0.2°;
(c) a chiral purity of greater than about: (i) 90%, (ii) 95%, (iii) 97%, (iv) 99%, (v) 99.5%, (vi) 99.7%, or (vii) 99.9%; and
(d) a chemical purity of greater than about: (i) 80%, (ii) 90%, (iii) 95%, (iv) 97%, (v) 99%, (vi) 99.5%, (vii) 99.7%, or (viii) 99.9%.

In various embodiments, the present inventions provide a crystalline form of (S)-amisulpride ethyl acetate solvate characterized by an XRPD pattern comprising peaks, in terms of 2-theta, at 6.4±0.2°, 8.3±0.2°, and 20.8±0.2°. In various embodiments, the present inventions provide a crystalline form of (S)-amisulpride ethyl acetate solvate characterized by three or more peaks in its XRPD pattern selected from those at 6.4±0.2°, 8.3±0.2°, 8.9±0.2°, 14.1±0.2°, 20.8±0.2°, and 25.3±0.2°. In various embodiments, the present inventions provide a crystalline form of (S)-amisulpride ethyl acetate solvate characterized by an XRPD pattern substantially in accord with FIG. 8.

In various embodiments, the present inventions provide a crystalline form of (S)-amisulpride ethyl acetate solvate characterized by the following properties, an XRPD pattern comprising peaks, in terms of 2-theta, at 6.4±0.2°, 8.3±0.2°, and 20.8±0.2°, a chiral purity of greater than about 99%, and a chemical purity greater than about 99%.

In various embodiments, the present inventions provide a crystalline form of (R)-amisulpride ethyl acetate solvate characterized by the following properties, an XRPD pattern comprising peaks, in terms of 2-theta, at 6.4±0.2°, 8.3±0.2°, and 20.8±0.2° and one or more of the following:
(a) the powder x-ray diffraction pattern further comprising a peak, in terms of 2-theta, at 14.1±0.2°;
(b) the powder x-ray diffraction pattern further comprising peaks, in terms of 2-theta, at 25.3±0.2°;
(c) a chiral purity of greater than about: (i) 90%, (ii) 95%, (iii) 97%, (iv) 99%, (v) 99.5%, (vi) 99.7%, or (vii) 99.9%; and
(d) a chemical purity of greater than about: (i) 80%, (ii) 90%, (iii) 95%, (iv) 97%, (v) 99%, (vi) 99.5%, (vii) 99.7%, or (viii) 99.9%.

In various embodiments, XRPD information and patterns are used to characterize Form B and Form B'. FIGS. 5 and 8 present XRPD patterns for, respectively, (R)-amisulpride ethyl acetate solvate Form B, and (S)-amisulpride ethyl acetate solvate Form B'. Tables 7-8 present further information and details on XRPD patterns obtained for Forms B and B'.

The XRPD patterns of both (R)-amisulpride ethyl acetate solvate Form B (FIG. 5) and (S)-amisulpride ethyl acetate solvate Form B' (FIG. 8) show prominent peaks, in terms of 2-theta, at 6.4±0.2°, 8.3±0.2°, 14.1±0.2°, 14.9±0.2°, 20.8±0.2°, and 25.3±0.2°.

The XRPD patterns of FIGS. 5 and 8 were obtained with a Rigaku MiniFlex II Desktop X-Ray diffractometer using Cu radiation (Cu Kα λ=1.54184 Å). The tube voltage and amperage were set to 30 kV and 15 mA, respectively. The scattering slit was fixed at 1.25° and the receiving slit was fixed at 0.3 mm. Diffracted radiation was detected by a NaI scintillation detector. A θ-2θ continuous scan at 1.0°/min with a step size of 0.02-0.05° from 3 to 45° 2θ was used. Data were collected and analyzed using Jade 8.5.4. Each sample was prepared for analysis by placing it in a low background, round, 0.1 mm indent sample holder. In FIGS. 5 and 8, 2-Theta angles in degrees (x-axis) are plotted against peak intensity in terms of the count rate per second (y-axis).

Crystals of (R)-amisulpride ethyl acetate solvate Form B
FIG. 5 presents an XRPD for (R)-amisulpride ethyl acetate solvate of Form B, and a listing of the peaks of the XRPD of FIG. 5 are listed in Table 7.

TABLE 7

| (R)-amisulpride ethyl acetate solvate Form B Crystal XRPD (FIG. 5) Peak List | |
|---|---|
| 2-Theta | Relative Height |
| 6.48 | 100 |
| 6.69 | 2.7 |
| 6.96 | 3.2 |
| 8.36 | 17.7 |
| 8.96 | 5.7 |
| 11.72 | 0.9 |
| 12.92 | 2.7 |
| 13.30 | 1 |
| 14.08 | 16.6 |
| 14.84 | 14.8 |
| 16.80 | 9.1 |
| 16.98 | 11.7 |
| 17.3 | 5.7 |
| 18.17 | 2.1 |
| 19.41 | 5.9 |
| 20.04 | 9.9 |
| 20.40 | 15.7 |
| 20.76 | 51.3 |
| 21.10 | 11.8 |
| 21.58 | 2.2 |
| 22.06 | 2.4 |
| 23.24 | 3.7 |
| 23.68 | 3.3 |
| 23.86 | 4.3 |
| 24.23 | 3 |
| 25.32 | 56.7 |
| 25.52 | 21.7 |
| 25.94 | 5.8 |
| 26.98 | 10.8 |
| 28.13 | 0.7 |
| 29.64 | 0.6 |
| 29.92 | 1.8 |
| 30.20 | 4.3 |
| 31.83 | 1.1 |
| 32.32 | 1.6 |
| 32.88 | 0.8 |

TABLE 7-continued

| (R)-amisulpride ethyl acetate solvate Form B Crystal XRPD (FIG. 5) Peak List | |
|---|---|
| 2-Theta | Relative Height |
| 33.68 | 1.9 |
| 34.31 | 2.9 |
| 35.44 | 0.9 |
| 35.68 | 0.8 |
| 36.60 | 1 |
| 38.60 | 1.6 |
| 38.96 | 2.1 |
| 39.28 | 2.3 |
| 41.09 | 1.5 |
| 42.22 | 0.8 |
| 43.14 | 1.8 |
| 44.16 | 1.1 |
| 44.32 | 1.1 |

Crystals of (S)-amisulpride ethyl acetate solvate Form B'
FIG. 8 presents an XRPD for (S)-amisulpride ethyl acetate solvate of Form B', a listing of the peaks of the XRPD of FIG. 8 are listed in Table 8.

TABLE 8

| (S)-amisulpride ethyl acetate solvate Form B' Crystal XRPD (FIG. 8) Peak List | |
|---|---|
| 2-Theta | Relative Height |
| 6.50 | 41.7 |
| 8.36 | 36.8 |
| 8.70 | 2.8 |
| 8.98 | 14.9 |
| 10.59 | 1.8 |
| 11.87 | 0.6 |
| 12.92 | 1.7 |
| 13.76 | 5.1 |
| 14.06 | 11.4 |
| 14.86 | 11.8 |
| 15.10 | 2.5 |
| 15.40 | 4.1 |
| 16.48 | 3.3 |
| 16.8 | 7.4 |
| 17.00 | 18.7 |
| 17.38 | 2.4 |
| 18.22 | 2.4 |
| 19.36 | 4.8 |
| 19.77 | 0.8 |
| 20.01 | 3.3 |
| 20.80 | 32.4 |
| 21.12 | 12 |
| 21.38 | 2.7 |
| 23.30 | 4.8 |
| 23.68 | 2.4 |
| 23.88 | 1.7 |
| 24.22 | 2.6 |
| 25.34 | 100 |
| 25.60 | 3.3 |
| 25.96 | 8.7 |
| 26.98 | 12 |
| 27.34 | 1.3 |
| 28.40 | 0.7 |
| 28.81 | 0.6 |
| 29.04 | 0.5 |
| 29.98 | 3.1 |
| 30.24 | 5.4 |
| 30.68 | 1.2 |
| 31.89 | 1.2 |
| 32.28 | 1.9 |
| 33.37 | 0.8 |
| 33.70 | 2.7 |
| 34.30 | 1.9 |
| 35.44 | 0.7 |
| 36.20 | 1.1 |
| 36.71 | 1 |
| 37.88 | 0.6 |

TABLE 8-continued (S)-amisulpride ethyl acetate solvate
Form B' Crystal XRPD (FIG. 8) Peak List

| 2-Theta | Relative Height |
|---|---|
| 38.13 | 1.1 |
| 38.60 | 1.5 |
| 39.10 | 0.9 |
| 39.30 | 0.8 |
| 39.60 | 0.8 |
| 41.11 | 1 |
| 43.14 | 1 |
| 43.66 | 0.7 |
| 44.40 | 0.6 |

In various embodiments, the present inventions provide a crystalline form of (R)-amisulpride ethyl acetate solvate characterized by an XRPD pattern comprising peaks, in terms of 2-theta, at two or more of 6.4±0.2°, 8.3±0.2°, and 20.8±0.2°.

In various embodiments, the present inventions provide a crystalline form of (S)-amisulpride ethyl acetate solvate characterized by an XRPD pattern comprising peaks, in terms of 2-theta, at two or more of 6.4±0.2°, 8.3±0.2°, and 20.8±0.2°.

In various embodiments, the present inventions provide a crystalline form of (R)-amisulpride 2-butanone solvate characterized by an XRPD pattern comprising peaks, in terms of 2-theta, at 6.6±0.2°, 8.5±0.2°, and 15.4±0.2°. In various embodiments, the present inventions provide a crystalline form of (R)-amisulpride 2-butanone solvate characterized by three or more peaks in its XRPD pattern selected from those at 6.6±0.2°, 8.5±0.2°, 9.1±0.2°, 13.9±0.2°, 15.4±0.2°, 16.6±0.2°, 17.1±0.2°, 21.0±0.2°, and 25.4±0.2°. In various embodiments, the present inventions provide a crystalline form of (R)-amisulpride 2-butanone solvate characterized by an XRPD pattern substantially in accord with FIG. 18.

In various embodiments, the present inventions provide a crystalline form of (R)-amisulpride 2-butanone solvate characterized by the following properties, an XRPD pattern comprising peaks, in terms of 2-theta, at 6.6±0.2°, 8.5±0.2°, and 15.4±0.2°, and a chiral purity of greater than about 99%, and a chemical purity greater than about 99%.

In various embodiments, the present inventions provide a crystalline form of (R)-amisulpride 2-butanone solvate characterized by the following properties, an XRPD pattern comprising peaks, in terms of 2-theta, at 6.6±0.2°, 8.5±0.2°, and 15.4±0.2°, and one or more of the following:
  (e) the powder x-ray diffraction pattern further comprising a peak, in terms of 2-theta, at 13.9±0.2°;
  (f) the powder x-ray diffraction pattern further comprising peaks, in terms of 2-theta, at 15.4±0.2°;
  (g) a chiral purity of greater than about: (i) 90%, (ii) 95%, (iii) 97%, (iv) 99%, (v) 99.5%, (vi) 99.7%, or (vii) 99.9%; and
  (h) a chemical purity of greater than about: (i) 80%, (ii) 90%, (iii) 95%, (iv) 97%, (v) 99%, (vi) 99.5%, (vii) 99.7%, or (viii) 99.9%.

The XRPD pattern of FIG. 18 was obtained with a Rigaku MiniFlex II Desktop X-Ray diffractometer using Cu radiation (Cu Kα λ=1.54184 Å). The tube voltage and amperage were set to 30 kV and 15 mA, respectively. The scattering slit was fixed at 1.25° and the receiving slit was fixed at 0.3 mm. Diffracted radiation was detected by a NaI scintillation detector. A θ-2θ continuous scan at 1.0°/min with a step size of 0.02-0.05° from 3 to 45° 2θ was used. Data were collected and analyzed using Jade 8.5.4. Each sample was prepared for analysis by placing it in a low background, round, 0.1 mm indent sample holder. In FIG. 18 2-Theta angles in degrees (x-axis) are plotted against peak intensity in terms of the count rate per second (y-axis).

FIG. 18 presents an XRPD for (R)-amisulpride 2-butanone solvate, and a listing of the peaks of the XRPD of FIG. 18 are listed in Table 14.

TABLE 14

(R)-amisulpride 2-butanone solvate
crystal XRPD (FIG. 18) peak list

| 2-Theta (degree) | Relative Height (%) |
|---|---|
| 6.56 | 50.5 |
| 8.48 | 42.9 |
| 9.06 | 27.2 |
| 11.91 | 2.7 |
| 13.86 | 26.9 |
| 15.36 | 73.8 |
| 16.62 | 38.1 |
| 17.14 | 31.2 |
| 18.32 | 3.5 |
| 19.46 | 16.2 |
| 20.06 | 34 |
| 20.98 | 86 |
| 22.8 | 4 |
| 23.5 | 5.2 |
| 23.94 | 16 |
| 25.44 | 100 |
| 26.08 | 13.3 |
| 27.12 | 10 |
| 28.82 | 2.7 |
| 29.3 | 2.7 |
| 30.1 | 8 |
| 30.52 | 5 |
| 30.85 | 3.4 |
| 32.32 | 5.2 |
| 33.55 | 2.1 |
| 33.85 | 5.4 |
| 34.42 | 4.1 |
| 35.04 | 2.8 |
| 37.76 | 3.1 |
| 38.68 | 4.6 |
| 39.39 | 3.7 |
| 40.14 | 1.4 |
| 42.78 | 3.1 |

In various embodiments, (R)-amisulpride 2-butanone solvate can be converted to crystalline (R)-amisulpride Form A, e.g., treat the solvate in high vacuum at 35° overnight.

In various embodiments, the present inventions provide a crystalline form of (R)-amisulpride L-tartrate characterized by an XRPD pattern comprising peaks, in terms of 2-theta, at 9.1±0.2°, 10.4±0.2°, and 12.8±0.2°. In various embodiments, the present inventions provide a crystalline form of (R)-amisulpride L-tartrate characterized by three or more peaks in its XRPD pattern selected from those at 9.1±0.2°, 10.4±0.2°, 12.4±0.2°, 12.8±0.2°, 15.3±0.2°, 15.9±0.2°, 17.3±0.2°, 18.3±0.2°, 19.5±0.2°, 21.5±0.2°, 22.1±0.2°, 22.6±0.2°, 23.1±0.2°, 24.4±0.2°, and 24.9±0.2°. In various embodiments, the present inventions provide a crystalline form of (R)-amisulpride L-tartrate characterized by an XRPD pattern substantially in accord with FIG. 22.

In various embodiments, the present inventions provide a crystalline form of (R)-amisulpride L-tartrate characterized by a DSC substantially in accord with FIG. 23. In various embodiments, the present inventions provide a crystalline form of (R)-amisulpride L-tartrate characterized by an endothermic event at about 78° C.

In various embodiments, the present inventions provide a crystalline form of (R)-amisulpride L-tartrate characterized by the following properties, an XRPD pattern comprising peaks, in terms of 2-theta, at 9.1±0.2°, 10.4±0.2°, and 12.8±0.2°, and a chiral purity of greater than about 99%, and a chemical purity greater than about 99%.

In various embodiments, the present inventions provide a crystalline form of (R)-amisulpride L-tartrate characterized by the following properties, an XRPD pattern comprising peaks, in terms of 2-theta, at 9.1±0.2°, 10.4±0.2°, and 12.8±0.2°, and one or more of the following:
  (i) the powder x-ray diffraction pattern further comprising a peak, in terms of 2-theta, at 15.9±0.2°;
  (j) the powder x-ray diffraction pattern further comprising peaks, in terms of 2-theta, at 19.5±0.2°;
  (k) a chiral purity of greater than about: (i) 90%, (ii) 95%, (iii) 97%, (iv) 99%, (v) 99.5%, (vi) 99.7%, or (vii) 99.9%; and
  (l) a chemical purity of greater than about: (i) 80%, (ii) 90%, (iii) 95%, (iv) 97%, (v) 99%, (vi) 99.5%, (vii) 99.7%, or (viii) 99.9%.

In various embodiments, the present inventions provide a crystalline form of (S)-amisulpride D-tartrate characterized by an XRPD pattern comprising peaks, in terms of 2-theta, at 9.1±0.2°, 10.4±0.2°, and 12.8±0.2°. In various embodiments, the present inventions provide a crystalline form of (S)-amisulpride D-tartrate characterized by three or more peaks in its XRPD pattern selected from those at 9.1±0.2°, 10.4±0.2°, 12.3±0.2°, 12.8±0.2°, 15.3±0.2°, 15.9±0.2°, 17.2±0.2°, 18.3±0.2°, 19.5±0.2°, 21.4±0.2°, 22.1±0.2°, 22.5±0.2°, 23.1±0.2°, 24.4±0.2°, and 24.8±0.2°. In various embodiments, the present inventions provide a crystalline form of (S)-amisulpride D-tartrate characterized by an XRPD pattern substantially in accord with FIG. 20.

In various embodiments, the present inventions provide a crystalline form of (S)-amisulpride D-tartrate characterized by a DSC substantially in accord with FIG. 21. In various embodiments, the present inventions provide a crystalline form of (S)-amisulpride D-tartrate characterized by an endothermic event at about 82° C.

In various embodiments, the present inventions provide a crystalline form of (R)-amisulpride L-tartrate characterized by the following properties, an XRPD pattern comprising peaks, in terms of 2-theta, at 9.1±0.2°, 10.4±0.2°, and 12.8±0.2°, and a chiral purity of greater than about 99%, and a chemical purity greater than about 99%.

In various embodiments, the present inventions provide a crystalline form of (R)-amisulpride L-tartrate characterized by the following properties, an XRPD pattern comprising peaks, in terms of 2-theta, at 9.1±0.2°, 10.4±0.2°, and 12.8±0.2°, and one or more of the following:
  (m) the powder x-ray diffraction pattern further comprising a peak, in terms of 2-theta, at 15.9±0.2°;
  (n) the powder x-ray diffraction pattern further comprising peaks, in terms of 2-theta, at 19.5±0.2°;
  (o) a chiral purity of greater than about: (i) 90%, (ii) 95%, (iii) 97%, (iv) 99%, (v) 99.5%, (vi) 99.7%, or (vii) 99.9%; and
  (p) a chemical purity of greater than about: (i) 80%, (ii) 90%, (iii) 95%, (iv) 97%, (v) 99%, (vi) 99.5%, (vii) 99.7%, or (viii) 99.9%.

In various aspects, provided are methods of making enantiomeric amisulpride crystalline polymorphs of Form A and Form A', and methods of making solvates of enantiomeric amisulpride crystalline polymorphs of Form B and Form B'. Various embodiments of the methods described below produce novel crystal forms and various embodiments of these methods are in themselves novel.

In addition, in various aspects, provided are novel methods of resolving enantiomeric amisulpride from non-enantiomerically pure mixtures of amisulpride, e.g. substantially racemic amisulpride. In some embodiments, a method of resolving a non-enantiomerically pure mixture of amisulpride, comprises the steps of: (a) providing a starting material comprising a non-enantiomerically pure mixture of amisulpride; (b) forming a solution of the starting material in a solvent comprising an enantiomeric tartaric acid; (c) isolating from the mixture of step (b) a tartaric acid salt of one enantiomer of the starting material; (d) freeing the one enantiomer of the starting material from the tartaric; and (e) isolating from the mixture of step (d) the free base of the one enantiomer of the starting material. In some embodiments, the tartaric acid is one or more of tartaric acid, dibenzoyl tartaric acid, and di-p-toluoyl tartaric acid. In some embodiments, the tartaric acid is a derivative of tartaric acid. In some embodiments, the one enantiomer is (S)-amisulpride and the tartaric acid is levorotatory. In some embodiments, the one enantiomer is (R)-amisulpride and the tartaric acid is dextrorotatory. In some embodiments, the solvent is one or more of acetonitrile, methanol and water. In some embodiments, the step of freeing the one enantiomer of the starting material from the tartaric acid comprises: (a) solvating of the tartaric acid salt of one enantiomer of the starting material in a second solvent, wherein the second solvent is a carbonyl containing compound having 5 carbons or less; and (b) freeing the solvated starting material from the second solvent by adding a third solvent other than water to form a mixture with a starting material solubility of less than about 20 wt/wt %. In some embodiments, the step of isolating from the mixture of step (d) the free base of the one enantiomer of the starting material comprises: isolating from the mixture comprising the free base of the one enantiomer of the starting material a crystalline form of the one enantiomer of the starting material having a powder x-ray crystal pattern comprising peaks, in terms of 2-theta, at least at 7.0±0.2°, 9.7±0.2°, and 19.4±0.2°.

As used in the context of the methods of the present inventions, the term "Form A" or "Form A'" refers to a method that produces a crystalline form of enantiomeric amisulpride having a powder x-ray crystal pattern comprising peaks, in terms of 2-theta, at least at 7.0±0.2°, 9.7±0.2°, and 19.4±0.2°; and preferably with additional peaks, in terms of 2-theta, at two or more of: 15.4±0.2°, 20.1±0.2°, 21.0±0.2°, 23.2±0.2°, and 29.3±0.2°; and in various preferred embodiments an powder x-ray crystal pattern substantially in accord with FIG. 2B, in the case of (R)-amisulpride, and FIG. 3B in the case of (S)-amisulpride.

As used in the context of the methods of the present inventions, the term "Form B" or "Form B'" refers to a method that produces a ethyl acetate solvate crystalline form of enantiomeric amisulpride having a powder x-ray crystal pattern comprising peaks, in terms of 2-theta, at least at 6.4±0.2°, 8.3±0.2°, and 20.8±0.2°; and preferably with additional peaks, in terms of 2-theta, at one or more of: 14.1±0.2°, 14.9±0.2°, 20.8±0.2°, and 25.3±0.2°; and in various preferred embodiments an powder x-ray crystal pattern substantially in accord with FIG. 5, in the case of (R)-amisulpride, and FIG. 8 in the case of (S)-amisulpride.

Producing high yields of a specific crystalline form, and thus high purity of that crystalline form, is often limited by the formation of amorphous products and other crystalline forms that may, for example, be kinetically favored. It has been discovered through experimentation that making crystalline enantiomeric amisulpride is complicated by the fact that traditional methods result in non-crystalline (amorphous) enantiomeric amisulpride, including methods that produce crystalline racemic amisulpride.

It has been discovered that formation of certain enantiomeric amisulpride solvates as intermediates followed by conversion to the free base allows for isolation of a crystalline form of enantiomeric amisulpride (having a powder x-ray crystal pattern comprising peaks, in terms of 2-theta, at least at 7.0±0.2°, 9.7±0.2°, and 19.4±0.2° that is greater than 90% by weight, greater than 95% by weight, greater than 97% by weight, greater than 99% by weight; or greater than 99.5% by weight of the enantiomeric amisulpride starting material.

In various embodiments, methods of making crystalline enantiomeric amisulpride, characterized by an XRPD pattern comprising peaks, in terms of 2-theta, at least at 7.0±0.2°, 9.7±0.2°, and 19.4±0.2°, comprise: (a) providing either (R)-amisulpride or (S)-amisulpride as a starting material, where (R)-amisulpride is provided as the starting material when crystalline (R)-amisulpride is the desired product and (S)-amisulpride is provided as the starting material when crystalline (S)-amisulpride is the desired product; (b) solvating the starting material with a first solvent where the first solvent is a carbonyl containing compound having 5 carbons or less; (c) freeing the solvated starting material from the first solvent by adding a second solvent other than water to form a mixture with a starting material solubility of less than about 20 wt/wt %; and then (d) isolating the crystalline form of the starting material having a powder x-ray crystal pattern comprising peaks, in terms of 2-theta, at least at 7.0±0.2°, 9.7±0.2°, and 19.4±0.2°.

In various embodiments, the methods start with the provision of either (R)-amisulpride or (S)-amisulpride to make, respectively, crystalline (R)-amisulpride or crystalline (S)-amisulpride. It is to be understood that there are many acceptable ways to separate the enantiomers of amisulpride to provide an enantiomeric starting material for the methods of the present inventions. For example, Example 1 herein provides one way by which enantiomeric amisulpride starting material can be obtained, and Examples 2 and 3 provide methods for further purification of the amisulpride enantiomers. In addition, for example, Examples 5 and 8 provide an in situ method for making enantiomerically enriched amisulpride starting material.

In addition, in various aspects, the present inventions include novel methods for resolution of enantiomeric amisulprides from a mixture of enantiomers, such as for example, a racemic mixture. In various embodiments, these novel resolution methods provide enantiomeric amisulpride having a chiral purity of greater than about 90%, greater than about 91%, greater than about 92%, greater than about 93%, greater than about 94%, greater than about 95%, greater than about 96%, greater than about 97%, greater than about 98%, greater than about 99%, or greater than about 99.2%. Examples 10 and 11 provide non-limiting examples of these novel methods for, respectively, resolution of (R)-amisulpride and (S)-amisulpride from racemic amisulpride.

It is to be understood that the enantiomeric amisulpride starting materials of the present invention are not necessarily crystalline, and may be amorphous or a mixture of amorphous and crystalline form. In addition to separation of enantiomers from a racemic starting material, suitable enantiomeric starting materials for the methods of the present inventions can also be directly synthesized.

It is to be understood that the ultimate chiral purity of the crystalline form of the starting material is limited by the chiral purity of the starting material. However, in various embodiments, it has been found that the methods produce the crystalline form of the starting material that has a chiral purity that is no less than the chiral purity of the starting material. Thus, in various embodiments, the present methods of making crystalline enantiomeric amisulpride (characterized by an XRPD pattern comprising peaks, in terms of 2-theta, at least at 7.0±0.2°, 9.7±0.2°, and 19.4±0.2°) provide said crystalline enantiomeric amisulpride having one or more of: a greater than about 90% chiral purity where the starting material has a greater than about 90% chiral purity; a greater than about 95% chiral purity where the starting material has a greater than about 95% chiral purity; a greater than about 97% chiral purity where the starting material has a greater than about 97% chiral purity; a greater than about 99% chiral purity where the starting material has a greater than about 99% chiral purity.

It has been unexpectedly found that by proper selection of the first solvent, an intermediate solvate can be formed that upon subsequent conversion to the free base can provide an amisulpride product where greater than 90% by weight, greater than 95% by weight, greater than 97% by weight, greater than 99% by weight; or greater than 99.5% by weight of amisulpride product is in the form of crystalline enantiomeric amisulpride of starting material, characterized by an XRPD pattern comprising peaks, in terms of 2-theta, at least at 7.0±0.2°, 9.7±0.2°, and 19.4±0.2°.

The first solvent is a carbonyl containing compound having 5 carbons or less. The inventors have unexpectedly found that larger carbonyl containing solvents interfere with, and can even prohibit, proper crystallization of Form B and B'. Examples of such larger carbonyl containing solvent include cyclohexanone. Preferably, the first solvent has a water content of less than 3% by weight, more preferably less than 1% by weight, and more preferably less than 0.5% by weight. It has been found that excess water in the first solvent interferes with, and can even prohibit, proper crystallization. In various embodiments, the first solvent is an aldehyde, ketone or ester. In various embodiments, the first solvent is ethyl acetate, propyl acetate, or methyl ethyl ketone; and in various preferred embodiments the first solvent is ethyl acetate.

In various embodiments, the ratio of ethyl acetate to amisulpride is 1:3 in Form B. In various embodiments, the ratio of ethyl acetate to amisulpride is 1:3 in Form B'.

In various embodiments, the step of solvating includes basifying; for example, by addition of a basic aqueous solution. In various embodiments, a basic solution sufficient to raise the pH to greater than 9.5, preferably to about 10, and in various embodiments between about 9.5 and about 11, is added. In various embodiments, aqueous solutions of potassium carbonate are employed. It is to be understood that a variety of basic solutions can be used to basify including, but not limited to, potassium carbonate, sodium carbonate, sodium hydroxide, and the like.

In various embodiments, the solvating step comprises multiple separations between any aqueous phase and organic phase of the solvent system of the solvating step, as may result, for example, from basifying; the desired products being preferentially partitioned into the organic phase. In various embodiments, the aqueous/organic solvent system is heated to 30-40° C. to facilitate separation.

In various embodiments, subsequent to basifying, the organic phase is concentrated and an excess of the first solvent is added one or more times to facilitate complete conversion to the solvate. In addition, in various embodiments, repeated concentration and addition of the first solvent facilitates producing a concentrated solvate solution having less than about 1 wt % water, less than about 0.7 wt % water, or less than about 0.4 wt % water, as determined by Karl Fischer titration.

For example, in various embodiments, the first solvent forms an azeotrope with water. First solvent is added and water removed, and the process is repeated such that upon each addition of first solvent and removal of water (e.g. by distillation) the concentration of water is lowered and the process repeated until the desired level of water is reached. In various preferred embodiments, the first solvent is ethyl acetate.

In various embodiments, the reaction mixture is seeded prior to addition of the second solvent. In various embodiments, the step of solvating includes formation of a slurry by, for example, seeding the reaction mixture and cooling the reaction mixture below about 40° C., in various embodiments below about 30° C., and preferably below about 20° C.

It is to be understood that crystalline form of the seed in all the various aspects and embodiments of the present inventions is not critical, and that enantiomeric crystalline amisulpride of either enantiomer can be used (i.e., of Form A and/or Form A'), as well as enantiomeric crystalline amisulpride ethyl acetate solvate of either enantiomer (i.e., of Form B and/or Form B') can be used. It has been discovered by the present inventors that seed crystals of Form B, or Form B', can, in various embodiments convert, respectively, to crystalline amisulpride of Form A, or Form A', during the recrystallization. It is to be understood that it is preferred that the seed be of the same enantiomeric confirmation as the desired product to minimize introduction of chiral impurity into the desired product. In various embodiments, a nucleation center is sufficient as a seed to induce appropriate crystallization although one of ordinary skill in the art will understand that such nucleation centers are to be used in the lowest amounts practicable to minimize introduction of impurities in the final desired product.

Following formation of the enantiomeric starting material solvate, (i.e., (R)-amisulpride solvate with the first solvent or a (S)-amisulpride solvate with the first solvent) the solvate is freed from the enantiomeric starting material to form the free base of the enantiomeric starting material under conditions that allow for the isolation of crystalline enantiomeric amisulpride characterized by an XRPD pattern comprising peaks, in terms of 2-theta, at least at 7.0±0.2°, 9.7±0.2°, and 19.4±0.2°. In various embodiments, the reaction mixture is seeded prior to addition of the second solvent. In various embodiments, the step of freeing comprises cooling the reaction mixture to below about 40° C.

As used herein, the term "solvating" refers to the combination of (R)-amisulpride or (S)-amisulpride with a solvent.

As used herein, the terms "isolating" and "freeing" refer to separating the desired product from the environment in which it was formed or detected. For example, separation can include compositions containing at least about 50%, at least about 60%, at least about 70%, at least about 80%, at least about 90%, at least about 95%, at least about 97%, or at least about 99% by weight of the desired product.

In various embodiments, a second solvent (other than water) is added to form a mixture with a starting material solubility of less than about 20 wt/wt %; less than about 10 wt/wt %; or less than about 5 wt/wt %. One of skill in the art will understand that in various embodiments the second solvent can be considered an anti-solvent as it lowers the solubility of the mixture with respect to the desired product. It is to be understood that a variety of compounds can be used as a second solvent including, but not limited to, methyl t-butyl ether, toluene, heptane, isopropanol, and the like. In various embodiments the second solvent is methyl t-butyl ether (MtBE). In various embodiments, the second solvent is added in excess to increase the yield.

A variety of procedures can be used to isolate the desired enantiomeric crystalline form of the starting material. In various embodiments, the step of isolating comprises one or more of: (a) adding an anti-solvent; (b) cooling the mixture to below about 30° C., and in various embodiments between about 10° C. and about 20° C.; and (c) adding seed crystal of the R-enantiomer of either Form A or Form B or the S-enantiomer of either Form A' or Form B'. In various embodiments, the step of isolating comprises adding an anti-solvent and/or cooling the reaction mixture. In various embodiments use is made of seed crystals of the crystalline formed desired, and seed crystals can be obtained by one of skill in the art using the teachings provided herein.

For example, Examples 4A and 4B teach methods of producing crystalline (R)-amisulpride ethyl acetate solvate of Form B. The product of these examples upon drying above about 30° C., desolvates and converts to crystals of crystalline (R)-amisulpride free base of Form A and amorphous. Similarly, for example, Example 7 teaches a method producing crystalline (S)-amisulpride ethyl acetate solvate of Form B'. The product of these examples upon drying above about 30° C., desolvates and converts to crystals of crystalline (S)-amisulpride free base of Form A' and amorphous. Although the fraction of the solvate that converts to Form A or Form A' in the above examples is low, it is sufficient for obtaining seed crystals.

In various embodiments, the step of isolating the crystalline form comprises seeding the reaction mixture prior to addition of the second solvent, and, in various embodiments, a slurry is then formed by cooling the reaction mixture below about 40° C., in various embodiments below about 30° C., and preferably below about 20° C.

Without being held to theory, it is believed that seeding prior to addition of the second solvent results in formation of a enantiomeric amisulpride ethyl acetate solvate crystal form (e.g., Form B or B') that conversion to the free base (e.g., displacement of the solvate solvent) converts to the respective free base crystalline form, e.g. Form A for Form B conversion and to Form A' for Form B' conversion.

In various embodiments, the step of isolating comprises filtering a slurry comprising the desired crystalline form of the enantiomeric amisulpride free base, washing the solid residue with a solvent system comprising the second solvent and the first solvent, and drying the residue. In various embodiments, the wt/wt ratio of the second solvent to first solvent (second solvent:first solvent) is greater than about 1:9, and in various embodiments between about 1:9 to about 4:1. In various embodiments where the second solvent is MtBE and the first solvent ethyl acetate, the MtBe:ethyl acetate ratio is preferably about 3:1.

In various embodiments, the methods of the present inventions for making crystalline enantiomeric amisulpride, characterized by an XRPD pattern comprising peaks, in terms of 2-theta, at least at 7.0±0.2°, 9.7±0.2°, and 19.4±0.2°, comprise recrystallization. In the Examples, example methods that do not show a recrystallization step are noted as forming a "crude freebase," however it is to be understood that this nomenclature is only for distinguishing the examples.

Recrystallization can be performed by a variety of techniques. In various embodiments, a step of recrystallization comprises (a) dissolving the crystalline enantiomeric amisulpride material in a solvent/anti-solvent solution; (b) cooling the solution comprising the starting material and the solvent/anti-solvent solution; and (c) adding a seed crystal of the R or S crystalline enantiomeric amisulpride of Form A, Form A', Form B Form B'. In various embodiments the step of dissolving includes heating of the solution, to a temperature greater than 40° C. and below about 70° C., and preferably between about 50° C. and about 65° C., and preferably about 60° C.

A variety of solvent/anti-solvent systems can be used. For example, in various embodiments the solvent is acetone and the anti-solvent is methyl t-butyl ether. In various embodiments, the solvent is isopropanol (IPA) and the anti-solvent is heptane. As understood by those of skill in the art, care must be taken in selection of the solvent/anti-solvent system. For example, the inventors have found that in the IPA/heptane system a second liquid phase can form before seeding if the heptane to IPA ratio is greater than 1:1, that if a large excess of IPA is added the seeds will dissolve then crystallize upon addition of heptane antisolvent and cooling, and that a preferred IPA:heptane:product ratio is 36:32:32. In various embodiments, the IPA:heptane:product ratios range from about 28:19:53 to about 44:34:22, where in various preferred embodiments the ratio of IPA to heptane is greater than 1:1.

Non-limiting examples of various embodiments of making crystalline enantiomeric amisulpride of Form A and Form A', or characterized by an XRPD pattern comprising peaks, in terms of 2-theta, at least at 7.0±0.2°, 9.7±0.2°, and 19.4±0.2°, are further illustrated and described in Examples 5, 6, 8 and 9.

In various aspects, provided are novel methods of making ethyl acetate solvated crystal forms of amisulpride enantiomers, the solvated crystalline form of amisulpride having a powder x-ray crystal pattern comprising peaks, in terms of 2-theta, at least at 6.4±0.2°, 8.3±0.2°, and 20.8±0.2°. In various embodiments, these methods provide for isolation of a crystalline form of crystalline enantiomeric ethyl acetate solvates (having a powder x-ray crystal pattern comprising peaks, in terms of 2-theta, at least at 6.4±0.2°, 8.3±0.2°, and 20.8±0.2°) that is greater than 90% by weight, greater than 95% by weight, greater than 97% by weight, greater than 99% by weight; or greater than 99.5% by weight of the enantiomeric amisulpride starting material.

In various embodiments, methods of making ethyl acetate solvated crystal forms of amisulpride enantiomers, characterized by a powder x-ray crystal pattern comprising peaks, in terms of 2-theta, at least at 6.4±0.2°, 8.3±0.2°, and 20.8±0.2°, comprise: (a) providing a starting material comprising either R-4-Amino-N-[(1-ethyl-2-pyrrolidinyl)methyl]-5-(ethylsulfonyl)-2-methoxybenzamide or S-4-Amino-N-[(1-ethyl-2-pyrrolidinyl)methyl]-5-(ethylsulfonyl)-2-methoxybenzamide; (b) solvating the starting material with a ethyl acetate to form an ethyl acetate solvate with the starting material and first solvent; and (c) isolating from the mixture of step (b) an ethyl acetate solvated crystalline form of the starting material having a powder x-ray crystal pattern comprising peaks, in terms of 2-theta, at least at 6.4±0.2°, 8.3±0.2°, and 20.8±0.2°.

In various embodiments, the methods start with the provision of either (R)-amisulpride or (S)-amisulpride to make, respectively, crystalline (R)-amisulpride ethyl acetate solvates or crystalline (S)-amisulpride ethyl acetate solvates. There are many acceptable ways to provide (R)-amisulpride or (S)-amisulpride starting materials, including but not limited to those discussed elsewhere herein. In addition, for example, Examples 4A, 4B and 7 provide methods for making enantiomerically enriched amisulpride starting material.

It is to be understood that the ultimate chiral purity of the solvated crystalline form of the starting material is limited by the chiral purity of the starting material. Thus, in various embodiments, the present methods of making crystalline enantiomeric amisulpride ethyl acetate solvates (characterized by an XRPD pattern comprising peaks, in terms of 2-theta, at least at 6.4±0.2°, 8.3±0.2°, and 20.8±0.2°) provide said crystalline enantiomeric amisulpride ethyl acetate solvates having one or more of: a greater than about 90% chiral purity where the starting material has a greater than about 90% chiral purity; a greater than about 95% chiral purity where the starting material has a greater than about 95% chiral purity; a greater than about 97% chiral purity where the starting material has a greater than about 97% chiral purity; a greater than about 99% chiral purity where the starting material has a greater than about 99% chiral purity.

It has been unexpectedly found that ethyl acetate forms crystalline solvates with enantiomeric amisulpride. Preferably, the ethyl acetate has a water content of less than 3% by weight, more preferably less than 1% by weight, and more preferably less than 0.5% by weight. It has been found that excess water in the first solvent interferes with, and can even prohibit, proper crystallization.

In various embodiments, the step of solvating includes basifying; for example, by addition of a basic aqueous solution. In various embodiments, a basic solution sufficient to raise the pH to greater than 9.5, preferably to about 10, and in various embodiments between about 9.5 and about 11, is added. In various embodiments, aqueous solutions of potassium carbonate are employed. It is to be understood that a variety of basic solutions can be used to basify including, but not limited to, potassium carbonate, sodium carbonate, sodium hydroxide, and the like.

In various embodiments, the solvating step comprises multiple separations between any aqueous phase and organic phase of the solvent system of the solvating step, as may result, for example, from basifying; the desired products being preferentially partitioned into the organic phase. Preferably the, the aqueous/organic solvent system is not heated during separation.

In various embodiments, subsequent to basifying, the organic phase is concentrated and an excess of ethyl acetate is added one or more times to facilitate complete conversion to the solvate. The ethyl acetate forms an azeotrope with water. The process is repeated such that upon each addition of ethyl acetate and removal of water (e.g. by distillation) the concentration of water is lowered and the process repeated until the desired level of water is reached.

The isolation from the mixture of an ethyl acetate solvated crystalline form of the starting material (having a powder x-ray crystal pattern comprising peaks, in terms of 2-theta, at least at 6.4±0.2°, 8.3±0.2°, and 20.8±0.2°) can be accomplished in various ways. In various embodiments, the step of isolating comprises one or more of comprises: (a) using a solvent/anti-solvent solution system; (b) cooling the solution; and (c) adding a seed.

In various preferred embodiments, crystals of enantiomeric amisulpride ethyl acetate solvate are isolated by cooling the reaction mixture to below about 10° C., and preferably to about −10° C., until a slurry is formed. The slurry is slowly warmed and agitated for at least 1 hour at a temperature less than about 10° C., then filtered and washed with ethyl acetate at room temperature, and the resultant residue allowed to dry to isolate the desired crystalline enantiomeric amisulpride ethyl acetate solvate having a powder x-ray crystal pattern comprising peaks, in terms of 2-theta, at least at 6.4±0.2°, 8.3±0.2°, and 20.8±0.2°. It is important in the filtration and drying process the maintain the temperature below 30° C., as it has been found that Form B can desolvate to Form A and amorphous (and that Form B' can desolvate to Form A' and amorphous) upon drying at temperatures above about 30° C.

Non-limiting examples of various embodiments of making crystalline enantiomeric amisulpride ethyl acetate solvates of Form B and Form B', or characterized by an XRPD pattern comprising peaks, in terms of 2-theta, at least at 6.4±0.2°, 8.3±0.2°, and 20.8±0.2°, are further illustrated and described in Examples 4A, 4B and 7.

In addition, in various aspects, provided are novel methods of resolving enantiomeric amisulpride from non-enantiomerically pure mixtures of amisulpride, e.g. substantially racemic amisulpride.

Non-limiting examples of various embodiments of methods of resolving enantiomeric amisulpride from non-enantiomerically pure mixtures are further illustrated and described in Examples 10-12.

In some embodiments, provided herein is (S)-4-amino-N-((1-ethylpyrrolidin-2-yl)methyl)-5-(ethylsulfonyl)-2-methoxybenzamide (2R,3R)-bis((4-methylbenzoyl)oxy)succinic acid salt. In various embodiments, the present inventions provide a crystalline form of (S)-4-amino-N-((1-ethylpyrrolidin-2-yl)methyl)-5-(ethylsulfonyl)-2-methoxybenzamide (2R,3R)-bis((4-methylbenzoyl)oxy)succinic acid salt characterized by an XRPD pattern comprising peaks, in terms of 2-theta, at 5.3±0.2°, 7.0±0.2°, and 8.4±0.2°. In various embodiments, the present inventions provide a crystalline form of (S)-4-amino-N-((1-ethylpyrrolidin-2-yl)methyl)-5-(ethylsulfonyl)-2-methoxybenzamide (2R,3R)-bis((4-methylbenzoyl)oxy)succinic acid salt characterized by three or more peaks in its XRPD pattern selected from those at 5.3±0.2°, 7.2±0.2°, 8.4±0.2°, 10.6±0.2°, 12.4±0.2° and 12.9±0.2°. In various embodiments, the present inventions provide a crystalline form of (S)-4-amino-N-((1-ethylpyrrolidin-2-yl)methyl)-5-(ethylsulfonyl)-2-methoxybenzamide (2R,3R)-bis((4-methylbenzoyl)oxy)succinic acid salt characterized by three or more peaks in its XRPD pattern selected from those at 5.3±0.2°, 7.2±0.2°, 8.4±0.2°, 10.6±0.2°, 12.4±0.2°, 12.9±0.2°, 14.0±0.2° 16.0±0.2°, 17.2±0.2°, and 19.7±0.2°. In various embodiments, the present inventions provide a crystalline form of (S)-4-amino-N-((1-ethylpyrrolidin-2-yl)methyl)-5-(ethylsulfonyl)-2-methoxybenzamide (2R,3R)-bis((4-methylbenzoyl)oxy)succinic acid salt characterized by an XRPD pattern substantially in accord with FIG. 11B.

In various embodiments, the present inventions provide a crystalline form of (S)-4-amino-N-((1-ethylpyrrolidin-2-yl)methyl)-5-(ethylsulfonyl)-2-methoxybenzamide (2R,3R)-bis((4-methylbenzoyl)oxy)succinic acid salt characterized by the following properties, an XRPD pattern comprising peaks, in terms of 2-theta, at 5.3±0.2°, 7.0±0.2°, and 8.4±0.2°, a chiral purity of greater than about 99%, and a chemical purity greater than about 99%.

In various embodiments, the present inventions provide a crystalline form of (S)-4-amino-N-((1-ethyl pyrrolidin-2-yl) methyl)-5-(ethylsulfonyl)-2-methoxybenzamide (2R,3R)-bis((4-methylbenzoyl)oxy)succinic acid salt characterized by the following properties, an XRPD pattern comprising peaks, in terms of 2-theta, at 5.3±0.2°, 7.0±0.2°, and 8.4±0.2° and one or more of the following:
- (a) the powder x-ray diffraction pattern further comprising a peak, in terms of 2-theta, at 10.6±0.2°;
- (b) the powder x-ray diffraction pattern further comprising peaks, in terms of 2-theta, at 12.4±0.2°;
- (c) the powder x-ray diffraction pattern further comprising peaks, in terms of 2-theta, at 12.9±0.2°;
- (d) a chiral purity of greater than about: (i) 90%, (ii) 95%, (iii) 97%, (iv) 99%, (v) 99.5%, (vi) 99.7%, or (vii) 99.9%; and
- (e) a chemical purity of greater than about: (i) 80%, (ii) 90%, (iii) 95%, (iv) 97%, (v) 99%, (vi) 99.5%, (vii) 99.7%, or (viii) 99.9%.

In various embodiments, the present inventions provide a crystalline form of (S)-4-amino-N-((1-ethylpyrrolidin-2-yl)methyl)-5-(ethylsulfonyl)-2-methoxybenzamide (2R,3R)-bis((4-methylbenzoyl)oxy)succinic acid salt characterized by an XRPD pattern comprising peaks, in terms of 2-theta, at 5.3±0.2°, 7.0±0.2°, and 8.4±0.2°. In various embodiments, the present inventions provide a crystalline form of (S)-4-amino-N-((1-ethylpyrrolidin-2-yl)methyl)-5-(ethylsulfonyl)-2-methoxybenzamide (2R,3R)-bis((4-methylbenzoyl)oxy)succinic acid salt characterized by three or more peaks in its XRPD pattern selected from those at 5.3±0.2°, 7.2±0.2°, 8.4±0.2°, 10.6±0.2°, 12.4±0.2° and 12.9±0.2°.

In some embodiments, the crystalline compounds provided herein, e.g., Form A, Form A', Form B, and Form B', have particle size of about 1 μm to about 500 μm. In some embodiments, the particle size is about 5 μm to 200 μm. In some embodiments, the particle size is about 10 μm to about 100 μm. In some embodiments, the particle size is about 20 μm to about 80 μm.

The present disclosure also provides the following embodiments:

Embodiment 1A. A crystalline form of (R)-(+)-amisulpride characterized by a powder x-ray diffraction pattern comprising peaks, in terms of 2-theta, at 7.0±0.2°, 9.7±0.2°, and 19.4±0.2°.

Embodiment 2A. The crystalline (R)-(+)-amisulpride of embodiment 1A, further characterized by the powder x-ray diffraction pattern further comprising peaks, in terms of 2-theta, at 15.4±0.2°, and 29.3±0.2°.

Embodiment 3A. The crystalline (R)-(+)-amisulpride of embodiments 1A or 2A, further characterized by the powder x-ray diffraction pattern further comprising peaks, in terms of 2-theta, at 20.1±0.2°, 21.0±0.2°, and 23.2±0.2°.

Embodiment 4A. A crystalline form of (R)-(+)-amisulpride characterized by a powder x-ray diffraction pattern comprising peaks, in terms of 2-theta, at 7.0±0.2°, 9.7±0.2°, and 15.4±0.2°.

Embodiment 5A. The crystalline (R)-(+)-amisulpride of embodiment 4A, further characterized by the powder x-ray diffraction pattern further comprising peaks, in terms of 2-theta, at 9.3±0.2°, and 19.4±0.2°.

Embodiment 6A. The crystalline (R)-(+)-amisulpride of embodiments 5A or 6A, further characterized by the powder x-ray diffraction pattern further comprising peaks, in terms of 2-theta, at 14.9±0.2°, 16.9±0.2°, and 20.1±0.2°.

Embodiment 7A. The crystalline (R)-(+)-amisulpride of any one of embodiments 4A-6A, further characterized by the powder x-ray diffraction pattern further comprising peaks, in terms of 2-theta, at 19.0±0.2°, 21.0±0.2°, and 23.2±0.2°.

Embodiment 8A. The crystalline (R)-(+)-amisulpride of any one of embodiments 1A-7A, characterized by a powder x-ray diffraction pattern substantially in accord with FIG. 2B.

Embodiment 9A. The crystalline (R)-(+)-amisulpride of any one of embodiments 1A-8A, further characterized by having a melting point at about 102±3° C.

Embodiment 10A. The crystalline (R)-(+)-amisulpride of any one of embodiments 1A-8A, having a differential scanning calorimetry thermogram comprising a peak at 101±3° C.

Embodiment 11A. The crystalline (R)-(+)-amisulpride of any one of embodiments 1A-10A, having a differential scanning calorimetry thermogram substantially in accord with FIG. 2A.

Embodiment 12A. A crystalline form of (S)-(−)-amisulpride characterized by a powder x-ray diffraction pattern comprising peaks, in terms of 2-theta, at 7.0±0.2°, 9.7±0.2°, and 19.4±0.2°.

Embodiment 13A. The crystalline (S)-(−)-amisulpride of embodiment 12A, further characterized by the powder x-ray diffraction pattern further comprising peaks, in terms of 2-theta, at 15.4±0.2° and 29.3±0.2°.

Embodiment 14A. The crystalline (S)-(−)-amisulpride of embodiments 12A or 13A, further characterized by the powder x-ray diffraction pattern further comprising peaks, in terms of 2-theta, at 20.1±0.2°, 21.0±0.2°, and 23.2±0.2°.

Embodiment 15A. A crystalline form of (S)-(−)-amisulpride characterized by a powder x-ray diffraction pattern comprising peaks, in terms of 2-theta, at 7.0±0.2°, 9.7±0.2°, and 15.4±0.2°.

Embodiment 16A. The crystalline (S)-(−)-amisulpride of embodiment 15A, further characterized by the powder x-ray diffraction pattern further comprising peaks, in terms of 2-theta, at 9.3±0.2°, and 19.4±0.2°.

Embodiment 17A. The crystalline (S)-(−)-amisulpride of embodiments 15A or 16A, further characterized by the powder x-ray diffraction pattern further comprising peaks, in terms of 2-theta, at 14.9±0.2°, 16.9±0.2°, and 20.2±0.2°.

Embodiment 18A. The crystalline (S)-(−)-amisulpride of any one of embodiments 15A-17A, further characterized by the powder x-ray diffraction pattern further comprising peaks, in terms of 2-theta, at 19.1±0.2°, 21.0±0.2°, and 23.2±0.2°.

Embodiment 19A. The crystalline (S)-(−)-amisulpride of any one of embodiments 12A-18A, characterized by a powder x-ray diffraction pattern substantially in accord with FIG. 3B.

Embodiment 20A. The crystalline (S)-(−)-amisulpride of any one of embodiments 12A-19A, further characterized by having a melting point at about 102±3° C.

Embodiment 21A. The crystalline (S)-(−)-amisulpride of any one of embodiments 12A-19A, having a differential scanning calorimetry thermogram comprising a peak at 101±3° C.

Embodiment 22A. The crystalline (S)-(−)-amisulpride of any one of embodiments 12A-21A, having a differential scanning calorimetry thermogram substantially in accord with FIG. 3A.

Embodiment 23A. A crystalline (R)-(+)-amisulpride or (S)-(−)-amisulpride characterized by single crystal x-ray diffraction having a P1 space group and cell formula units (Z) of 4.

Embodiment 24A. The crystalline form of (R)-(+)-amisulpride of embodiment 23A, wherein the P1 space group has unit cell parameters: a is about 12.3 Å, b is about 12.8 Å, c is about 14.1 Å, α is about 64.0°, β is about 73.4°, and γ is about 75.9°.

Embodiment 25A. The crystalline form of (S)-(−)-amisulpride of embodiment 23A, wherein the P1 space group has unit cell parameters: a is about 12.4 Å, b is about 12.8 Å, c is about 14.1 Å, α is about 64.2°, β is about 73.6°, and γ is about 75.8°.

Embodiment 26A. A composition comprising the crystalline (R)-(+)-amisulpride of any one of embodiments 1A-11A, 23A and 24A, wherein the chiral purity of (R)-(+)-amisulpride is greater than about 90% and (R)-(+)-amisulpride is of crystalline Form A with a polymorph purity of greater than about 90%.

Embodiment 27A. A composition comprising the crystalline (R)-(+)-amisulpride of any one of embodiments 1A-11A, 23A, 24A, and 26A, wherein the chemical purity of the composition is greater than about 99% (R)-(+)-amisulpride.

Embodiment 28A. A composition comprising the crystalline (S)-(−)-amisulpride of any one of embodiments 12A-23A, and 25A, wherein the chiral purity of (S)-(−)-amisulpride is greater than about 90% and (S)-(−)-amisulpride is of crystalline Form A' with a polymorph purity of greater than about 90%.

Embodiment 29A. A composition comprising the crystalline (S)-(−)-amisulpride of any one of embodiments 12A-23A, 25A, and 28A, wherein the chemical purity of the composition is greater than about 99% (S)-(−)-amisulpride.

Embodiment 30A. A crystalline form of (R)-(+)-amisulpride ethyl acetate solvate characterized by a powder x-ray diffraction pattern comprising peaks, in terms of 2-theta, at 6.4±0.2°, 8.3±0.2°, and 20.8±0.2°.

Embodiment 31A. The crystalline (R)-(+)-amisulpride ethyl acetate solvate of embodiment 30A, further characterized by the powder x-ray diffraction pattern further comprising a peaks, in terms of 2-theta, at 14.1±0.2° and 25.3±0.2°.

Embodiment 32A. The crystalline (R)-(+)-amisulpride ethyl acetate solvate of embodiments 30A or 31A, further characterized by the powder x-ray diffraction pattern further comprising a peak, in terms of 2-theta, at 14.1±0.2°.

Embodiment 33A. The crystalline (R)-(+)-amisulpride ethyl acetate solvate of any one of embodiments 30A-32A, characterized by a powder x-ray diffraction pattern substantially in accord with FIG. 5.

Embodiment 34A. A composition comprising the crystalline (R)-(+)-amisulpride ethyl acetate solvate of any one of embodiments 30A-33A, wherein the chiral purity of (R)-(+)-amisulpride ethyl acetate solvate is greater than about 90% and (R)-(+)-amisulpride ethyl acetate solvate is of crystalline Form B with a polymorph purity of greater than about 80%.

Embodiment 35A. A composition comprising the crystalline (R)-(+)-amisulpride ethyl acetate solvate of any one of embodiments 30A-34A wherein the chemical purity of the composition is greater than about 95% (R)-(+)-amisulpride ethyl acetate solvate.

Embodiment 36A. A crystalline form of (S)-(−)-amisulpride ethyl acetate solvate characterized by a powder x-ray diffraction pattern comprising peaks, in terms of 2-theta, at 6.4±0.2°, 8.3±0.2°, and 20.8±0.2°.

Embodiment 37A. The crystalline (S)-(−)-amisulpride ethyl acetate solvate of embodiment 36A, further characterized by the powder x-ray diffraction pattern further comprising peaks, in terms of 2-theta, at 14.1±0.2° and 25.3±0.2°.

Embodiment 38A. The crystalline (S)-(−)-amisulpride ethyl acetate solvate of embodiments 36A and 37A, further characterized by the powder x-ray diffraction pattern further comprising a peak, in terms of 2-theta, at 14.1±0.2°.

Embodiment 39A. The crystalline (S)-(−)-amisulpride ethyl acetate solvate of any one of embodiments 36A-38A, characterized by a powder x-ray diffraction pattern substantially in accord with FIG. 8.

Embodiment 40A. A composition comprising the crystalline (S)-(−)-amisulpride ethyl acetate solvate of any one of embodiments 36A-39A, wherein the chiral purity of (S)-(−)-amisulpride ethyl acetate solvate is greater than about 90% and (S)-(−)-amisulpride ethyl acetate solvate is of crystalline Form B' with a polymorph purity of greater than about 80%.

Embodiment 41A. A composition comprising the crystalline (S)-(−)-amisulpride ethyl acetate solvate of any one of embodiments 36A-40A, wherein the chemical purity of the composition is greater than about 95% (S)-(−)-amisulpride ethyl acetate solvate.

Embodiment 42A. A method of making an enantiomerically pure crystalline form of amisulpride having a powder x-ray crystal pattern comprising peaks, in terms of 2-theta, at least at 7.0±0.2°, 9.7±0.2°, and 19.4±0.2°, the method comprising the steps of:
(a) providing a starting material comprising either R-4-Amino-N-[(1-ethyl-2-pyrrolidinyl)methyl]-5-(ethylsulfonyl)-2-methoxybenzamide or S-4-Amino-N-[(1-ethyl-2-pyrrolidinyl)methyl]-5-(ethylsulfonyl)-2-methoxybenzamide;
(b) solvating the starting material with a first solvent to form a solvate of the starting material and first solvent, wherein the first solvent is a carbonyl containing compound having 5 carbons or less;
(c) freeing the solvated starting material from the first solvent by adding a second solvent other than water to form a mixture with a starting material solubility of less than about 20 wt/wt %; and
(d) isolating from the mixture comprising the free base of the starting material a crystalline form of the starting material having a powder x-ray crystal pattern comprising peaks, in terms of 2-theta, at least at 7.0±0.2°, 9.7±0.2°, and 19.4±0.2°.

Embodiment 43A. The method of embodiment 42A, further comprising a step of recrystallizing the crystalline form of the starting material of step (d).

Embodiment 44A. The method of embodiment 43A, wherein the step of recrystallizing comprises one or more of:
(a) dissolving the material in step (d) and adding an anti-solvent;
(b) cooling the mixture to −10±2° C.; and
(c) seeding the mixture.

Embodiment 45A. A method of making an enantiomerically pure ethyl acetate solvate crystalline form of amisulpride having a powder x-ray crystal pattern comprising peaks, in terms of 2-theta, at least at 6.4±0.2°, 8.3±0.2°, and 20.8±0.2°, the method comprising the steps of:
(a) providing a starting material comprising either R-4-Amino-N-[(1-ethyl-2-pyrrolidinyl)methyl]-5-(ethylsulfonyl)-2-methoxybenzamide or S-4-Amino-N-[(1-ethyl-2-pyrrolidinyl)methyl]-5-(ethylsulfonyl)-2-methoxybenzamide;
(b) solvating the starting material with a ethyl acetate to form an ethyl acetate solvate with the starting material and first solvent; and
(c) isolating from the mixture of step (b) an ethyl acetate solvated crystalline form of the starting material having a powder x-ray crystal pattern comprising peaks, in terms of 2-theta, at least at 6.4±0.2°, 8.3±0.2°, and 20.8±0.2°.

Embodiment 46A. The method of embodiment 45A, wherein the step of isolating comprises one or more of:
(a) adding an anti-solvent;
(b) cooling the mixture to −10±2° C.; and
(c) seeding the mixture.

Embodiment 47A. A method of resolving a non-enantiomerically pure mixture of amisulpride, comprising the steps of:
(a) providing a starting material comprising a non-enantiomerically pure mixture of amisulpride;
(b) forming a solution of the starting material in a solvent comprising an enantiomeric tartaric acid;
(c) isolating from the mixture of step (b) a tartaric acid salt of one enantiomer of the starting material;
(d) freeing the one enantiomer of the starting material from the tartaric; and
(e) isolating from the mixture of step (d) the free base of the one enantiomer of the starting material.

Embodiment 48A. A pharmaceutical composition comprising (R)-(+)-amisulpride, wherein more than about 90% of the (R)-(+)-amisulpride is in Form A.

Embodiment 49A. A pharmaceutical composition comprising (S)-(−)-amisulpride, wherein more than about 90% of the (S)-(−)-amisulpride is in Form A'.

The present disclosure also provides the following embodiments:

Embodiment 1. A crystalline form of (R)-(+)-amisulpride characterized by a powder x-ray diffraction pattern comprising peaks, in terms of 2-theta, at 7.0±0.2°, 9.7±0.2°, and 19.4±0.2°.

Embodiment 2. The crystalline (R)-(+)-amisulpride of embodiment 1, further characterized by the powder x-ray diffraction pattern further comprising peaks, in terms of 2-theta, at 15.4±0.2°, and 29.3±0.2°.

Embodiment 3. The crystalline (R)-(+)-amisulpride of embodiment 2, further characterized by the powder x-ray diffraction pattern further comprising peaks, in terms of 2-theta, at 20.1±0.2°, 21.0±0.2°, and 23.2±0.2°.

Embodiment 4. A crystalline form of (R)-(+)-amisulpride characterized by a powder x-ray diffraction pattern comprising peaks, in terms of 2-theta, at 7.0±0.2°, 9.7±0.2°, and 15.4±0.2°.

Embodiment 5. The crystalline (R)-(+)-amisulpride of embodiment 4, further characterized by the powder x-ray diffraction pattern further comprising peaks, in terms of 2-theta, at 9.3±0.2°, and 19.4±0.2°.

Embodiment 6. The crystalline (R)-(+)-amisulpride of embodiment 5, further characterized by the powder x-ray diffraction pattern further comprising peaks, in terms of 2-theta, at 14.9±0.2°, 16.9±0.2°, and 20.1±0.2°.

Embodiment 7. The crystalline (R)-(+)-amisulpride of embodiment 6, further characterized by the powder x-ray diffraction pattern further comprising peaks, in terms of 2-theta, at 19.0±0.2°, 21.0±0.2°, and 23.2±0.2°.

Embodiment 8. The crystalline (R)-(+)-amisulpride of any one of embodiments 1-7, characterized by a powder x-ray diffraction pattern substantially in accord with FIG. 2B.

Embodiment 9. A crystalline (R)-(+)-amisulpride characterized by single crystal x-ray diffraction having a P1 space group and cell formula units (Z) of 4.

Embodiment 10. The crystalline (R)-(+)-amisulpride of embodiment 9, wherein the P1 space group has unit cell parameters: a is about 12.3 Å, b is about 12.8 Å, c is about 14.1 Å, α is about 64.0°, β is about 73.4°, and γ is about 75.9°.

Embodiment 11. The crystalline (R)-(+)-amisulpride of any one of embodiments 1-10, further characterized by having a melting point at about 102±3° C.

Embodiment 12. A crystalline (R)-(+)-amisulpride characterized by a differential scanning calorimetry thermogram comprising an endothermic event at 101±3° C.

Embodiment 13. The crystalline (R)-(+)-amisulpride of any one of embodiments 1-12, having a differential scanning calorimetry thermogram substantially in accord with FIG. 2A.

Embodiment 14. A composition comprising the crystalline (R)-(+)-amisulpride of any one of embodiments 1-13, wherein the chiral purity of (R)-(+)-amisulpride is greater than about 90% and (R)-(+)-amisulpride is of crystalline Form A with a polymorph purity of greater than about 90%.

Embodiment 15. A composition comprising the crystalline (R)-(+)-amisulpride of any one of embodiments 1-13, wherein the chiral purity of (R)-(+)-amisulpride is greater than about 92% and (R)-(+)-amisulpride is of crystalline Form A with a polymorph purity of greater than about 90%.

Embodiment 16. A composition comprising the crystalline (R)-(+)-amisulpride of any one of embodiments 1-13, wherein the chiral purity of (R)-(+)-amisulpride is greater than about 95% and (R)-(+)-amisulpride is of crystalline Form A with a polymorph purity of greater than about 90%.

Embodiment 17. A composition comprising the crystalline (R)-(+)-amisulpride of any one of embodiments 1-13, wherein the chiral purity of (R)-(+)-amisulpride is greater than about 99% and (R)-(+)-amisulpride is of crystalline Form A with a polymorph purity of greater than about 90%.

Embodiment 18. A composition comprising the crystalline (R)-(+)-amisulpride of any one of embodiments 1-13, wherein the chiral purity of (R)-(+)-amisulpride is greater than about 99.5% and (R)-(+)-amisulpride is of crystalline Form A with a polymorph purity of greater than about 90%.

Embodiment 19. A composition comprising the crystalline (R)-(+)-amisulpride of any one of embodiments 1-13, wherein the chiral purity of (R)-(+)-amisulpride is greater than about 99.7% and (R)-(+)-amisulpride is of crystalline Form A with a polymorph purity of greater than about 90%.

Embodiment 20. A composition comprising the crystalline (R)-(+)-amisulpride of any one of embodiments 1-13, wherein the chiral purity of (R)-(+)-amisulpride is greater than about 99.9% and (R)-(+)-amisulpride is of crystalline Form A with a polymorph purity of greater than about 90%.

Embodiment 21. A composition comprising the crystalline (R)-(+)-amisulpride of any one of embodiments 1-20, wherein the chemical purity of the composition is greater than about 99% (R)-(+)-amisulpride.

Embodiment 22. A composition comprising crystalline (R)-(+)-amisulpride of any one of embodiments 1-20, wherein the chemical purity of the composition is greater than about 99.5% (R)-(+)-amisulpride.

Embodiment 23. A composition comprising crystalline (R)-(+)-amisulpride of any one of embodiments 1-20, wherein the chemical purity of the composition is greater than about 99.7% (R)-(+)-amisulpride.

Embodiment 24. A composition comprising crystalline (R)-(+)-amisulpride of any one of embodiments 1-20, wherein the chemical purity of the composition is greater than about 99.9% (R)-(+)-amisulpride.

Embodiment 25. A crystalline form of (S)-(−)-amisulpride characterized by a powder x-ray diffraction pattern comprising peaks, in terms of 2-theta, at 7.0±0.2°, 9.7±0.2°, and 19.4±0.2°.

Embodiment 26. The crystalline (S)-(−)-amisulpride of embodiment 25, further characterized by the powder x-ray diffraction pattern further comprising peaks, in terms of 2-theta, at 15.4±0.2° and 29.3±0.2°.

Embodiment 27. The crystalline (S)-(−)-amisulpride of embodiment 26, further characterized by the powder x-ray diffraction pattern further comprising peaks, in terms of 2-theta, at 20.1±0.2°, 21.0±0.2°, and 23.2±0.2°.

Embodiment 28. A crystalline form of (S)-(−)-amisulpride characterized by a powder x-ray diffraction pattern comprising peaks, in terms of 2-theta, at 7.0±0.2°, 9.7±0.2°, and 15.4±0.2°.

Embodiment 29. The crystalline (S)-(−)-amisulpride of embodiment 28, further characterized by the powder x-ray diffraction pattern further comprising peaks, in terms of 2-theta, at 9.3±0.2°, and 19.4±0.2°.

Embodiment 30. The crystalline (S)-(−)-amisulpride of embodiment 29, further characterized by the powder x-ray diffraction pattern further comprising peaks, in terms of 2-theta, at 14.9±0.2°, 16.9±0.2°, and 20.2±0.2°.

Embodiment 31. The crystalline (S)-(−)-amisulpride of embodiment 30, further characterized by the powder x-ray diffraction pattern further comprising peaks, in terms of 2-theta, at 19.1±0.2°, 21.0±0.2°, and 23.2±0.2°.

Embodiment 32. The crystalline (S)-(−)-amisulpride of any one of embodiments 25-31, characterized by a powder x-ray diffraction pattern substantially in accord with FIG. 3B.

Embodiment 33. A crystalline (S)-(−)-amisulpride characterized by single crystal x-ray diffraction having a P1 space group and cell formula units (Z) of 4.

Embodiment 34. The crystalline (S)-(−)-amisulpride of embodiment 33, wherein the P1 space group has unit cell parameters: a is about 12.4 Å, b is about 12.8 Å, c is about 14.1 Å, α is about 64.2°, β is about 73.6°, and γ is about 75.8°.

Embodiment 35. The (S)-(−)-amisulpride of any one of embodiments 25-34, further characterized by having a melting point at about 102±3° C.

Embodiment 36. A crystalline (S)-(−)-amisulpride characterized by a differential scanning calorimetry thermogram comprising an endothermic event at 101±3° C.

Embodiment 37. The crystalline (S)-(−)-amisulpride of any one of embodiments 25-36, having a differential scanning calorimetry thermogram substantially in accord with FIG. 3A.

Embodiment 38. A composition comprising the crystalline (S)-(−)-amisulpride of any one of embodiments 25-37, wherein the chiral purity of (S)-(−)-amisulpride is greater than about 90% and (S)-(−)-amisulpride is of crystalline Form A' with a polymorph purity of greater than about 90%.

Embodiment 39. A composition comprising the crystalline (S)-(−)-amisulpride of any one of embodiments 25-37, wherein the chiral purity of (S)-(−)-amisulpride is greater than about 92% and (S)-(−)-amisulpride is of crystalline Form A' with a polymorph purity of greater than about 90%.

Embodiment 40. A composition comprising the crystalline (S)-(−)-amisulpride of any one of embodiments 25-37, wherein the chiral purity of (S)-(−)-amisulpride is greater than about 95% and (S)-(−)-amisulpride is of crystalline Form A' with a polymorph purity of greater than about 90%.

Embodiment 41. A composition comprising the crystalline (S)-(−)-amisulpride of any one of embodiments 25-37, wherein the chiral purity of (S)-(−)-amisulpride is greater than about 99% and (S)-(−)-amisulpride is of crystalline Form A' with a polymorph purity of greater than about 90%.

Embodiment 42. A composition comprising the crystalline (S)-(−)-amisulpride of any one of embodiments 25-37, wherein the chiral purity of (S)-(−)-amisulpride is greater than about 99.5% and (S)-(−)-amisulpride is of crystalline Form A' with a polymorph purity of greater than about 90%.

Embodiment 43. A composition comprising the crystalline (S)-(−)-amisulpride of any one of embodiments 25-37, wherein the chiral purity of (S)-(−)-amisulpride is greater than about 99.7% and (S)-(−)-amisulpride is of crystalline Form A' with a polymorph purity of greater than about 90%.

Embodiment 44. A composition comprising the crystalline (S)-(−)-amisulpride of any one of embodiments 25-37, wherein the chiral purity of (S)-(−)-amisulpride is greater than about 99.9% and (S)-(−)-amisulpride is of crystalline Form A' with a polymorph purity of greater than about 90%.

Embodiment 45. A composition comprising the crystalline (S)-(−)-amisulpride of any one of embodiments 25-44, wherein the chemical purity of the composition is greater than about 99% (S)-(−)-amisulpride.

Embodiment 46. A composition comprising the crystalline (S)-(−)-amisulpride of any one of embodiments 25-44, wherein the chemical purity of the composition is greater than about 99.5% (S)-(−)-amisulpride.

Embodiment 47. A composition comprising crystalline (S)-(−)-amisulpride of any one of embodiments 25-44, wherein the chemical purity of the composition is greater than about 99.7% (S)-(−)-amisulpride.

Embodiment 48. A composition comprising crystalline (S)-(−)-amisulpride of any one of embodiments 24-44, wherein the chemical purity of the composition is greater than about 99.9% (S)-(−)-amisulpride.

Embodiment 49. A crystalline form of (R)-(+)-amisulpride ethyl acetate solvate characterized by a powder x-ray diffraction pattern comprising peaks, in terms of 2-theta, at 6.4±0.2°, 8.3±0.2°, and 20.8±0.2°.

Embodiment 50. The crystalline (R)-(+)-amisulpride ethyl acetate solvate of embodiment 49, further characterized by the powder x-ray diffraction pattern further comprising a peaks, in terms of 2-theta, at 14.1±0.2° and 25.3±0.2°.

Embodiment 51. The crystalline (R)-(+)-amisulpride ethyl acetate solvate of embodiment 49, further characterized by the powder x-ray diffraction pattern further comprising a peak, in terms of 2-theta, at 14.1±0.2°.

Embodiment 52. The crystalline (R)-(+)-amisulpride ethyl acetate solvate of any one of embodiments 49-51, characterized by a powder x-ray diffraction pattern substantially in accord with FIG. 5.

Embodiment 53. A composition comprising the crystalline (R)-(+)-amisulpride ethyl acetate solvate of any one of embodiments 49-52, wherein the chiral purity of (R)-(+)-amisulpride ethyl acetate solvate is greater than about 90% and (R)-(+)-amisulpride ethyl acetate solvate is of crystalline Form B with a polymorph purity of greater than about 80%.

Embodiment 54. A composition comprising the crystalline (R)-(+)-amisulpride ethyl acetate solvate of any one of embodiments 49-52, wherein the chiral purity of (R)-(+)-amisulpride ethyl acetate solvate is greater than about 92% and (R)-(+)-amisulpride ethyl acetate solvate is of crystalline Form B with a polymorph purity of greater than about 80%.

Embodiment 55. A composition comprising the crystalline (R)-(+)-amisulpride ethyl acetate solvate of any one of embodiments 49-52, wherein the chiral purity of (R)-(+)-amisulpride ethyl acetate solvate is greater than about 95% and (R)-(+)-amisulpride ethyl acetate solvate is of crystalline Form B with a polymorph purity of greater than about 80%.

Embodiment 56. A composition comprising the crystalline (R)-(+)-amisulpride ethyl acetate solvate of any one of embodiments 49-52, wherein the chiral purity of (R)-(+)-amisulpride ethyl acetate solvate is greater than about 99% and (R)-(+)-amisulpride ethyl acetate solvate is of crystalline Form B with a polymorph purity of greater than about 80%.

Embodiment 57. A composition comprising the crystalline (R)-(+)-amisulpride ethyl acetate solvate of any one of embodiments 49-52, wherein the chiral purity of (R)-(+)-amisulpride ethyl acetate solvate is greater than about 99.5% and (R)-(+)-amisulpride ethyl acetate solvate is of crystalline Form B with a polymorph purity of greater than about 80%.

Embodiment 58. A composition comprising the crystalline (R)-(+)-amisulpride ethyl acetate solvate of any one of embodiments 49-52, wherein the chiral purity of (R)-(+)-amisulpride ethyl acetate solvate is greater than about 99.7% and (R)-(+)-amisulpride ethyl acetate solvate is of crystalline Form B with a polymorph purity of greater than about 80%.

Embodiment 59. A composition comprising the crystalline (R)-(+)-amisulpride ethyl acetate solvate of any one of embodiments 49-52, wherein the chiral purity of (R)-(+)-amisulpride ethyl acetate solvate is greater than about 99.9% and (R)-(+)-amisulpride ethyl acetate solvate is of crystalline Form B with a polymorph purity of greater than about 80%.

Embodiment 60. A composition comprising the crystalline (R)-(+)-amisulpride ethyl acetate solvate of any one of embodiments 49-60, wherein the chemical purity of the composition is greater than about 95% (R)-(+)-amisulpride ethyl acetate solvate.

Embodiment 61. A composition comprising the crystalline (R)-(+)-amisulpride ethyl acetate solvate of any one of embodiments 49-60, wherein the chemical purity of the composition is greater than about 99% (R)-(+)-amisulpride ethyl acetate solvate.

Embodiment 62. A composition comprising the crystalline (R)-(+)-amisulpride ethyl acetate solvate of any one of embodiments 49-60, wherein the chemical purity of the composition is greater than about 99.5% (R)-(+)-amisulpride ethyl acetate solvate.

Embodiment 63. A composition comprising the crystalline (R)-(+)-amisulpride ethyl acetate solvate of any one of embodiments 49-60, wherein the chemical purity of the composition is greater than about 99.7% (R)-(+)-amisulpride ethyl acetate solvate.

Embodiment 64. A composition comprising the crystalline (R)-(+)-amisulpride ethyl acetate solvate of any one of embodiments 49-60, wherein the chemical purity of the composition is greater than about 99.9% (R)-(+)-amisulpride ethyl acetate solvate.

Embodiment 65. A crystalline form of (S)-(−)-amisulpride ethyl acetate solvate characterized by a powder x-ray diffraction pattern comprising peaks, in terms of 2-theta, at 6.4±0.2°, 8.3±0.2°, and 20.8±0.2°.

Embodiment 66. The crystalline (S)-(−)-amisulpride ethyl acetate solvate of embodiment 65, further characterized by the powder x-ray diffraction pattern further comprising peaks, in terms of 2-theta, at 14.1±0.2° and 25.3±0.2°.

Embodiment 67. The crystalline (S)-(−)-amisulpride ethyl acetate solvate of embodiment 65, further characterized by the powder x-ray diffraction pattern further comprising a peak, in terms of 2-theta, at 14.1±0.2°.

Embodiment 68. The crystalline (S)-(−)-amisulpride ethyl acetate solvate of any one of embodiments 65-67, characterized by a powder x-ray diffraction pattern substantially in accord with FIG. 8.

Embodiment 69. A composition comprising the crystalline (S)-(−)-amisulpride ethyl acetate solvate of any one of embodiments 65-68, wherein the chiral purity of (S)-(−)-amisulpride ethyl acetate solvate is greater than about 90% and (S)-(−)-amisulpride ethyl acetate solvate is of crystalline Form B' with a polymorph purity of greater than about 80%.

Embodiment 70. A composition comprising the crystalline (S)-(−)-amisulpride ethyl acetate solvate of any one of embodiments 65-68, wherein the chiral purity of (S)-(−)-amisulpride ethyl acetate solvate is greater than about 92% (S)-(−)-amisulpride ethyl acetate solvate and (S)-(−)-amisulpride ethyl acetate solvate is of crystalline Form B' with a polymorph purity of greater than about 80%.

Embodiment 71. A composition comprising the crystalline (S)-(−)-amisulpride ethyl acetate solvate of any one of embodiments 65-68, wherein the chiral purity of (S)-(−)-amisulpride ethyl acetate solvate is greater than about 95% and (S)-(−)-amisulpride ethyl acetate solvate is of crystalline Form B' with a polymorph purity of greater than about 80%.

Embodiment 72. A composition comprising the crystalline (S)-(−)-amisulpride ethyl acetate solvate of any one of embodiments 65-68, wherein the chiral purity of (S)-(−)-amisulpride ethyl acetate solvate is greater than about 99% and (S)-(−)-amisulpride ethyl acetate solvate is of crystalline Form B' with a polymorph purity of greater than about 80%.

Embodiment 73. A composition comprising the crystalline (S)-(−)-amisulpride ethyl acetate solvate of any one of embodiments 65-68, wherein the chiral purity of (S)-(−)-amisulpride ethyl acetate solvate is greater than about 99.5% and (S)-(−)-amisulpride ethyl acetate solvate is of crystalline Form B' with a polymorph purity of greater than about 80%.

Embodiment 74. A composition comprising the crystalline (S)-(−)-amisulpride ethyl acetate solvate of any one of embodiments 65-68, wherein the chiral purity of (S)-(−)-amisulpride ethyl acetate solvate is greater than about 99.7% and (S)-(−)-amisulpride ethyl acetate solvate is of crystalline Form B' with a polymorph purity of greater than about 80%.

Embodiment 75. A composition comprising the crystalline (S)-(−)-amisulpride ethyl acetate solvate of any one of embodiments 65-68, wherein the chiral purity of (S)-(−)-amisulpride ethyl acetate solvate is greater than about 99.9% (S)-(−)-amisulpride ethyl acetate solvate and (S)-(−)-amisulpride ethyl acetate solvate is of crystalline Form B' with a polymorph purity of greater than about 80%.

Embodiment 76. A composition comprising the crystalline (S)-(−)-amisulpride ethyl acetate solvate of any one of embodiments 65-76, wherein the chemical purity of the composition is greater than about 95% (S)-(−)-amisulpride ethyl acetate solvate.

Embodiment 77. A composition comprising the crystalline (S)-(−)-amisulpride ethyl acetate solvate of any one of embodiments 65-76, wherein the chemical purity of the composition is greater than about 99% (S)-(−)-amisulpride ethyl acetate solvate.

Embodiment 78. A composition comprising the crystalline (S)-(−)-amisulpride ethyl acetate solvate of any one of embodiments 65-76, wherein the chemical purity of the composition is greater than about 99.5% (S)-(−)-amisulpride ethyl acetate solvate.

Embodiment 79. A composition comprising the crystalline (S)-(−)-amisulpride ethyl acetate solvate of any one of embodiments 65-76, wherein the chemical purity of the composition is greater than about 99.7% (S)-(−)-amisulpride ethyl acetate solvate.

Embodiment 80. A composition comprising the crystalline (S)-(−)-amisulpride ethyl acetate solvate of any one of embodiments 65-76, wherein the chemical purity of the composition is greater than about 99.9% (S)-(−)-amisulpride ethyl acetate solvate.

Embodiment 81. A method of making an enantiomerically pure crystalline form of amisulpride having a powder x-ray crystal pattern comprising peaks, in terms of 2-theta, at least at 7.0±0.2°, 9.7±0.2°, and 19.4±0.2°, the method comprising the steps of:
(a) providing a starting material comprising either R-4-Amino-N-[(1-ethyl-2-pyrrolidinyl)methyl]-5-(ethylsulfonyl)-2-methoxybenzamide or S-4-Amino-N-[(1-ethyl-2-pyrrolidinyl)methyl]-5-(ethylsulfonyl)-2-methoxybenzamide;
(b) solvating the starting material with a first solvent to form a solvate of the starting material and first solvent, wherein the first solvent is a carbonyl containing compound having 5 carbons or less;
(c) freeing the solvated starting material from the first solvent by adding a second solvent other than water to form a mixture with a starting material solubility of less than about 20 wt/wt %; and
(d) isolating from the mixture comprising the free base of the starting material a crystalline form of the starting material having a powder x-ray crystal pattern comprising peaks, in terms of 2-theta, at least at 7.0±0.2°, 9.7±0.2°, and 19.4±0.2°.

Embodiment 82. The method of embodiment 81, wherein the staring material is R-4-Amino-N-[(1-ethyl-2-pyrrolidinyl)methyl]-5-(ethylsulfonyl)-2-methoxy benzamide.

Embodiment 83. The method of embodiment 81, wherein the staring material is S-4-Amino-N-[(1-ethyl-2-pyrrolidinyl)methyl]-5-(ethylsulfonyl)-2-methoxybenzamide.

Embodiment 84. The method of embodiment 81, wherein the staring material has a greater than about 95% chiral purity and the crystalline form of the starting material of step (d) has a greater than about 95% chiral purity.

Embodiment 85. The method of embodiment 81, wherein the staring material has a greater than about 99% chiral purity and the crystalline form of the starting material of step (d) has a greater than about 99% chiral purity.

Embodiment 86. The method of embodiment 81, wherein the first solvent is an aldehyde, ketone or ester.

Embodiment 87. The method of embodiment 81, wherein the first solvent has a water content of less than about 3% by weight.

Embodiment 88. The method of embodiment 81, wherein the first solvent has a water content of less than about 1% by weight.

Embodiment 89. The method of embodiment 81, wherein the first solvent has a water content of less than about 0.5% by weight.

Embodiment 90. The method of embodiment 81, wherein the first solvent is ethyl acetate.

Embodiment 91. The method of embodiment 81, wherein the first solvent is propyl acetate.

Embodiment 92. The method of embodiment 81, wherein the first solvent is methyl ethyl ketone.

Embodiment 93. The method of embodiment 81, wherein the first solvent is ethyl acetate having a water content of less than about 1% by weight.

Embodiment 94. The method of embodiment 81, wherein the step of solvating comprises basifying the first solvent starting material mixture to raise the pH to greater than about 9.5.

Embodiment 95. The method of embodiment 94, where the step of basifying comprises adding an aqueous solution of potassium carbonate.

Embodiment 96. The method of embodiment 95, where the aqueous solution of potassium carbonate is about 40% by weight potassium carbonate.

Embodiment 97. The method of embodiment 81, wherein the second solvent is methyl t-butyl ether.

Embodiment 98. The method of embodiment 81, wherein the step of freeing the solvated starting material comprises forming a mixture with a starting material solubility of less than about 10 wt/wt %.

Embodiment 99. The method of embodiment 81, wherein the step of freeing the solvated starting material comprises forming a mixture with a starting material solubility of less than about 5 wt/wt %.

Embodiment 100. The method of embodiment 81, wherein the crystalline form of the starting material of step (d) has a greater than about 90% chemical purity.

Embodiment 101. The method of embodiment 81, wherein the crystalline form of the starting material of step (d) has a greater than about 95% chemical purity.

Embodiment 102. The method of embodiment 81, wherein the crystalline form of the starting material of step (d) has a greater than about 99% chemical purity.

Embodiment 103. The method of embodiment 81, wherein after step (d) greater than 95% by weight of the starting material is in the crystalline form having a powder x-ray crystal pattern comprising peaks, in terms of 2-theta, at least at 7.0±0.2°, 9.7±0.2°, and 19.4±0.2°.

Embodiment 104. The method of embodiment 81, wherein after step (d) greater than 99% by weight of the starting material is in the crystalline form having a powder x-ray crystal pattern comprising peaks, in terms of 2-theta, at least at 7.0±0.2°, 9.7±0.2°, and 19.4±0.2°.

Embodiment 105. The method of embodiment 81, wherein the step of isolating comprises one or more of:
(a) adding an anti-solvent;
(b) cooling the mixture to −10±2° C.; and
(c) seeding the mixture.

Embodiment 106. The method of embodiment 105, wherein the anti-solvent is methyl t-butyl ether.

Embodiment 107. The method of embodiment 81, further comprising a step of recrystallizing the crystalline form of the starting material of step (d).

Embodiment 108. The method of embodiment 107, wherein the step of recrystallizing comprises one or more of:
(a) dissolving the material in step (d) and adding an anti-solvent;
(b) cooling the mixture to −10±2° C.; and
(c) seeding the mixture.

Embodiment 109. The method of embodiment 107, wherein the step of recrystallizing comprises:
(a) dissolving the material in step (d) in a solvent/anti-solvent solution;
(b) cooling the solution comprising the starting material and the solvent/anti-solvent solution; and
(c) adding a seed crystal.

Embodiment 110. The method of embodiment 109, wherein the solvent of the solvent/anti-solvent solution is acetone and the anti-solvent is methyl t-butyl ether and the step of dissolving comprises heating.

Embodiment 111. The method of embodiment 109, wherein the solvent of the solvent/anti-solvent solution is isopropanol and the anti-solvent is heptane and the step of dissolving comprises heating.

Embodiment 112. The method of embodiment 111, wherein isopropanol:heptane:material of step (d) ratio is 36±10: 32±10:32±10.

Embodiment 113. The method of embodiment 107, wherein the crystalline form of the starting material of step (d) has a greater than about 99% chemical purity.

Embodiment 114. The method of embodiment 107, wherein the crystalline form of the starting material of step (d) has a greater than about 99.5% chemical purity.

Embodiment 115. The method of embodiment 107, wherein the crystalline form of the starting material of step (d) has a greater than about 99.7% chemical purity.

Embodiment 116. The method of embodiment 107, wherein the crystalline form of the starting material of step (d) has a greater than about 99.9% chemical purity.

Embodiment 117. The method of embodiment 107, wherein after recrystallization greater than 99% by weight of the starting material of the isolating step (d) is in the crystalline form having a powder x-ray crystal pattern comprising peaks, in terms of 2-theta, at least at 7.0±0.2°, 9.7±0.2°, and 19.4±0.2°.

Embodiment 118. The method of embodiment 107, wherein after recrystallization greater than 99.5% by weight of the starting material of the isolating step (d) is in the crystalline form having a powder x-ray crystal pattern comprising peaks, in terms of 2-theta, at least at 7.0±0.2°, 9.7±0.2°, and 19.4±0.2°.

Embodiment 119. A method of making an enantiomerically pure ethyl acetate solvate crystalline form of amisulpride having a powder x-ray crystal pattern comprising peaks, in terms of 2-theta, at least at 6.4±0.2°, 8.3±0.2°, and 20.8±0.2°, the method comprising the steps of:
(a) providing a starting material comprising either R-4-Amino-N-[(1-ethyl-2-pyrrolidinyl)methyl]-5-(ethylsulfonyl)-2-methoxybenzamide or S-4-Amino-N-[(1-ethyl-2-pyrrolidinyl)methyl]-5-(ethylsulfonyl)-2-methoxybenzamide
(b) solvating the starting material with a ethyl acetate to form an ethyl acetate solvate with the starting material and first solvent; and
(c) isolating from the mixture of step (b) an ethyl acetate solvated crystalline form of the starting material having a powder x-ray crystal pattern comprising peaks, in terms of 2-theta, at least at 6.4±0.2°, 8.3±0.2°, and 20.8±0.2°.

Embodiment 120. The method of embodiment 119, wherein the staring material is R-4-Amino-N-[(1-ethyl-2-pyrrolidinyl)methyl]-5-(ethylsulfonyl)-2-methoxybenzamide.

Embodiment 121. The method of embodiment 119, wherein the staring material is S-4-Amino-N-[(1-ethyl-2-pyrrolidinyl)methyl]-5-(ethylsulfonyl)-2-methoxybenzamide.

Embodiment 122. The method of embodiment 119, wherein the staring material has a greater than about 95% chiral purity and the crystalline form of the starting material of step (c) has a greater than about 95% chiral purity.

Embodiment 123. The method of embodiment 119, wherein the staring material has a greater than about 99% chiral purity and the crystalline form of the starting material of step (c) has a greater than about 99% chiral purity.

Embodiment 124. The method of embodiment 119, wherein the ethyl acetate has a water content of less than about 3% by weight.

Embodiment 125. The method of embodiment 119, wherein the ethyl acetate has a water content of less than about 1% by weight.

Embodiment 126. The method of embodiment 119, wherein the ethyl acetate has a water content of less than about 0.5% by weight.

Embodiment 127. The method of embodiment 119, wherein the step of solvating comprises basifying the ethyl acetate starting material mixture to raise the pH to greater than about 9.5.

Embodiment 128. The method of embodiment 127, where the step of basifying comprises adding an aqueous solution of potassium carbonate.

Embodiment 129. The method of embodiment 128, where the aqueous solution of potassium carbonate is about 40% by weight potassium carbonate.

Embodiment 130. The method of embodiment 119, wherein the ethyl acetate solvated crystalline form of the starting material of step (c) has a greater than about 90% chemical purity.

Embodiment 131. The method of embodiment 119, wherein the ethyl acetate solvated crystalline form of the starting material of step (c) has a greater than about 95% chemical purity.

Embodiment 132. The method of embodiment 119, wherein the ethyl acetate solvated crystalline form of the starting material of step (c) has a greater than about 99% chemical purity.

Embodiment 133. The method of embodiment 119, wherein after step (c) greater than 90% by weight of the starting material is in the crystalline form having a powder x-ray crystal pattern comprising peaks, in terms of 2-theta, at least at 6.4±0.2°, 8.3±0.2°, and 20.8±0.2°.

Embodiment 134. The method of embodiment 119, wherein after step (c) greater than 95% by weight of the starting material is in the crystalline form having a powder x-ray crystal pattern comprising peaks, in terms of 2-theta, at least at 6.4±0.2°, 8.3±0.2°, and 20.8±0.2°.

Embodiment 135. The method of embodiment 119, wherein the step of isolating comprises one or more of:
(a) adding an anti-solvent;
(b) cooling the mixture to −10±2° C.; and
(c) seeding the mixture.

Embodiment 136. A method of resolving a non-enantiomerically pure mixture of amisulpride, comprising the steps of:
(a) providing a starting material comprising a non-enantiomerically pure mixture of amisulpride;
(b) forming a solution of the starting material in a solvent comprising an enantiomeric tartaric acid;
(c) isolating from the mixture of step (b) a tartaric acid salt of one enantiomer of the starting material;
(d) freeing the one enantiomer of the starting material from the tartaric; and
(e) isolating from the mixture of step (d) the free base of the one enantiomer of the starting material.

Embodiment 137. The method of embodiment 136, where in the tartaric acid is one or more of tartaric acid, dibenzoyl tartaric acid, and di-p-toluoyl tartaric acid.

Embodiment 138. The method of embodiment 136, wherein the one enantiomer is (S)-amisulpride and the tartaric acid is levorotatory.

Embodiment 139. The method of embodiment 136, wherein the one enantiomer is (R)-amisulpride and the tartaric acid is dextrorotatory.

Embodiment 140. The method of embodiment 136, wherein the solvent is one or more of acetonitrile, methanol and water.

Embodiment 141. The method of embodiment 136, wherein the step of freeing the one enantiomer of the starting material from the tartaric acid comprises:
(a) solvating of the tartaric acid salt of one enantiomer of the starting material in a second solvent, wherein the second solvent is a carbonyl containing compound having 5 carbons or less; and
(b) freeing the solvated starting material from the second solvent by adding a third solvent other than water to form a mixture with a starting material solubility of less than about 20 wt/wt %.

Embodiment 142. The method of embodiment 136, wherein the step of isolating from the mixture of step (d) the free base of the one enantiomer of the starting material comprises:
(a) isolating from the mixture comprising the free base of the one enantiomer of the starting material a crystalline form of the one enantiomer of the starting material having a powder x-ray crystal pattern comprising peaks, in terms of 2-theta, at least at 7.0±0.2°, 9.7±0.2°, and 19.4±0.2°.

Embodiment 143. A pharmaceutical composition comprising (R)-(+)-amisulpride, wherein more than about 90% of the (R)-(+)-amisulpride is in Form A.

Embodiment 144. The pharmaceutical composition of embodiment 143, wherein the chiral purity of the (R)-(+)-amisulpride is greater than about 95%.

Embodiment 145. A pharmaceutical composition comprising (S)-(−)-amisulpride, wherein more than about 90% of the (S)-(−)-amisulpride is in Form A'.

Embodiment 146. The pharmaceutical composition of embodiment 145, wherein the chiral purity of the (S)-(−)-amisulpride is greater than about 95%.

Aspects, embodiments, and features of the inventions may be further understood from the following examples, which should not be construed as limiting the scope of the inventions.

Example 1: Separation of Amisulpride Enantiomers 903 g of racemic 4-Amino-N-[(1-ethyl-2-pyrrolidinyl)methyl]-5-(ethylsulfonyl)-2-methoxybenzamide was dissolved in acetonitrile containing 0.1% v/v diethylamine. The solution was separated on 8×110 g columns packed with Chirolcel OZ arranged in a simulated moving bed configuration eluting with acetonitrile containing 0.1% v/v diethylamine at 35 bar and the temperature at 30° C. This yielded 3752.2 g of 1:5 wt % (S)-4-Amino-N-[(1-ethyl-2-pyrrolidinyl)methyl]-5-(ethylsulfonyl)-2-methoxybenzamide in acetonitrile, having a yield of 88%, and purity of 99.7% as determined by chiral HPLC; and 2346 g of 25 wt % (R)-4-Amino-N-[(1-ethyl-2-pyrrolidinyl)methyl]-5-(ethylsulfonyl)-2-methoxybenzamide in acetonitrile.

It is to be understood that Example 1 is one of many acceptable ways to separate the enantiomers of amisulpride to provide an enantiomeric starting materials for the methods of the present inventions. It is to be understood that the enantiomeric amisulpride starting materials of the present invention are not necessarily crystalline, and may be amorphous or a mixture of amorphous and crystalline form. In addition to separation of enantiomers from a racemic starting material, suitable enantiomeric starting materials for the methods of the present inventions can also be directly synthesized. Examples 2 and 3 further describe a method of purifying enantiomers separated substantially in accord with the procedure of Example 1.

Example 2: Purification of R-4-Amino-N-[(1-ethyl-2-pyrrolidinyl)methyl]-5-(ethylsulfonyl)-2-methoxybenzamide Obtained from Example 1

2308 grams of the 25 wt % (R)-4-Amino-N-[(1-ethyl-2-pyrrolidinyl)methyl]-5-(ethylsulfonyl)-2-methoxybenzamide solution in acetonitrile (obtained substantially by Example 1) was added to a reactor with nitrogen purge, temperature gauge and agitator. The solution was distilled to 600 mL, maintaining the temperature below 40° C. 624 g of acetone was added to the reactor. 2401 g of methyl t-butyl ether (MtBE) was then added to the reactor. The solution was cooled to 0° C., agitated and seeded, and distilled to 1.8 L. The solution was then diluted with 4810 g of methyl t-butyl ether, agitated and distilled to a volume of 1.8 L. The solution was diluted with 4866 g of methyl t-butyl ether and distilled to a volume of 1.8 L. 4796 g methyl t-butyl ether was added and the reactor then refluxed to remove residue from the vessel walls and the slurry was then slowly cooled to −10° C. After agitation at −10° C., the slurry was filtered and dried. 453 grams of R-4-Amino-N-[(1-ethyl-2-pyrrolidinyl)methyl]-5-(ethylsulfonyl)-2-methoxybenzamide was obtained as a mixture of Form A and amorphous R-4-Amino-N-[(1-ethyl-2-pyrrolidinyl)methyl]-5-(ethylsulfonyl)-2-methoxybenzamide having a chemical purity greater than 99.8%.

Example 3: Purification of S-4-Amino-N-[(1-ethyl-2-pyrrolidinyl)methyl]-5-(ethylsulfonyl)-2-methoxybenzamide Obtained from Example 1

3863 grams of 15 wt % S-4-Amino-N-[(1-ethyl-2-pyrrolidinyl)methy]-5-(ethylsulfonyl)-2-methoxybenzamide solution in acetonitrile (obtained substantially by Example 1) was added to a reactor with nitrogen purge, temperature gauge and agitator. The solution was distilled to 800 mL, maintaining the temperature below 40° C. 600 g of acetone was added to the reactor. 2396 g of methyl t-butyl ether (MtBE) was then added to the reactor, and the solution cooled to 0° C., agitated and seeded. The mixture was agitated further and then distilled to 1.8 L. The solution was then diluted with 4820 g of methyl t-butyl ether, agitated and distilled to a volume of 1.8 L. The solution was then diluted with 4846 g of methyl t-butyl ether and distilled to a volume of 1.8 L. 4780 g methyl t-butyl ether was added and the reactor was then refluxed to remove residue from the vessel walls and the slurry was then slowly cooled to −10° C. After agitation at −10° C., the slurry was filtered and dried. 528 grams of S-4-Amino-N-[(1-ethyl-2-pyrrolidinyl)methyl]-5-(ethylsulfonyl)-2-methoxybenzamide was obtained as a mixture of Form A and amorphous S-4-Amino-N-[(1-ethyl-2-pyrrolidinyl)methyl]-5-(ethylsulfonyl)-2-methoxybenzamide.

Example 4A: Synthesis of R-4-Amino-N-[(1-ethyl-2-pyrrolidinyl)methyl]-5-(ethylsulfonyl)-2-methoxybenzamide (Ethyl Acetate Solvate Form B)

10 g of 4-amino-5-(ethylsulfonyl)-2-methoxybenzoic acid, 100 mL of acetone and 5.3 mL of 4-methyl morpholine were placed in a flask equipped with a stir bar, a thermocouple and a nitrogen line. The solution was cooled to 0° C., and then 4.4 mL of ethyl chloroformate was added to the reactor. The mixture was agitated at −10° C. and then 5.42 g of (R)-(1-ethylpyrrolidin-2-yl)methanamine was added dropwise. The mixture was agitated at −10° C. for 1 hour then warmed to ambient. The reaction was concentrated and 100 mL of water and 100 mL of ethyl acetate were added. The mixture was agitated and the organic layer removed. 100 mL of ethyl acetate and 40 mL of 10 wt % aqueous potassium carbonate were then added. The mixture was agitated and the phases were allowed to separate and the aqueous layer was removed. The ethyl acetate layer was then washed with 50 mL of water two times. The organic layer was transferred to a flask with a mechanical stirrer, a thermocouple and distillation head. The organic layer was concentrated to dryness and 10 g of ethyl acetate was added. The mixture was stirred then cooled to −10° C. and agitated until a slurry formed. The mixture was warmed to 0° C. and stirred at 0° C. for 2h. The slurry was then filtered, washed with ethyl acetate and dried at ambient temperature. 7 g of (R)-4-Amino-N-[(1-ethyl-2-pyrrolidinyl)methyl]-5-(ethylsulfonyl)-2-methoxybenzamide ethyl acetate solvate, having greater than 99% chiral purity, and greater than 99% chemical purity, was obtained.

An NMR spectrum of the (R)-4-Amino-N-[(1-ethyl-2-pyrrolidinyl)methyl]-5-(ethylsulfonyl)-2-methoxybenzamide ethyl acetate solvate obtained in Example 4A is illustrated in FIG. 4A, having the following characteristics: $^1$H NMR (400 MHz, CHLOROFORM-d) δ ppm 1.11 (t, J=7.24 Hz, 3H) 1.23-1.27 (m, 3H), 1.25 (t, J=7.17 Hz, 0.91H) 1.55-1.77 (m, 3H) 1.82-1.92 (m, 1H), 2.04 (s, 0.93H), 2.14-2.27 (m, 2H) 2.58-2.64 (m, 1H) 2.84 (dd, J=12.13, 7.43 Hz, 1H) 3.07-3.28 (m, 4H) 3.69 (ddd, J=13.50, 7.24, 2.74 Hz, 1H) 3.93 (s, 3H) 4.11 (q, J=7.17 Hz, 0.64H) 5.52 (s, 2H) 6.21 (s, 1H) 7.26 (s, 1H) 8.04 (br d, J=5.09 Hz, 1H) 8.52 (s, 1H).

Example 4B: Synthesis of R-4-Amino-N-[(1-ethyl-2-pyrrolidinyl)methyl]-5-(ethylsulfonyl)-2-methoxybenzamide (Ethyl Acetate Solvate, Form B)

50 g of 4-amino-5-(ethylsulfonyl)-2-methoxybenzoic acid, 300 g of acetone were placed in a flask equipped with a stir bar, a thermocouple and a nitrogen line. The solution was cooled to −10° C., and then 24 g of ethyl chloroformate was added to the reactor. 27 mL of 4-methyl morpholine was added slowly and the mixture was agitated at −10° C. for 1 h and then 25 g of (R)-(1-ethylpyrrolidin-2-yl)methanamine was added dropwise. The mixture was then agitated at −10° C. then warmed to ambient. The reaction was concentrated and 300 mL of water and 200 mL of ethyl acetate were added. The mixture was agitated and the organic layer removed. Then 300 mL of ethyl acetate and 100 mL of 20 wt % aqueous potassium carbonate were added to the organic layer. The mixture was agitated, the phases allowed to separate and the aqueous layer removed. The ethyl acetate layer was washed with 200 mL of water two times. The organic layer was then transferred to a flask with a mechanical stirrer, a thermocouple and distillation head. The organic layer was concentrated to dryness and 120 g of ethyl acetate added. The mixture was stirred then cooled to −10° C. and agitated until a slurry formed. The mixture was warmed to 10° C. and stirred at 10° C. for 1 h. The slurry was then filtered, washed with 120 g of ethyl acetate and dried at ambient temperature. 16 g of crystalline (R)-4-Amino-N-[(1-ethyl-2-pyrrolidinyl)methyl]-5-(ethylsulfonyl)-2-methoxybenzamide ethyl acetate was obtained. XRPD analysis showed a pattern in accordance with Form B and that of FIG. 5.

An NMR spectrum of the (R)-4-Amino-N-[(1-ethyl-2-pyrrolidinyl)methyl]-5-(ethylsulfonyl)-2-methoxybenzamide ethyl acetate solvate obtained in Example 4B is illustrated in FIG. 4B, having the following characteristics: 1H NMR (400 MHz, CHLOROFORM-d) δ ppm 1.10 (t, J=7.24 Hz, 3H) 1.21-1.26 (m, 4H) 1.54-1.73 (m, 3H) 1.81-1.92 (m, 1H) 2.01-2.03 (m, 1H) 2.11-2.26 (m, 2H) 2.60 (tt, J=8.75, 2.59 Hz, 1H) 2.82. (dq, J=12.13, 7.43 Hz, 1H) 3.06-3.27 (m, 4H) 3.67 (ddd, J=13.60, 7.14, 2.74 Hz, 1H) 3.92 (s, 3H) 4.10 (q, J=7.04 Hz, 1H) 5.57 (s, 2H) 6.23 (s, 1H) 7.25 (s, 1H) 8.05 (br d, J=4.70 Hz, 1H) 8.50 (s, 1H)

Referring to FIG. 5 presents data on crystalline R-4-Amino-N-[(1-ethyl-2-pyrrolidinyl)methyl]-5-(ethylsulfonyl)-2-methoxybenzamide ethyl acetate solvate, (R)-amisulpride ethyl acetate solvate, obtained in Example 4A. FIG. 5 is a XRPD pattern for crystalline (R)-amisulpride ethyl acetate solvate obtained in Example 4A.

Example 5: Synthesis of R-4-Amino-N-[(1-ethyl-2-pyrrolidinyl)methyl]-5-(ethylsulfonyl)-2-methoxybenzamide (Crude Freebase)

150 g of 4-amino-5-(ethylsulfonyl)-2-methoxybenzoic acid and 2000 g of acetone were placed in a flask. The solution was cooled to −9° C., and 74.3 mL of ethyl chloroformate was added to the flask. Then 88.9 mL of 4-methyl morpholine was added over 1 hour. 81.4 g of (R)-(1-ethylpyrrolidin-2-yl)methanamine was added and the mixture stirred for 16h. The reaction was then concentrated and 800 g of water and 300 g of ethyl acetate were added. The mixture was agitated and the organic layer removed, which contained the R-4-Amino-N-[(1-ethyl-2-pyrrolidinyl)methyl]-5-(ethylsulfonyl)-2-methoxybenzamide starting material. The solution containing the starting material was basified by the addition of aqueous 20 wt % potassium carbonate and 2.5 L of ethyl acetate was added. The aqueous layer was removed. The organic layer was washed twice with water and concentrated to dryness. Then 800 g of ethyl acetate was added and the mixture was concentrated. This was repeated once. The resulting oil was dissolved into 800 g of ethyl acetate and concentrated to 600 mL. The solution was stirred at 30° C. and a slurry formed. The resulting slurry was cooled to 20° C. and agitated. 600 g of methyl t-butyl ether was added and the mixture stirred. The slurry was then filtered, washed with 3:1 wt/wt methyl t-butyl ether:ethyl acetate and dried. 165 g of R-4-Amino-N-[(1-ethyl-2-pyrrolidinyl)methyl]-5-(ethylsulfonyl)-2-methoxybenzamide was obtained as a crystalline solid.

Example 6: Recrystallization of R-4-Amino-N-[(1-ethyl-2-pyrrolidinyl)methyl]-5-(ethylsulfonyl)-2-methoxybenzamide (Freebase Crystal Form A)

603.05 g of R-4-Amino-N-[(1-ethyl-2-pyrrolidinyl)methyl]-5-(ethylsulfonyl)-2-methoxybenzamide (prepared substantially according to Example 5) and 500.3 g of isopropanol were added to a flask with a stir bar and stopper. The flask was heated to 40° C. to form a solution. The solution was then polish filtered and transferred to a reactor at 40° C. with agitator, nitrogen line, thermocouple and cooling water, using 122.81 g of isopropanol to rinse the flask and polish filter. 603.2 g of heptane was added and the solution was agitated. The reactor was cooled to a jacket temperature of 35° C. and 6.91 g of isopropanol was added to the reactor drop wise to create a clear solution. The solution was agitated and then seeded with 972 mg of R-4-Amino-N-[(1-ethyl-2-pyrrolidinyl)methyl]-5-(ethylsulfonyl)-2-methoxybenzamide (Form A) and then agitated. The reactor was then cooled to 20° C. and then agitated. 1889.24 g of heptane was added using an external pump. Following agitation, the slurry was filtered, washed with 15:85 wt/wt isopropanol:heptane and dried. 531.7 g of R-4-Amino-N-[(1-ethyl-2-pyrrolidinyl)methyl]-5-(ethylsulfonyl)-2-methoxybenzamide of crystal Form A, having greater than 97% chiral purity, and greater than 99% chemical purity, was obtained, representing a yield of about 88%.

An NMR spectrum of the R-4-Amino-N-[(1-ethyl-2-pyrrolidinyl)methyl]-5-(ethylsulfonyl)-2-methoxybenzamide obtained in Example 6 is illustrated in FIG. 6, having the following characteristics: $^1$H NMR (400 MHz, CHLOROFORM-d) δ ppm 1.12 (t, J=7.24 Hz, 3H) 1.26 (t, J=7.43 Hz, 3H) 1.56-1.76 (m, 3H) 1.84-1.94 (m, 1H) 2.15-2.29 (m, 2H) 2.59-2.66 (m, 1H) 2.81-2.90 (m, 1H) 3.08-3.29 (m, 4H) 3.70 (ddd, J=13.69, 7.24, 2.93 Hz, 1H) 3.94 (s, 3H) 5.53 (s, 2H) 6.22 (s, 1H) 8.06 (br d, J=4.70 Hz, 1H) 8.53 (s, 1H).

Referring to FIGS. 2A, 2B and 2C, FIGS. 2A, 2B and 2C present data on the R-4-Amino-N-[(1-ethyl-2-pyrrolidinyl)methyl]-5-(ethylsulfonyl)-2-methoxybenzamide, (R)-amisulpride, of crystal Form A obtained in Example 6. FIG. 2A is a DSC thermogram for crystal Form A of (R)-amisulpride obtained in Example 6; FIG. 2B a XRPD pattern for crystal Form A of (R)-amisulpride obtained in Example 6; and FIG. 2C a micrograph image crystals of crystal Form A of the (R)-amisulpride obtained in Example 6.

Example 7: Synthesis of S-4-Amino-N-[(1-ethyl-2-pyrrolidinyl)methyl]5-(ethylsufonyl)-2-methoxybenzamide (Ethyl Acetate Solvate)

50 g of 4-amino-5-(ethylsulfonyl)-2-methoxybenzoic acid, and 280 g of acetone were placed in a flask equipped with a stir bar, a thermocouple and a nitrogen line. Then 24 g of ethyl chloroformate was added to the reactor. The solution was cooled to −10° C., and then 28 g of 4-methyl morpholine was added slowly. The mixture was agitated at −10° C. for 1 h and then 27 g of (S)-(1-ethylpyrrolidin-2-yl)methanamine was added dropwise. The mixture was agitated at −10° C. then warmed to ambient. The reaction was concentrated and 300 mL of water and 200 mL of ethyl acetate were added. The mixture was agitated and the organic layer removed. 300 mL of ethyl acetate and 100 mL of 20 wt % aqueous potassium carbonate were added. The mixture was agitated, the phases are allowed to separate and the aqueous layer removed. The ethyl acetate layer was then washed with 200 mL of water two times. The organic layer was transferred to a flask with a mechanical stirrer, a thermocouple and distillation head. The organic layer was concentrated to dryness and 120 g of ethyl acetate added. The mixture was stirred then cooled to −10° C. and agitated until a slurry formed. The mixture was warmed to 10° C. and stirred at 10° C. for 1h. The slurry was then filtered, washed with 30 g of ethyl acetate and dried at ambient temperature.

49 g of (R)-4-Amino-N-[(1-ethyl-2-pyrrolidinyl)methyl]-5-(ethylsulfonyl)-2-methoxybenzamide ethyl acetate was obtained. XRPD analysis showed a pattern in accordance with Form B' and that of FIG. 8.

An NMR spectrum of the S-4-Amino-N-[(1-ethyl-2-pyrrolidinyl)methyl]-5-(ethylsulfonyl)-2-methoxybenzamide ethyl acetate solvate obtained in Example 7 is illustrated in FIG. 7, having the following characteristics: $^1$H NMR (400 MHz, CHLOROFORM-d) δ ppm–0.02-0.00 (m, 1H) 1.11 (t, J=7.24 Hz, 3H) 1.22-1.28 (m, 4H) 1.55-1.74 (m, 4H) 1.82-1.92 (m, 1H) 2.03 (s, 1H) 2.13-2.27 (m, 2H) 2.58-2.64 (m, 1H) 2.84 (dq, J=12.08, 7.32 Hz, 1H) 3.07-3.28 (m, 4H) 3.66-3.74 (m, 1H) 3.93 (s, 3H) 5.48 (s, 2H) 6.19 (s, 1H) 8.03 (br d, J=4.30 Hz, 1H) 8.52 (s, 1H).

Referring to FIG. 8, FIG. 8 presents data on crystalline S-4-Amino-N-[(1-ethyl-2-pyrrolidinyl)methyl]-5-(ethylsulfonyl)-2-methoxybenzamide ethyl acetate solvate, (S)-amisulpride ethyl acetate solvate, obtained in Example 7. FIG. 8 is a XRPD pattern for crystalline (S)-amisulpride ethyl acetate solvate obtained in Example 7.

Example 8: Synthesis of S-4-Amino-N-[(1-ethyl-2-pyrrolidinyl)methyl]-5-(ethylsulfonyl)-2-methoxybenzamide (Crude Freebase)

153 g of 4-amino-5-(ethylsulfonyl)-2-methoxybenzoic acid and 789 g of acetone were placed in a flask fitted with a stir bar, a thermocouple and a nitrogen line. The solution was cooled to –8° C., and then 70.4 g of ethyl chloroformate was added to the flask. An addition funnel was fitted to the flask and 79.3 g of 4-methyl morpholine was added drop wise, maintaining the temperature below 0° C. The mixture was agitated at –8° C. and then 55 g of (S)-(1-ethylpyrrolidin-2-yl)methanamine was added drop wise. The mixture was agitated at 0° C. for 1 hour, warmed to ambient temperature and then further agitated at ambient temperature to provide S-4-Amino-N-[(1-ethyl-2-pyrrolidinyl)methyl]-5-(ethylsulfonyl)-2-methoxybenzamide starting material. The reaction was then concentrated to minimum volume and 822 g of water, followed by 311 g of ethyl acetate, was added. The mixture was agitated and the organic layer removed. The solution was heated to 35° ° C. and 755 g of ethyl acetate and 326 g of 40 wt % potassium carbonate (aq) were added. The mixture was agitated, the phases allowed to separate, and the aqueous layer removed. Then 296 g of water of water was added, the mixture agitated, the phases allowed to separate and the aqueous layer removed. 302 g of water was added, the mixture agitated, the phases allowed to separate and the aqueous layer removed. The organic layer was transferred to a flask with a mechanical stirrer, a thermocouple and a nitrogen line. The organic layer was concentrated to dryness and 531 g of ethyl acetate was added. After agitation, the solution was concentrated to 400 mL. Then 305 g of ethyl acetate was added and the solution was concentrated to 400 mL and was 0.35 wt % water by Karl Fischer titration. The solution was then cooled to 30° C. and seeded with 300 mg of S-4-Amino-N-[(1-ethyl-2-pyrrolidinyl)methyl]-5-(ethylsulfonyl)-2-methoxybenzamide and a slurry formed. The solution was then cooled to 20° C. and agitated, and 495 g of methyl t-butyl ether was added. The slurry was then filtered, washed with 3:1 wt/wt methyl t-butyl ether:ethyl acetate and dried. 160.7 g of S-4-Amino-N-[(1-ethyl-2-pyrrolidinyl)methyl]-5-(ethylsulfonyl)-2-methoxybenzamide was obtained as a crystalline solid, representing a yield of about 74%.

Example 9: Recrystallization of: S-4-Amino-N-[(1-ethyl-2-pyrrolidinyl)methyl]-5-(ethylsulfonyl)-2-methoxybenzamide (Freebase Crystal Form A')

300.19 g of S-4-Amino-N-[(1-ethyl-2-pyrrolidinyl)methyl]-5-(ethylsulfonyl)-2-methoxybenzamide (prepared substantially according to Example 8) and 240.2 g of isopropanol were added to a flask with a stir bar and stopper. The flask was heated to 40° C. to form a solution. The solution was then polish filtered and transferred to a reactor at 40° C. with agitator, nitrogen line, thermocouple and cooling water, using 59.8 g of isopropanol to rinse the flask and polish filter. 300.4 g of heptane was added and the solution agitated. The reactor was cooled to a jacket temperature of 35° C. and 6.91 g of isopropanol was added to the reactor drop wise to create a clear solution. The solution was agitated and then seeded with 602 mg of S-4-Amino-N-[(1-ethyl-2-pyrrolidinyl)methyl]-5-(ethylsulfonyl)-2-methoxy benzamide (Form A') and then agitated for 30 min. The reactor was then cooled to 20° C. and agitated for 30 min. 1399.86 g of heptane was added using an external pump. Following agitation, the slurry was filtered, washed with 15:85 isopropanol:heptane and dried. 281.03 g of S-4-Amino-N-[(1-ethyl-2-pyrrolidinyl)methyl]-5-(ethylsulfonyl)-2-methoxybenzamide of crystal Form A' having greater than 97% chiral purity, and greater than 98% chemical purity, was obtained, representing a yield of about 91%.

An NMR spectrum of the S-4-Amino-N-[(1-ethyl-2-pyrrolidinyl)methyl]-5-(ethylsulfonyl)-2-methoxybenzamide obtained in Example 9 is illustrated in FIG. 9, having the following characteristics: $^1$H NMR (400 MHz, METHANOL-$d_4$) δ ppm 1.12-1.23 (m, 6H) 1.57-1.66 (m, 1H) 1.68-1.80 (m, 2H) 1.95 (dq, J=12.18, 8.33 Hz, 1H) 2.20-2.36 (m, 2H) 2.68 (dtd, J=8.61, 6.26, 6.26, 3.91 Hz, 1H) 2.91 (dq, J=12.08, 7.32 Hz, 1H) 3.12-3.27 (m, 3H) 3.32-3.48 (m, 1H) 3.60 (dd, J=13.30, 3.91 Hz, 1H) 3.97 (s, 3H) 6.49 (s, 1H) 8.28 (s, 1H).

Referring to FIGS. 3A, 3B and 3C, FIGS. 3A, 3B and 3C present data on the S-4-Amino-N-[(1-ethyl-2-pyrrolidinyl)methyl]-5-(ethylsulfonyl)-2-methoxybenzamide, (S)-amisulpride, of crystal Form A' obtained in Example 9. FIG. 3A is a DSC thermogram for crystal Form A' of (S)-amisulpride obtained in Example 9; FIG. 3B a XRPD pattern for crystal Form A' of (S)-amisulpride obtained in Example 9; and FIG. 3C a micrograph image showing crystals of crystal Form A' of the (S)-amisulpride obtained in Example 9.

Example 10A: Resolution of (R)-amisulpride 60 g of racemic 4-Amino-N-[(1-ethyl-2-pyrrolidinyl)methyl]-5-(ethylsulfonyl)-2-methoxybenzamide and 62.53 g of Di-p-toluoyl-D-tartaric acid were added to a 2000 mL jacketed flask equipped with reflux condenser, nitrogen purge, thermocouple and mechanical stirrer. 1615 mL of acetonitrile was added to the flask and the reaction heated to 70° C. The mixture was held for 2 hours at 70° C. and cooled to room temperature at a rate of 1° C. per minute. The mixture was held at room temperature (r.t.) for 1 hour and then filtered. The cake was rinsed with 200 mL of acetonitrile. The solid (termed first stage solid in this example) contained a 91.75:8.25 ratio of (R):(S) enantiomers by chiral HPLC. The solid was then transferred back into the 2000 mL flask equipped with a reflux condenser, nitrogen purge, thermocouple and mechanical stirrer and 1200 mL of acetonitrile was added. The mixture was then heated to 70° C. and water added dropwise to create a clear solution. The solution was cooled to room temperature, stirred for 1 hour and the resultant slurry filtered and rinsed with 200 mL of acetonitrile and then dried. 45.17 g of Dextrorotary Di-p-toluoyl tartrate of 4-Amino-N-[(1-ethyl-2-pyrrolidinyl)methyl]-5-(ethylsulfonyl)-2-methoxybenzamide was obtained representing about a 73% yield from the first stage solid. The solid contained a 99.25:0.75 ratio of (R):(S) enantiomers by chiral HPLC.

Example 10B

Alternative Resolution of (R)-amisulpride: 30.00 kg of 4-amino-N-[(1-ethyl-2-pyrrolidinyl)methyl]-5-(ethylsulfonyl)-2-methoxybenzamide and 32.00 kg of di-p-toluoyl-D-tartaric acid was added to a 1000 L glass-lined reactor equipped with reflux condenser, nitrogen purge, thermocouple and retreat curve impeller. 630.2 kg of acetonitrile was added to the reactor and stirred. 40.80 kg of water was then added to the reaction slurry and heated to 75 C. The mixture was held for 30 minutes at 75° C. and cooled to 15° C. at a rate of 0.25 C per minute. The mixture was then held at 15° C. for 17 hours and then filtered. The resultant cake was washed twice with 90.00 kg of acetonitrile and then dried with a nitrogen flow. 29.78 kg of crude Di-p-toluoyl-D-tartrate of (R)-(+)-4-amino-N-[(1-ethyl-2-pyrrolidinyl)methyl]-5-(ethylsulfonyl)-2-methoxybenzamide was obtained. The solid contained enantiomers as R:S=95.83:4.17 ratio by chiral HPLC. (yield=49%)

The 29.68 kg of crude Di-p-toluoyl-D-tartrate of (R)-(+)-4-amino-N-[(1-ethyl-2-pyrrolidinyl)methyl]-5-(ethylsulfonyl)-2-methoxybenzamide and 341.3 kg of methanol was charged into a 1000 L glass-lined reactor equipped with reflux condenser, nitrogen purge, thermocouple and retreat curve impeller. The mixture was heated to 64° C. and a clear solution was created. The solution was cooled to 58° C. and 0.58 kg of seed added. A slurry formed seeding. The slurry was agitated for 1 hours, then cooled to 0° C. at a rate of 0.3 C per minute. The slurry was held at 0° C. for 15 hour and then filtered. The cake was washed with 103.9 kg of methanol and then dried with a nitrogen flow. 26.73 kg of Di-p-toluoyl-D-tartrate of (R)-(+)-4-amino-N-[(1-ethyl-2-pyrrolidinyl)methyl]-5-(ethylsulfonyl)-2-methoxybenzamide was obtained. The solid contained enantiomers as R:S=99.24:0.76 ratio of by chiral HPLC. (yield=90%). The DSC of the solid obtained is shown in FIG. 19, indicating an endothermic event at 147° C.

An NMR spectrum of Di-p-toluoyl-D-tartrate of (R)-(+)-4-amino-N-[(1-ethyl-2-pyrrolidinyl)methyl]-5-(ethylsulfonyl)-2-methoxybenzamide was obtained in Example 10B, having the following characteristics: $^1$H NMR (400 MHz, DMSO-$d_6$) δ ppm 1.07-1.15 (m, 6H) 1.59-1.67 (m, 1H) 1.73-1.87 (m, 2H) 1.97-2.07 (m, 1H) 2.35 (s, 6H) 2.81-2.96 (m, 2H) 3.09-3.21 (m, 3H) 3.37-3.59 (m, 4H) 5.67 (s, 2H) 6.46 (s, 1H) 6.54 (s, 2H) 7.29 (d, J=7.93 Hz, 4H) 7.82 (d, J=8.54 Hz, 4H) 8.08 (s, 1H) 8.36 (br s, 1H).

26.23 kg of Di-p-toluoyl-D-tartrate of (R)-(+)-4-amino-N-[(1-ethyl-2-pyrrolidinyl)methyl]-5-(ethylsulfonyl)-2-methoxybenzamide was charged into a 500 L glass-lined reactor equipped with reflux condenser, nitrogen purge, thermocouple and retreat curve impeller. 128.8 kg of methyl tert-butyl ether and 63.3 kg of 1N HCl was added to the reactor and agitated for 15 minutes. The phases were allowed to separate, then the organic layer was removed. 156.70 kg of ethylacetate and 35.84 kg of 40 wt % aqueous potassium carbonate were charged into a 500 L glass-lined reactor equipped with reflux condenser, nitrogen purge, thermocouple and retreat curve impeller. The previously obtained aqueous layer was added to the reactor and agitated for 15 minutes. The phases were allowed to separate, then the aqueous layer was removed. 5.25 kg of water was then added to the reactor and agitated for 15 minutes. The phases were allowed to separate, then the aqueous layer was removed. The organic layer was concentrated to 26 kg and 76.80 kg of 2-propanol added. The solution was then filtered and rinsed with 4.51 kg of 2-propanol then transferred into a 200 L glass-lined reactor equipped with reflux condenser, nitrogen purge, thermocouple and retreat curve impeller. The solution was concentrated to 21.91 kg, then 2.56 kg of 2-propanol was added. 2.38 kg of n-heptane was then added and 64.2 g of seed added at 20° C. then the thin slurry stirred for 1 hour and 9.51 kg of n-heptane was added slowly over 80 minutes. The slurry was agitated for 1 hour and 91.60 kg of n-heptane was added slowly over 60 minutes. The slurry was agitated for 19 hours at 20° C. and filtered. The resultant cake was washed with 25.6 kg of 4:1 volume ratio of n-heptane/2-propanol and dried with a nitrogen flow. 12.13 kg of (R)-(+)-4-amino-N-[(1-ethyl-2-pyrrolidinyl)methyl]-5-(ethylsulfonyl)-2-methoxybenzamide was obtained. The solid contained enantiomers as R:S=99.72:0.28 ratio by chiral HPLC. The chemical purity was 99.5% by HPLC.

Example 11: Resolution of (S)-amisulpride 45.17 g of Dextrorotary Di-p-toluoyl tartrate of racemic 4-Amino-N-[(1-ethyl-2-pyrrolidinyl)methyl]-5-(ethylsulfonyl)-2-methoxybenzamide was added to a 500 mL flask equipped with mechanical stirrer and nitrogen purge along with 264 mL ethyl acetate, 53.84 g of 40 wt % potassium carbonate and 100 mL of water, and agitated for 30 minutes. The phases were allowed to separate, the aqueous layer was removed and 60 mL of water added. The phases were allowed to separate, the aqueous layer is removed, 60 mL of water added and the aqueous layer was again removed. The organic layer was concentrated to 60 mL and 145 g of ethyl acetate added and then the solution was concentrated to 60 mL. The resultant solution contained 0.0012 wt % water. The solution was cooled to 30° C., seeded, cooled to room temperature (r.t.) and 98 mL of methyl t-butyl ether was added slowly over 20 minutes. A slurry formed after seeding. The slurry was agitated for 2 hours at r.t and filtered. The cake was washed with 24.26 g of 3:1 methyl t-butyl ether/ethyl acetate and dried, and 10.85 g of 4-Amino-N-[(1-ethyl-2-pyrrolidinyl)methyl]-5-(ethylsulfonyl)-2-methoxybenzamide was obtained representing about a 50% yield from the racemic starting material. The solid contained a 98.90:1.10 ratio of (S):(R) enantiomers by chiral HPLC.

Example 12: Resolution of (S)-amisulpride 60.0 g of racemic amisulpride, 60.52 g of (−)-Di-p-toluoyl-L-tartaric acid, and 1604 mL (1260.7 g) acetonitrile were added to a 2000 mL jacketed flask. The slurry was heated to 70° C. and water was added to the mixture until it became a solution at 70° C. (a total of 115.6 g water was added). The solution was held at 70° C. for an additional 15 mins then cooled back down to room temperature at a rate of 1° C./min. (The solution became a slurry at 47° C.). The mixture was stirred at ambient for 1 hr then filtered, washed with 200 mL of acetonitrile, and dried in vacuo to yield 52.7 g of solid. 50.0 g of the solid and 800 mL of 8.5% water in acetonitrile were added to a 2000 mL jacketed flask. The slurry was heated to 70° C. The mixture was a slurry at 70° C. and more 8.5% water in acetonitrile was added until the all the solid dissolved (311 mL [245.9 g] of additional 8.5% H2O in CH3CN were added). The solution was held at 70° C. for 15 minutes and cooled to room temperature at a rate of 1° C./min. The mixture was stirred at room temperature for an hour then filtered, washed with acetonitrile and dried in vacuo to obtain 39.7 g of (S)-4-amino-N-((1-ethylpyrrolidin-2-yl)methyl)-5-(ethylsulfonyl)-2-methoxybenzamide (2R,3R)-bis((4-methylbenzoyl)oxy)succinic acid salt (79.4% yield, >99% enantiomeric purity as determined by chiral HPLC).

An NMR spectrum of the (S)-4-amino-N-((1-ethylpyrrolidin-2-yl)methyl)-5-(ethylsulfonyl)-2-methoxybenzamide (2R,3R)-bis((4-methylbenzoyl)oxy)succinic acid salt obtained in Example 12 is illustrated in FIG. 10, having the following characteristics: $^1$H NMR (400 MHz, DMSO-d6) δ ppm 1.15-1.22 (m, 6H) 1.69 (br dd, J=12.52, 6.26 HZ, 1H) 1.80-1.95 (m, 2H) 2.07-2.17 (m, 2H) 2.44 (s, 6H) 2.99 (dt, J=13.30, 6.65 Hz, 2H) 3.14-3.32 (m, 3H) 3.47 (br dd, J=13.69, 6.26 Hz, 2H) 3.52-3.59 (m, 1H) 3.59-3.76 (m, 1H) 3.94 (s, 3H) 5.77 (s, 2H) 6.54 (s, 1H) 6.63 (br s, 2H) 7.36-7.41 (m, 4H) 7.92 (br d, J=7.04 Hz, 4H) 8.16 (s, 1H) 8.49 (br s, 1H).

Referring to FIGS. 11A-11B, these figures present data on the (S)-4-amino-N-((1-ethylpyrrolidin-2-yl)methyl)-5-(ethylsulfonyl)-2-methoxybenzamide (2R,3R)-bis((4-methylbenzoyl)oxy)succinic acid salt obtained in Example 12. FIG. 11A is a DSC thermogram (S)-4-amino-N-((1-ethylpyrrolidin-2-yl)methyl)-5-(ethylsulfonyl)-2-methoxybenzamide (2R,3R)-bis((4-methylbenzoyl)oxy)succinic acid salt obtained in Example 12. FIG. 11B is a XRPD pattern for a crystalline form of (S)-4-amino-N-((1-ethylpyrrolidin-2-yl)methyl)-5-(ethylsulfonyl)-2-methoxybenzamide (2R,3R)-bis((4-methylbenzoyl)oxy)succinic acid salt obtained in Example 12, and a listing of the peaks of the XRPD of FIG. 11B are listed in Table 9.

30 g of the product ((S)-4-amino-N-((1-ethylpyrrolidin-2-yl)methyl)-5-(ethylsulfonyl)-2-methoxybenzamide (2R,3R)-bis((4-methylbenzoyl)oxy)succinic acid salt), 200 g ethyl acetate, 15 g 40 wt % $K_2CO_3$, and 15 g water were added to a 1000 mL jacketed flask. It was stirred for 30 minutes and the bottom, aqueous phase was separated using a 1000 mL separation funnel. The organic layer was set aside, and the aqueous layer was added back to the 1000 mL jacketed flask along with another 50 mL ethyl acetate. The solution in the flask was stirred for 15 minutes and the aqueous layer was separated again. The organic layer was washed with 30 mL water and the aqueous layer was separated again. This organic layer and the previously separated organic layer were dried via rotary evaporation to obtain 14.5 g oil. The oil as well as 56 mL ethyl acetate were added to a 250 mL jacketed flask. The solution was stirred at ambient for 1 hr, 60 g methyl tert-butyl ether was added, and it was stirred for another 2 hrs. It was then filtered, washed with 33 g 3:1 methyl tert-butyl ether:ethyl acetate and dried in vacuo. This yielded 3.70 g of (S)-4-amino-N-((1-ethylpyrrolidin-2-yl)methyl)-5-(ethylsulfonyl)-2-methoxybenzamide (of Form A') (25.2% yield, >99% enantiomeric purity as determined by chiral HPLC).

TABLE 9

(S)-4-amino-N-((1-ethylpyrrolidin-2-yl) methyl)-5-(ethylsulfonyl)-2-methoxybenzamide (2R,3R)-bis((4-methylbenzoyl)oxy) succinic acid salt crystal XRPD (FIG. 11B) Peak List

| 2-Theta | Relative Height |
| --- | --- |
| 5.32 | 36.9 |
| 5.51 | 0.7 |
| 7.02 | 42.3 |
| 7.20 | 0.7 |
| 8.18 | 7.8 |
| 8.36 | 33.1 |
| 10.28 | 7.4 |
| 10.64 | 71.6 |
| 10.96 | 3.2 |
| 11.08 | 6.1 |
| 12.00 | 8.4 |
| 12.44 | 56.5 |
| 12.92 | 71 |
| 14.04 | 23.1 |
| 14.42 | 3.2 |
| 15.96 | 81.5 |
| 16.24 | 6.8 |
| 16.76 | 79.4 |
| 17.20 | 42.3 |
| 17.70 | 40.2 |
| 18.06 | 2.3 |
| 18.58 | 6.8 |
| 19.00 | 2.1 |
| 19.72 | 100 |
| 20.60 | 22.2 |
| 21.06 | 74.7 |
| 21.28 | 13.2 |
| 21.98 | 79.7 |
| 22.28 | 48.2 |
| 22.48 | 24.7 |
| 22.78 | 21.7 |
| 23.30 | 5.2 |
| 23.62 | 18 |
| 24.30 | 52.4 |
| 24.78 | 35.1 |
| 24.94 | 19.9 |
| 26.24 | 37.9 |
| 26.76 | 11.4 |
| 27.07 | 3.8 |
| 27.48 | 24.1 |
| 27.92 | 16.4 |
| 28.40 | 20.8 |
| 29.02 | 11.9 |
| 29.35 | 4.1 |
| 29.88 | 21.2 |
| 30.12 | 7.2 |
| 30.7 | 4.1 |
| 31.00 | 6.4 |
| 31.35 | 4.1 |
| 31.72 | 7.4 |
| 32.22 | 6.9 |
| 32.66 | 1.9 |
| 32.84 | 3.3 |
| 33.16 | 13.5 |
| 33.80 | 3.3 |
| 34.52 | 7.4 |
| 34.70 | 11.2 |
| 35.12 | 2.5 |
| 35.54 | 7.8 |
| 36.16 | 2.6 |
| 36.64 | 2.8 |
| 36.92 | 5.6 |
| 37.34 | 4.6 |
| 37.88 | 4.1 |
| 38.54 | 8.5 |
| 38.94 | 2.8 |
| 39.58 | 7.9 |
| 40.18 | 3 |
| 40.88 | 7 |
| 41.20 | 8.3 |
| 41.80 | 2.2 |
| 42.30 | 4.1 |
| 42.51 | 3.9 |
| 43.36 | 34.6 |
| 43.86 | 2.7 |
| 44.50 | 6.2 |

Example 13: General Overview of Preparation of R-4-Amino-N-[(1-ethyl-2-pyrrolidinyl)methyl]-5-(ethylsulfonyl)-2-methoxybenzamide In overview, R-4-Amino-N-[(1-ethyl-2-pyrrolidinyl)methyl]-5-(ethylsulfonyl)-2-methoxybenzamide of Form A can be prepared in two steps: Step 1 Preparation of Crude (R)-amisulpride; and Step 2 Recrystallization of the Crude (R)-amisulpride to crystalline (R)-amisulpride of Form A.

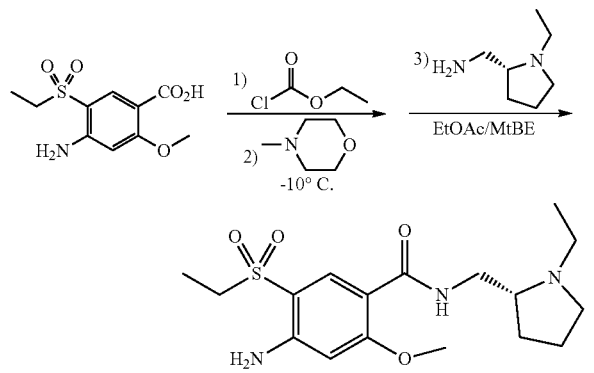

Step 1, Examples 13 and 14

Step 1 in general comprises mixing 4-Amino-5-(ethylsulfonyl)-2-methoxybenzoic acid with ethyl chloroformate and then reacting with (R)-(1-ethyl pyrrolidin-2-yl)methanamine to form R-4-Amino-N-[(1-ethyl-2-pyrrolidinyl)methyl]-5-(ethylsulfonyl)-2-methoxybenzamide hydrochloride. Other coupling reagents such as methyl, isopropyl and isobutyl chloroformates and dimethoxytriazinechloride are also suitable for carrying out the coupling reaction. The resulting product is extracted into water and washed with ethyl acetate. The R-4-Amino-N-[(1-ethyl-2-pyrrolidinyl)methyl]-5-(ethylsulfonyl)-2-methoxybenzamide hydrochloride is converted to freebase, dissolved into ethyl acetate and washed with base and water. The ethyl acetate solution is then dried and concentrated. The ethyl acetate solvate of R-4-Amino-N-[(1-ethyl-2-pyrrolidinyl)methyl]-5-(ethylsulfonyl)-2-methoxybenzamide crystallizes and is converted to R-4-Amino-N-[(1-ethyl-2-pyrrolidinyl)methyl]-5-(ethylsulfonyl)-2-methoxybenzamide (crude freebase) by the addition of methyl-tert butyl ether. The R-4-Amino-N-[(1-ethyl-2-pyrrolidinyl)methyl]-5-(ethylsulfonyl)-2-methoxybenzamide (crude freebase) is then isolated by filtration. The reaction can be performed on a large scale. For example, 96 kg of 2-methoxy 4-amino 5-ethylsulfonyl benzoic acid was converted to 102 kg of (R)-4-Amino-N-[(1-ethyl-2-pyrrolidinyl)methyl]-5-(ethylsulfonyl)-2-methoxybenzamide.

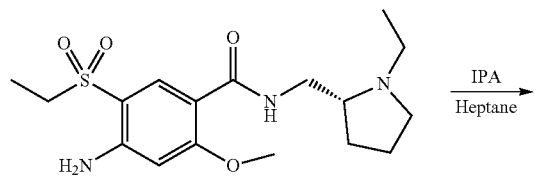

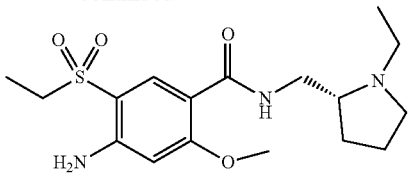

Step 2, Examples 13 and 14

Step 2 in general comprises dissolving the R-4-Amino-N-[(1-ethyl-2-pyrrolidinyl)methyl]-5-(ethylsulfonyl)-2-methoxybenzamide (crude freebase) of Step 1 into isopropanol and polish filtering. The isopropanol solution is concentrated, diluted with n-heptane and seeded with Form A to yield R-4-Amino-N-[(1-ethyl-2-pyrrolidinyl)methyl]-5-(ethylsulfonyl)-2-methoxybenzamide freebase crystals. The mixture is then cooled and filtered to yield crystalline R-4-Amino-N-[(1-ethyl-2-pyrrolidinyl)methyl]-5-(ethylsulfonyl)-2-methoxybenzamide substantially of Form A.

It is to be understood that during the crystallization of R-4-Amino-N-[(1-ethyl-2-pyrrolidinyl)methyl]-5-(ethylsulfonyl)-2-methoxybenzamide (crude) ethyl acetate solvate the amount of water in the ethyl acetate solvent affects the crystallization and is preferably less than 0.5%. Accordingly the water content is preferably monitored during the distillation of the ethyl acetate solution, such as for example by coulometric titration (Karl Fischer). For example, in various embodiments coulometric titration (Karl Fischer) was performed by non-aqueous, perchloric acid titration where approximately 300 mg of sample, accurately weighed, was dissolved in about 50 mL of glacial acetic acid and titrated with 0.1 N perchloric acid and the end-point determined potentiometrically. The weight of sample was corrected for water content and residual solvent content prior to assay calculation. The drying of the isolated solid is also preferably monitored. In various embodiments, the reaction of Step 1 is considered complete when the amount of 4-amino-5-(ethylsulfonyl)-2-methoxybenzoic acid in the reaction mixture is less than or equal to 10 A % (where A % refers to Area % by HPLC) and/or when the amount of 4-amino-5-(ethylsulfonyl)-2-methoxybenzoic acid in the reaction mixture is less than or equal to 10 mol %.

Example 14: Detailed Overview of Preparation of R-4-Amino-N-[(1-ethyl-2-pyrrolidinyl)methyl]-5-(ethylsulfonyl)-2-methoxybenzamide of Form A Step 1: To a mixture of 4-amino-5-(ethylsulfonyl)-2-methoxybenzoic acid in acetone at −10° C. and ethyl chloroformate, 4-methylmorpholine is added at a rate (exothermic) so as to maintain the internal temperature below −5° C. The reaction is stirred for 1 hour at −10° C. and then (R)-(1-ethyl pyrrolidin-2-yl)methanamine is added. After stirring for 2 hours the reaction mixture is concentrated and diluted with water and ethyl acetate. The ethyl acetate layer is removed and the aqueous layer is basified with potassium carbonate. Ethyl acetate is added and the aqueous layer removed. The organic layer is washed with water twice and concentrated. The mixture is diluted with ethyl acetate and concentrated until water content of the ethyl acetate solution is below 0.5%. The solution is seeded at 31° C. with 1 wt % Form A and stirred at the nucleation temperature for 2 h. The mixture is cooled to 20° C. and stirred for 1 h. The slurry is diluted with methyl tert butylether (MtBE) and stirred for 2 h at 20 C. The suspension is filtered and the product cake is washed with MtBE/ethyl acetate. The wet-cake is dried under vacuum at 40° C.±5° C. to constant weight to yield R-4-Amino-N-[(1-ethyl-2-pyrrolidinyl)methyl]-5-(ethylsulfonyl)-2-methoxybenzamide (crude).

Step 2: Isopropanol and R-4-Amino-N-[(1-ethyl-2-pyrrolidinyl)methyl]-5-(ethylsulfonyl)-2-methoxybenzamide (crude) are mixed together. The mixture is heated to 50° C. to achieve dissolution and then passed through a filter. The filtrate is concentrated and cooled to 40° C. n-Heptane is added and the resulting solution is cooled to 28° C. and seeded with Form A. The resulting slurry is cooled to 23° C. and stirred for 1.5 h at this temperature. More n-heptane is added and the slurry is stirred at 22° C. for 13h. The suspension is filtered and the product cake is washed with isopropanol/N-heptane. The wet-cake is dried under vacuum at 40° C.±5° C. to constant weight to yield R-4-Amino-N-[(1-ethyl-2-pyrrolidinyl)methyl]-5-(ethylsulfonyl)-2-methoxybenzamide of Form A.

An NMR spectrum of the R-4-Amino-N-[(1-ethyl-2-pyrrolidinyl)methyl]-5-(ethylsulfonyl)-2-methoxybenzamide of Form A obtained by the methods of Examples 13 and 14 is illustrated in FIG. 12A, and FIG. 12B provides the number scheme used for the assignments of Table 10 based on the NMR spectrum of FIG. 12A, where the following notation is used in Table 10: s: singlet, d: doublet, br s: broad singlet, br d broad doublet, ddd: doublet of doublets of doublets, t: triplet, q: quadruplet; m: multiplet, tt: triplet of triplets; dq: doublet of quadruplets.

TABLE 10

Assignment of $^1$H NMR Spectrum of FIG. 12A

| Carbon (see FIG. 11B) | Chemical Shift | Details |
|---|---|---|
| 1 | 1.19-1.20 | t, J = 7.24 Hz, 3 H |
| 2 | 3.02-3.08 | q, J = 7.43 Hz, 2 H |
| 5 | 6.28 | s, 1 H |
| 8 | 8.45 | s, 1 H |
| 10a, b | 3.18-3.23 | ddd, J = 13.50, 4.89, 2.74 Hz, 1 H |
|  | 3.60-3.66 | ddd, J = 13.69, 7.04, 2.74 Hz, 1 H |
| 11 | 2.53-2.64 | m, 1 H |
| 12a, b | 1.52-1.59 | m, 1 H |
|  | 1.79-1.85 | m, 1 H |
| 13 | 1.64-1.69 | m, 2 H |
| 14a, b | 2.09-2.15 | m, 1 H |
|  | 3.12-3.17 | m, 1 H |
| 15a, b | 2.18-2.21 | m, 1 H |
|  | 2.74-2.81 | dq, J = 11.93, 7.37 Hz, 1 H |
| 16 | 1.04-1.06 | t, J = 7.04 Hz, 3 H |
| 17 | 3.88 | s, 3 H |
| 18 | 5.71 | s, 2 H |
| 19 | 8.05-8.07 | br dd, J = 7.04, 2.35 Hz, 1 H |

A $^{13}$C NMR spectrum of the R-4-Amino-N-[(1-ethyl-2-pyrrolidinyl)methyl]-5-(ethylsulfonyl)-2-methoxybenzamide of Form A obtained by the methods of Examples 13 and 14 is illustrated in FIG. 13A, and FIG. 1.3B provides the number scheme used for the assignments of Table 11 based on the $^{13}$C NMR spectrum of FIG. 13A.

TABLE 11

| Assignment of $^{13}$C NMR Spectrum of FIG. 13A | |
|---|---|
| Chemical Shift (ppm) | Assignment (see FIG. 12B) |
| 7.15 | 1 |
| 49.45 | 2 |
| 112.24 | 3 |
| 111.83 | 4 |

TABLE 11-continued

| Assignment of $^{13}$C NMR Spectrum of FIG. 13A | |
|---|---|
| Chemical Shift (ppm) | Assignment (see FIG. 12B) |
| 98.53 | 5 |
| 162.44 | 6 |
| 150.84 | 7 |
| 136.04 | 8 |
| 164.17 | 9 |
| 41.29 | 10 |
| 62.14 | 11 |
| 28.39 | 12 |
| 22.82 | 13 |
| 53.54 | 14 |
| 47.82 | 15 |
| 14.14 | 16 |
| 56.03 | 17 |

Example 15: General Overview of Preparation of S-4-Amino-N-[(1-ethyl-2-pyrrolidinyl)methyl]-5-(ethylsulfonyl)-2-methoxybenzamide In overview, S-4-Amino-N-[(1-ethyl-2-pyrrolidinyl)methyl]-5-(ethylsulfonyl)-2-methoxybenzamide of Form A' can be prepared in two steps: Step 1 Preparation of Crude (S)-amisulpride; and Step 2 Recrystallization of the Crude (S)-amisulpride to crystalline (S)-amisulpride of Form A'.

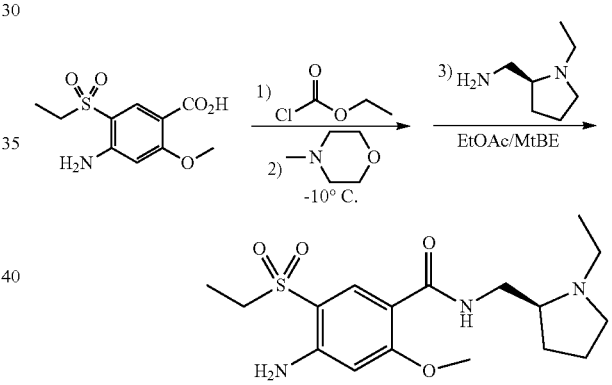

Step 1, Examples 15 and 16

Step 1 in general comprises reacting 4-Amino-5-(ethylsulfonyl)-2-methoxybenzoic acid with ethyl chloroformate and then adding (S)-(1-ethyl pyrrolidin-2-yl)methanamine to form S-4-Amino-N-[(1-ethyl-2-pyrrolidinyl)methyl]-5-(ethylsulfonyl)-2-methoxybenzamide hydrochloride. The resulting product is extracted into water and washed with ethyl acetate. S-4-Amino-N-[(1-ethyl-2-pyrrolidinyl)methyl]-5-(ethylsulfonyl)-2-methoxybenzamide hydrochloride is converted to freebase by the addition of aqueous potassium carbonate, dissolved into ethyl acetate and washed with water. The ethyl acetate solution is dried and concentrated. The ethyl acetate solvate of S-4-Amino-N-[(1-ethyl-2-pyrrolidinyl)methyl]-5-(ethylsulfonyl)-2-methoxybenzamide crystallizes and is desolvated by the addition of methyl-tert butyl ether. The S-4-Amino-N-[(1-ethyl-2-pyrrolidinyl)methyl]-5-(ethylsulfonyl)-2-methoxybenzamide (crude freebase) is isolated by filtration. The reaction can be performed on a large scale. For example, 96 kg of 2-methoxy 4-amino 5-ethylsulfonyl benzoic acid was converted to 101 kg of (S)-4-Amino-N-[(1-ethyl-2-pyrrolidinyl)methyl]-5-(ethylsulfonyl)-2-methoxybenzamide.

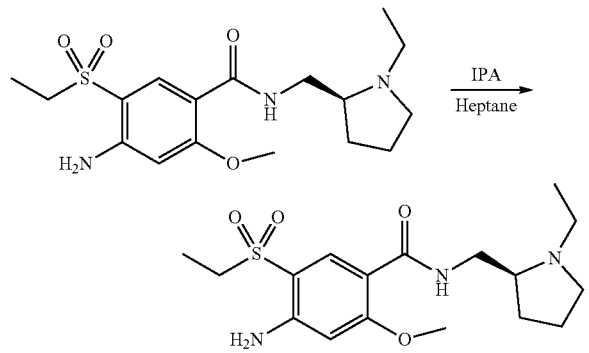

Step 2, Examples 15 and 16

Step 2 in general comprises dissolving the S-4-Amino-N-[(1-ethyl-2-pyrrolidinyl)methyl]-5-(ethylsulfonyl)-2-methoxybenzamide (crude freebase) of into isopropanol and polish filtering. The isopropanol solution is concentrated, diluted with n-heptane and seeded with Form A' to yield a slurry of S-4-Amino-N-[(1-ethyl-2-pyrrolidinyl)methyl]-5-(ethylsulfonyl)-2-methoxybenzamide. The mixture is cooled and filtered to yield crystalline S-4-Amino-N-[(1-ethyl-2-pyrrolidinyl)methyl]-5-(ethylsulfonyl)-2-methoxybenzamide substantially of Form A'.

It is to be understood that during the crystallization of S-4-Amino-N-[(1-ethyl-2-pyrrolidinyl)methyl]-5-(ethylsulfonyl)-2-methoxybenzamide (crude freebase) the amount of water in the ethyl acetate solvent affects the crystallization and is preferably less than 0.5%. Accordingly the water content is preferably monitored during the distillation of the ethyl acetate solution, such as for example by coulometric titration (Karl Fischer). For example, in various embodiments coulometric titration (Karl Fischer) was performed by non-aqueous, perchloric acid titration where approximately 300 mg of sample, accurately weighed, was dissolved in about 50 mL of glacial acetic acid and titrated with 0.1 N perchloric acid and the end-point determined potentiometrically. The weight of sample was corrected for water content and residual solvent content prior to assay calculation. The drying of the isolated solid is also preferably monitored. In various embodiments, the reaction of Step 1 is considered complete when the amount of 4-amino-5-(ethylsulfonyl)-2-methoxybenzoic acid in the reaction mixture is less than or equal to 10 A % (where A % refers to Area % by HPLC) and/or when the amount of 4-amino-5-(ethylsulfonyl)-2-methoxybenzoic acid in the reaction mixture is less than or equal to 10 mol %.

Example 16: Detailed Overview of Preparation of S-4-Amino-N-[(1-ethyl-2-pyrrolidinyl)methyl]-5-(ethylsulfonyl)-2-methoxybenzamide of Form A'

Step 1: To a solution of 4-amino-5-(ethylsulfonyl)-2-methoxybenzoic acid in acetone at −10° C. is added ethyl chloroformate. 4-Methylmorpholine is added at a rate (exothermic) so as to maintain the internal temperature below −5° C. The reaction is stirred for 1 hour at −10° C. and then (S)-(1-ethyl pyrrolidin-2-yl)methanamine is added. After stirring for 2 hours the reaction mixture is concentrated and diluted with water and ethyl acetate. The ethyl acetate layer is removed and the aqueous layer is basified with potassium carbonate. Ethyl acetate is then added and the aqueous layer removed. The organic layer is washed with water twice and concentrated. The mixture is diluted with ethyl acetate and concentrated until the water content of the ethyl acetate solution is below 0.5%. The solution is seeded at 31° C. with 1 wt % S-4-Amino-N-[1-ethyl-2-pyrrolidinyl)methyl]-5-(ethylsulfonyl)-2-methoxybenzamide of Form A' and stirred at the nucleation temperature for 2 h. The mixture is cooled to 20° C. and stirred for 1 h. The slurry is then diluted with methyl tert butylether (MtBE) and stirred for 2 h at 20° C. The suspension is then filtered and the product cake is washed with MtBE/ethyl acetate. The wet-cake is dried under vacuum at 40° C.±5° C. to constant weight to yield S-4-Amino-N-[(1-ethyl-2-pyrrolidinyl)methyl]-5-(ethylsulfonyl)-2-methoxybenzamide (crude).

Step 2: Isopropanol is added to S-4-Amino-N-[(1-ethyl-2-pyrrolidinyl)methyl]-5-(ethylsulfonyl)-2-methoxybenzamide (crude) and the mixture is heated to 50° C. to achieve dissolution. The resulting solution is then passed through a filter. The filtrate is concentrated and cooled to 40° C. n-Heptane is then added and the resulting solution is cooled to 28° C. and seeded with Form A'. The resulting slurry is cooled to 23° C. and stirred for 1.5 h at this temperature. More n-heptane is added and the slurry is stirred at 22° C. for 13 h. The suspension is then filtered and the product cake is washed with isopropanol/n-heptane. The wet-cake is dried under vacuum at 40° C.±5° C. to constant weight to yield S-4-Amino-N-[(1-ethyl-2-pyrrolidinyl)methyl]-5-(ethylsulfonyl)-2-methoxybenzamide substantially of Form A'.

An NMR spectrum of the S-4-Amino-N-[(1-ethyl-2-pyrrolidinyl)methyl]-5-(ethylsulfonyl)-2-methoxybenzamide of Form A' obtained by the methods of Examples 15 and 16 is illustrated in FIG. 14A, and FIG. 14B provides the number scheme used for the assignments of Table 12 based on the NMR spectrum of FIG. 14A, where the following notation is used in Table 12: s: singlet, d: doublet, br s: broad singlet, br d broad doublet, ddd: doublet of doublets of doublets, t: triplet, q: quadruplet; m: multiplet, tt: triplet of triplets; dq: doublet of quadruplets.

TABLE 12

Assignment of $^1$H NMR Spectrum of FIG. 14A

| Carbon (see FIG. 13B) | Chemical Shift | Details |
| --- | --- | --- |
| 1 | 1.21-1.25 | t, J = 7.43 Hz, 3 H |
| 2 | 3.05-3.11 | q, J = 7.30 Hz, 2 H |
| 5 | 6.20 | s, 1 H |
| 8 | 8.50 | s, 1 H |
| 10a, b | 3.22-3.26 | ddd, J = 13.69, 4.89, 2.93 Hz, 1 H |
|  | 3.64-3.70 | ddd, J = 13.69, 7.04, 2.74 Hz, 1 H |
| 11 | 2.57-2.61 | m, 1 H |
| 12a, b | 1.57-1.64 | m, 1 H |
|  | 1.83-1.88 | m, 1 H |
| 13 | 1.66-1.72 | m, 2 H |
| 14a, b | 2.12-2.16 | m, 1 H |
|  | 3.13-3.18 | m, 1 H |
| 15a, b | 2.19-2.23 | m, 1 H |
|  | 2.79-2.84 | dq, J = 12.13, 7.43 Hz, 1 H |
| 16 | 1.07-1.11 | t, J = 7.24 Hz, 3 H |
| 17 | 3.91 | s, 3 H |
| 18 | 5.51 | br s, 2 H |
| 19 | 8.02-8.03 | br d, J = 5.1 Hz, 1 H |

A $^{13}$C NMR spectrum of the S-4-Amino-N-[(1-ethyl-2-pyrrolidinyl)methyl]-5-(ethylsulfonyl)-2-methoxybenzamide of Form A' obtained by the methods of Examples 15 and 16 is illustrated in FIG. 15A, and FIG. 15B provides the number scheme used for the assignments of Table 13 based on the $^{13}$C NMR spectrum of FIG. 15A.

TABLE 13

Assignment of $^{13}$C NMR Spectrum of FIG. 15A

| Chemical Shift (ppm) | Assignment (see FIG. 14B) |
|---|---|
| 7.23 | 1 |
| 49.67 | 2 |
| 112.81 | 3 |
| 112.30 | 4 |
| 98.44 | 5 |
| 162.41 | 6 |
| 150.54 | 7 |
| 136.35 | 8 |
| 164.05 | 9 |
| 41.31 | 10 |
| 62.23 | 11 |
| 28.43 | 12 |
| 22.90 | 13 |
| 53.63 | 14 |
| 47.89 | 15 |
| 14.23 | 16 |
| 56.00 | 17 |

Example 17: Production Attempt of crystalline S-(−)-4-Amino-N-[(1-ethyl-2-pyrrolidinyl)methyl]-5-(ethylsulfonyl)-2-methoxybenzamide D-tartrate The present inventors have discovered that previously described methods for production of crystalline S-(−)-4-Amino-N-[(1-ethyl-2-pyrrolidinyl)methyl]-5-(ethylsulfonyl)-2-methoxybenzamide D-tartrate, as described in U.S. Pat. No. 6,187,807 ("the '807 Patent") and U.S. Pat. No. 4,294,828 ("the '828 Patent") yielded a crystalline solid that is different from that reported in the '807 patent and '828 patent. The present inventors have also discovered that previously described methods for production of S-(−)-4-Amino-N-[(1-ethyl-2-pyrrolidinyl)methyl]-5-(ethylsulfonyl)-2-methoxybenzamide in the '807 patent and the '828 patent did not yield a crystalline solid. S-(−)-4-Amino-N-[(1-ethyl-2-pyrrolidinyl)methyl]-5-(ethylsulfonyl)-2-methoxybenzamide and crystalline D-tartrate of S-(−)-4-Amino-N-[(1-ethyl-2-pyrrolidinyl)methyl]-5-(ethylsulfonyl)-2-methoxybenzamide productions were attempted substantially in accord with Example V of the '828 Patent and Example 1 of the '807 Patent.

95 g of 2-methoxy-4-amino-5-ethylsulphonylbenzoic acid was dissolved in 370 ml of acetone, in the presence of 37 g of triethylamine, treated with 40 g of ethyl chloroformate and then treated with 57 g of (S)-(−)-1-ethyl-2-aminomethylpyrrolidine. (S)-(−)-N-(1-ethyl-2-pyrrolidinylmethyl)-2-methoxy-4-amino-5-ethylsulphonylbenzamide was obtained as an oil.

More specifically, 95.4 g of 2-methoxy 4-amino 5-ethylsulfonyl benzoic acid and 291.7 g acetone was placed into a jacketed flask fitted with a thermometer, and an addition funnel. 37.7 g triethylamine was added and the mixture was cooled to 0° C. 39.69 g of ethyl chloroformate was added dropwise via addition funnel. The mixture was agitated for 30 minutes and then 57.1 g (S)-1-ethyl 2-aminomethylpyrrolidine was added drop wise while maintaining the temperature between 5 and 10° C. The mixture was warmed to 10° C. and agitated for 5 minutes and then warmed to 22° C., and agitated for 18 hours. The slurry was filtered to remove the triethylamine hydrochloride and then the acetone was removed on a rotovap. The residue was dissolved in 500 mL of water and 200 mL of 2N NaOH was added. The mixture contained two layers (aqueous and oil). After 30 minutes, the water was decanted off and an additional 283.9 g water was added to the oil and the mixture was stirred then allowed to separate for 30 minutes. The water was again decanted off and 157.1 g water was added and the mixture stirred then allowed to settle for 30 minutes. The water was again decanted off and the resulting product was obtained as an oil.

133 g of the (S)-(−)-N-(1-ethyl-2-pyrrolidinylmethyl)-2-methoxy-4-amino-5-ethylsulphonylbenzamide obtained was dissolved in 500 ml of methanol, then 54 g of D-(−)-tartaric acid dissolved in 80 ml of methanol was added.

For example, the oil of (S)-(−)-N-(1-ethyl-2-pyrrolidinylmethyl)-2-methoxy-4-amino-5-ethylsulphonylbenzamide was dissolved in 500 mL of methanol. 54.01 g of D-(−)-tartaric acid in 80 mL of methanol was added. An additional 70.4 g methanol was added to ensure all of the D-(−)-tartaric acid was added. A thick slurry formed and was agitated for 45 minutes at 22° C. The slurry was then vacuum filtered and washed with 156.1 g methanol, then 164.3 g methanol, and finally 149.7 g of methanol. 199.3 g wet cake was dried in a vacuum oven overnight at 40° C. for 18 hours. After drying 111.01 g of white solid was obtained.

The 111.01 g of solid and 367.25 g of methanol were placed into a 1000 mL reactor. The solution was heated and the mixture became a solution at 56° C. The solution was held at 70° C. for 20 minutes and then cooled back down to 22° C. The solution was became a slurry at 25° C. The slurry was stirred for 1.5 hours, vacuum filtered, and washed with 34.7 g of methanol. The wet cake was dried in a vacuum oven at 40° C. for 20 h. This resulted in 109.48 g of the product.

An NMR spectrum of D-tartrate (S)-(−)-N-(1-ethyl-2-pyrrolidinylmethyl)-2-methoxy-4-amino-5-ethylsulphonylbenzamide was obtained in Example 17, having the following characteristics: $^1$H NMR (400 MHz, METHANOL-d$_4$) δ ppm 1.21 (t, J=7.43 Hz, 3H) 1.37 (t, J=7.43 Hz, 3H) 1.91-2.12 (m, 3H) 2.20-2.27 (m, 1H) 3.10-3.19 (m, 4H) 3.33 (m, 3H) 3.46-3.53 (m, 1H) 3.65-3.74 (m, 3H) 3.82-3.88 (m, 1H) 3.99 (s, 3H) 4.40 (s, 2H) 6.51 (s, 1H) 8.29 (s, 1H).

The solid obtained was confirmed to be D-tartrate of S-(−)-4-Amino-N-[(1-ethyl-2-pyrrolidinyl)methyl]-5-(ethylsulfonyl)-2-methoxybenzamide by chiral HPLC and had a melting point of 80° C., as compared to the melting point of 100° C. reported in the '828 and '807 Patents.

FIG. 21 shows the DSC thermogram of D-tartrate of S-(−)-4-Amino-N-[(1-ethyl-2-pyrrolidinyl)methyl]-5-(ethylsulfonyl)-2-methoxybenzamide, with an endothermic event at 82° C. having an onset at 77° C.

FIG. 20 shows the XRPD pattern of D-tartrate of S-(−)-4-Amino-N-[(1-ethyl-2-pyrrolidinyl)methyl]-5-(ethylsulfonyl)-2-methoxybenzamide. Table 15 below shows the XRDP peaks. The XRPD pattern of FIG. 20 was obtained with a Rigaku MiniFlex II Desktop X-Ray diffractometer using Cu radiation (Cu Kα λ=1.54184 Å). The tube voltage and amperage were set to 30 kV and 15 mA, respectively. The scattering slit was fixed at 1.25° and the receiving slit was fixed at 0.3 mm. Diffracted radiation was detected by a NaI scintillation detector. A θ-2θ continuous scan at 1.0°/min with a step size of 0.02-0.05° from 3 to 45° 2θ was used. Data were collected and analyzed using Jade 8.5.4. Each sample was prepared for analysis by placing it in a low background, round, 0.1 mm indent sample holder. In FIG. 20 2-Theta angles in degrees (x-axis) are plotted against peak intensity in terms of the count rate per second (y-axis).

TABLE 15

| 2-Theta (degree) | Relative height % |
|---|---|
| 6.44 | 4 |
| 7.5 | 6.4 |
| 9.1 | 30.8 |
| 10.36 | 98.2 |
| 12.34 | 16.5 |
| 12.76 | 100 |
| 13.34 | 4.9 |
| 13.76 | 25.5 |
| 15.06 | 12.5 |
| 15.3 | 24 |
| 15.88 | 69 |
| 16.38 | 25.7 |
| 17.24 | 42.7 |
| 17.64 | 18.4 |
| 17.96 | 17.6 |
| 18.26 | 26.7 |
| 19.46 | 71.4 |
| 20.44 | 3.7 |
| 21.44 | 87.3 |
| 22.12 | 66.7 |
| 22.52 | 71.1 |
| 23.08 | 22.4 |
| 23.46 | 6.4 |
| 24.44 | 65.2 |
| 24.8 | 23.8 |
| 25.26 | 24.2 |
| 25.68 | 34.5 |
| 26.18 | 8.6 |
| 27.08 | 31.7 |
| 27.72 | 9.6 |
| 28.28 | 25.8 |
| 28.84 | 14.1 |
| 29.54 | 5.6 |
| 30.66 | 17.8 |
| 31.1 | 9.2 |
| 31.59 | 6.6 |
| 32.28 | 5.6 |
| 32.75 | 5.5 |
| 33.36 | 21.6 |
| 34.08 | 35.6 |
| 34.52 | 27.3 |
| 35.58 | 7.2 |
| 36.92 | 9.6 |
| 37.56 | 11.2 |
| 38.01 | 3.4 |
| 38.36 | 6.1 |
| 39.07 | 5 |
| 39.44 | 9.8 |
| 40.16 | 11.3 |
| 41.32 | 4 |
| 41.88 | 7.5 |
| 42.62 | 4.9 |
| 42.88 | 3.9 |
| 43.7 | 23.5 |
| 44.19 | 5.4 |

Example 18: Production Attempt of crystalline R-(+)-4-Amino-N-[(1-ethyl-2-pyrrolidinyl)methyl]-5-(ethylsulfonyl)-2-methoxybenzamide L-tartrate The present inventors have discovered that previously described methods for production of crystalline R-(+)-4-Amino-N-[(1-ethyl-2-pyrrolidinyl)methyl]-5-(ethylsulfonyl)-2-methoxybenzamide L-tartrate, as described in U.S. Pat. No. 4,294,828 ("the '828 Patent") yielded a crystalline solid that is different from that in the '828 patent. R-(+)-4-Amino-N-[(1-ethyl-2-pyrrolidinyl)methyl]-5-(ethylsulfonyl)-2-methoxybenzamide and L-tartrate of R-(+)-4-amino-N-[(1-ethyl-2-pyrrolidinyl)methyl]-5-(ethylsulfonyl)-2-methoxybenzamide productions were attempted substantially in accord with Example IV of the '828 Patent.

104 g of 2-methoxy 4-amino 5-ethylsulphonyl benzoic acid and 380 g acetone was placed into a jacketed flask fitted with a thermometer, and an addition funnel. 55 g triethylamine was added and the mixture was cooled to 0° C. 41 g of ethyl chloroformate was added drop wise via addition funnel. The mixture was agitated for 1 h and then 57 g (R)-1-ethyl 2-aminomethylpyrrolidine was added drop wise while maintaining the temperature between 5° and 10° C. The mixture was warmed to 22° C., and stirred for 18 h at 22° C. The slurry was filtered to remove the triethylamine hydrochloride and then the acetone was removed on a rotovap. The residue was dissolved in 500 mL of water and 100 mL of 2N NaOH was added (pH>12). The mixture contained two layers (aqueous and oil). 250 mg of (R)-(+)-N-(1-ethyl-2-pyrrolidinylmethyl)-2-methoxy-4-amino-5-ethylsulphonylbenzamide was added and the mixture stirred for 1 d (R)-(+)-N-(1-ethyl-2-pyrrolidinylmethyl)-2-methoxy-4-amino-5-ethylsulphonylbenzamide dissolved into the oil. The resulting mixture contained 2 layers (aqueous and oil). The water was decanted off and the resulting product is an oil even after seeding with 0.5 g of (R)-(+)-N-(1-ethyl-2-pyrrolidinylmethyl)-2-methoxy-4-amino-5-ethylsulphonylbenzamide.

The oil (R)-(+)-4-Amino-N-[(1-ethyl-2-pyrrolidinyl)methyl]-5-(ethylsulfonyl)-2-methoxybenzamide was dissolved into 500 g of methanol. L-(+)-tartaric acid in 120 g of methanol was added. The mixture was stirred at 22° C. and 100 mg of R-(+)-4-Amino-N-[(1-ethyl-2-pyrrolidinyl)methyl]-5-(ethylsulfonyl)-2-methoxybenzamide L-tartrate was added. The resulting very thick slurry was stirred for 2 h at 22° C. filtered and washed with 150 g of methanol. After drying 110 g of white solid was obtained. The 110 g of solid and 500 g of methanol were placed into a 1 L jacketed flask equipped with a mechanical stirrer and thermocouple. The flask was heated and the mixture became a solution at 60° C. The solution was polish filtered and returned to the flask. The solution was cooled to 22° C. and became a slurry at 38° C. The slurry was stirred for 16 hours, filtered and washed with 150 g of methanol. The solid was dried in vacuo at 35° C. for 20 h. This yielded 92.5 g of white solid.

The solid obtained had a melting point of 78° C., as compared to the melting point of 98-108° C. reported in the '828 and '807 Patents.

An NMR spectrum of L-tartrate R-(+)-4-Amino-N-[(1-ethyl-2-pyrrolidinyl)methyl]-5-(ethylsulfonyl)-2-methoxybenzamide was obtained in Example 18, having the following characteristics: $^1$H NMR (400 MHz, METHANOL-d$_4$) δ ppm 1.21 (t, J=7.43 Hz, 3H) 1.37 (t, J=7.24 Hz, 3H) 1.90-2.05 (m, 2H) 2.05-2.15 (m, 1H) 2.17-2.33 (m, 1H) 3.05-3.29 (m, 4H) 3.34 (s, 2H) 3.39-3.58 (m, 2H) 3.60-3.78 (m, 3H) 3.79-3.93 (m, 1H) 3.99 (s, 3H) 4.39 (s, 2H) 6.51 (s, 1H) 8.30 (s, 1H).

FIG. 23 shows the DSC thermogram of L-tartrate of R-(+)-4-Amino-N-[(1-ethyl-2-pyrrolidinyl)methyl]-5-(ethylsulfonyl)-2-methoxybenzamide, with an endothermic event at 78° C. having an onset at 75° C.

FIG. 22 shows the XRPD pattern of L-tartrate of R-(+)-4-Amino-N-[(1-ethyl-2-pyrrolidinyl)methyl]-5-(ethylsulfonyl)-2-methoxybenzamide. Table 16 below shows the XRDP peaks. The XRPD pattern of FIG. 22 was obtained with a Rigaku MiniFlex II Desktop X-Ray diffractometer using Cu radiation (Cu Kα λ=1.54184 Å). The tube voltage and amperage were set to 30 kV and 15 mA, respectively. The scattering slit was fixed at 1.25° and the receiving slit was fixed at 0.3 mm. Diffracted radiation was detected by a NaI scintillation detector. A θ-2θ continuous scan at 1.0°/min with a step size of 0.02-0.05° from 3 to 45° 2θ was used. Data were collected and analyzed using Jade 8.5.4. Each sample was prepared for analysis by placing it in a low background, round, 0.1 mm indent sample holder. In FIG. 22 2-Theta angles in degrees (x-axis) are plotted against peak intensity in terms of the count rate per second (y-axis).

TABLE 16

| 2-Theta (degree) | Relative height % |
| --- | --- |
| 6.41 | 3 |
| 7.5 | 6.4 |
| 9.12 | 32.4 |
| 10.38 | 86.1 |
| 12.42 | 21.9 |
| 12.8 | 100 |
| 13.8 | 15.8 |
| 15.32 | 30 |
| 15.9 | 78.4 |
| 16.4 | 17 |
| 17.26 | 34.4 |
| 17.6 | 12.4 |
| 18.26 | 33.3 |
| 19.48 | 87.8 |
| 21.48 | 95.1 |
| 22.12 | 79.8 |
| 22.6 | 68.6 |
| 23.14 | 24.8 |
| 23.49 | 5.9 |
| 24.44 | 79.8 |
| 24.86 | 28.4 |
| 25.34 | 13.7 |
| 25.7 | 35.8 |
| 26.96 | 30.8 |
| 27.48 | 11 |
| 27.74 | 6.2 |
| 28.34 | 26.9 |
| 28.86 | 10.6 |
| 30.84 | 24.6 |
| 31.58 | 7.9 |
| 32.43 | 2.9 |
| 32.86 | 7 |
| 33.42 | 23.5 |
| 34.16 | 47.7 |
| 34.54 | 30.2 |
| 35.66 | 6.2 |
| 36.96 | 12.9 |
| 37.72 | 9.3 |
| 38.44 | 6.3 |
| 39.5 | 8.3 |
| 40.24 | 11.9 |
| 41.92 | 7.2 |
| 42.64 | 4.6 |
| 43.74 | 27.8 |

Example 19: Production Attempt of crystalline S-(+4-Amino-N-[(1-ethyl-2-pyrrolidinyl)methyl]-5-(ethylsulfonyl)-2-methoxybenzamide The present inventors have discovered that previously described methods for production of allegedly crystalline S-(−)-4-Amino-N-[(1-ethyl-2-pyrrolidinyl)methyl]-5-(ethylsulfonyl)-2-methoxy-benzamide, as described in CN Publication CN 10189899 ("the '899 Patent") do not yield a crystalline solid. Crystalline S-(+)-4-Amino-N-[(1-ethyl-2-pyrrolidinyl)methyl]-5-(ethylsulfonyl)-2-methoxybenzamide production was attempted substantially in accord with Examples 1-4 of the '899 Patent.

Example 1 of the '899 Patent

A jacketed 250 mL round bottom was charged with 60 g of glycerin, 54 g of (S) (−)-1-ethyl-2-amino-methylpyrrolidine and 90 g of methyl 4-amino-5-(ethanesulfonyl)-2-methoxybenzoate. The slurry was stirred at 87° C. for 12 hours, HPLC analysis indicated an 18:82 ratio of methyl 4-amino-5-(ethanesulfonyl)-2-methoxybenzoate and 4-amino-5-(ethanesulfonyl)-N-[(1-ethylpyrrolidin-2-yl) methyl]-2-methoxybenzamide in the mixture. The mixture was cooled to 0° C. and stirred at 0° C. for 3 hours. The resulting mixture was a thick oil. Even stirring the mixture at 0° C. for a total of 48 hours, the resulting mixture was a still thick oil.

Example 2 of the '8499 Patent

A jacketed 250 mL round bottom was charged with 60 g of glycerin, 54 g of (S) (−)-1-ethyl-2-amino-methylpyrrolidine and 90 g of methyl 4-amino-5-(ethanesulfonyl)-2-methoxybenzoate. The slurry was stirred at 93° C. for 9 hours. HPLC analysis indicated an ratio of 18:82 methyl 4-amino-5-(ethanesulfonyl)-2-methoxybenzoate and 4-amino-5-(ethanesulfonyl)-N-[(1-ethylpyrrolidin-2-yl) methyl]-2-methoxybenzamide in the mixture. The mixture was cooled to 0° C. and stirred at 0° C. for 3 hour. The resulting mixture was a thick oil. Even stirring the mixture at 0° C. for a total of 4 hours, the resulting mixture was a thick oil.

Example 3 of '899 Patent

A jacketed 250 mL round bottom was charged with 60 g of glycerin, 54 g of (S) (−)-1-ethyl-2-amino-methylpyrrolidine and 90 g of methyl 4-amino-5-(ethanesulfonyl)-2-methoxybenzoate. The slurry was stirred at 74° C. for 12 hours. HPLC analysis indicated an 37:63 ratio of methyl 4-amino-5-(ethanesulfonyl)-2-methoxybenzoate and 4-amino-5-(ethanesulfonyl)-N-[(1-ethylpyrrolidin-2-yl) methyl]-2-methoxybenzamide in the mixture. The mixture was cooled to 0° C. and stirred at 0° C. for 3 hours. The resulting mixture was a slurry in a thick oil. Even stirring the mixture at 0° C. for a total of 48 hours, showed no change with the resulting mixture being a slurry in a thick oil. An attempt to filter the slurry was performed. The slurry was filtered, which took 2 days, and the solid washed with ethanol. The solid was analyzed and found to be the starting material methyl 4-amino-5-(ethanesulfonyl)-2-methoxybenzoate.

Example 4 of the '899 Patent

A jacketed 250 mL round bottom was charged with 60 g of glycerin, 54 g of (S) (−)-1-ethyl-2-amino-methylpyrrolidine and 90 g of methyl 4-amino-5-(ethanesulfonyl)-2-methoxybenzoate. The slurry was stirred at 102° C. for 16 hours. HPLC analysis indicated a 3:97 ratio of methyl 4-amino-5-(ethanesulfonyl)-2-methoxybenzoate and 4-amino-5-(ethanesulfonyl)-N-[(1-ethylpyrrolidin-2-yl) methyl]-2-methoxybenzamide in the mixture. The mixture was cooled to 0° C. and stirred at 0° C. for 3 hours. The resulting mixture was a thick oil. The thick oil was place in a refrigerator at 4° C. for 2 days (still oil).

Example 5 of the '899 Patent was not attempted because the conditions are the same as Examples 2 and 4.

Although the invention has been described with reference to a specific embodiment this description is not meant to be construed in a limiting sense. The invention being thus described, it is apparent that the same can be varied in many ways. Such variations are not to be regarded as a departure from the spirit and scope of the present invention, and all such modifications, alternatives, and equivalents as would be obvious to one skilled in the art are intended to be included within the scope of the following claims.

What is claimed is:

1. A crystalline form of (R)-(+)-amisulpride characterized by a powder x-ray diffraction pattern comprising peaks, in terms of 2-theta, at 7.0±0.2°, 9.7±0.2°, and 15.4±0.2°, wherein the crystalline form of (R)-(+)-amisulpride has a chiral purity greater than about 95%.

2. The crystalline form of (R)-(+)-amisulpride of claim 1, wherein the chiral purity is greater than about 97%.

3. The crystalline form of (R)-(+)-amisulpride of claim 2, wherein the chiral purity is greater than about 99%.

4. The crystalline form of (R)-(+)-amisulpride of claim 1, characterized by the powder x-ray diffraction pattern further comprising peaks, in terms of 2-theta, at 9.3±0.2°, and 19.4±0.2°.

5. The crystalline form of (R)-(+)-amisulpride of claim 1, characterized by a powder x-ray diffraction pattern substantially in accord with FIG. 2B.

6. The crystalline form of (R)-(+)-amisulpride of claim 1, characterized by a differential scanning calorimetry thermogram comprising an endothermic event at 101±3° C.

7. A crystalline form of (R)-(+)-amisulpride characterized by a powder x-ray diffraction pattern comprising peaks, in terms of 2-theta, at 7.0±0.2°, 9.7±0.2°, and 15.4±0.2°, wherein the crystalline form of (R)-(+)-amisulpride has a chemical purity greater than about 95%.

8. The crystalline form of (R)-(+)-amisulpride of claim 7, wherein the chemical purity is greater than about 97%.

9. The crystalline form of (R)-(+)-amisulpride of claim 8, wherein the chemical purity is greater than about 99%.

10. The crystalline form of (R)-(+)-amisulpride of claim 7, characterized by the powder x-ray diffraction pattern further comprising peaks, in terms of 2-theta, at 9.3±0.2°, and 19.4±0.2°.

11. The crystalline form of (R)-(+)-amisulpride of claim 7, characterized by a powder x-ray diffraction pattern substantially in accord with FIG. 2B.

12. The crystalline form of (R)-(+)-amisulpride of claim 7, characterized by a differential scanning calorimetry thermogram comprising an endothermic event at 101±3° C.

13. A crystalline form of (R)-(+)-amisulpride characterized by a powder x-ray diffraction pattern comprising peaks, in terms of 2-theta, at 7.0±0.2°, 9.7±0.2°, and 15.4±0.2°, wherein the crystalline form of (R)-(+)-amisulpride has a polymorph purity greater than about 90%.

14. The crystalline form of (R)-(+)-amisulpride of claim 13, characterized by the powder x-ray diffraction pattern further comprising peaks, in terms of 2-theta, at 9.3±0.2°, and 19.4±0.2°.

15. The crystalline form of (R)-(+)-amisulpride of claim 13, characterized by a powder x-ray diffraction pattern substantially in accord with FIG. 2B.

16. The crystalline form of (R)-(+)-amisulpride of claim 13, characterized by a differential scanning calorimetry thermogram comprising an endothermic event at 101±3° C.

17. A crystalline form of (R)-(+)-amisulpride characterized by a powder x-ray diffraction pattern comprising peaks, in terms of 2-theta, at 7.0±0.2°, 9.7±0.2°, and 15.4±0.2°, wherein the crystalline form of (R)-(+)-amisulpride has a chiral purity greater than about 97%, a chemical purity greater than about 97%, and a polymorph purity greater than about 90%.

18. A crystalline form of (S)-(−)-amisulpride characterized by a powder x-ray diffraction pattern comprising peaks, in terms of 2-theta, at 7.0±0.2°, 9.7±0.2°, and 15.4±0.2°, wherein the crystalline form of (S)-(−)-amisulpride has a chiral purity greater than about 95%.

19. The crystalline form of (S)-(−)-amisulpride of claim 18, wherein the chiral purity is greater than about 97%.

20. The crystalline form of (S)-(−)-amisulpride of claim 19, wherein the chiral purity is greater than about 99%.

21. The crystalline form of (S)-(−)-amisulpride of claim 18, characterized by the powder x-ray diffraction pattern further comprising peaks, in terms of 2-theta, at 9.3±0.2°, and 19.4±0.2°.

22. The crystalline form of (S)-(−)-amisulpride of claim 18, characterized by a powder x-ray diffraction pattern substantially in accord with FIG. 3B.

23. The crystalline form of (S)-(−)-amisulpride of claim 18, characterized by a differential scanning calorimetry thermogram comprising an endothermic event at 101±3° C.

24. A crystalline form of (S)-(−)-amisulpride characterized by a powder x-ray diffraction pattern comprising peaks, in terms of 2-theta, at 7.0±0.2°, 9.7±0.2°, and 15.4±0.2°, wherein the crystalline form of (S)-(−)-amisulpride has a chemical purity greater than about 95%.

25. The crystalline form of (S)-(−)-amisulpride of claim 24, wherein the chemical purity is greater than about 97%.

26. The crystalline form of (S)-(−)-amisulpride of claim 25, wherein the chemical purity is greater than about 99%.

27. The crystalline form of (S)-(−)-amisulpride of claim 24, characterized by the powder x-ray diffraction pattern further comprising peaks, in terms of 2-theta, at 9.3±0.2°, and 19.4±0.2°.

28. The crystalline form of (S)-(−)-amisulpride of claim 24, characterized by a powder x-ray diffraction pattern substantially in accord with FIG. 3B.

29. The crystalline form of (S)-(−)-amisulpride of claim 24, characterized by a differential scanning calorimetry thermogram comprising an endothermic event at 101±3° C.

30. A crystalline form of (S)-(−)-amisulpride characterized by a powder x-ray diffraction pattern comprising peaks, in terms of 2-theta, at 7.0±0.2°, 9.7±0.2°, and 15.4±0.2°, wherein the crystalline form of (S)-(−)-amisulpride has a polymorph purity greater than about 90%.

31. The crystalline form of (S)-(−)-amisulpride of claim 30, characterized by the powder x-ray diffraction pattern further comprising peaks, in terms of 2-theta, at 9.3±0.2°, and 19.4±0.2°.

32. The crystalline form of (S)-(−)-amisulpride of claim 30, characterized by a powder x-ray diffraction pattern substantially in accord with FIG. 3B.

33. The crystalline form of (S)-(−)-amisulpride of claim 30, characterized by a differential scanning calorimetry thermogram comprising an endothermic event at 101±3° C.

34. A crystalline form of (S)-(−)-amisulpride characterized by a powder x-ray diffraction pattern comprising peaks, in terms of 2-theta, at 7.0±0.2°, 9.7±0.2°, and 15.4±0.2°, wherein the crystalline form of (S)-(−)-amisulpride has a chiral purity greater than about 97%, a chemical purity greater than about 97%, and a polymorph purity greater than about 90%.

35. A pharmaceutical composition comprising the crystalline form of claim 1 and a pharmaceutically acceptable carrier or diluent.

36. A pharmaceutical composition comprising the crystalline form of claim 7 and a pharmaceutically acceptable carrier or diluent.

37. A pharmaceutical composition comprising the crystalline form of claim 13 and a pharmaceutically acceptable carrier or diluent.

38. A pharmaceutical composition comprising the crystalline form of claim 17 and a pharmaceutically acceptable carrier or diluent.

39. A pharmaceutical composition comprising the crystalline form of claim 18 and a pharmaceutically acceptable carrier or diluent.

40. A pharmaceutical composition comprising the crystalline form of claim 24 and a pharmaceutically acceptable carrier or diluent.

41. A pharmaceutical composition comprising the crystalline form of claim 30 and a pharmaceutically acceptable carrier or diluent.

42. A pharmaceutical composition comprising the crystalline form of claim 34 and a pharmaceutically acceptable carrier or diluent.

\* \* \* \* \*